US011766476B2

(12) United States Patent
Gladue et al.

(10) Patent No.: US 11,766,476 B2
(45) Date of Patent: Sep. 26, 2023

(54) GENOMIC DELETION IN AFRICAN SWINE FEVER VACCINE ALLOWING EFFICIENT GROWTH IN STABLE CELL LINES

(71) Applicant: The United States of America, as represented by the Secretary of Agriculture, Washington, DC (US)

(72) Inventors: Douglas P. Gladue, Guilford, CT (US); Manuel V. Borca, Westbrook, CT (US)

(73) Assignee: The United States of America, as represented by The Secretary of Agriculture, Washington, DC (US)

(*) Notice: Subject to any disclaimer, the term of this patent is extended or adjusted under 35 U.S.C. 154(b) by 206 days.

(21) Appl. No.: 17/130,814

(22) Filed: Dec. 22, 2020

(65) Prior Publication Data

US 2022/0193217 A1 Jun. 23, 2022

(51) Int. Cl.

| | |
|---|---|
| ***C12N 7/00*** | (2006.01) |
| ***A61K 39/12*** | (2006.01) |
| ***C12N 7/04*** | (2006.01) |
| *A61K 39/00* | (2006.01) |

(52) U.S. Cl.

CPC ................ *A61K 39/12* (2013.01); *C12N 7/04* (2013.01); *A61K 2039/5254* (2013.01); *C12N 2710/12021* (2013.01); *C12N 2710/12034* (2013.01)

(58) Field of Classification Search

None

See application file for complete search history.

(56) References Cited

FOREIGN PATENT DOCUMENTS

| | | | | |
|---|---|---|---|---|
| CN | 114555793 A | * | 5/2022 | ............ A61K 39/12 |
| WO | WO-2022090131 A1 | * | 5/2022 | |

OTHER PUBLICATIONS

Bosch Camos et al., "African swine fever vaccines: a promising work still in progress," Porcine Health Management, 6:17 at https://doi.org/10.1186/s40813-020-00154-2 (Year: 2020).*

Sang et al., "Progress Toward Development of Effective and Safe African Swine Fever Virus Vaccines," Frontiers in Veterinary Science, 7:84 doi: 10.3389/fvets.2020.00084 (Year: 2020).*

WIPO English translation of CN114555793A (Year: 2022).*

* cited by examiner

*Primary Examiner* — M Franco G Salvoza

(74) *Attorney, Agent, or Firm* — John D. Fado; Mark D. McNemar

(57) ABSTRACT

Provided herein are details on the construction of a recombinant African Swine Fever Virus (ASFV) live attenuated vaccine for prevention of ASF caused by various strains of ASFV, such as the highly virulent Georgia 2007 isolate ("ASFV-G"). An exemplary vaccine comprises a deletion of multiple genes allowing for industrial-scale growth in stable cell lines.

16 Claims, 3 Drawing Sheets

Specification includes a Sequence Listing.

SEQUENCE LISTING

```
<160> NUMBER OF SEQ ID NOS: 4

<210> SEQ ID NO 1
<211> LENGTH: 180835
<212> TYPE: DNA
<213> ORGANISM: Artificial Sequence
<220> FEATURE:
<223> OTHER INFORMATION: Chemically Synthesized

<400> SEQUENCE: 1

actgctgtag gcgtcaaaga ttaaaattat tactactgct gtaggcgtta aacattaaaa      60

ttattactac tgctgtaggc gttaaagatt aaaaatatta gtactgctgc aggcgttaaa     120

gattaaaaat attagtactg ctgcaggcgt taaacattaa aattattgta ctgctgtagg     180

cgttaaacat taaaattatt actactgctg taggcgtcaa agattaaaat tattactact     240

gctgtaggcg ttaaacatta aaattattac tactgctgta ggcgttaaag attaaaaata     300

ttagtactgc tgcaggcgtt aaagattaaa attattacta ctgctgtagg tgtcaaagat     360

taaaattatt actgtaggcg ttcatttcac aagatgcgga attatttcgc aaagattatt     420

ttttgaaacg ccgcggccgg aaatattttt ttttgcggtt gtaattgatt tttttttgcg     480

gctgggcggc gggccagaca aaattgacca taactggtgt tacgccgccg gtaataaacc     540

ctaccgtaaa tacttttttt tggggcggcc agagagacat tatcgccgta ggtatcaatt     600

actgctgtag gtatcaatta ttatactaca ggcgttaaac attattagta cacaggcgtc     660

aaagaagcta aaacttaatg ttttttcgtc aaaaatcgcc atgaatatct atcttgtgtg     720

gtttctctac atactattgg ggaacctgat attagcagta atatattgcg tcatagatga     780
```

-continued

```
ggtggtgtgt gacaatatcc atataaaaaa aaatgttgcc gcccctgaga tgccgcggcg    840
gttctaaatt ttaatgtttt tttcggcgaa catttttcac atatgcgata ttggcgctaa    900
agcgagcgta ttaccgcttg taacaacatt ttttttcgat cggcaataga taagtagaat    960
ataccatatt attgctattg ccatcaatga gaatgccacg taggcatagg tcatcctatg   1020
gccggaccaa tccatggctg cacttaaaaa tatcaaaaaa agtttaagtt ttgggccggc   1080
gttaaaattt aaaccttttc tggttgatct ttagccatgt atagctgcga tgtttggtgc   1140
cttatctaca tgctattggc attcctgata ttcgcactaa agtgctatgt tacaaccgtc   1200
ttatgcgtga tttttatcca ccttattggc cgaagggccg ccttgtattt cctgttaggt   1260
ggtttggccg tattctactg gtggcaagca gctatcaata aaatttaatg gctctcactt   1320
aagatccttg ctgtaagcgg gcgtttacat actttgatca agaaaaaaaa attatttttg   1380
gacccccccc catgttttat acaaaaatca tataataaag tggcgacaat caacatatta   1440
atcaaccaca gcattttatg atgtgttaat caacatatac catattaatc aaccacagca   1500
ttttatgatg cgtcaatcaa catattatta cggagagcgt caatcaatat aatattgaga   1560
acagcgactt gataccgtgt atggtggtgg cggcggcatg ttgtttgtaa cagcattttt   1620
catcattcga agcttacaaa agatatgtat aagatagcat attaatgtta ttaacagtaa   1680
tatcaataag gcgtagctat agatcttcac tttggtagac caataatcca tggttgcgct   1740
taaaaatacc aaaaaaaaca ttaagttttg gagggtaaga ttggtttttc accattggta   1800
aagattatta ttctaaatgt ttaccccata gatgtgaaac aatgattctt catatattaa   1860
catatttttt gacttatact tttcttcatc tagtaaggcg ttaatttttt ccggatctgt   1920
cgtttttatt gataaaagag aagagtctgg actgtaattt ttaaataata agatatttat   1980
taatatccaa ttattcgttt ggctcgctat ttccatgctc tcttcgaaag catcagctcc   2040
taaatctata caaaggaata agttaccttc acaaaaattc attaccgagg taatcattgc   2100
ccgattaatg tcagccccca acataaaaca ataatatata gttgtataat tacaatcata   2160
catacaggcc aactgcatca tttcatcaat gtctatattt gtcttctctt tgttataaat   2220
ttcatgaagg tcaaagacgt tgttataagc aaccccacat attaaccgcc aatctttaaa   2280
atgactatat cgttgataaa aatattggat ggcttcagta agcttatata gtatcgccat   2340
actataccaa tacctagtta gcatttcgtt gaatgaaata ttatccaatg taaagttaat   2400
tgataatgta tctagttcac caaaaattct taatttcagt tgagcattat ttaggaaaag   2460
gggattatca gataataatt catggcatag aataatatta ctgctagttt taacatactg   2520
tacattataa aatatttcta aaattttatt ttcactcaaa gctttcctcg cacctaactt   2580
ttggcatagg tcctggtgca ctccatattg acagtaacca acccaaagct gatgtctgca   2640
ccccattcgg taaacagctc tattaaacca tgattgtttt cctgtacagc cttcattaat   2700
gcaacattta atgttaaacc atgtttaaaa cttgctgttt ttattaatat ttgttcatct   2760
atacaagtat gataaatcgt aattggggct tcatgccacc acaaaccaca acgctctaaa   2820
atacaataat catcttttaa cacaggctgt gtagctagta ctttttttagt aagtgcttgt   2880
aaagtagatg gcatcttcta tctgcaaaat aattatttcc gaaaaaaaaa tcaaattaaa   2940
atactaaatt ctattttttt ttttaataaa gcctgtaaat tatataataa atctcgccca   3000
ccgtattatt tccggacaca actttttata cctcattata tttttagatc tatagttttt   3060
taacaaggca ttaatttttt ctggatctgt cgtttttaaa gataaaagag agacgtttga   3120
actataataa tctttaaatg ataatatttc tactaatata tcatgattct tttgttttgc   3180
```

-continued

```
taattctaag ctctcttcga aagcattagc tcctaaatct atacaaaaga acaagttatt   3240
catataaaag ttttttaccg aggtaaccat tgcccgattg atgtcagccc ccaatacaaa   3300
acaatagtaa atggttaaaa aattgctatc tctcatacag gccagatata tcatttcatc   3360
aatattcata tcaacctttt ttatatgata catttcatga agatcagaca cgttattaaa   3420
agaaagccca catattagcc gccaatcttt aaaatgacta tatcgttgat aaaaatattg   3480
gatggcttca gtaagcttac atagtatcgc tatactatac caatatctag ttagcatttc   3540
gttgaatgtt atttcattca atataaagtt gatcgatatc ttctctagaa aacaacaaat   3600
tattactttt aattcctcta tattctggaa aaggggatta ttagataaca atttatggca   3660
taaaataata ttactactag ttttaatacg atgtatttta taaaatattt gtacaatatc   3720
catttcattc aaaatttttg cgcctaactc ccggcagaaa ttccaagtat gctccgtatt   3780
gacagtgact aagctagagt tgatgtctgc accccattca gtaaacaact ctattagatc   3840
atagttgttt tcctgcacag ttttcattaa tgcgagattt aactctaaac catctttaaa   3900
aattgctgat tttatcatca attgattatc ctcattagta gaaagcataa ttggagctcc   3960
atgccaccac aaaccacaat atttcaaaat aaagtagtgt tctttagata tgtgctgtgt   4020
ggccagtatt tttttagcaa gagcctgcag agaaattgga gtagacatat tttttttttgc   4080
aaaatggttt aagtttttca agaatacaga ttggataaat taggttgttg acttagttac   4140
aggaggtatt aaatattatg tagacataaa aatgagatcc tccaaaaaaa taaacaacaa   4200
aaaaaaatat gtttaatatt aaaatgacaa tttctacatt gcttattgct cttattatac   4260
tacttattat tattttagta gtgtttttat actataagaa acaacaacca ccgaaaaagg   4320
tctgtaaagt agataaagat tgtggtagtg gagagcattg tgttcgtgga tcatgtagct   4380
cattgagctg cttagatgcc gtaaaaaatgg acaaacgaaa tattaagata gattctaaga   4440
tttcctcatg cgaattcact cccaattttt accgttttac ggatactgct gctgatgagc   4500
agcaagaatt tggaaaaaca cggcatccta taaaaataac tccatctcca agtgaatccc   4560
atagccccca agaggtgtgt gaaaaatatt gttcatgggg aaccgatgac tgtacaggtt   4620
gggaatatgt tggtgatgaa aaggagggaa catgttatgt atataataat ccacatcacc   4680
cggttcttaa atatggtaag gatcacatca tagccttacc tagaaatcat aaacatgcat   4740
aaataaatac attaggctca tcgtatcttt ttaaaatcca taaatattcg tttgatatat   4800
gctgaaattt ttataaaaaa aaataactat ttcctataaa tcatctagaa atagtcctcg   4860
ttttgatcgg tttatatctt ataatattgt gcatcgatgc acaactgctt tttttggtcc   4920
ttctggaaca tcattatatt ttctttcatt aatataccat tcagatgtaa acgttgaata   4980
atttttatgg caacaatcta ccattgaatt atatttagta acatctaata catcgtttgt   5040
tttatcaggc tcagctctat aatcttgata atttttgtta tcagcttcta aagctccatc   5100
attatttttc aaagaagtat ccataattat gtttggtaaa aatactttaa gttttaatgt   5160
gatatttaaa atggttgtta tataaattta ccgcttacag gtaatcttta ttcagtgtca   5220
taaactatac ttttgatgat tcagtatttt gtgaatcagt acatttatta tcattaatat   5280
ttttaggctg tttttccaat gttttattgt tgcaatgagc ctgctcctcc tttgacgagg   5340
aagtgtctgt tggagtcatc tgtttaggaa gagtatcatc catatctatt atgaagaaaa   5400
tatataaata ttgatataca atcaaaaata tttttgatca cgtctttgtt atctatcgat   5460
attgttgata acgtcttgaa taacctacat catttttttta cataaaaaaa tagatataat   5520
```

-continued ttttattata tctcaattat tttaaagata attatcaata cagcaaatat cataagctaa 5580
catatttttc gaataatagt tttttagtaa agtattaatc ttttcaggat tggtttcttt 5640
tgataataag ataggattcg ctttataaat ttttaaagat aatatattca caatgataga 5700
ataaccgtat atatctgcta atgtcttact gtgttcaata acattagccc ctaaatccat 5760
acaaaagaac atattttcaa tacaaaagtt ttttaccgag attaacattg ctcgattagc 5820
gttggctccc aatgcaaaac agtagtaaat ggtcaaaaaa ttattatcgc gcatacaggc 5880
cagctccatc attttattaa tactcatatg aattttcgtt gtgttacata tttcatgaag 5940
gtcaaacaca ttgttgaaag aaagtgcaca aattaatcgc cattcatcaa aatgcctgta 6000
ttcttgacaa aaatattgaa tagcttcttt aagattatat tttaccgcta tgccatacca 6060
atatttggtt agcatctcac taaatgagat ctcatttaac atagaatttg ttgttaaatc 6120
cttcaactcc caataaatga tcatccttaa atccaccatg tttacatttt gtaaaaaagg 6180
gttattagaa aataattcat gacacaaaat gacattacta cttgttattt tacactttgt 6240
ttcaaagaaa aatcgtaaaa tttcacttgt ctcaagctct tctttagctc ccaattttcg 6300
gcataggttt cgagtatgct cgttattaat aaaaagtaac ccataattaa tatttgcacc 6360
ccattcagta aacaacatga ttagatcatc attgttttcc ttaactgcca ataccaatgc 6420
agtattaagc cttataccct ctttaaagca taatgtcctt atcattattt gattatcatc 6480
atctatatac attgagatag gagcttcatg ccaccataaa ccataacgct ctaaaatata 6540
ataatcatct ttagatacgt gttgcgtggc caatgccctt ttagcaagtg cttgtaaagt 6600
cgatggctgc atgtttattc tgttaaaaaa aaatcaaatt atcgggtaaa cataaggatc 6660
aacccgtagt taatatttgc agtagtattt tttaacaatg aattataata aaaaaataat 6720
tcattactat ctattataaa acccatcttt aactttaaag aagaactaga tcatcttttt 6780
ttttgttgtg tcagaacttc ttcaatttat tacccacatt ttatctaaaa aaaataaaaa 6840
ctacatcata tcttgtttct tcatcaaatt atcataccat ttatagggtg taggttggga 6900
acattccatc atgtggtaat cagggtattt atatattttt tgatagtaac atctatttgg 6960
cagatgtatt gtccaacaat catgtctaat aaaatcattt tcacctatgg gggaatcatc 7020
ttaaaaacct tattcctaca gattccattt tgacagtccc agcaaaagtc acaatatttt 7080
ccatgagtac accaatgttc aagctctctt tcgggaggaa tgctgccaat tttatgtttt 7140
ttagcttcta actctctgta caacatcagt tgggaaagca gaaagaagat taccaggaga 7200
accattaaat atataatagt ctgcaaacta cgtttgcgaa tgtaatttgc aactaaaaca 7260
caacccacaa ggtaaaatcc ataagttaat aacttttgcc attttcgtat gacagcctcg 7320
tgccattcat ggttgtgttg tgggcattct gttcggtaaa cttcatgagg ctttatagaa 7380
gttacatagt aggtacagaa ttcattgtga cgaaaaacac tgcagttagc tatgtagtca 7440
ttttcaagaa tgggagaatg gttttcaaag accttattct tacagatgcc atcttgacag 7500
tcccaacaga acctacaatg atttgcatag gtgcaccagt attcaagctc cttttcagga 7560
ggggttcttg ttagatccag gagctctagc tcatatgtat aaagaagagt tggaatggat 7620
agtaaagtaa atatttgcag accaagcatg gctacttgtg aacaagtggc tgctcgtcaa 7680
caaatagctg tttatcagca aatagctgtt tatcagcaac aactaattat cagcaaatgc 7740
tgcttgtggg taagccaata aataggccat acccttgaaa ggagaattca gtttgataaa 7800
aaaaataacg agttttctaa taacccggtc aagcatttaa taaatgaata gcatcacacg 7860
tctgcatcgt gcattctgcc tggaaaatgg gcccatctct aatatattta cactgacggt 7920

-continued

```
gaatcataca gtgttccatg ggatagctat gctcctgtac aggaggcata tcttttagaa   7980
ctttattctt acaaagacca tcttgacaag cccagcaaaa ccgacaattt ttcacatatt   8040
gacaccagta tctaagctcc tcttccaggg gattgtcggt cgaaaacccc tgtagactag   8100
ctaggccagc tagcagcaag ccgaggtaac taaagaacct cattgtagtg ttatattacg   8160
aaaaaacatg ttaaaatttg gaaaaaaaag cccttttat agatctggaa aaaaattttc   8220
acaaatctaa ttaaaagcct tacagatcat ccttttcata aattttcatt aacaattggt   8280
gggggcggtt gtgaggtact ggatcagaac aatccataac atggtaatgt ccatttcctt   8340
caccatatgt acactggtta taccagcgag aaacctcaca agatgtcaaa taactgttct   8400
caacaatcaa tggcatgctc ttattcacct tgttcttgca aattccatgt gcacattccc   8460
agcaaaactt gcagttttcc atgtaagtac accagtatcc aagttcttct tgtggaggat   8520
tatccgttga acgaagatgc cctcctgcct gagtaggtag tcctaagacc tgattggcca   8580
gcaggccaag aatttccaag aagatcacca acattgctac ggctggctga acagctggca   8640
gatagctagc taattagcaa accaagtgac tcgccctctc tactcttaat atgagaattt   8700
aagattcggt ccggcttttt tcccatgttt tacagggaaa aggtattttt agcctatgaa   8760
tgtacatggt tccgcacatt aaaaaaaaat aaaagaaatt atttaatatt ggctgttatt   8820
ttctttcaac tagcaacaag ccaggtaact aaagaacttc attgtagttt tatattacgg   8880
aaaaggttaa attttggaca aaaaaaatca tatctaatta aaaatcctca cagatctttc   8940
ttttcataaa ttttcattaa caattggtag gggcggttgt gaggtactgg atcagaacaa   9000
tccataacat ggtaatgccc atttccttca ccatatgtac actggttata ccagcgagaa   9060
acctcacatg ttgtcaagta gctgttttca ataatcaatg gcatgctatt attcaccttg   9120
ttcttgcaaa ttccatgtgc acattcccag caaaacttgc acctttccat gtaagtgcac   9180
cagtatccaa gttcttcttg tggaggatta tccgttgaac gaagatgccc tcctgcctga   9240
gtaggtagtc ctacgacctg attggccagc aggccaagaa ttcccaagaa gactaccaac   9300
attgctacgg ctggctgaac agctggcaga tagctagcta attagcaaac caagtgactc   9360
accctctcta ctcttaatat gagaatttaa gatccggtcc gacatttttc cgatatttta   9420
caagaaaaag atatttttag ctacaaatac acttcatata tccctaaaaa aaacaaaaat   9480
ttatttaatt ttaactatta ttttctttcc actctctctt taagattttg taaggattcc   9540
agggctttgg ttcagaacag gccattacat ggtgaatccc ctgtcctaga tcatacatac   9600
atttatttag ccagcgggaa actatacatg attgcacata ctcattttca agaattgttg   9660
tattctccaa tttgccctca caaaggccat tttgacaatt ccagcaaaac ttgcagtttt   9720
ctgtataagt gcaccagtat tcaagttctt cttgtggagg attatccgtt ggatgaagtt   9780
gtccagctgg ttgattaggt agccctaaga cctggttgca attcatggta tggtagatac   9840
ccttatctaa atcatacata catttatcca gccaacggga aaccagacat gatttcacat   9900
actcattctt gtaaattact gacccatcta ttttgtttat acaagtgccg tcttggcagt   9960
cccagcaaaa ttggcaactt tccatgtagg cacaccagta ttcgagttct tcctctggag  10020
gctcctctgt tggacgaagt tgtccaacga gctgacttga aacctggctg gccagaaggc  10080
caagaattcc caagaagatc accaacattg ctacggctgg ctgaacagct gactgaatag  10140
ctagccaatt agcaatccac tgtacttttc ataagatcat ttaagattcg gtcggcattt  10200
tttcaatagt ttgctaggaa aaaattttta attttataga ttcacactac ttcattctca  10260
```

-continued

```
tgcttaggaa aaaaacaaac taaatcttac aatgtatctg gatctaatga gaagctagaa  10320
ttcatctttt ttcaaatcct ttctgggatg ttcattcttt ttccactcct tccttgcaat  10380
tttataagga ttccagggct ttgggtcaga acagttcatg ctatggtaaa tgtgctcctc  10440
cacatcatat ctacataggt caccccagcg ggaaacctca caatatttta catagtcatt  10500
ctcaataata cttgtggagt tgtttcccca aaccctgctg gtacaaatcc catcttcaca  10560
atcccagcag aaccgacagc tttccacata agtgcaccag tatccaagtt cattctctgg  10620
gggttcaaat gttagaggaa gatgtccacc tacccgagta gaagtggagg atgaaaccag  10680
gttgctactg gccagcaggc caataattcc caggataatc accagcattg tgctcaacca  10740
gcaacggcta gcaacgacta gcaactgact agcaatagct agaaatggct agcaatcagt  10800
agtagctaac gctctactct ttataagaaa atttaaaatt cgatcagatt tttttagaat  10860
tgagaatgag taaaacgctt atattctttt tctagctaga aaaaataagc tagtttaaga  10920
taggatttcc cttactaacg gtttaatttt tagcaaaggt ataggtaaaa tacacttgta  10980
cttagctgca aaaaaataag cttatggcgt ataagccgcc ataagtttat ttaattaaaa  11040
tgttaaactc tgtgataaga ctggaatctt aggcaggttt gatgtggaga acagcatgaa  11100
atacaagagt gcctgttaca cgaataagtt ctctcaaacc ggggatggtc atactcacat  11160
ctatgaaatc ctggtctagg agattcattt gatgcatgat ggccgcaccc acacttatga  11220
gacactgaag aactaaaggg tttaattttg atctgaatgg tactatatag gatgatggca  11280
atccatatca agattagagc aatcaaaatc acctcctcaa gaagcatgat gtagccttaa  11340
atcttagact gctttaaacc ttaggccctc actatcttta atgaaggagt ttaaattttg  11400
atcccttttt caagacccat ttagaagaaa aaaataaagt ttatatcaat ctaattcata  11460
agtcatctct ttcataaatc ttcatgtatt ctctatgtgg ataagtatgg gatgttggat  11520
ttgcgcagtc catttgatga tctgtatggt ttttgggtcc ttcataataa ctacatatac  11580
cattccagcg ggaaaccgtg caatttataa tccagtcatt ttgatgaata actggccaat  11640
ctgtttgaat cctgtttcgg cagataccgt ggacgcattc ccagcaaaag tcacattggt  11700
ttgcgtaagt gcaccaataa actagctcat gttcaggagg ataacgggtt ggtagtaaat  11760
cttctaattt acgtatagga gcggcttgaa ggacaaccac ccccagtagt actagaatca  11820
gtacctttat agtggccacc ctacactaga cctctaagtt gaagacaaag aactaaaatt  11880
tagagccgtt taattactac taataattat attttttatt gtctacaata ggattctatt  11940
aaaaaataat gatttttacc aagaaatatt tttataaaaa attaatatat tttgtaataa  12000
actttatttc caatgactgt taaaataagg aaactatcct tagttagtcg aggaagatgg  12060
ttaggttatt tcgcaatccg ataaaatgtt tattttatcg taggtctcgt aaaatccagg  12120
aaaaaaaatt acggaagagt ttaaaaaagc taaattttta ccaccctcca gaagattgtt  12180
gtcaaatata tcgtttgcta gaaaatgttc ctggaggaac ttactttatt acagaaaata  12240
tgacgaatga tttaattatg gtcgtaaagg attcggtgga taaaaaaatt aaaagcatta  12300
aattatatct tcatggaagt tatattaaga ttcatcagca ctattatatt aatatttata  12360
tgtatcttat gagatatacc caaatttata aatatccctt aatttgtttt aacaaatatt  12420
ataacatcta agtaaatatt cttggaatgg attttcttat agaatggtta caggatatgt  12480
cagcgacagg cttaataaca aatttgttaa tattttttttg ttaaataaat gaacaggcca  12540
ccatttaata ttacccgttg caaaataaga aaaaaaaaac aaacttatag ttacaaatca  12600
tcttgattaa tcacatgtcg ttttaactca atgaaccatt ctaaatcttt gggttgtgaa  12660
```

-continued caattcatgt tatgttgata gtgtatccta aagtgagctt catacataca ccggtcatgc 12720
caccgggaaa ctgtacaatt aacaatataa tcattttgcg taataatagg gtggtcacta 12780
aacactttat ttttacacat tccatcttta caggtccagc agaagtcaca gtgttttgca 12840
taggtgcacc agaacttgag atccctttca ggaggcctac gcatttgcat cggattatct 12900
gtggaaagag gtaggttcat tattatgttc gtcatcaaaa ttcctaaaag aacatagaag 12960
ccaagaaaga taagcagtct tgtagcggct tgcattcgca ttcgtgagta ttgtttgcga 13020
acatagctta tgagagcaat ggtagctatc atacaaagac aagtatgttt gatattctca 13080
gtgtcaatga ccctatcctc ctttatttgc attaactcat caaaccaatc ataatatgtg 13140
ggatttgtac agctcatgat gtgaaagcgg cgtatcctag agtctgtaaa gtagctacat 13200
ctttcattat agcgagaaac cctacatatt tgtatgtaat catttttttt gatgagaggg 13260
tgtttttcaa aaaccttatt tttacaaacc ccgtgtcgac aattccagca gaagtcacac 13320
gattttgcat aggtgcacca atactcaagc tctctctttg gaggtctccg ggtcattggt 13380
aactctcctg ttcctggaaa agattggctt tgaatgaccg gctgcatgac cgccagtacc 13440
aaaaggaaca caatcacctt catggctgca acttataagt tgcaacttat gggttgcaat 13500
actgcaacgt ataggttgca ccttatagat cgcgactcaa aaggtatgaa aaccttaccc 13560
tcaatacaga atttaagttt taatcctgat aatgtatctg tttatgaaaa aaaatttttt 13620
ttactcatgt atgaattctt atacgaatca taatatgtag gctgagaata ataattcata 13680
tacggtgttg cgggctcaat aaaaattttg ttaccacaaa aaataaatgc tggattttta 13740
agatatatat ctattaatga ctaaaccctt tatacgctgt aggctgaaaa caatccatat 13800
aatgaatata cggtgatttg ggtttaataa aatacataca acggtcaaaa tagcgggcaa 13860
tactacattg actaatataa tcattttgtt taataagagg catatcatcc cacactttat 13920
ttttacaaat accgttccta cattcccagc agaaatcaca gtgttttcca tacgtgcacc 13980
agtattcaag ctctcttata ggaggcgtat aagtccttgg taaattttgt ttcatataaa 14040
agatggaaag gggtcgattt aaacccggct gagatagcca aatcaaaata cataaaagag 14100
caagtagttt catagtggta tttagatgta aatttttata gtatgcaaat acaatgtaac 14160
ctacaaatac aatactaaat acaaggtaaa aacaacaatg tcttataatg attggccaat 14220
aatcaccccc ccccccattt ttccatgaat atttcatttc ctgtataggg tctaggatgt 14280
gaacactcca tgttatgatg attaggcatt ttaactgata tttcataaaa acaccccccag 14340 gaattgcgat taactataca gtttacaatc gaattcatcg aattagactc atttgttatc 14400
ttatttttac aaatgccatt ttgacaatcc cagcagaagt cacaattctt tacatacgta 14460
caccaatatg gaagctcctc cttaggagga tgctgggttc ttggtaattc tggtaattca 14520
tgtgcaagaa tgaggactga gtagcccaac aaaagtccta gaaccttcat gttgtgtcca 14580
aatggcacct gtcattttaa aaaagattta aattttgcta ccgcaaaaaa aaatccagta 14640
tgtatttttt taatacatat aattattgaa gtcttataag ataaagccga gaacactata 14700
ttttgtatag atgatgtatc cggtattcaa actctcttat aagtacatgt aggaaatggt 14760
caattattca agattggctg agataacaac aaaaccaaaa tactcaaaag cataagtaat 14820
ttcatggttg tactcagtcg tagatttttg cagatcgcaa atgcaacgca accagcaaat 14880
acaaagctaa atacaaggta aaaacaataa taccttataa tgattggcca attcttatcc 14940
ctccattttt ccatgaacat ttcatgttca taaagtctag gatacgaaca acatttcatg 15000
ctatgatgat taggtatttt aagtgatatt tcataaaaac accacggggt tgttggtgat 15060
tgataggtaa gaataaggat ggttgaataa cctagtaaaa gtcctagaaa aaccttcata 15120
ttgcgttcat accacagatg ttatttaaaa aaaatataaa ttttacagta tgtgatatac 15180
acataccaca aaaatgttct tatattaact aaaatatgtg ggcagagagc aattcatata 15240
atgaatatat ggtattttag gctcaataaa gtacatacaa cgatcaataa aacgggtaat 15300
actacattta ctgatgtaat cattttgaac aataagaggc atatcatcca aaaccttatt 15360
tttacaaata ccattcttac aatcccagca gaaatcacag tgttttccat acgtacacca 15420
atattcaagt tctctcatag gaggcgtata ggtccttggt aaaatttgtt tcgtataaaa 15480
gatggaaagg ggtcgattta aaactggctg tgctaaccaa accaaaatac tcaaaagaac 15540
gaaaagtttc atggttgtac tcagacgcag attcttacaa agcgcacata caaagcagcc 15600
tgtatatgca ataccaatga tgaaatagag acagtattgc tttatagata attgttgatg 15660
gtcacccccc cccccccccc atgtttgcat gaatatttca tttcctgtat agggtctagg 15720
atgtaaacat tccatgctaa agtgattagg cattttagat gaaatttcat ataaacagga 15780
ttgagtcttg gaatcacgga aaactctaca gtttacaata gaatgattgg agtcaatgaa 15840
acgagattcc gttatcttat ttttgcaaat gccatcttga cagtcccaac agaaatcgca 15900
ttgtggtaca tacgtacacc aatatgaaag ctcactcttg ggaggatgct gggttcttgg 15960
taagtctggt aattcatgtg cgagaatgag gactgagtag cccaacaaaa gtcccagaag 16020
aaccttcatg ttgcgtctaa atgacacctg cacttacaaa aaaaaattta aattttgaat 16080
ataacacaaa aaaaccacct taaaatttct tatattattt cttggatctg ccccgacgtc 16140
atacaatgta ttaaaattat agaccaatca tctttttgta tataggctaa tcatctttat 16200
atatagattt tagatgtttg cttgttgtat caacttaact gctagcgaag aaaatggata 16260
aaaactttct gtatttttat aggttgaaat cattttatgc acatcgctag gatctaatat 16320
tttattttga agaaccgaat gtgggcttaa aatttttttc ttagaaaaaa gtagaatcat 16380
aatattgcta tgtttttgtt taatgatttc ttgtatcttt tttgtatacg ggttggcacc 16440
caaacctata caaaaatata cattactcaa ataactacct tctatacata atcttttttc 16500
cccacgtatt ttcctattta tttccctatt tatggaatta aaggatatca atctctctaa 16560
ggcacggtca aggtctgcgc ctaaggcaaa acaataaatat atacctaatt tattcccagg 16620
gcgtgcacag gcaagaaaca tcatgacgtt tagccctaaa cgtatatttt cctgaaaata 16680
cgcatgatga acttcatcaa tattacctaa gtatatggcc gtttgtaaac gccaaagatc 16740
taaatgagga aattttttac taagataatg aataggtttt gtgagattaa aatctatggc 16800
gattccaaga ttatagtttt gtatggaaac aagcatggct tgattgatgt tggctcccat 16860
gataaaacag tagtaaatgg ccgaatagct ataatcttgg atgcaggcta tgtgcatcat 16920
ttcatcaata tccatgcgga ccctttctat ttcgtacagc tcgtgaaggt cgaacacgtt 16980
gttgtaaaaa agggcgcaca tgagccgcca cctatgtaga cgcgggtatt tctggtaaaa 17040
gtagcggata gcatctttga ggtcatagtc caccgctatc gcgtaccagt atttggttaa 17100
aacagtgcta aagctatcat catggtccag catgaaggtt atctccatga gccctcttaa 17160
ctcccacatg atttcccccc tcagatccag attatctata atccttaaat tggggttatt 17220
ggaaaacacc tcgtggcaaa agataatatt gctactggtt ttatcgcgcg ttgtatcaaa 17280
gaaaattttt aaaatatact ctctttctaa atattctttg gctcccagct ctttgcacag 17340
atcacgggta ttttccgtga gagcacaaat cattccatag ttaatatctg caccccattc 17400

```
agtaaacagc tttatcaagt catgattatt ctccttcacg gctttcatca gtcctatgtt  17460
taactcgata ccttgactaa aacaggttga ccttataaat aatttattgc gtcgaatatg  17520
aagcataatg gggccattat gccaccacag gccacaacac ttcaggacat gatattgatc  17580
taccggtata cactgcccgg ccagtacttt cttcgtgagg gattgcaggg aaggcaacat  17640
gcctttccat cctttgacgg aaatcaaatt atctactaat aactatcagt gtttatatta  17700
agtatttaga tattatcccg ggctggatac gtagtatcgc tattcacatg tacttccaac  17760
tctagccgga gcctgcaggg tcatttattt ttaatattga ttcttttttg tatttaatca  17820
tttagagaag gtcatcatag gagccagatg ttctctctcc agaacttatg tcgaaaaaca  17880
ttacctaacc gtaaacttcc tgaatttttt gacgaatata tattacaact gctgggatta  17940
tactgggaaa accatggaac tattcaacga gcaggaaaca actgtgtgct tatacagcaa  18000
cataccctca ttcccgtaaa tgaagccctg agaacagcag catctgaaga aaattatgag  18060
atcgtgagcc ttttattagc gtgggagggg aacctttact atgctattat aggggctcta  18120
gagggcaacc gccacgactt aattcgtaaa tatgatgacc aaatcaagga ccatcatgaa  18180
attctgccat tcattgacga tccagtcata tttcacaaat gccatatcat gcggcaatgc  18240
tttttgatt gtattttata tcaagctgta aaatatagta agtttcgcgt tcttctttac  18300
tttaaacata gattagagga tgatttgccc ttcactcatt tacttattga aaaggcatgt  18360
aaagatcata attatgaagt tattaaatgg atatatgaaa acctacatat ctacaatatg  18420
atagatacct ttgaatgtgc tattgcccat aaggatctac atctatattg tttggggtat  18480
agatttatat ataacagaat cgtacccgat aagtatcatc atttagatat tcgcatgctt  18540
tcaagcctac aactcctaca taaggtggca gccaaaggat acttagattt tatcctagaa  18600
accttaaagt atgatcataa taaagataat ataaatatta ttctaacaca agctgcaacc  18660
tataaccata gaaaaatttt aatctatttc attcctcaat caacccacgc acagatagaa  18720
caatgtttac tagtggcgat aaaagcaaaa tcttccagga aaaccttgaa cttactactg  18780
tctcacctaa acctttccat caacctcatc aaaaaaataa gccattatgt tgccacttac  18840
aattcaacaa atataatagg cattctgagt atgcggcgga aaaagaagat atatttagat  18900
atcatattga caaaatttgt aaaaaaagct atttttaata agtttgtcgt tcgatgtatg  18960
gatacatttt ctataaaccc ggaaagaatc cttaaaatag ccgcgcgaat aaataggatg  19020
atgttagtga aaaaaatatc tgaacatgtt tggaaaaatc atgcggttag acttaaatac  19080
cttaaacatg cggtacacac gatgaagcat aaagatggga aaaatagact catgaacttt  19140
atctatgatc gctgttatta ccatatgcaa ggggaagaaa tctttagcct cgcaagattt  19200
tatgcaatcc atcatgcacc aaagttgttt gacgtttttt atgattgttg tatcctagat  19260
acgatacgat tcaaaagcct tcttttagat tgttcacata tcataggtaa aaacgctcat  19320
gatgctacca atatcaacat cgtgaacaag tatatcggca acctgtttgt tatgggagtt  19380
cttagcaaaa aagaaatctt acaggactat ccatccattt attctaaaca atacatgcct  19440
tagtttattt tttttgcggc cgaaacatta ttcttaccct agaaaacgct tatagtcatc  19500
ttaaatcata ggtaaggaag atcatcatat tttttgaaac gtaatttttt aacgcatgat  19560
ctatgatttc agggtccgtg cttttaggca acggggtggt ggccggacta taaatcttta  19620
gggataaaat gttctttata agctcatacc cttcccctaa agctgtagta ccctcttcga  19680
aaacatcagc cccagatct atacaaaaga acatgttttc tatattatag tactgtattg  19740
```

-continued agctaagcat ggcttgattg atgttggcgc ccaggacata gcagtagtac atggttgaaa 19800
ggttgtggtc tttgatgcag gcgatccgca tcatctcttc tatgtccata tggatcttgt 19860
ccttttcata cgcctcatga aggtcaaaca cattattaaa acaaagagca catgttaacc 19920
gccacgtatt caggtgtgta tatttttggt aaaaatactg tatggcctct ttcaggttat 19980
agcgtatggc tatagcgtac cagtatttga gtagtaatgt actgagcgaa aactcattat 20040
ttagcagatc ggtttttact attaactccc ttaactccca gaaaatttct atcctcattt 20100
ttatattatt tactttttgt aatatcggat tgttggaaaa cacctcatgg cataaaataa 20160
tgttactact agttttatga aactttagat ctataaaaat ttgtaaaatt tcttcttcat 20220
tcaaggtttc cttggcacct agctctcgac agaggtccca ggtgtgctcc gtgttgacag 20280
ataccagccc gtagttgatg tccgcccccc actctgcaaa cagttttata aggttgtagt 20340
tgttttccct tacagccttc actaacgccg tatttaggtt taagccctct ttaatacctg 20400
ctgattttat gagccttagg ttatgatcaa acgtgatcgg agcatcatgc caccataggt 20460
cataacactt taaaagataa tgttggttcg tgggcacgca ttgtccagcc aacacctttt 20520
tggtcagaga ttgcagggaa ggcaacatgt ctcttcatct tttaaaaaaa aatcaaatta 20580
attagccgaa taaatttttc tttcgagggc tttttaaaag agctctttaa gagctcttta 20640
agagcttttt aagagattaa aaaattattc ttgctggcat tctgccaagt atgcggcatt 20700
cctatcatct atagtatatt atgagaatat tcccaaatga tggataagtt ttttgattta 20760
taatctttta ataaactgct tatttcttcg gggtccttta agtttagtgg caaggaagca 20820
tctgagctgt aaatatccaa agccaaacta tggctcagaa aattataacc tttttgttcc 20880
gctatggcac gaccctcttc aaaggcatta ccacccaaat ctatacagaa aaatatatta 20940
ccgatgttat aatattgtac tgaagtaagc atagcttggt tgatgttgcc ccccagcgcg 21000
taacagtaat atattgttaa tggattgtta tccttggtag aagccagaca tatcatgtca 21060
tggacgtcta tttggatgtt ttccttgtgg tacatctcat gaagctcata tattttgtta 21120
taatacagga gacattttaa tcgccattca ttaagatccg tatatttctc atctagaaaa 21180
caaatggcgt ccttacaatc gtattgtact gctttggcgt accaatactt cactagtaaa 21240
ccatttaact cgtccgtttc ttttatttct atgagccccc atagtctttt ataaattaag 21300
ccccttaatt gtataacaaa tttgttttct aaaataggat tattcataaa aatttcatgg 21360
cacaaaataa tactgccgct ggttttattg tgcattatcc tggtaaaaat acggaaaata 21420
tcgttgtcct ctagagtttc tttggcgcct agctgtctac acaactctcg gatgtgcttc 21480
gtattgatag aaagcaaacc atagttgata tttgcgcccc actctgtaaa gagctttatc 21540
agactatagt tgttttcctt aacagctatt attaatgcca cacgaaggtc tatatcttct 21600
cctaaaaatc ctgattttat ttgtattcgg ccacgatcca tacaaagctt gagaggagca 21660
tcatgccacc ataggccaca atatttcaaa atgcagtgtt catctattga caaacactgg 21720
ctggctatcg tctttttgac gagggtctgc agagagagcg gcaacgacat gtttcttttt 21780
caccaaaaaa aaatcaaatg ttctcgtctt taaaggttaa ttcatgttct taaaatgttc 21840
atttcatgat agtgattaat aatatggttt aataacgcta gaaggcttgt ttataagaca 21900
gtcataagca gtctataaga cagtctataa gcagtctata agacagtcta tgacttagtc 21960
tataactata atttctggat gggctgtaag atactcttcg gctcgtttca gattttttga 22020
agtatatgtc tttagcatat catatatttc ctggggttcg gttacatcta ataccaaggt 22080
cacatcacgg ctgaaaagct gctttactaa gaaaatgttg ctcaagttat acatataagc 22140

```
tttgtgcgca atgagttgtg ccctatcaaa atcggcagcc cccaaatcaa tacagaaaaa  22200
catgtttaaa gtattattgt tatagataga aagattcatg ccataatcga gactagcccc  22260
caacctatga cagtaataaa tggccgcgta atttttttcc cgcaagcaag caaatttcat  22320
catcagatta gggctgatgc aaatctcttt ttcacgacac aactcgtgta tgtcaaaaat  22380
gttattaaaa taaaggctac aagctacccg ccaatagagg tgatttttat gccttttata  22440
gaaatagtga atagcctttg taaaattatg tcgtaatgcc agggcaaacc aaaactttgt  22500
taataggtgg tgcgccgtat cccccgtcaa cggaatgttt gaacaggtgt acgtaactgt  22560
gtctaaagtg gttctagtta cggtttccaa gagtggatta tgacaaaaca tgtcataacc  22620
cagcagaact cctgcacagg attttagcct ggccacttct tttaaaattt ccagaagacg  22680
gggttcggat acaggcgtta agcctcccag ttccgcacac agccgcttta gatacacggc  22740
aggaacacgt ataagcccat attcaggatt tgcgccccaa tccacaaata aacgtataag  22800
ttcaagatta tcgctcttca cggcctttac tagcgccgct tcgagacaaa gatcatcctc  22860
agaaaaacac tgtaaatgtt tatacgaaaa aacttgctta caattgttac ataggtgaat  22920
aggacctaaa tcccaccaca aaccaaaacg ctgcaacgta taatcatagt cacttgaaag  22980
ataattgcat gccacaactt ttttggccaa cgtttgtaaa gacaacatac taagtttaaa  23040
acatcttaaa tctaagctag ctaactttca agaaaaccct ctatccctaa gaatatatct  23100
tataactaga cttatagcag taaaaatcaa ctttggttat tctttttaat ataaaacgtc  23160
taattacttg caaaggacta taaagcccat tttcctcagc tagaattttt atttttttaat  23220
gaagtagggg gatatgtttt cccttcaaga cctttgccga aagcatcttt ttattcttcc  23280
cgatgttttt ggcgagcatg tactacaacg attaggactg tattggagat gtcacggctc  23340
ccttcaacgc ataggagacg accacatact catacgacgg gatctcatcc tttccaccaa  23400
cgaggcctta agaatggcgg gagaggaagg aaacaatgaa gtagtaaagc tcttgttact  23460
gtggaaggga aatcttcatt acgccgtcat aggagccttg cagggtgatc aatatgacct  23520
gatccataag tatgaaaacc aaatcggcga ctttcatttt atcttaccat tgattcaaga  23580
cgcgaatacg tttgaaaaat gccacgcttt agaacgtttt tgtggtgttt catgtctgct  23640
aaaacatgct acaaaataca acatgctccc tattctccaa aaataccaag aagagctgtc  23700
tatgagagcg tatcttcacg aaaccctatt tgaactagca tgcctatggc agaggtatga  23760
tgtccttaaa tggatagagc aaaccataca tgtttacgac ctaaagatta tgtttaatat  23820
tgccatctcc aagagggatc tgactatgta ctccttagga tatattttcc tttttgatag  23880
agggaacacc gaagctacgt tgctaacgca acatctcaag aagacagcgg ccaaagggct  23940
cctccacttt gtgctagaaa cgttaaaata cggcggcaac atagataccg tcctgaccca  24000
agccgtaaag tacaatcata gaaaactttt agattatttt ctgcgtcaac tacctcgtaa  24060
acatattgaa aaactttttgt tgctggccgt gcaggaaaag gcttctaaaa aaacattgaa  24120
cttactgttg tcacatttaa actactccgt gaaacgcatc aaaaaactac cgcgctatgt  24180
gatagagtac gagtccacct tggtgataaa gattttatta aaaaaaagag tgaacctgat  24240
agatgccatg ttggaaaaga tggtaagata tttttctgcg acgaaagtga ggacgatcat  24300
ggatgagctt tcgattagtc cggaaagagt cattaagatg gctatacaga aaatgagaac  24360
ggatatcgta atccatactt cttatgtttg ggaggatgat ctagaacgtc ttactcgtct  24420
taaaaatatg gtatacacca taaagtacga acatgggaaa aaaatgttaa ttaaagtcat  24480
```

gcacggcata tacaaaaact tattatacgg cgaaagggaa aaagtcatgt tttatttagc 24540
caagctctat gttgctcaaa acgcggccac ccaattcaga gacatttgta aggactgtta 24600
caaactggat gtggcacggt ttaaaccgcg gtttaagcaa ctaatattag actgtttaga 24660
aattattact aaaaaatctt gctatagtat cctggaaatc ttagaaaaac atattatttc 24720
cctgtttact atgaaagtta tgactgaaga agaaaaaaac ctatgtttag aaatattata 24780
taaagtaatt cattataaaa caatacaatg ttaaaattca atagatatcc atcattaata 24840
ttgattatat tttcgaatat tatcttctat ggtgcaagat aatcatctag cgcgtgaaac 24900
atgtcctctt ctcttcagga actttgtcga aaaaagctgc ctgactgcat acttccagag 24960
ttttttgacg actatgtatt gcaactgtta ggactgcact ggcaagatca tggttccctt 25020
cagcgtatcg agaagaacca gatacttgtt caacaggaac ccatccatat caatgaagca 25080
ctcaaagtag cagcatcgga agggaactat gaaatcgtag agctgttgtt gtcatgggag 25140
gcagatcccc gctacgccgt cgtaggagcc ctagaaagca aatactatga cctggtttac 25200
aaatactatg accaagttaa agactgccat gatatcttgc cgctgattca aaatccggaa 25260
acattcgaaa gatgtcatga gttaaacagc acctgttcac tgaaatgctt attcaagcat 25320
gctgtgataa atgacatgct gccgattctt caaaaatata cagactatct ggataggtgg 25380
gagtattgca gccagatgct gttcgaactg gcatgtagta aaaaaaaata tgagatggtt 25440
gtgtggatag agggagttct aggcgtcggc aaagttacat ctcttttcac cattgcgatt 25500
agcaacagag acctacagct gtattctctg ggctactcaa ttatccttga gaatttgtac 25560
tcctgtggac aggaccccaa gtttttacta aatcatttcc tgcgagacgt ttcaataaaa 25620
gggcttctac cctttgtaat caaaaccata gaatatggtg gaagcaagga gatagccata 25680
actctggcta aaaaatatca gcataaacat attttgaaat acttcgaaac ctgggaaagc 25740
taggttcagt atggtgtact cactattgta gtgaatcgta tcctgtaaat tttgtaaaaa 25800
agcttaaact tttgaccaca tcatattgtt ttagaaatct caaaccagtg aacaacagtc 25860
ttatcataca ttaaaattcc agtaaaattt atattttttt tggtaaacaa atgttttctc 25920
ttcaagacat ctgtcggaaa catctttttc aacttcctga cgcttttgat gaatatatat 25980
tacaagcgct aggactatac tgggaaaaac acggatctct tcaacgaata agaaaggacg 26040
ctgtgtttgt acagcgaaac atcgtccttt ctaccaatga ggccctgaga atcgcagcct 26100
cagagggaaa cgaaagggta ataaaacttc tgttatcatg ggagggaaat tttcattatg 26160
tgatcatagg agctctagag ggtgaccaat atgacctaat tcataagtat gatagtcaaa 26220
ttaaagacta ccacatgatt ttatcattga tccaaaatgc aaataccttt gaaaagtgtc 26280
atcagttatc caatagtaat atgtggtgtc ttatacagaa tgctataaaa tataatatgc 26340
tccctattct ccaaaaacac agaaatattc tgacacatga gggagagaat caggaattgt 26400
ttgagatggc atgtgaggaa cagaaatatg acatagtttt atggatagga caaaccctaa 26460
tgttaaatga gccggagttt atttttgata tcgccttcga acggatagat ttttctttat 26520
taacaatggg ttatagcctt ctttttgata acaagatgag tagtatagac attcatgatg 26580
aagaagatct tacttcatta ccaacagaac acctcgaaaa agcagccact aagggatgtt 26640
tcttctttat gctagaaact ttaaaacatg gtggaaatgt aaatatggca gtcttatcta 26700
aagctgttga gtataatcat agaaaaattt tagaccattt tattcggcgg caaaaatgtt 26760
tatcacgtga agagattgaa aacctattat taaccgccat aaccaattgt gcatccataa 26820
aaacgttaaa cttactcttg tcttacctaa actattccgt aaaaaatatc attggaaaaa 26880

```
tagtacaaca tgtcataaaa gatggtgatt ataccatcat attactttta aaaaaaaaga  26940
aaataaacct agtggaacct gttttaacag gttttataga ttattactat agctattgtt  27000
ttataaaaca ttttatccaa gagtttgcta ttcgtccgga aaaactgatt aaaatggccg  27060
cgcgaaaagg taaactaaat atgattatcg aattccttaa cgaaaaatat gttcataaag  27120
atgatcttgg aactatattt aaatatctca aaaccctagt atgtaccatg aaacataaaa  27180
aaggaaaaga gacattaatt gttcttattc ataaaatata tcaagatatt catctggaga  27240
ctaaagaaaa atttaaatta ttaagatttt atgtcatgca tgatgcaact atccaatttc  27300
tatctatgtg caaagactgt tttaatttag ccggttttaa accatttgtt ttagaatgtt  27360
tggatattgc tattaaaaaa aattaccctg atatgataca atatatagaa attctatcga  27420
aatctgagta aaatttattt ttttgatcag agtaagaaaa tgttctccct ccaggagatc  27480
tgtcgaaaga acatctactt tctacctgac tggctcggtg agcatgtgat tcagcgacta  27540
ggtctgtact gggaaaaaca tggttctctt cagcgaatcg gagacaacta tgtacttata  27600
caacaggacc tcatcatccc catcaatgaa gccctaagaa tggcagggga ggaggggaat  27660
gatgaggtgg tacaactcct attactatgg gagggaaaca ttcattatgc catcatagga  27720
gctttggaga gtgaccatta tagcctaata cgtaagctct atgaccaaat cgaagactgt  27780
cacgacatcc ttcccttgat tcaagaccca aaactctttg aaaaatgcca tgaattagat  27840
aaatcttgta acattttatg tctcgtatta cacgccgtaa aaaacgatat gctttgcatt  27900
cttcaagagt ataaaatgca tctaagtgga gaggatattc aagtggtgtt tgaaacagca  27960
tgccgttcac aaaaaaacga tattgtgtca tggatgggac aaaatattgc aatatacaac  28020
cccgaagtta tttttgatat tgcctttgat aagatgaatg tgtccttatt atctataggg  28080
tatacgcttc ttttcaatca tcatataaat aatacgaacg aaaatattaa ttctttattg  28140
acacaacatc ttgaatgggc tgccggcatg ggccttcttc attttatgct ggaaacttta  28200
aagtatggcg gggatgtaac gataatagtc ttgtctgagg ccgtaaaata tgaccacaga  28260
aagattttag attattttct ccgtcgaaaa aacttgtacc aagaagatct tgaagaacta  28320
ttattgttgg cgatacgtgc agattgttct aaaaagacct taaacttgtt attatcttac  28380
ttaaactatt ccataaacaa tatccgtaaa aaaatattac aatgtgtaaa agaatatgaa  28440
acgaccgtta ttataaaaat tttacggaaa agaaagataa atctgataga gcccattttg  28500
gcagacttta taggatatca tagctatacc tatatggtag attttatgcg tgagttttcc  28560
atccatccgg aaaaaatgat caaaatggct gcacgagaat cgagggagga cttgatcata  28620
aaattttcca aaaaagtttg caaagagcct aaagatagac ttcactatct caaaagctta  28680
gtgtatacta tgcgacataa agaaggcaaa caactgttaa tttatacaat ccataactta  28740
tacaaagctt gtcatctaga gagtaaagaa atgtttaatt tggcacgatt tttatgcacgg  28800
cataatgcag tgatccagtt caaatcgatt tgccacgatc tctccaagct caatattaat  28860
atcaaaaact tgttgttaga atgtttaggt attgctatta aaaaaaatta ctttcaactt  28920
atcaaaacaa tagaaacgga tatgcgttat gagtaacatt tttagatgag ggaagattct  28980
accaaactaa ctaagacctt tcgctagaat gtatcttatt gttaatatag atgagatatg  29040
tcattgtgaa aaaatagatt aggtaggttg tgaaaaacag attaaactta aaattatgtg  29100
tattatgtaa aattttagaa ataaaaattt attttttttt attgagggta cggaaaatgt  29160
tctccctaca ggacctctgt cggaagaaca ttttcttcct tccaaatgat tttagcaagc  29220
```

-continued

```
ataccctaca atggctggga ttatattgga aagagcatgg atccgtccat cgagcagaaa  29280
aagacagcat aatgatacag aatgaattgg ttctttctat caatgatgct ttacagcttg  29340
caggagagga gggggacaca gatgtagtac agctcttgtt attatgggag ggaaatctgc  29400
attatgccat cataggagcc ttgaagactg aaaaatataa cctaatatgt gagtatcata  29460
gccaaattca ggactggcat attctcctac ccatgattca agatccagaa acattcgaaa  29520
aatgtcatga tttaagcctt ggatgtgact ttatttgcct tctccaacat gctgtaaaat  29580
acaacatgct ttctattctt gtcaaatata aggaggatct actaaatgca aggattaggc  29640
atcgtatcca atccctgttt gttttggcat gcgaaaatcg gagaattgaa attattgatt  29700
ggataggcca aaatctgcca attcctgaac ctgatgccat ttttagcatt gctgttgcta  29760
caagagattt agaactgttt tccttagggt acaagattat ttttgattac atgcaaagac  29820
agggaatcat tcaattaacc aatggagttc gcatggttgt gctaaatcgt cacattagca  29880
tggcaataga taatggtctt ttacctttttg ttctggaaac tttaaaacat ggtgggaata  29940
tacatagagc cttatcttat gcagtaacac acaatagaag aaaaattctg gattatctta  30000
ttcgccagaa aaatatagcc cctaatacaa ttgaaagact tttatatctg gccgtgaaaa  30060
atcaatcttc caggaaaact ttgaacttgt tgctatctta cataaattac aaggtgaaaa  30120
atgttaaaaa gctggtagag catgtagtaa atgagaaatc cactcttgtg ttaaaaattt  30180
tattagaaaa aaaggaaaat ctagtggatg ctgttttaac aagacttgta aaacattcta  30240
catatttcca ggtgagagaa tttatccagg agttttccat cagcccagaa aaattcatta  30300
aaatagctgt gcgggaaaag aaaaatgtgt taatcgaggc tatttctgaa gatatttggg  30360
aaaatcccac agaaagaatt acttatctca aacagatagt gcacaccata aaatatgaaa  30420
gtggaaggcg atttttggta gacatcattc acagcattta ccaaagttac tcactaaaac  30480
acgaagatat tcttaaactg gcaacatttt atgtcaaaca caatgcaatc acccatttta  30540
aagacctctg caaatatctt tggctgaaca gaggaacaga aagtaagaaa ctgtttttag  30600
agtgtttaga aattgctgat gagaaggagt ttcctgatat taaaagtatt gtgagtgaat  30660
atattaacta cttgtttact gcaggagcta ttaccaagga agaaatcatg caagcctatg  30720
atgctttaga gtagccatgt attaacattc tgaaagtaga ataaaatata ctatatacta  30780
aaaaccaaat tagccatttt taactatctt cttcttaaaa actctggata aaaatttatt  30840
ttttttaat ttgggtaggg aaaatgttct ccccttcagga cctctgtcgg aagaacacct  30900
tcttccttcc aagtgatttt agcaagcata ccctgcattt gctggggtta tactggaagg  30960
ggcatggatc tatccaaagg ataaagaatg atggtgtgct tatagagcat gatcttactc  31020
tttccatcaa tgaagcctta attcttgcag gagaagaggg aaacaatgaa gtagtaaagc  31080
tcttgttact atgggaagga aatcttcatt atgccatcat aggagctttg aggactgaga  31140
actataacct agtatgtgag taccatagtc aaattcagga ctggcatgtt ctcctcccctt  31200
tgattcaaga tccagaaaca ttcgaaaaat gtcatgattt aagccttgaa tgtgatcttt  31260
catgccttct ccaacatgct gtaaaatata acatgctttc gattcttgtt aaatataaag  31320
aggatctact aaatgtacta tttaggcaac aaattcaagg actatttatt ttagcatgtg  31380
aaaatcggaa gcttgagatt cttacgtgga tgggtcaaaa tctgccaatt cctgatcctg  31440
agcctatttt tagcattgct gttgtcacaa aagatttaga aatgttttcc ttagggtaca  31500
agattgtttt tgaatacatg gaaaaccaag gacttcattt aacccaggta gttcgtatgg  31560
ttatgctaaa tcatcacttt ggcatggtaa taaataaagg acttttaccc tttgtgctgg  31620
```

-continued

```
aaattttaaa ttatggtggg aatgtaaata gagccttatc ttatgctgtc acacaaaata  31680
aaagaaagat tttagaccat gttgttcgcc aaaagaatat accccataaa accattgaaa  31740
gaatgttgca tctggctgta aaaaagcatg ctcccaggaa aactctgaac ttgttactat  31800
cttacataaa ttacaaggtg aaaaatgtta aaaagttgtt agaacatgta gtgaaataca  31860
actctactct tgtgataaga ctcttgttag aaaaaaagaa aaacctgctg gatgctactt  31920
tgacaagata tgtcaaagat tctacatact ttcaggtgaa agaatttatg caagacttct  31980
ccatcagccc agaaaaattc attaaaatag ctgtgcggga aaagagaaat gtgttgatca  32040
agggtatttc tgaagatatt tgggaaaatc ccgcggaaag aatcaggaat cttaagcaga  32100
tagtgtgtac cataaaatat gaaagtggaa gacaattcct gataaatatc attcacacca  32160
tttaccagag ttattctttg aaacctgaag aaattcttaa attggcaaca ttttatgtca  32220
aacacaatgc aaccacccat tttaaagatc tctgcaaata tctttggctg aacagaagaa  32280
cagaaagtaa gaaactgttt ttagagtgct tggaaattgc tgataagaag gagtttcctg  32340
atattaaaag tattgtgagt gaatacatta actatttgtt tactgcagga gctattacca  32400
aggaagaaat catgcaagcc tatgctttgg agtatgccat gtattaaatt tctgaatcag  32460
taagcaatag atagatttta gaatatgctg tattaagtta gtttctgaat aagtaattaa  32520
tagatagatt ttagtttatg taaaaatgtt aacatttgtt cataagtttt agataccatt  32580
ttagagttac ttttttagat attactattt tagccattat tatcttaaat aatcactatt  32640
ttagataggt ccccgtatta aaaaccaaat taaccattat ctatgttttt aataatactt  32700
tttaaaaacc ctccataaaa atttattttt ttttcataaa agtagagaaa atgttctccc  32760
tacaggatct ctgtcggaag aaccttttt c ttccacttga gcccttaggc aagcatgtgg  32820
ttcaacggct gggattatac tgggaaggcc atggttcagt taaacgagtg ggtgattgct  32880
ttatatgtgt agaccagatt tggatgctat caatccataa ggctatacaa attgcagcct  32940
cggaaggaaa tgagaacatt gtcaagcttt tcttactatg gaaggggagt ctacaatatg  33000
ccatcatagg agccttagag ggcaggcaat atgatctgat tcaaaaatat tacaaccaaa  33060
ttggggactg ccatcagatt ctaccactga ttcaagatcc agaaatttac gaaagatgtc  33120
atgaattaaa tgttacatgt acctttcaat gcttatttca acatgctata agagataaca  33180
tgctgcccat tttccaaaaa tatggagaag atctgaatgg aaacaggaga atggttcaac  33240
ttctgtatga gatggcatgc cgattacaaa attatgatat catcaaatgg ataggatcta  33300
acctgcatgt ttataacttg gaagccattt ttagcattgc ttttgttaga aaggatttaa  33360
ctttgtattc tttaggctac atgcttcttc tgggtagaat gagtactgaa gatagaaact  33420
ttatctcaat cataacacgc catcttgaat acgcatcaaa aaagggactt tttgactttg  33480
tactagaatc tttgaaatat ggaggtcaag tggatacagt gttgtttcag gctgtaaaat  33540
acaaccatag gaaaatttg gcccatttta ttcatgaaat tccccgtgaa acggttgaaa  33600
agctgatact ccatgctgtg gagtcacggg cctccagaaa aacattcaac ctgcttttat  33660
cttccataaa ctactgtgtg aacccttttg tcaaaaaact actgcacgct gtggtgaaac  33720
acaagtacat gcttatcata aagcttttgc tcgagcggcc caaaaagaag ataaacctgg  33780
tagatgctgc tctattcaaa cttgtaaaat actctactta tacagaaata gtaaaataca  33840
tgggtgagtt ttctgtggac ccaaaaaggg tggtcaaaat ggcagcacga ctcatgagag  33900
tggacctgat taaaaagatt tctaatgatg catgggaaga taaactagag agaatcaagc  33960
```

accttaaaca gatggtaaat accatgaacc acagaaatgg aaaaaatcta ttgatgtaca 34020
atattcacaa tattactgga tatacctatc tgaacaccaa agaagcattt aacttaacaa 34080
gattttatgc tgtccacaat gcaacatgtt tgtttaaaga aatgtgtaaa agctgttttg 34140
tacatgataa aatacagctc agagaattgc ttgaagattg tttacatatt gctaataggc 34200
atgattatat ccagattgca gaaaccgcag atgaatgtat caaatatata gatcttatta 34260
catttaagta aaccatgtat atatcaagta aatccagatt aaatcaggct aattgtaaat 34320
agttgtagat accatataat gaatgtttta ttaggatagt agttcagtta agatagtagt 34380
ttagttaaga tagtagttta gttaagatag tagttatgtt aagatagtag ttctgttaag 34440
ataatagttt agttaaaact agttcatgtt aagttaatag ttttgttaag acaatagttc 34500
atttaagtca atagttcagt taagtcaata gttttgttaa gtcaatagtt tagttaagtc 34560
aatagtttag ttaagtcaat agtttagtta agtcaatagt tatattaaga cattagttct 34620
gctaatacat tagttttgtt aagataataa aaatttattt tttttcatc agggtagaga 34680
aaatgttctc cctacaggag ctctgccgga agaacattta cattcttcct taccccttgg 34740
ctaagcatgt acttcaacaa ctagggctgt actggaaggg acatggatct cttcaacgaa 34800
tcggagatga ccatgtactc ttacagcagg acctgatctt ttccatcaac gaggccttaa 34860
gaatggcagg agaggaagga aacaatgaag tagtaaagct cttgttacta tgggagggaa 34920
accttcatta tgccatcata ggagctttag agggcgaccg atatgacctt atccataaat 34980
attatgatca aattggggac tgccacaaga ttcttccttt aatccaagac ccgcaaatct 35040
ttgaaaaatg ccatgaattg agtaactcct gtaatattcg atgcctttta gaacatgcag 35100
taaaacacga catgctttct attcttcaaa aacacaagga gcaaataaga ttacacatgg 35160
cattaaccca aatactattt gaattggcgt gtcatgaacg taaaaatgac atcattagat 35220
ggatcggtta ttccctgcac atacaccatc tagagactat ttttgatgtt gcattcgccc 35280
ataaaaattt atccttatac gttttagggt atgaacttct catgcacaaa gtaaatacag 35340
aggctgcata tatagaatta cccaatttgc tatcatatca ccttcgaact gcggcggcag 35400
gaggtcttct taactttatg ttagaaacaa taaagcatgg tggatatctg gataaaacgg 35460
ttttatccgc ggctatcagg tacaagcata ggaaaattgt ggctcatttt attcatcagg 35520
ttccccgtaa aaccgttaaa aaactgttac tctatgctgt gcaggctcgg gcccccaaaa 35580
aaacactgaa cctactttta tcttccttaa actactccgt gcacaccatc accaaacaac 35640
tcgtacacaa tgtcgtcatc tacagttcca cgcttatcgt aaagctttta ctcatgcggc 35700
gaaaaaacaa gttaaaccta gtagatgccg ttttagccag acttgtaaaa tattccacct 35760
atacagacat tgtacaattc atgggtgagt tttctgtgag cccagaaagg gtgatcaaaa 35820
tggctgcacg ggaatccagg acctttctga ttgaaatgat ctccaaagct gcttggggaa 35880
atcacccaca gacgttgatt catcatctca aacaactaac caataccatg aagcctcaat 35940
ctggaaaaga ccacatcata tataccatcc actatattta tctaaactct aatatgctgg 36000
tagcggagga ggaaaaaaat atttttaaat tagcaaaatt ttatgcgaat cataatgcgg 36060
taaacaggtt taaacaaatt tgtgaagact attatatatt agatgcacga tttaaaacac 36120
ttattttaga atgttttgaa attgccgtcc agaaaaacta tcctagaatt gcaaatattg 36180
tggatgacta tattcgattc ctttttttaca ggggaaatat aaccgaggaa gaaattcgtg 36240
aagcctattc tttaaaagat gctgaggttt atgtagattt aaaatggtta caacaaggag 36300
aaatggttta aaccaaatcc ggtttaaact aaatccaatt taaactacat ttggtttatc 36360
attagtcatt gaaaccatcg aaaaaaaagc tatttgttta tccccataaa ctcatctttt 36420
ttttgtctca aagtttgaca ctaaaattca gtgttttata gtgtttataa ttaagtgttt 36480
tgcatgcatt gcagaaattt tcatcttttt taattggttc aataccacat gtcatacaat 36540
atgttgtttg attatcaaga ttaactttat gaaaggaaag taagtgagcc gcaaatttaa 36600
aagtaaaata tctttcattt aaaatgatct tatgaatgta ttttcgataa ggaggaatga 36660
aagcatttgc caaaataaat cgcataaaag gcttggaaaa acccatatct tctaatcttt 36720
tgtgggtata aaccctattt tggtgtttta caaaaacttc attgttataa tagtcgttat 36780
agctatcaat catttttta agtcctataa tgcccaaggt tgcacgcata aagccacagt 36840
ttctgctcca aaaagcatgc acctgtaaag ggtgcttttc atataaccaa ttacaaaatt 36900
tcattccgca acagtagcat gttatttcag tgggggatgt atagaataat ccggcattcg 36960
aaaatttttc ataatttttt atgtcatgga ttgcgaagct ttgatttcgt gcatctatgg 37020
agctatagcc tacatattta ggttttactt caaataatcg caaagagatg tatggatcta 37080
tcgtatttat tttaggaaac atttcataat tttaaattct tatatataat ataaaaaaaa 37140
ttacaaacat ttgtaatgat catcctcaat tgaaggctga gttgtaggct ttatttttct 37200
aattatacga agaaggtagg ttctcataaa gccttcaaga tgactattga tgtttccaat 37260
acattttctc aatgagttca taaacccaga cattttgcta atggcttggc aaagtgccaa 37320
caagttgtcc acaaagtact ggtagattgc cactagctat agctagctat agtgagccaa 37380
cctctctgta tgtattttat atatttcatt ttttaataga tttaatattt ttataaaaaa 37440
atatttagtt ttttatacaa gaatgtcgac aaaaaaaaag cccacaatta ccaagcaaga 37500
gctttactcc ttagtagcgg cagataccca gttaaataaa gcattgattg aaagaatctt 37560
tacaagtcag caaaaaataa tacaaaatgc tttaaagcac aatcaagaag ttattatacc 37620
acccggaatc aagttcaccg tcgttacggt gaaagctaaa cctgctcgcc agggccataa 37680
tcccgccaca ggagagccta ttcaaattaa agctaaacct gaacataaag ccgtaaagat 37740
acgagcattg aaacctgtcc atgatatgtt aaactaaact ataaagtcat attcttcttt 37800
atcgttatta tcttcaatat atttttgcca atcgaaatcg aataaattca gatcctggac 37860
atttaaatac ttatcatcgt acattttaat ataatttaaa catgagttgt tgtcaaaaac 37920
ttttagcgtt tttgttaaaa ttatcatatg aataatttcc ttattaagag ttgccggaat 37980
aatacaaaac ctatttttag gtacatcatc catgataata gtaaaattag taaaaattgt 38040
ttcttgtttt tcttttgttt caaataaacg ttgtaaggtt aaaggtttct cgttcaatgg 38100
tttctttgaa gataaaaaga atgtataatc tggtttaaag gtatttttgg tttcaatcgt 38160
gattccatct gcttgagcat atactaaacc agaccaaata taacggtcca ctattacaat 38220
ataatttagc ttaagtagca ctgcaatttc tgcgataaat tcactacgat gttttgtaaa 38280
taatttatgt aattgttccg atgacatttc tatggtttta tttaacacct gcaatataag 38340
atcaccggtg gtcgtgtctg gattaggaaa atgtatacat atagcattat aatccatgca 38400
ttccaatgtt tcttttaatt tcattgcctg tgtgcttttt cccacaccat tgattccctc 38460
gatggcaatg agtattccac gcatgattaa taaaaggaaa aaaagaattc agtttttaac 38520
atttcttaca aatctttttt tatacaacat tgtacaacac tgcattagcg gtatatgatg 38580
ttatagcttc attaaatatt tgcttttata taatctttac caacctatat ttggtagatc 38640
actgcagatg gtcataaata ggccataact aagataaaaa ttatttcaga cgctactacg 38700

-continued

```
gtagtattat taaaatcatg tgtggcaatg tatgacgtct taatagataa aacatttaag  38760
gaaaacaaat ttgaataaaa aaaataattg ttatgatggc gttgttacac aaagaaaagc  38820
ttatagagtg catctatcat gagctagaaa atggcgggac aatattgctt ctaacaaaaa  38880
atattgttgt gtcagaaatt tcatacattg gcaatactta taaatatttt acctttaatg  38940
acaatcatga tctgataagc aaagaagatc ttaaaggagc aacatccaaa aacattgcta  39000
aaatgattta taattggatt ataaaaaatc ctcaaaataa taagatttgg agtggtgagc  39060
cgcgtactca aatttatttt gaaaatgatt tatatcatac aaattacaat cataaatgta  39120
taaaagattt ttggaatgtt tcaacttcag tcggtcctca tatctttaat gatcgtagca  39180
tttggtgtac taaatgcaca tccttttacc catttaccaa cattatgtcg cccaatatat  39240
tccaataaat tagatatctt tgctattaaa atagttaaaa accttatagg ataattaggt  39300
actttattac gataaattat gatattttat aattagttac tttattataa ttaatctctt  39360
tattaatgaa ttatcataag ataactaatt atttttttcc atatatcaga taataaatct  39420
gatatgggct aaaagtatgt ttcaaactat ttacaataga atttctgtta agaaaacata  39480
cataatttga ataaaatttt tttaaatatc accgaaacaa tcaacatggt gttaatagag  39540
tttttaacag gtttcttcta tttatatgga aagagactgt tttccattag taaagtcatg  39600
gacatgatat gtctagacta ttataccatt attcctgctc ctctggcgat gatgttagcg  39660
gcaagactaa aaaactatga cctcatgaaa cgactgcacg aatgggaaat ctctattgac  39720
tacgctctac ttgtagtaga tgatgtgccg tctattgact attgcttaag tcttggcgct  39780
agatccccga ctagagcaca aaaaagagaa ctgctgaggg acaacacgtt taatcccgtg  39840
tataagtatc ttatgaactg ttccggcttc ccaacaaaga gagaaaaaaa cattccttgt  39900
gatgttcaat gcgaaagact gcaaaaaaac attataaaag aactggtatt taactgctct  39960
gtactgcttg aaatggtact gcacacagaa agagaatatg catacgccct acactgtgct  40020
gcaaaacata accaattgcc catcctcatg tattgttggc aacaatccac agacgcggaa  40080
tctattttgt tgaaaacctg ctgttctgat aagaacatca attgttttaa ctattgtatt  40140
ctatatggcg gcgcccaaaa tttggatgct gcaatggtgg aagcggcaaa gcacgatgcc  40200
cggatgctga taaactactg tgtcatgctt ggtggaagat ccttaaacga agcaaaagaa  40260
acggctgcca tgtttggaca cattgaatgc gcacaacact gttttaaact gcagtcttac  40320
gtcgtggaca catcgaatac agacgacact gattaaagcg acaatcttac gtcatgaacg  40380
actgtctttt gagtatctat acttacatta tattttttta tgaaaaaaat ataaaggttg  40440
tatacaaacc tttgtataca agaaatttgg atcattaaac aataattaat ttggacacag  40500
gaaacgatct agatcgatca aaaagctatt ttttttgcac acagaacatt tagataattg  40560
agagattact ttccatactt gttaagcttt tttacacaca ggaactttgg attctgttca  40620
ggaagttttt catagacatt atgtttacag ccagtaataa taattttggg ctttttctta  40680
aaccaccggt ggaaaacatc cagcttgtaa agagggaaat gcatgtagag aggttttggt  40740
agtcatggtt aagagatttg actaactcca tgtttcctgt aaagactgcc cagtcccaag  40800
cagtaaaacc tctatgatag tctttttgag tcggatctgc tccaaatttt atgagagaaa  40860
gcatatttaa agaacggccc cgtattgcgg ccttcatcac aggagtcatc ccattaaaat  40920
tcggtaaaca aattctggtc ccattttttc cgaaatagcc caacacccct tccaggatta  40980
aatgattttt tttctcagct aaataatgta aagcagagtt tccatcttta tccctcctat  41040
gagggttaat tatttctcca ggataagatt cttgttcaaa aagaaatttt aaaaagtcta  41100
```

tacgtccgta gatgcatatc cacatgaata ccgaggatcc atttttatcg catctattga 41160
caatccacgg atctgtttta aaaaattcct caaatagtgt aagattccca tttctaatat 41220 gtttttaat ccatttaaca aacaagtttt ctatctccct ttctggaaac atgtgttcca 41280
ttttgaatgt cgcccctact ccactatatg attttactcc tttaattttt aatgtccttt 41340
tttttcggac ttctttggat aagctgttta ttaccatctt taaatgcctt atagcgggga 41400
ggagccaggc ccttttccca tatgtgcggt aattcttggt gtttatgctt gcctttggca 41460
taaccaggcc agtatttttc gatatattca gggtttgttt ttacgtattc tttaaaggtc 41520
cgataggctt cttgaataca ggtaggctca ccggtataat ttccatgttc atcttccttt 41580
aaaaagccat taaccctgtc ctttctccac ttaagattgt gctttccaaa aatgcgatca 41640
agatcttgcg cctgctgggg tggaatcata aatccctttt taggtcgaag ctttttattt 41700
tttccatagc ttcggccatc gcgttgcgaa acagtggtta ggacgcctga tagtctttcc 41760
atgggcgtcg catctaatcc tatccatcca ccctgatgaa tatcaatggc aacaagctct 41820
cctttatttt gggcaagcca agtttccaag aatgccatgc tttcttccca gggataaggc 41880
ccgccaacac cacgggttgt ccaatcttgc aaggactcca ggtccgacac ctggtaaggc 41940
tctaaagaag acggttcctt gtttttgtac tgcaaataag atttaatgac ccatttatac 42000
catgtgtcga accgcagcgt ggcgcctcca aagtgaaagc cgtcgttgat tttaggatat 42060
ctgcaacata tttcaaccgt acgtttgagt tctgcaaaag cggccttcca aggaagtctt 42120
tcgctgcggg taagacggtc tattttgccc tgcgtgccat agcgtatggc atgtcgtgcc 42180
aattgcaaca attctgacac cgatccgtgg gccccgatcc agtttatcgg ataggcaacc 42240
tccgaagggt ttaaaagatg ctcgtaaaag cgtggatctt cagatgccaa ggcgtctgca 42300
aaggggataa tgctagaaaa cctgtctaga catacgtttt ctgtgtttac ttctaaaggt 42360
agaaaaatgg ttgcgtgagg cttttgaacc tgcttgttca gcggtctgca tatgctttga 42420
ataatgtctc taggactatg tcgcggcgct gcaaaaaata ccgcgtttag ttctggaacc 42480
tctacgccct cttgaaagag tcgacagttt aataaaataa cgggttcctt tgaggaacaa 42540
aattctgtaa atgttttgag gataacctgt cgcggcaggg ttgagtgagc tatcagggca 42600
tagacccctt ggtctaccaa cgccgcgtat agctccttgg cctgtttaat atcacgggta 42660
aataccagca ttttaggagc cggtatattg gtttttaaat aggctaaggc cattataatt 42720
tgctttacta tgatctgttt cgtggtctcc tctttggtac tcggttggtg ggccaattta 42780
ggcgcggcta ccatctgcaa ttcaaaatca tttacatagc cggcctctat gccttctcgc 42840
agatagtagc gaaaggcaac gccgccaaaa agttcacgat tttcatgga aagcggggtg 42900 tcgtacctgg gcgttgccgt taaaaaaagt cggtgccctt ttttaaagtt gagcaacacg 42960
tgggtaaagg gccgtgtctc ccattcgccg caaatccggt gacattcatc gctaataata 43020
agatcgaaat catccaccag tagcgtggag gattggtagg tggcaatcac aagaagagaa 43080
ggggcctccc gtatccgttt tgcaataaag acaggattgg tggtcatttc tatattgtcg 43140
tgatttagca caatgcgggt ctggtcagac cccacaagca aaacgttctt caaagaaatt 43200
ccatactgat agagtttttc cagagtctgc cgtagtaggg acaggcccgg caccaggtac 43260
aaaacttttc cttgaagata attggagagg ataagatagg cgacgcgagt tttgccgcat 43320
cggcaggcca tctgcagaat ggccctccca cttcgccgca gctcctgata gcccatattg 43380
gccgcctcct tctgataaag tcgatcctcg attgcagtcc gtgtctcatc tgtagaaaaa 43440

-continued

```
aataatacgt catctgcgaa atgttcatct tccacaggag ttatcaccag gtgtctcagt  43500
ttctccttgc ttatcagcgg atcagagggc aaagatggct caaccactat cgtggaatca  43560
ttcatctcat aggcgggaga atcacacaaa gtatagctta tgtccagaca gtttgcaaca  43620
tcctcagcca attgttttat tttttcgggt aaaagacata cgagttcttt gtttttgacg  43680
cgaaaaaact gtgcacaata taacacccct gcttcaattt tttgcgcatc cttctttgta  43740
gatgtttcca atgtgaaaca atacttccat tcatccgtaa aacaggttgt ataagatcca  43800
tcatgaagcc tagcggccaa gtttcctgtg tgcccaactt tatgtaagga ttgggcctcc  43860
agccagggat gaaccgccac gtaaaatcct gcgcacatgc tatatcaaat tgcagtttct  43920
taataactgt acacaggatc tgaaaaacat gtgattacaa aatttagata agaaatattt  43980
aatattaaaa atcacagaat acatgtcact gtgtagagag aaagccaaaa actcctcttg  44040
accgccgtgg gaaatcatcc agggtagtag gttgtgtttc ataaagttgt atgccgtagt  44100
gatcaccgtg gactccagat ggttattggc atctttgcaa tactttgcca tcttggcaga  44160
aaagacgata aatccacaaa ttctacccca gttgataaga tccttaaaca gctcagtcac  44220
aaccccagta aactgggttt taatttcttg aacactcgta agagaaaagg taattgtaac  44280
ctgtttgttc aaacactcat cataataggt taaaattttt tttatttgtt gttgatatgg  44340
gctaagctca tgctctgaaa tatcattaat gtaatattta atatatccca ctagtatttc  44400
attaatgata ttatgatata ttaactcttc tccctccata gcggcaccct atattttttt  44460
atttaggttt caatgttatc acaattgcga tacaattgtg atacaattgt gacacaactg  44520
tgttgtatac aacaaatgtt aggccacgta tagcaaccta tatgttaaga aatattttta  44580
tcccaacatt agttggaaac gagcagccgc aaagaagtca tttaaaataa gccatttaaa  44640
gatttagaat ttatatgtat acaactgtac aatggaagca gttcttacca aactcgacca  44700
ggaggaaaaa aaggctctcc aaaattttca tcgttgtgct tgggaagaaa ctaaaaatat  44760
tataaacgat tttcttgaaa tccctgagga acgatgcacc tataaattca actcatacac  44820
aaaaaaaatg gagcttttat ttacccctga attccacacc gcctggcatg aagttcctga  44880
gtgcagagag ttcatattaa actttttgag actcatttcg ggacatcgag tggtattaaa  44940
aggccctaca tttgttttta caaaagagat caagaatctg ggcattccta gtaccatcaa  45000
tgttgacttt caggccaaca ttgaaaatat ggatgatcta cagaagggaa atctcatcgg  45060
caagatgaat atcaaagaag gctaaataaa acaactaaca tcaaaaaaca ttaaaggcta  45120
tgttgtggac gatgcctttg tctcaatagt ttcgaggtca tccaataact catgtaacgt  45180
aaaaaagttg gtccattttt ttgaaaacat taaaagacgt tcgtcttcat aaataaaaaa  45240
gtcattcgaa ggaaaaatga tatactcaat accatagtct tgtaatattt tttttaggtc  45300
tctcagggtc cagggattta ccaggcttct acgcgaagtg agcatcataa aaatatctaa  45360
tattttttgc gccataagcc agcgcggatt ctcattggcc cacaaatcaa caataattct  45420
cttatcaacc gtgagcattc ctacttgatt cgaagaaatg attagatgcc cagcagtcca  45480
ccccatgagt agataacgca gcgttgtaga aatgtcacat atggaaggca ttcctccaca  45540
acatgaaccc aaattaggat gcgtgtgaaa cacaaacata gcaggcttgt tggccaccct  45600
gctataaata tcagcaggca tcatagcctc gctgccaaaa taaatgttct ctcctgccct  45660
ataggggctt ggaatgattt ccactatctc gggtacaccg tttatcatat taatgcggcc  45720
gcaccattca cggtcatcgt ccaaaaattt tttgatggca ccccgaacat tgtcccagtt  45780
aagcaacaga gtattcacaa tctcattacg ctccgcccag tattccttaa aacttctttt  45840
```

agacttgctg agctgttccc aggattcgaa ctcagtccaa tgttttttttt cttttgggga 45900
agacttccct tttgaaacat tttttgcggc tccaccatct acactatgat tttccaaaat 45960
aatctccttc atcgtttgag ttatatgggc attgctaagc accttagtgg taacctgttt 46020
acctatgtga tttagcagaa aaccaagttt gtccatttgt gtctcaacca tttattctta 46080
acaaaacaaa aaaaaattaa aaatcatcgt cgtttaaaaa gagtttgaag gcaaacgcat 46140
catccttaac acagttctga tactgcgtag gtcttaactc gaaaaagttg gttttttcta 46200
cttcattaag aaagaattta gtcatctgag gaaaagggtt tcccacctta taaatgcttt 46260
tgcactgcat catgaagcac aaattatctg taaagtagcg tatatattga aatagcattt 46320
cttttgaaaa accgggaact cttcctcttg ccttgtcaaa ggcatagtta ataaactcat 46380
ccaccaactc cacagcctcc ttcaaaattt tgtgaatgat cttttcctcg ggaatgttat 46440
acacgtaatt tgagataaga aaacacgcaa aactacagtg catcccttca tcacgtgaga 46500
taaactcatt atagcttaca agccccggca taatattctg ttccttaaga aactggatcg 46560
ccacaaagtg gttttgaaat aaaatgcctt ctacggcggc gaagcccacc agccgctcac 46620
ctagagtgtt cctgtcgggg tccatccact gccgcaccca ctgcgccatt tttttatga 46680
tagggtgttt ttcaatgccg ctaaagatgc gctgttgttc cttctcatcc gggatcagcg 46740
tttttacctg tattgagtag gcttcgctat gaacgcactc ttgggcagcc tgcattgtat 46800
aaaagtataa cacttccttt actttaattt cgcgcataaa attggttaaa aggttttcga 46860
taacaatttc gtcggcaaca acaaagaagg ctaaaatttg tttataaaat tcgcgctgtg 46920
gctttggcat ggcttcccaa tcatcaatgt ccttacacat gtccacctcc tgcgccgtcc 46980
acgtcaaact ttctaatttt ttataccagt tccaacattc ggggtgctga ataggaaaaa 47040
tagtgaaacg ttgggaattt tcaattagta attcctccat atttgaaata aatattaaca 47100
tcttcaaatt tattggctgc catggagacg ttttttattg agacgttggc atctgatgtg 47160
tatggaaagg cgttaaatgt tgatttagat agactatcgc aggcgcaggt taaatatacc 47220
cttcaagagc ttatttccta ctgcagcgct ctaaccattt tacattatga ctattcaacc 47280
cttgcggcgc gtctttcggt gtaccagctg caccagtcaa cggcctcctc cttctcaaag 47340
gcggtgaggc tgcaggccgc acaatcctgc tcacgcctgt ccccccagtt tgtggacgtc 47400
gtttacaagt acaaagccat ttttgacagc tacattgact atagcagaga ttacaagctg 47460
tccctcctgg ggatagaaac catgaaaaat tcttatttgt taaaaaataa agatggggtc 47520
atcatggaac gcccgcagga tgcttatatg cgggttgcca tcatgatcta tgggatggga 47580
agagtggtca atatgaaaat gattctgcta acctatgacc tgctttccca gcacgtcatc 47640
acacacgcgt cgcccaccat gttcaatgca ggcaccaaaa agccacaact ctccagctgt 47700
ttcctgctaa atgtaaatga taatttagaa aatttatatg atatggtcaa aacggccggc 47760
atcatttcag gcggcggcgg tggaataggg ctgtgcttgt caggaatacg ggcaaagaat 47820
agttttattt ctggtagtgg tcttaaaagt aacggcatac agaattatat tgtgctgcaa 47880
aatgcttcac aatgctacgc gaaccaggga ggcctacgtc ccggagccta cgccgtctac 47940
ttagagctgt ggcaccaaga catctttaca tttttacaaa tgcctcgcct aaaaggacaa 48000
atggctgaac aacggcttaa tgcccctaat ctcaagtacg gcctatgggt ccccgaccta 48060
ttcatggaaa tacttgaaga ccaaatacac aacagaggcg acggcaaatg gtacctcttt 48120
tcgccggatc aggcccccaa tctacataag gtctttgatt tggaacggtc gcagcacgaa 48180

-continued

```
aacgcacacc gcgaatttaa aaagctttac tatcagtatg ttgctgaaaa aaggtacacc  48240
ggcgtcacaa cggccaaaga gattatcaaa gagtggttca aaacagttgt tcaagtaggg  48300
aatccctata tcgggtttaa agatgccata aatcgtaaaa gtaatctttc acatgtaggc  48360
actatcacga actccaatct ttgtattgaa gtcacaatcc cctgctggga gggtgataag  48420
gctgaacaag gtgtttgtaa tctggccgca gtaaatctag ccgcctttat acgtgaaaat  48480
ggctacgact accgtgggct catagaagca tcaggcaatg tcacagaaaa tttagataat  48540
attatagata atggctacta ccccacagaa gccacgcgga gaagcaatat gcgtcaccga  48600
cctattggca tcggggtctt tggcctagcc gacgtgtttg cgtctttaaa aatgaaattt  48660
ggttcacccg aggccattgc catggatgag gccatccatg cggccctata ctacggggcc  48720
atgcgacgat ccatagaact tgcaaaagaa aaaggaagtc atcccagctt tccggggtct  48780
gcggcctcaa agggtctact gcagcccgac ctatgggttc gctgtggtga tttagtttcc  48840
tcctgggaag aacgcgtggc acagacgacg cagggtgtgt tgacgccgaa aaggtggtcg  48900
cagctacgcc tggcggctat gcagggactt cgaaatggat atgtcacagc tcttatgccc  48960
accgcaacct cctcaaattc tacaggaaaa aacgaatgtt ttgagccctt tacatccaat  49020
ctatatacac gtagaacgtt aagcggggag tttattgttt taaataagta tttaatagac  49080
gatttaaaag aaattaatct ttggacagaa gccattcaac agcagctact aaatgcggga  49140
ggtagcattc agcacatttt ggatataccg gccgagatcc gcgatcggta taaaacctcc  49200
agggaaatga atcaaaaaat tttaacaaaa cacgcggccg cacgaaaccc ctttgtatcc  49260
caaagtatgt ccttgaacta ttacttttat gaacctgaac taagccaggt acttacagtg  49320
ctcgtcctag gctggaaaaa aggtttaact accggttcct attactgtca ttttagccct  49380
ggagcgggta cccaaaaaaa gattataaga aactctgaga aagcgtgtaa tgcggactgc  49440
gaggcgtgtc ttctgtaggt gtctcgcggt aaaagagcag cggggaccat atggtaaacc  49500
ccaacaagag gataatgaat aaaaaaagta aacaggcatc cattagttcc atattaaatt  49560
tttttttctt ctatataatg gaatattttg ttgcggtaga caatgaaacc tccttggggg  49620
tttttacttc tatagagcaa tgtgaagaaa cgatgaaaca ataccccggc ctccattatg  49680
tcgtttttaa gtatatgtgt ccggcggatg cagaaaatac agatgttgta tatttaatac  49740
cctcgttaac cttgcatacc cccatgtttg tagaccactg tccaaatcgt accaaacaag  49800
cacgacacgt attgaaaaaa ataaacttag tgttcgagga agagtctatt gaaaattgga  49860
aggtttcagt aaatactgtg ttcccccatg ttcacaacag attatctgcg ccgaaacttt  49920
ccatcgacga ggctaatgaa gccgtagaaa agtttttgat acaagcagga cgactcatgt  49980
ctctgtaaat gtctcttcct ttatgggtga cgtctcttcc tttgccgagg aagtctctgt  50040
tatgggcaag aggtttgaaa caacgcaagg actctgctta atctgctgtc tcacaaaggg  50100
aatcaaacta cctgctttcg tatttttaat gtagtaatta cccttgttgt gatgaatttt  50160
aagaccatag cgtagtccca gtactttatt aatgaatttt aaaattgttt gagggtccgt  50220
tttattgggc tttttaagct taaactcaaa gctgatcgcg cttaaatcat actgaacaaa  50280
ttcatcaacg agtttcgtca ttaattgttc attggtcaat atattagggt cctgaacgca  50340
tttaaagccg cacttagtta atagcataat agcgtacata tgagattgaa aactataatt  50400
aaattgtaga tcatgatgct ctgcgtgttg catggcccat tgatgaaagt ttaattcctg  50460
agtttgtaac atagtgagcg actcgtatac tgtctttccg cggcttattt ggacacggcc  50520
agtatagttc tgttttgtca taaaactatt gtattgttca acaaatttgg gagtaatttt  50580
```

atgaccgtgc catgcataaa attcgagtag tttatacttt tcatacgcaa ataggtcttg 50640
ctggtctact gtgatgcctt cctttaagtt ttgtttaatt tgtaaagctt tattggcatc 50700
aatggtttca gccgaggcaa tgtttacata gtcctggtgt ttaatttcca ttttaatgct 50760
tgtatattgt ttgactgtct ccagcttttc acccgtcagt ataaacacct tagcgccggt 50820
gtcggcgatc tggttaataa atcgggttat aaagtgattt tttgatagat gttgtatccg 50880
cattgtttcg agccatagat ggtagtatgg agttttataa tatatcggcc tacctgtttc 50940
cttactatac gtgaaggaaa gctggtgatt gcttatggtc tgaaaaaggg tgtcacgttt 51000
ttgtaacgta aacatttcaa tgtcttcgat ggtttctgga tagtaatttt gtttcccctg 51060
taagcagatt ttataacact tactttttaa ttcacgcacg cggcccaaca tttggcaaca 51120
tgtttctacg tcacacgaca tattgttaaa aaagccgtat aaaacatcaa atctcttatc 51180
ttcgtatgaa acacccgctg aaatcgtggg cgtatagata aggatatcaa cgagccccca 51240
ataatacgat acattattaa aatgggattc ccgttcatga gcagtgcttt tagaactata 51300
aaacccaatt tttttttccg gaaacttttt ttggataaat gattgcaaca gccgggcctc 51360
cattaatgaa tttgtaggga taacaatttt tttgtcttct agcaaatcct ttaaaaggtt 51420
atttaaccaa gtttctcgtg aagaggtaaa ataatacgtg tcatgctggg ccctttttata 51480
ttgattccag tgaaagaaga tagggacatc cccgcgaaaa cgctgtagaa tattatacgt 51540
tcgatttcct aggtttgcgt ccaagcatat aacataattt gccgtttcga gcatccacat 51600
gaaaatggca aaagagggag caaagtattt gtgcaggccg ctattgaatt gattaaaaat 51660
cgattctacc tcatccaaaa taagtaggtc tacaggctcg gctgtggagg ttagccggaa 51720
aagtgattct acctgaatga tgactctttc gtagctgtcc aaatctccag ttacttcgct 51780
gtacaatgtg aaattcggta gccgggattg tatatttttt gagaagatct gtcgaaacgt 51840
cacaaaccgt atggtttgtt gttttgaaat agaattattg ccgtagtatt tttgcaaata 51900
gttgcgcagt tggacggttt tacctatttt catttgagcc tttacaacaa gcgtagggac 51960
tcgttcatat tctcgcatac tactttcatc atagatgtgt ttttgagtat caggcagttc 52020
ttcaaagaga atggactcat gaacctctat gctctttgtc atcacttggt ccacatatgt 52080
ttccacaaaa ttatttgtgc cggaaaggct gcccatgaga aggctatgtt tattgtcatg 52140
gcgacagtgt tgatacactt tgtttcccgt gactcttaaa attagggtat tgtccttatc 52200
atgcatacgc ttacatattt cgcagtaact tggacttgta cgtttaaaca atactaaatt 52260
tttatgaaca cggaggaagc aatgattttt acatagtgtt cctgcaaatt ttaatacctc 52320
ttcaagttca ctttgttgga tagtatcgca ggaactcggt gttgtttctt ttacatttgt 52380
gaagatacaa ggtaaacacg tcgtttcaaa gggggttgct ataagggtat cactcttttt 52440
cgtggttgta ctggtctcaa acacctctgc aagctcctca ttaaacattt taacacgcat 52500
gctacctttt ttatgagacc ctatgatgcg aaaattttga atacttttgt tgacctgggg 52560
gtcaacaaaa ggataaacgt gtttgggaag attttctaac actttggatg taaagacttt 52620
ggcctcatta ttgtttaata ctgagtatgt ataaagtatg atatgaaagg agtatttaag 52680
ttctcgcttt ttatttaatc cgatagaatc tgttagcaaa atttgttcac gcgttagatt 52740
gatgttataa ggtaaagaat atgtctcgta aaatacatcc atgatgacgt taattatcat 52800
gtcaaggatg tcatagacat tgtcttcgac attatcattg tcatcaacat tgtcatcaga 52860
gtatgactta tttaccggaa agtcgatgtc aaattttaag cgctgaggca aaaacccaaa 52920
taccacttcg tggaaacact tctgctcaaa gggctgagcc gcctcccact cccaaaagtc 52980
atcacgactt gaaaaaactc taaaaagatt attatattca tctcgcacca cgaagtgatt 53040
ctttaaggtt tcgagagaat atttatcctc tacggcttct ccttgggagt tacagcgaag 53100
aaacttgaat gtttcttgca ttttgatatt taaaattaaa tcaattatga tgcggccgct 53160
aatgcggcgg ttgacgcggc cgcgccgctg acgcagccat catacataaa gcggcatggc 53220
cgttttataa cgactagtcg gccgttatat gacgaactat ataaaaatga attcttttaa 53280
ttagagttaa gtattgttga ttgtataatc catcatggtt gagccacgcg aacagttttt 53340
tcaagatctg ctttcagcag tggatcaaca aatggacact gtaaaaaatg acataaaaga 53400
cattatgaaa gaaaaaacgt cttttatggt atcattcgaa aactttatag aacgttacga 53460
taccatggaa aaaaatattc aagaccttca gaataagtac gaagaaatgg cggccaacct 53520
tatgaccgtc atgacggata caaaaattca gcttggagcc attatcgccc aacttgagat 53580
tctaatgata aatggcactc cacttccggc aaaaaagaca acaattaagg aggctatgcc 53640
cttaccttca tcaaacacga ataatgaaca aacgagtcct cccgcctcag gcaaaacaag 53700
tgaaacacct aaaaaaaatc ccacgaatgc gatgttcttc acgcgtagcg aatgggcatc 53760
ctcgaatact tttcgagaaa agtttttaac accagaaatt caagccatat tggatgagca 53820
gtttgcaaac aagaccggga tcgaaagatt gcatgccgag ggtctttaca tgtggagaac 53880
ccaattctct gacgaacaga agaaaatggt caaagagatg atgaagaagt aatatttttg 53940
gtaaaaatat ttttatcaaa attttttac caaataataa aaaatatttt ttactttttt 54000
ttcttcataa tatacataga atgcctacaa aagctggcac aaaaagtacc gcaaataaaa 54060
aaacaacgaa gggctcctcc aaatctggtt cttccagagg ccacaccggc aaaacccatg 54120
cttcttcgtc catgcattcc gggatgctct ataaagatat ggtaaatatt gctagatcta 54180
gaggcattcc gatttaccag aatggatcgc gtcttactaa aagtgaattg gagaaaaaaa 54240
ttaaacggtc aaaatgaata taatcaggaa acttaagcct ggaacaatta gccttgtgct 54300
gggacccatg tttgccggca aaactacgtt tcttattcat tgcatttaca tgctcgaacg 54360
tttggaaaaa aaagtagtct tcataaaatc taccaaaaac acccgagaca aaactattaa 54420
aacacactcc ggtatacagc tacgacccaa acaatgtaaa atcatagaaa gcacacagtt 54480
atctgacgtg ggttctctca ccgatatcca tgcagttgtc gtagatgaag cgcatttttt 54540
tgacgattta atcacatgcc gcacttgggc agaggaagaa aaaattatta ttcttgcggg 54600
actcaatgct tccttcgagc agaaaatgtt tccgcccatc gttcgtattt ttccttactg 54660
cagctgggtt aagtatattg gccgcacctg tatgaaatgt aaccaacata atgcatgctt 54720
taatgtgcgt aagaacgcag acaagacgct tatccttgcg ggaggaagtg aactgtacgt 54780
aacatgttgt aacaactgtc taaaaaatac atttattaag cagttgcaac ctattaaata 54840
ttaaaaatct tatacaataa tggatcatta tcttaaaaaa ttacaagata tttatacgaa 54900
gctcgagggt catccctttc tttttagccc gtcgaaaacc aatgaaaaag agtttattac 54960
tctgctaaac caggccttgg cctcaacgca gctttaccgc agcatacaac agctgttttt 55020
aacgatgtat aagctagatc ccattgggtt tattaactat attaaaacga gtaaacaaga 55080
gtatttatgc ctgttaatta atcctaaact cgttactaag tttttaaaaa taacgagctt 55140
taaaatttac attaatttca ggctgaaaac tttttatata agtcctaata agtataataa 55200
tttttacacc gctccctctg aagaaaagac taaccatctt ctaaaagaag aaaaaacttg 55260
ggcaaagatt gttgaagaag gaggagaaga atcctaagtc gcttacattt ttttttgcta 55320

-continued

```
tttttataga atgtacacgc atgttgatgt tgtcggaata gctgaagcct cagcggccct  55380
ctacgtgcaa aaagataggg atcgctactt agacgtgcta acaaccattg aaaactttat  55440
ttaccaacac aaatgcatca taacagggga aagcgcccac ctactctttt taaaaaaaaa  55500
tatttatctt tacgaatttt actccaacaa tgtggcggag cacagcaagg ctttggcgac  55560
cctgctttat aaacttgatc cggaatacct cactcgttac acagtactca ttaccaaaat  55620
tcccaaccat tggtatgtga ttaacgtaga tcagcgagaa tttgtgcgcc tatatgccat  55680
cccggcagtt aaacaacact taccgattcc cattttaccc ttctattgca ccagcgcact  55740
cacccagcaa gaattgtttt gtttaggacc tgaactgcag ttaatacaaa tatattccaa  55800
gctctgtaac cccaactttg tcgaggaatg gcctacgttg ctcgactacg aaaaaagcat  55860
gcggatgtta tttttagaac agtttccgca aagattggaa atgacgggcg ggaagaagga  55920
ggagaaggaa aagcatgaaa gtatcattaa aaaaataata ctagaaatgg tctctacccg  55980
tcagcgaatc gttgttgggg gttacataca aaaaaacctg tacaaccatg tactcaagaa  56040
tagaaatcgt ttacagctta ttacgagctt aaatatttat gaagaaaaag atatcatcca  56100
gcaattttgt gattcaaatg gactgaagat caaaatacgt atcaacaatc cgctcttgcc  56160
tacaaatccg gaattacggc gtttgactat ttattttaat cataataatg atgatgatca  56220
gtcatatcta atagtagata tgtacaacac gggaagctat gagctagtgc ctacaaatca  56280
gataaacacg cttgatggca gctttttaat aggaacaccc ttcgtgcaag cgcgattttt  56340
gttggtagag atctgggtgc ttatgcttat tgcgcagcaa actaaaaagg acaccaaaaa  56400
aataatacaa tttttataa atcaatatga aatgcttatg aatagtcctt ggcccagtat  56460
ggaggccctt tttccctcaa gcagtaaaag atatttaggc aactatgtag accctaacgc  56520
gctcataaag tgggcacaac tcaaattaaa aagaataccg ccttttatc ctggaaagcc  56580
ggatgaagaa tcatgttaag ccgattaaaa aatcatgtta agctggttga aaaatcatgt  56640
taagctggtt gaaaaactct tggtgaaagc acggatgtaa tattaacatt ggccgctcgc  56700
atttcgtgtt gaaatacgat ggaagagcga cggctatcta ccatgccgat atcggcctgg  56760
acatcacagt tcatgcactt gtagatggga tgactcgcgt tatagatggc aggctcgcca  56820
cagtttctac agatgtagga gatgcagcca tccgagtcgt cgtgcgattt ttctatgatg  56880
gtttgcatgg cgccctgcgc cgtaagcacc caatgctcca tttctcccag acgaagacct  56940
ccgtgcgatc gtttgccgtc caacggctgg cctgtgaggg catccgtggg cccatagctt  57000
gcaacggcgt atcggtcatc cagcacaaat ttttgcaggc gctggtgata ggtcggtcct  57060
atgaagatgg ccgcatcaaa gtactcgccg gtctggccgt tgaacatttt ttggcatcca  57120
ttgaagcgta gaccttcttg cgccagtctt tctgaaagaa gctgcacatt aataggcagg  57180
aatgcggtgc cgtctgttac cacccccctgt agggcatttg ctagaccaac cgtggtttct  57240
atcatttgac cgttggtcat tcgggaggga tgtgagtggg ggtttacaat gaggtcgggc  57300
tgcaatccgt cctctgtgaa gggcatgtct gaagtgggca gggccagcgc cgcaatgccc  57360
ttgttcccgc tgcgagaact cattttgtcg cctatattga gatttctttc atagcgcagg  57420
cgcatgaggc caaagatctc gtcattaggc ccatggggac gcatcacagc atccacgacg  57480
gccggctcat cgaagccgta catgacagac cggtcgatgt atttgttgag ttcgtctttt  57540
tcgccccgta ttttggccac ttttcctata atgatgtcgc cctttttgac caccgttcct  57600
acgggcacga atccatctac aagcttttcg taattagcac caggcttaag atttttggtg  57660
```

-continued

```
attaaagggt cgggcttccc aaacgactct atatcgcttt ctaattctac tttttcttct  57720
cggtagaagg tgccggcaaa gccgcccctg tcaataaagg actgcgacac gatcacagag  57780
tcctcctgat tgtagccgcc gtagatcata taagccacaa tggtattaag cccgttgggt  57840
atgacatagt tatgtgctat ggtctttaca agcggcattt cattgtaaaa ctggaagaag  57900
cggttcatgt cgacacgata tggccagcta aagcaatacc agccccccgt ttgccggcct  57960
tggtttgttt cataggtaac acgcgcaggt tgggtacagt ttgcgtaggg ggacactagg  58020
gcggcaaggc ccaaaatagc ttggggcacg tccacgtgtg tgaaacgacg cgttacatca  58080
tgtttatgtt tgcgtagctc gatgatggag aaggcaacaa gacagttttc cgcctcctcg  58140
ggggtaatga actcacagat gccctgtgct acgagatctt caagtgtaag cgttccggct  58200
aaaatgtctt ttgccatttg aggcgtaaat cgcgtatttt gaatgaaagg gattttatgt  58260
ttttcccagt ctttatcgcc ttttttttctg gcctctgcgg ccttgtagca ggcttgattg  58320
tatttttcaa tattattatc tacaatgagt agggggcggg tcagcctacc gacgtccaac  58380
caaaattcta cttcgtctac catgctatcc cagtagatgg tggtatgggg atgcacaacc  58440
ttgccctcac ggcgaagcat tctataccgc tgagcaagct caaaggcatt ggtgcagcag  58500
ccgatccatt ctccgttgat aaatacgcgc gctaggccct ttcgtacaat gtccttgttg  58560
gaaacatcgg ctaactgttg aatggccgga tctgatagaa ggcgttgttt taacgaaagt  58620
acttctccgg cggtgcagac attggcagtg atggctaact gtttagacat gcctactttt  58680
tcaccagtat cggctgactg ggctacgcag atgtatccag gataggatgc gtgcacgcga  58740
cgcatcatgt cagccctttc tgtttgtttg gatgcgttgg tggtgttatg agtatttacc  58800
gtacgcaatg ctgaaatggt atttaataaa ttttttcttt ccaaactttg agtagatact  58860
ctgtttacaa tggggcgctg tcgcaccatg atggttttat ttcctgaaat gatagactgt  58920
tccatactgc gattaagatc ggaggcggta ttttttgata aagcggcaga aaatgcctcg  58980
ataatgtttc gctgagtaag ctcctcaaag gctgtttgtt taagaagttc tttgaaccca  59040
ttgatgatgg gtgctatcac ggaagtatta aaaatagcct taaaggcctt ggcgagtgag  59100
acccctgagc cgtgcacccg cttggtgcgg tagctatcac ggtccgtggg tggaaacaca  59160
ttcataatga caagaagtat tttatgaata agcaggccta aaaagcgcag ctttcgtaca  59220
cgtgtatctg cggtttggcc catgtgtggc agcaatattt tgtctaaaat agtaagttgt  59280
ctttcattta agtattgtac cgcattttca tcgcttttgt aagcagatgg gtttgagaca  59340
aatttggaaa ccttctcgga taaaaactgg ataatttttt ctcggttcag ctcgtgttgg  59400
accggttgaa atatggggtc taaaacatga atggattttt ccagaatttc tatcatgaag  59460
gtattcacaa gggagttgga ttctagatca aataccactt gctcaatgat gctgtcatcg  59520
cctgtcattc caaacatgcg aaagatgaga taccaaggta tgcgaagttt tgagaacttg  59580
gtgctattga tttcaatggt aatggcgccg gtggtcatgt agcgtataat aatttgagag  59640
ctattttcga aggcacctcc cggttgggag ataaactcgc cgcgaatgat ttcattattc  59700
ccttgttgca tggtatggta atggatgtga agcgtgttaa agcggatgtt ttctaagagg  59760
tctacgaccc attccccgcc tcgggctata aagtagccgc cgggttcatt agggtcttct  59820
cctatttctt tttttgcggt ttttgatagg tgatgagtgt ggcagcggtt gctgccccgc  59880
atgatgggaa atgtagatac ctgaaaagga ggaatacttg ctcgttttac ctcctgccga  59940
ccattgctgt agtgcgccgt taaaataacc tcggcggcta gattaaccgg gcccgaatag  60000
gaaaggccac acaggcgtgc cttattgggt agtaaattta tcttgtttcc ctgtgaatag  60060
```

-continued

```
tttcgatgtt gcgggcgttc aatgttcaca tctgtaaagt taaattggat ctgaactgat  60120
tcccgaagct tatctatttc agtatggtcg cgttggtctt tataagtaat atccacgtta  60180
aacatttgtt ttacaatttg cggaattcca ttgtccataa gatcgtcgaa gcttttgatg  60240
ttataccccta tcaatcctgt agagtttact gcagcggaga taaagctcag catatcagcc  60300
tctgtaagct cctcattatc cacggtttca atggggccgt aggttatttg cggccgcaag  60360
ggttccatga ttatgaagta ctacattaat attcagttat tctttaaaat aaatctttat  60420
ttataaatct tatttataat ataagaatgc cttatgcaag agacatcaca aagtttatta  60480
cggcaacgga accagaggtg ggtcttcccc tgttggcgct gcagcgctcc aaatccatca  60540
taggggttat tcttcttgta ataagtttgt tatttatttt cattggcatt attatattat  60600
cagtgagtag tggtcatacc acagcagcct ctatatttat cgtattgagt cttatcctag  60660
gtggcggtgg tttttttctt atttataaag ataattctta acccacataa aatttgaaaa  60720
aatatagagt aagaaaatgt ccaattacta ttattactat ggcgggggga gatatgattg  60780
gttaaaaaca gtagaaccca ctaatttttt aaaaatcggg ttgccttacc aggcacaccc  60840
attacatctt caacatcagg caactactcc cccatctatc ttagaaaaat ttaaacgagc  60900
agacattctt cttaatgagg tgaaggccga aatggaccca ctcatgttac aaccagaaac  60960
cgaaaaaaaa ctattccaga tattgagtag tattgatatg ttcaaaggtc tgcgaaaaaa  61020
agtagaattc acgtacaatg ctcaaattgt tacgaatgct tggcttaaaa tgtatgagct  61080
gctaaatacc atgaatttta ataatacatc tcaggcattt tgcaattgtg agcttccagg  61140
agggtttata agtgcaatta accattttaa ttatacaatg atgcattacc ctacttttaa  61200
ctgggtagct tcctcccttt accccagttc ggaaacagat gccctggaag atcactatgg  61260
tctttatcag tgcaatccgg ataactggtt gatgcaatct cctttactga aaaaaaatat  61320
agattataat aacggggacg taaccatcgc tagcaatgta aaaaacctag cgcttagagc  61380
cacacaaagg ctgacgccca tccatctata tacggctgat gggggtatta atgtaggaca  61440
tgactacaat aaacaggaag aattaaatct taagcttcac tttggtcaag cccttacggg  61500
tttgttgagt cttagcaaag gcggaaacat gatactcaaa cactatacct taaatcatgc  61560
atttactctt tctttaatat gtgtattttc tcactttttt gaggaactat acattaccaa  61620
acctacctcc tctcggccca caaactctga aacctatatt gtgggtaaaa acagattacg  61680
cttatttacc cccaaggaag aacaagtcct tctaaaacgg ctagaatttt ttaatgatac  61740
gcccctcgta gacctaagtc tttaccaaaa tttacttgaa agcgtttact ttgccgtaga  61800
aacaatacat ctaaaacaac aaatagaatt tctaaacttc ggaatgaaat gttatcgaca  61860
tttttataac aagattaaac tacttaacga ttatttagct ccgaaaaaaa agatttttca  61920
ggataggtgg cgtgtgctta ataagcttta tgttcttgaa aaaaagcata aacttaagct  61980
ttgtgcctcc tagggatctg ttgcttaatt taacagatgc aatcttaaca gatgtaaact  62040
aaaaagtgtg ttcatacaag gattgtattt atgaatattt attaacatat aaggttgtga  62100
tgtaacactg tataacctat ataactacac tatgaagcac ggcgtataat aatttatatt  62160
gaacacgatg ttgactcatt tatttgcaaa caaatatttg tttgcaagac gtttgcatgc  62220
atttactaat atgttgttga ctagtttatt tgcaaactag atgtttgatt gcaaactaga  62280
tgtttgcacg tatttatttg aactaatata cactccttgt tttatttgtt atatacacag  62340
catacataag tgtatattgt ttacacttat gtttataact cgacgtaata acattttaca  62400
```

-continued

```
cgcttttttt ttgcaaatct taataatatt gtatgataaa tcaaacaatg tcttatatat  62460
gtggtttatt attttaggcg ccgcaagatg tactccattc tcattgcatg cttggtgtta  62520
ttactctgtc tagttatata tgtcggtcat cgtgccgatc atgcacgaaa atatttagaa  62580
ggaatgtggc atggagatcc ggtttttcta aaacagtcgg ggctacaatc cttttatctc  62640
tacatacaac ctgaccatac atgttttttt agcattgtga ataaaaatgg tgaaaagctg  62700
atggaaacca aaataccttg tacgataaca aataaaatat atatgttttt taaacctatt  62760
tttgaatttc atgttgtgat ggaagacata catagctact tccctaagca gtttaacttt  62820
ctgttagata gtacagaagg taaacttatt ttagaaaaca atcacgttat ttatgctgta  62880
ttgtataagg ataatttcgc caccgcacta ggaaaaacgg ttgaaaaata tataacacaa  62940
aattaatcat gttttctaac aaaaagtaca tcggtcttat caataagaag gagggtttga  63000
aaaaaaaaat agatgattat agtatattaa taattggaat attaattgga actaacatct  63060
taagccttat tataaatata ataggagaga ttaataaacc aatatgttac caaaatgatg  63120
ataagatatt ttattgccct aaagattggg ttggatataa taatgtttgt tattattttg  63180
gcaatgaaga aaaaaattat aataatgcaa gtaattattg taagcaatta aatagtacgc  63240
ttactaataa taatactatt ttagtaaatc ttactaaaac attaaatctt actaaaacat  63300
ataatcacga atctaattat tgggttaatt attctttaat taaaaatgag tcagtactat  63360
tacgtgatag tggatattac aaaaaacaaa aacatgtaag tttattatat atttgtagta  63420
aataatattt ttaattactt aaaattttta tatataagtt tttgatacta tattataaaa  63480
catatgttca taaaatgata atacttattt ttttaatatt ttctaacata gttttaagta  63540
ttgattattg ggttagtttt aataaaaacaa taattttaga tagtaatatt actaatgata  63600
ataatgatat aaatggagta tcatggaatt tttttaataa ttcttttaat acactagcta  63660
catgtggaaa agcaggtaac ttttgtgaat gttctaatta tagtacatca atatataata  63720
taacaaataa ttgtagctta actattttc ctcataatga tgtatttgat acaacatatc  63780
aagtagtatg gaatcaaata attaattata caataaaatt attaacacct gctactcccc  63840
caaatatcac atataattgt actaattttt taataacatg taaaaaaaat aatggaacaa  63900
acactaatat atatttaaat ataaatgata cttttgttaa atatactaat gaaagtatac  63960
ttgaatataa ctggaataat agtaacatta acaattttac agctacatgt ataattaata  64020
atacaattag tacatctaat gaaacaacac ttataaattg tacttattta acattgtcat  64080
ctaactattt ttatactttt tttaaattat attatattcc attaagcatc ataattggga  64140
taacaataag tattcttctt atatccatca taacttttt atctttacga aaaagaaaaa  64200
aacatgttga agaaatagaa agtccaccac ctgaatctaa tgaagaagaa caatgtcagc  64260
atgatgacac cacttccata catgaaccat ctcccagaga accattactt cctaagcctt  64320
acagtcgtta tcagtataat acacctattt actacatgcg tccctcaaca caaccactca  64380
acccatttcc cttacctaaa ccgtgtcctc cacccaaacc atgtccgcca cccaaaccat  64440
gtcctccacc taaaccatgt ccttcagctg aatcctattc tccacccaaa ccactaccta  64500
gtatcccgct actacccaat atcccgccat tatctaccca aaatatttcg cttattcacg  64560
tagatagaat tatttaatat gtactatata ttaattattt aacctttcaa gctggtcttc  64620
atttaaattt aaaatccact aataaaatgt attttctagt agcagatcat cgagaacatc  64680
atgtgattcc ttttcttaaa accgatttcc atcacatgca tcaaaatcct atacaaaaaa  64740
atcaagctct cctagaaatc aaacagcttt ttactggaga ttatctcatc tgcaaaagcc  64800
```

cttctaccat tctggcctgt attgaacgaa aaacctacaa agactttgcg gcttctttga 64860
aagatggacg ttataaaaat cgccaaaaaa tgctgtcgct gcgagaacaa accaactgtc 64920
aactttattt ttttgtagaa ggcccggcat ttcctaaccc tcaaaaaaaa attaatcacg 64980
ttgcctatgc aagcattatt actgctatga cgcatcttat ggttagagat catatttttg 65040
tcattcaaac gaaaaatgag gcccacagtt cccaaaagct tgtgcagctt ttttatgcct 65100
tttctaagga aatggtgtgc gtcgttccca cctccctcac ccccacggat gaagagctat 65160
gcatcaagct atggtcttct ctttctggta tttcaggcgt gataggtaaa atcttggcaa 65220
acacttgttc cgtagctcat ttggttcatg gaaagctttc atcgcagaat attgatcagt 65280
taaaaactcc ctccaaccga ccattcccca aaaaagtaaa acgtatgctt ataagcatta 65340
gcaaaggaaa taaggagtta gaaataaaat tgctctcggg ggttcccaat atcgggaaaa 65400
aattagctgc cgaaatttta aaagatcatg cgcttctttt ttttctaaat cagcccgtag 65460
aatgcttggc aaatatacaa atcgttcaaa aaacccgtac gattaagttg ggaatgaagc 65520
gagccgaagc gattcattat tttttaaact ggtgtggctc tgcccatgta accgatgata 65580
gccaaaatat cacagaggcg tcgcggtcca caatgcaggt cgcgacgcag tccgccgcaa 65640
tacagcccgc tgcaacgcag ccattgcacg aagtatcaga tgatgcatca tcagatgctt 65700
catcacccgt agggtatcaa acattatcta aagaaatgtt attgaacaca gcctgatgtt 65760
aataattcac tacatctaaa gaaatgttaa cctcgatact aaaaagtcat tgaacacaac 65820
tactggggcg ctaagttgtc caacacatct aaagaaatgt caacatcctc gatgctaaaa 65880
gggtcatcga gccggtcaat aatgtcttcc ccaaaaagtc cgggagaact gtaggccgag 65940
atgtcgtcca tggagctatc ttccccagag cacacaaagt cctctccaaa aatcataaag 66000
ttaaatgcac cgggcttact taacagcttt tcgctttgaa taatagtgtt gagttctgtc 66060
agcgcaaact ctctcacaat attcacaacc caggagggct ctttaatttc atacagcgtt 66120
aagaaactta tacataaaaa ttctatagag taaagcaagg cgctggcagg atctgttacc 66180
cgtaggtgtt taaatgtagt gtgatattca ttcacaacgt taggcagcac cttttccaaa 66240
tcctcctttt cctcgtacga caggtgcttt acaagccttt caacatgtat aggaggcttg 66300
ttaaatgtac taacgtgccg caaacagtta taattatata agaaaatacg tacggcagag 66360
tcgaccgcca tgagccttgg atcatccatt gaggtaggtg gtggcggggc accctggcct 66420
tccctgatgt ctgcgtagga gcgcccctcc atggccccta tggcctctat cacagcagga 66480
ctgatatcca aaatcttggc cgtcttgatt atttttccgt aatcgaaagt ccatggctcc 66540
tgtggaggct tgggttgtgt ttcggtggag ggcgtggtca tatctttctt tatttgaata 66600
gaacggatcg acatcttttc cttatcgtac tggtctttat aattattata atagtcatga 66660
actaattcgg gttgagaaag atgatcgtat ataatatagg taaaaagtcc gcacttgaca 66720 catttttat cctggaagtc gtgtaatcct cccttggggc agcgtgactc gtagaaggca 66780
taaaaggtgt taaattctaa gctcgccttt agggctgttt ggaccttttt tatgtttaat 66840
tgccccacct catgttgtag cacgtggcat acagaacagc gtagatcggc aagtgcataa 66900
tggttgtcaa ttttttttat gacgtctttg cgtgttactt caatctcggc gggtttctgc 66960
gaactgtcta cggccttgta aacgtaaatg gtccacttat gaggaagccc cctttcatcg 67020
tatagggttg aaatgggaag ccttttatac tcaaacagcc gagtccgttg gtcggctctt 67080
cctgtgttag gatcaaatat gttataaaat ccttgctgag caagcagggc cttttgctcg 67140

-continued

```
ccataagcat tttcgtacgt tttgaattct gcaagttcgg agttaaaatt aggtgcattt  67200
tgtaaatact taagaaataa ttcataggct ctaaggtaaa tgagagttga ggtttttttcc  67260
tcatcccgtc ctccccacca cacccgcagg ctttcttctt gaaaatagat gtcattcaga  67320
cgcgtcaact gcgtaaaatc aggccgatat ttagaggtat aaattttatc ataaaattct  67380
ttttgcgata atagctcggc cggggtacgt cctatcacgg ttttaaactc atattcagcc  67440
tccttgggag tccgtggttt gtgcataggg atgctgccgt caatacgggc cactgtggca  67500
gcataatcat acatggggtc cagcagaatc tctgtcaaaa gtaccttggt gtcgtcctgc  67560
acgctaagcc cttgtagccc attttggtgg ataatttttt tgaaagcctc ccgaaaatta  67620
ttagcaatcc actgatccgt aatctcagat agctgattta ttataccgct atattgctgc  67680
atcattttct ccaaaagaaa ggtcacgtat gcattcaaag agctatccgc cttcattcca  67740
tgaatggtaa tcgtaagaaa ttctttattt ttttgcgagc tataaatgag attcaaaata  67800
taggcataga tgtagatcac agcatacagc tgcgttaaag gatcgtaatc ctcttccttt  67860
ttaatatttt cgatgctata cacgagcggc aggcagacat ttacggctat attggcaaac  67920
tgtttcacgt ctacaagctt tccaaagtgg ataaacgtgc aggccttcat ggtttcctgc  67980
caaataaaaa cacggagctt actattaaga tcgccgatga tgcccacatc tgccgtacga  68040
tcctcttgaa taaaatgggc cagctcttcg ccacaaattt tgcaaaagta ggagtaaata  68100
agcccctggt tgttttcttt ctccttgttt attcctgaaa atttcattag cttggttcgc  68160
atggtgtcgt aggacgcttc tgccgcttga agctgtataa gcatgtccac atggggacaa  68220
agcagcttaa acccgcaggc tttgcataga ttccaattgg tggtattgtt tttttccttg  68280
tagagtacac gaatactttc taatactttt aataactccg cgtattgaag acccgaacgc  68340
aactgtttta ccagcttgag atgagcacat gcattttttt cttggagttc ccactgtttt  68400
ttaatgttta ggtattctgt tgtaataagt tctgcctcct gtttcccaca ggctttaatg  68460
acttcttgaa ggatgctgtt agggtcatcc actttaccct ccattgtaag aatttcacgt  68520
atagcatccg actgcaccct acctattttt tcttccataa ttttaaaata ctgtctcgcc  68580
tgggtaatga cctctgtgag cttcatgtcc acctgctgca gaatcatttg ctccttttca  68640
cgctgttcag catgttgtaa aaacttttgt tctacagggt tccaaagcac ctccaaatag  68700
cctgctctat ataggtcata aagcaagggc atgtatcccg atgtaaaaac cggggacacc  68760
gagtacatcg tagacaactc ttttaaaaaa aatatcacgc gcttaatgtt ctcctccggt  68820
tcaatctcct cggtttcaac gatattagat atatgactgc cctgatcctc acggtctagc  68880
tttcggtgta ccatctcctc tgctagccga ttaatgagcc agctatgccc gccgctccgc  68940
aaaaacttat aaagttcgat atactggtgc gtaaactgga tgatgttttc cttggtggtt  69000
acgacaaccc cttctccgtt ttttttccag gtttcttgat ccacgcattt cataaatact  69060
cgaataaaat tggtcaaatt ggctcctgag gcgacgtagc ccaaggtttc aggcgagaag  69120
gagcctatct cagccatacg cataaaacac tgcggggaaa aagtttttag ccgcaactta  69180
agtccataga tttcaatggg ggcttctgcg ggaacggcca ggtgcgtccc attaattaaa  69240
aaaatttctt tgcgtgtgct agggcgaaca cgtaattcct tttttttttc actcacgatg  69300
gggaccacat cggggtctac cagcagttga cgtatgtagg cctctatggg catggataga  69360
tcgggcagct ttgactgctc ggcgcgaaca tggttcacaa aatcttttag agtgaaaaga  69420
aagtctatta aacgtatgtt ttttatatca ttagaccctt taagggtaga gtagatttca  69480
tccactagtg cctcgatttc ctcattattg agcgataaga tatctgtgcc acggtggact  69540
```

```
atttgcgcga tcgtaattac ttcctccatt agatagaaac tgaatattat atttaaaata  69600
aatacaaaat gtcaaatgaa agttttcccg aaacgttgga aaacttactt tcaatgttac  69660
agaccaaaca gcaaaacgca attcagtcag aggtgattga atggctgcac agcttttgtg  69720
aaacctttca cttaaaaata cactgccata aacagtttat tcctagcggg gaaaaaaaac  69780
gagctaaaat acccgctcaa gaaacacagg gaaacacgca gccctcccac catgtgtacc  69840
gggttgttct ctccagagca cagccagtca aagcacagga atctctgcta acaaccatgt  69900
gcaacggact ggtgctagat gcaaacacat ggacatgcct agccattcct ccgcctgcgc  69960
cctttcaaca ggcgacccgc caggtccaac acttttaccg taacaatttc tacgaagtgg  70020
ttcccatcca ggatggcacc cttctcacaa tctaccactg ggatgaccct gaatatggcc  70080
cctcctggtg cctagcaagt acccacggat atgatgtgag taactactgt tggataggcg  70140
acaaaacctt cgccgagctt gtatacgaat tgctgcagca gcactctacc tgcgacgtca  70200
ccctggaaaa aaataaaacg cggggaacgc gtcttttctt tgataactta aatcccgatt  70260
actgctatac gattggaatc cggcaccata atttacagcc gctcatctat gaccctcaaa  70320
atatttgggc gattcaatct acaaacctaa aaacgcttaa aacggtatat ccagaatact  70380
acggctatat aggcattcca ggaattcaga gtcaagttcc tgagcttccc cagtatgatt  70440
taccttatct aatacgatct tataaaactg ctatgaatca agccaaaaat gctataaaaa  70500
atggcaaaaa agacaaggga tactttaatt atggctattt actcatttcg cgagcgcctg  70560
ccattactaa aagtacttct aatgttttgt taaaatcgcc tctgctggta tttttacaaa  70620
aaagtgtgta ccagaaaaaa cacaatatct ctaacagcca gcgactagaa tttattatac  70680
tgcaaaacta cttgatgcag cattttcgag atcatttcat tgctctattt ccgcagtaca  70740
tatcctatta tacgaaatac caaaacatgt tgaatatgat tatccatagt attgcaacta  70800
aagataaaga tcatcccttt gcaggagccg tggtaaaaaa agtgttggaa gatattgaaa  70860
acgccgaaaa cattattgat catacaacca ttcaaaacta tgcccatcaa agcaagtacg  70920
ccatgcttta cttgtcaatt atttcccatt tttaatctaa tacggccaaa gccgcgggtt  70980
ttttaataaa ctaacattta aaaaaactgt tttattaaaa attataatac ttttattata  71040
tatggaacat ccatctacaa actatactcc cgaacagcaa cacgaaaaat taaaacatta  71100
tgttttaatc cctaaacacc tttggtctta tattaaatac ggaacgcatg tccggtacta  71160
caccacacaa aatgttttcc gagtcggtgg ctttgtgctt caaaatccct acgaagccgt  71220
tataaaaaat gaggtaaaaa cagcaataag actgcaaaat agttttaaca caaaagcgaa  71280
agggcatgta acgtgggccg tcccatatga taatattagc aagctatatg ccaaaccaga  71340
tgcaattatg cttaccatac aagaaaatgt tgaaaaagct cttcatgctt taaaccaaaa  71400
cgtactgacg ctcgcatcaa aaatacgtta aatataattt ttgtagagga taaaaagcta  71460
ttttagctaa aaaataattc atatacgttt atgcagagga agaacggtgg ctttcaaatt  71520
cagattgcat ccacgtagac cgtagcgttt tttttgcttc tggtttatat cgtaaaccgt  71580
aataaacatc atcatttgta tccgttggat ctttttccca ctccggataa aaaatcggtt  71640
ttcttttttt ttggtcgttt tttgcagtaa gctgtaaatt aagggaatat agcttatcga  71700
aaagttgttc ctgatccata taaatagcag catatattaa aaaaaaataa aaaaagacgc  71760
ttcaacgagt cagtaccact gcttgccaac gatttacgtt ggttggtgca ttatggtgat  71820
atagtaatga gtgcctgcac aagtgcttgc acaagtgcct gcacaagtgc ttgcacaagt  71880
```

gcttgcacaa gtgcttacac aagtgcttgc acaagtgcct gtacacatta ctgcatcgcc 71940
aaagcacctg caatgcctac ttcctcaaca gagtacgata actaaatgct tttaagcacc 72000
gcttgcgtcg atgtgtcctt cggggcaatc gggttcaatt ggatccaata ttattagtca 72060
taattaccta atacttattc aattttatct tttttacctt gtaagattta aacagcgttt 72120
tagcttgttt aaagcaacgt ttaaaacaag ctaaaatgct gtttaaaaca acgttttaaa 72180
caagttaaaa caaataagct tataaatata ccatgacaaa attagcccaa tggatgtttg 72240
agcagtatgt caaagattta aacctaaaaa atcgagggtc cccctcgttc cgcaaatggc 72300
tcacattgca accctcactg ctgcgctatt cgggtgtgat gcgtgctaac gcctttgaca 72360
tcctaaaata tggctatcct atgcagcagt caggttatac ggttgctacg cttgaaatcc 72420
actttaaaaa tattaggtct tcctttgcca acatttactg gaaccgtgat agcgaggagc 72480
ctgagtacgt ctgctgttgt gccacctatc aatcgcacga tggcgaatac cggtatcgat 72540
ttgtttggta ccaacccttc atagaggctt ataatgccat agaggcggcc ctggatcccc 72600
tggaaaccat tatcctgaac ctcattgcgg cacgagatct agacttcgtt gttcacatat 72660
ttccttataa taagggccat gaagactatt tggcctccac gcaacttatt ctcaaaatct 72720
ttattgcgac gcttttaatg gacattttaa gaattaaaga caacacgttg gacgttcact 72780
taaattccga ctatattatt gtgatggagc ggctttggcc tcacataaag gatgccatag 72840
aacacttttt tgaagcccat aaggacttac tagggtactt aattgccttt cgcaatgggg 72900
ggaactttgc aggaagtctt agaccctcct gtgggcaaaa gattgttccc ctaacgattc 72960
gagaggtcct acaaatgaat gatattaatt tagccgtatg gcgggaggtg tttattatgc 73020
aggaatgttc cgacttagtc atcaatggga tagcgccctg tttcccccatt tttaacacgt 73080
ggacgtattt gcaaggtatt aaccagattt tttttgaaaa cacgtctttg caggagaaat 73140
ttaaaaaaga ttttattgcc cgagagcttt ccaaagaaat tatcaagggc caaaaaaacgt 73200
tgaatgacaa ggagtttaaa aagttaagcc tacatcaaat ccagtacatg gaatcctttc 73260
tacttatgtc ggatgttgcc attatgatta ccacagagta tgttggctat acccttcaat 73320
ccctgccggg tattatttcg cgatccagct atttatcccc catcgtgaaa aacattttga 73380
tggacgaaga ctcttttatg tccctactat ttgacctatg ctatggcgcc tacgtgttgc 73440
ataaaaaaga aaatgtgatt cacgcggatt tgcacctgaa taacatgacc tactaccatt 73500
tcaacccaac cagttttaca gatcgcaaca aaccaggaaa atacacctta aaggtcaaga 73560
atcctgtgat tgcctttata accgggccca aagtcgaaac cgaaacgtac gtgttcaagc 73620
acatagatgg gttcggctgc atcattgact ttagcagagc cattatgggg ccaaaccatg 73680
caatcaagct tgagcggcag tacggcctcg cttttgtaaa caccttttac cgcaatcaaa 73740
gtgagcatat tttaaaggta ttacggtact attttcctga aatgctaacc aatcgcgaaa 73800
acgaaataca gggggtgatt ttatcaaact ttaatttctt tttcaatagc attactgcca 73860
ttgattttta cgccattgct agaaacctac gtagtatgct ttctttggac tatttacaca 73920
cctctgaggt gaaacgaaac gtagaaattt cgcaaacatt tttggataca tgtcaatttt 73980
tggaggaaaa ggccgtggaa tttttgttta aaaatcttca tactgtctta tctggcaagc 74040
cggtcgaaaa aacggccggg gatgtgcttt tacccatcgt atttaaaaaa tttttatacc 74100
caaatattcc taaaaatata ttacggtctt ttaccgtaat agatgtatac aattataata 74160
atataaagcg ttattctggg aaagctatac aaacgtttcc accctgggct caaaccaaag 74220
aaatcttgac gcacgccgag ggtcgtacat ttgaagatat ttttcctaga ggagaattag 74280
tttttaaaaa ggcttacgca gaaaacaacc atttggacaa aattttacag cgtattcgtg 74340
agcagcttgc taatgaaaat ttgtaaggct tgcagttctt gtatggtcag aacctatgtc 74400
gatggaaaca ttatttttcg ctgcagctgc ggcgaaagcg ttcaagggga tagtcagaac 74460
ttgctcgtct ctagcaaggt gtaccacacc ggggaaatgg aagataagta caagattttt 74520
attaaaaatg caccctttga ccccacgaat tgccaaataa aaaaggattg cccaaattgt 74580
catttagact atttgacaca aatctgtatt ggaagccaaa aaatcattat attggtgtgc 74640
cgctgtggct atatgagcaa cagaggataa accatatcat cccaccgaat tatgacattc 74700
ctttaaaacc gtccgcctaa atagttttca cacctttggt ggcagactat tttataaaaa 74760
gtaatgttgg ttcatgaaga taaagtgtgc caaagaaact tttataaaca aatgattaat 74820
gtaggtgcta gtcgtgtgta cttaaacagg gtattctata gccaagtatt ttctatagcc 74880
aagtattttc tatagccagt attagtcaag tatttagatg tcagggtatt tttatagcca 74940
gtatttttct atatgtacaa actattccag taaacatatg tgtgttcttt attgagcagc 75000
atcatggcat taacaagttt attaaactgc tctaatgggc attaaatgac aactcggtgc 75060
ttagcaaaag tgcctatacc ttttaacaat tagggccggg aggcattccc agctttttc 75120
tataatcagc catacagtac ccctgagcct catacacggg aataaggtcc ttccattcct 75180
tgttgggatc ggcgggccag ctctcaaatg aggtgtgaat gtaagggtcc tgttcttttt 75240
ccttaatgaa gcgtttaatc tccatttgat gttgtttact tttttgtttg cggcggagcg 75300
tgttccgcac caatacgtaa aaaataccaa gaatcacaca taaaagaatt attaaaaaaa 75360
atatcatcat cgcggggttt aaaaaacgat cccatgcaac aggaatcgtt cttaaaacct 75420
tgtctggcag ggctgtaaac atgaagtctc ctcctataat cggggtggga ctgtagccta 75480
acagttcaag gtcctgtcgt tctagatact tattggcgaa ctgcccaccc tttgccccccg 75540
ttttttttatt aatcaagcag cgctgcattt tccaccattc taaatcttca ggagaaagct 75600
caatgccata tatcaacttt aacgttattg catctttttc aatatcctta tcaatttggc 75660
tgagcttttg agctttaagc gggtctagtg tgtacttcca tttaaactta gtgtcctgta 75720
gtttggctac atgaaatacg gaacatttcg gcggggcctt tgtgacgccc ttacactgcg 75780
gaagtttatc attaggacag gcgcatagat gagactgcgc cacagcatcg cgaactacat 75840
cgcagacgga gtacattttc ctcctatgtt aaacaataaa ttttttttcat agctgaaatt 75900
tgtgggccta tcttttccct tgcccggata ataattataa gggagtgttg aaacatctgg 75960
gagagaattg cttaaaaaat gggtttttgg gaggggtaac tgcgactgtt gtacgtcgtt 76020
ggccagggag attctatatg ccgggctaaa ggtgcaacgt tcctgtgaac aacttagtac 76080
gcgcgttgtt aatacaaatg gactggtatt agcaaacctc gtaaactctt ccggacttgt 76140
ttgtttttgt atgatgttta gcagggagtc tgccttttcg agaatccaaa gcgtcgcatt 76200
gtagtaaaat aaaaatagcg acttatcggc aggcgttgca aaagcgccgt atagaaaata 76260
aagcagtaag tactggggag acaccacaat aaggttatct tgaatgatag atatcgctag 76320
ctctttaaac atagtgctaa aaaaatgtat gtcgttcgtc ttgaatatag ggggactata 76380
gtccatgtag ggctcacata tctcagtcag gtgaaggccc atttctttta tgacttcttc 76440
cgggttgtac gtcgctaaca ccagcgcggg ataggctttg ggcatatcca cggtaagtgt 76500
tatgttttta tcattcttat ggtaggagta agatggttgt ggaaattctg ttttccactc 76560
cgggactttg caggtaattc tcagctcatt tagagtctgg tacaggaggg cgtatgccgc 76620

-continued

```
aaagccgtgt atggccactt gtttaaaggg aattgaaaac gttttacttt cgtatgtcga  76680
cttcacagga acaacgggaa tggggtaata tttttctatg aggttatacc gctgcaaatc  76740
ctttttaaac ctgctaaaaa catcttccct tggtgggtta tcaaaaggaa agcaaaatgc  76800
taggtgtagc ccggcccgct ggtaatcggg gtgaatgatt ttaaggtttt tatacgttaa  76860
tgtgggtatg gtgttaaaga tattgggggg catatatgaa agatcagcaa cccacacaaa  76920
gtccgtgcgc acccgcatgg tctgcacatg gatggcgcgc accgtgccca cctgcttgaa  76980
gccctttttca tacaaaatgt cagcaagttc gtaggcgtcc tcaacgtggt tgggggaaaa  77040
catatcaaag tcgggtcttt ctccctcggg ataaattgag ctgcctttaa gatgcagggc  77100
ataatcaatg gcaatccccc cgtacaaaat aagctttttc tttatgataa attcgcggac  77160
cacctccaaa gccgcctcaa tctccacggc atttgcctca cgtttttgag caatgagccg  77220
gtacttagaa acattaaaat cagtctttag taaagacgtc ataaatagtg tttaatatat  77280
attaaaggtt tgaataaaat actaaatagt aaaaatggat gccctattaa aggaaataga  77340
aaagttatcg cagccatcct tgcagaaaga aaacaatgat gtatgcgatc tctgttttat  77400
gcaaatgaaa aaaatttcta actatcagct tttatgcgaa gagtgcggtc agctgaagga  77460
ctggtttgaa cctgaatata atgaaaaatt cacggtatat tctcgtctaa agatcgtggg  77520
tgccaatagt tcctatcacc agcgcgattt ggacaaggcc aactcaagtg actatagctc  77580
cttgcaattt catcacattt tagaggagct caaatcccta aatgttaagt atatggatgc  77640
ggggcaaaag ccctttccta ttcaggtgtt aaaagaaact gctcacagtt ataaccaagt  77700
acaacaacat cgggtcatac gcagcattac aaagcttcag atcttagcca gtattctacg  77760
tagcatttgt ttaaaattaa acattgcttg tacggtggca gacgccgcga ggtttactca  77820
acttaatacc aaagggatct caaggggcat ggatcttctg cgctccctat ttgtagacaa  77880
taaaattact ttaaacgttg atttaaaccc tatagacagc tttattaata gtacctacag  77940
tgccttacaa attaaacaaa tccaccaaga actgcaggag gaaaatgttt ataatttaaa  78000
agaaattgtt aagagcttta tattatacgc ggatgagaag aacatcggcg tcgatcttaa  78060
caggagaacc gttgtgattg ctacgatgta taatgtttta cgccgtgcct actaccccat  78120
agaaattgat acggtggtgt atcaatgtaa aatacgaaaa aatacaatta cacgtgctct  78180
taaaatgtat gaggattact actcccactt taagtctctt tatgagcagt atcatttaaa  78240
cgcggcaaaa aaattaattt aaactaaacg tttaaactaa atgtttaaac taaacgttaa  78300
aactaaacat ttcgactaaa gtttaaaacc tagtctaaca gcgggatgcc catttccctg  78360
gggttccata tttcaacaat tttttgacct tcgggtgtta ccttgatgca gcgcatgacg  78420
agcagtggaa ttttcctatt aaagagttct tgcttagcta tatcaatagg actgctatat  78480
tttttttaa gcattgtaga tccattaatt gccaattgtt gcgctctaac ggcgaccaac  78540
cttgtggcct caaaggtggt taaaacgttg gaggtaatgc gctcgttatc gggtataatg  78600
accaatgttt gcgacgaggc ctgcacaaag ccctcgcaga tggacggaga ctccacgatc  78660
tcgtccttgt cctcggactc ctcctcactg tcgacgaggt tctcctcttc cgtttccaca  78720
tattcctcca cgaggtcatc catgataaga tcctcgttgt cattatcagc catattacac  78780
tgttatcaaa tgtactgttt aatacgcaaa tggatttact acgttttaat tgtatgtctt  78840
catgtgcagg ctctagtgga aagtaatttt ctcacaattt ttggcaccgt tacacttgtg  78900
cccacaaaaa cccgcgattt ttttatttta tattactttt ggaagtacga gtttaaccag  78960
tcgctttcaa accttatgcg tctatctcgc caaaaaacgc tcacagcggt gttggatatt  79020
```

-continued acctttaaaa aaataacatt aatttttacc acagagggcg tattgcgtat ggattctacg 79080
aataagccag gcgtgccact cgatatagac ccccagttca ttgaccttga tagtatttta 79140
atggaactgg atcattagga cctctcccgc ccatttaaat ttttagtttc tacaataata 79200
aaatgcgcga ggaatcatgg gaagaccacg ataccattca gctcaccgct cagcgcaaat 79260
acctcgccga ggtgcaagct ctagagaccc ttttgactcg agagctttca gtctttctca 79320
cagagccagg cagcaaaaaa acaaatatta ttaatagaat cacaggaaaa acctacgcac 79380
ttcccagcac agagctacta agactctacg agcatctcga gcaatgtcgc aagcaaggcg 79440
ccctcatgta ttttttggaa agacagggga cctactcggg tctcatgttg gactatgacc 79500
ttaaactcaa tacaaatgct gttcccccgc tggaaccccc cgcgctatca cggctttgcc 79560
atcgaatatt tgtgcatata aaaaacagca gtgtgctgcc tgagggcagc cataaaatcc 79620
acttcttttt tacattaaaa cctgaagtgg ttcagggcaa atatgggttc catgtgctca 79680
ttcctggtct caagctggcg gcttctacca aaaaaagcat tataggatcc ctacagcacg 79740
atgccaccgt acaaaaaatt ctacacgagc agggcgttac aaatcctgag tcctgtctgg 79800
acccccactc cgcctccgtt ccctcgctcc tctacggctc ctccaaacta aaccacaagc 79860
cctaccaact gaaaaccggc tttgagttag tctttgatag ctctgatccc gactacattc 79920
ccattcatca aataaaaaat ttagaatctt ataatttagt ttctgagttg agccttacga 79980
atgaacaggg aagccttgta agacctgtct attgcgcggc agacattgcc gctgagaagg 80040
aggaagagat cccgaccgag gatcactcgc tctccatatt aatgctacat gatcccgaag 80100
cccggtattt acataaaatt ttaaatctgc ttcctccgga gtattatgta gagtaccccc 80160
tatggagcaa cgtcgtattc gctttggcca atacatccgc taactatcgg cccctcgccg 80220
aatggttttc gcaaaaatgc cctgaaaaat ggaatacggg aggaaaagag aaactagaaa 80280
aactttggaa tgatgcctcg caccacactg aaaagaaaat caccaagcgg tccattatgt 80340
actgggccca caaacatgcc ccccagcaat acaaagaaat tgtagaacaa ggctactttt 80400
ccattctcgc tgaatatgtg tatagctata acggcatgct tgagcactac atgatcgcca 80460
aagtcatcta tgctatgatg ggcaacaagt ttgtagtgga cgtggattca aacgggaagt 80520
acgtttggtt cgaatttgtg ctaccgggcc agccaatgaa tcagggagaa atatggaagt 80580
ggcgcaagga ggtaaacccg gatgagctgc acatctatat ttccgaaaac ttttcaaggg 80640
tgatggaccg aatcacggag cacatcaaat accacctcag tcaaccccat gaaagcaata 80700
ttttaaatta ttataaaaaa ctattaaaag cctttgaacg ctctaaaagt aaaatcttta 80760
atgacagctt taaaaaggga gttatcaggc aagctgagtt tttatttcgc caaagaagct 80820
ttattcaaac tctggatacc aatccccacc tactgggggt tggcaacggg gttctctcca 80880
ttgagaccat cccggctaag ctcattaatc attttcacga gcatcccatt catcagtaca 80940
cacacatatg ttatgtgccc tttaatcccg aaaacccctg gacaaaacta ttattgaatg 81000
cactccaaga catcatccca gaacttgatg ctaggctgtg gatcatgttc tacctaagca 81060
cggccatatt tcgcggcctg aaggaggctc tgatgctttt gtggcttgga ggcggctgca 81120
atggaaaaac ttttctaatg cgacttgtgg ccatggtatt gggcgatcac tatgcctcca 81180
agctcaacat cagccttctt acaagctgca gagaaaccgc ggaaaaaccc aacagtgcct 81240
ttatgcggct taaggggcgg ggatatgggt actttgagga aaccaacaaa agcgaggttc 81300
taaatacgtc gcggctgaag gaaatggtaa atccgggcga tgtcaccgct cgagagctta 81360

```
atcaaaaaca ggaaagcttt cagatgacgg ccaccatggt cgccgcgtcc aactataact  81420
tcatcattga cacgacggac cacggcacat ggagaagact gcggcattat cggtcaaagg  81480
tgaaattctg ccataacccc gaccccagta acccctacga gaaaaaggaa gatcctcgct  81540
ttattcacga gtacatcatg gatccagact gccaaaacgc attcttcagc atactcgtct  81600
atttttggga gaagctacag aaggaataca acgggcagat taaaaaagtg ttttgtccca  81660
ccattgagag cgaaacggag gcgtacagaa agtcacaaga tacgctacat aggtttatca  81720
cagaaagagt cgtggagtcg ccctccgcag aaactgtgta caacctatcc gaggtcgtga  81780
cggcctacgc ggaatggtac aacaccaaca ttaacgtaaa gcgccatatt gccctcgagc  81840
tatcccagga gttagaaaac tctgtgctag aaaaatacct tcagtggtct cccaacaaaa  81900
cgcgaattct aaagggttgc cgtattttgc ataaatttga aacgctgcag cccggcgaat  81960
cctacattgg ggtgtccacg gccggcacac tcctaaacac acccatatgc gagccaaaaa  82020
ataaatggtg ggaatggtcc cctaatccct ctgcccctcc tgagaaagaa gcgtctgcac  82080
caactcctta gggaatatcc ttagaagcat gtctttcggc agagccatta ccggtagcaa  82140
aaaagcaaca ttgagtatat tatatgcctt agcctgctca taagcgtcct tttttttcat  82200
ggtattttat gtttttaaat atttttaatt atttttttaaa tacgatgaac agttcgtgct  82260
ccgaaggctg tttactaaaa atcggtgtga atccgcattc tttaaatatg gtttcccatt  82320
cggggatggt atggaaatcc atgtctctac gaatagtatg gtgcccaagt gcgtcctgca  82380
ggctgtgaag ccagaaggcc tcctgacctt gatgaaggtc gtacatgata agaaaaccat  82440
caggtttcaa cagatggtaa agcttgttaa aatcgtttat cgtaagatga tgcgccgcca  82500
taggtaaccc tatgagctcc acagagtttt catgctggac atcgtccata tcggtataaa  82560
acgtttcaca gtaaatgaga cgcttaaacg agtatcgatg acaaacattt atttccaagt  82620
aggtttgcac tacgttttta ggtatatcgg gaatcatgtt gattaaggtt gtttcgggaa  82680
acttaatcat ctgactaggc ttcattttca actctttaaa ggatttcccg gagaagtgaa  82740
aatgggtctt tacgtattta tgtaaaaata cctgaatggg cagagggggc tcctcctctt  82800
cgttctcgac gcctcccaaa atatttggaa tttcctgacg tggcaaaaga aagtttatgt  82860
ccacgtttac gaatccatcg aggacggaca caaagcttgg ctctaatctc cattccatat  82920
actgtttaga aacgggagat agcataatcc taggcgtcac aatgcacgaa gggtttttaa  82980
tcaccgcatc gtggtaagaa aagtgtattc catttcttcc agtataaaga agcctatgtt  83040
cgtcgtagca gaaacaatta aggcggtatg cctcatacat acactgtttc aaagtacaaa  83100
cacgttttaa aaaggtttct gcattggcgg aggccaagcg gttttgccat tggtggaagg  83160
ggttcaatcc tacaatggcc agctcgttta aaatatcttc gcggcgcgct aaaatctgca  83220
ccatagaaga atactttagc attttttttt cgcaccattc gcgaagatgt ttagctacat  83280
tattaacctt attattgata aagtatacga tggcatgttg gaagccttca aaaataaaga  83340
gcccctccaa aagatcatct gccaatagaa gatggatgtt ggtgtaagca ttgtcaatat  83400
tttgtagaaa cggcggaatg cctgccaaaa ccgcttcagc aagcatagct ccgttccgtt  83460
gtttactgtc caatagattc gtaagttttt tgtccgcaac agacacgacg gctaggatgg  83520
ttgcaatgtc agaaatggcg gcttgccaga aataacccga aaagcacatg cgcgcttctt  83580
ctatagataa aaacgaaaag cgagaggcaa tgtctccgag ctgcgtgagt tgaagacctt  83640
tttctcctct ggttaaaagg cctgccacaa tggcccgctc aatggctgat gccagcgcat  83700
ccgtgggggg aggatccagc atatcaatct cctctgcctt aaacacgcct tccttatttt  83760
```

```
ttttaatcgt ttctacgaca atgctaagaa aaatggcccc agggccttcc gtaatgattt  83820
caggatactg ctgcactggt atttgctcaa agacgtgttt tgtgtaaagc gggtaaaagt  83880
gcccaggaaa tactctccct acacgcccct ttctttgctc gatacggctt tgagccgcgg  83940
ggcgcgtaat aagccctccc gcccattcgg gatagtaggt ttcaatgctt ctgttccacc  84000
cgggatctat gacgtacttc agcgtttcaa tggtaaggcc cgtttccgca acaaccgtgg  84060
aaacaatgac ccttcttaaa ggtttttcca ctttagcggt taagggattt ttcacccaca  84120
gattcttaat ttccgctttc aggccaaggt aggcctcatt ttcctgcgca atcgcctcac  84180
tatcgatcgg caaaatcaac attaacggca gcttttcttt ggcaaggtcc atatttgcat  84240
tattcagcaa catcgaaagg aagcgtattt cagccatacc gggcatgaaa attaaaatat  84300
ctgcttccgt gggacgatca tgaatgtttt ctttatgaat agtgagagcc gtttcgcagg  84360
cggtcttaat gtagttgttg gtgttataca gcggccagtg ggtttccaca ccgtactgtc  84420
gtccttccac caaaataatg ttttcttttc cgataccaaa ataggttgag tatttatggg  84480
tatcaatggt ggcggaggtt aaaattacaa agggaatacg cagcgcccct atgcttcctc  84540
tttgcaacat gcgctgaagc atacttttaa tatacatgag cataaggtcg atgcctaggg  84600
ctcgctcatg ggcctcatct ataatcataa aggcatagcg ggaagctatc tcatcatccg  84660
tcattgtatg tagctgcgcc aacagaaccc ccgcggttgc ataaataagg ccccgattgg  84720
gtttttccgt cagaggcttc gtttggtagc ccactgtttg gcctaatatc atgtcggggt  84780
agtgggttga ggcgccgatg tctttggcga gggtcaccgc ggttaggact cttggctggg  84840
tacaaataac cgagcgtccc aagtattttt ggaaagaatg cgtgttttca tttctcagaa  84900
ttctgaacac gtgtacgggt aaggccgtgg attttccgga accagtgcgt gactttataa  84960
tgagcacccg gtctgcgagg gaggttggaa tggcccctcc aaactccggg agacgttgtt  85020
ttatccaagt gatgatgtaa tgaataggaa catcattctt gtgctcagcg ggcacgttat  85080
agagatgacc aggctccaat aaagtcggtt ttcccatatt ctattgtttt aaggattgat  85140
tgttcataaa tatttttata ctctgaccaa gaaattattt ttttattaag ccggttattt  85200
acgttgttat ggaacgcgaa ggtccagtac tgaaagtcct ccgagttgtt taatgtcaag  85260
ggattttttg taagatacga aaaggcgtgg tgctggcacc tggtgcatgg cagagactcg  85320
ataaagttca gtatccattg gatggcttca tatttttctt tccagctagg agcgtctgaa  85380
aaaaagatag catatagatg caaggatcgc cagtatttag gtccccaatg caacatttat  85440
aacctttga aaaatctcat tccatataga ggtaaatatt ttttttccat ggagaatttt  85500
tttgcactct tgaagggatt gcgccacatc gtcaaatgtt ttttgttttc catgtatttt  85560
ggcgtaattc cagccagtat ctgtgtcatg gtccttaatg tcatccgcta actgaaaggc  85620
atgtccaaaa caatgggcag ccctttcaat catcccaatg tcttcaacgg atccagttcc  85680
taaaacccag cccataataa acgcgatctt aaaaaaggga atggtttttt ctggagtgtc  85740
tactaactga ccggaacccg cgctgtttag agagtggctt acaaaggtac acagcagcgc  85800
tcccagttgg ttgggatccg gaaaccttgg acagtgttcc ttaatccagt cgatttgccg  85860
gcaaatattt tgaaatcctt gcatggttag cgccagagcg ctcatctgcg ccttggctac  85920
gccaaagcgg gcccacactg tatctttatt tcgccgcttc acatcgttgt caaaggaggg  85980
catatcatcg ataatcaaag aagctacgtg aaagtactcc gctgctaggg cggcctctgc  86040
cggataaata ggcgccccaa aggaatgttg caactgacag gcccgaacaa tttccatcag  86100
```

gataatggga cggatatact tcccacctct tagagcgtaa gagcaaggct ctgttagttg 86160
tcccttaaag tccccatctt caatagcatt atttaagatg gtctcaaact cttcactaaa 86220
ggttttataa tttttaggat tcagtggatg tattccatga aaaagcgcga cactacgcgg 86280
tgctgtgatt ctaaaatact taggtttgcg cgtataggat attaaaataa taataagaac 86340
tacaatgatg gagatataga tgagatgcaa catgctgagt tgtctccccg cagggaatgg 86400
tccttttccg cgcttgttaa cggtaccgag gaggcgttga aatctttagg aaaggtgctg 86460
tctagtttgg aatctccaat tcctcccgta tatttaggta tataattatt gtgtctagaa 86520
attgtttgct ttgaggtatc aaaatattca gcctgaccgc tatttctttt agaataattc 86580
ggtatagggc ttgagtagtt ggcaatactc ttaaaccggg gcaccaaggt aacaatattt 86640
tccatataat gggtttgata cgctttgttt aaaaatgggc ttaccggctt tatgcttgtt 86700
agttgtgcat tgagtaccgg tatgtcttct aggatttgtg gctttataga atgattagca 86760
aacacagaat gtagtatatt agatacttgt agcatatgtc tatttgcgga aaattcctgg 86820
tattctctgc cgtgttgcga atctttgggc ggaaggggac caagcatcgg cacgtccgtg 86880
taggtactgg tggattttat gagttcctgc tctatgttcg gtttgacatg tggatttcct 86940
aaaggaatac ctctacctgc aatccctttt tctaccgacg caggtagatt gtgcgctaaa 87000
cacaaaatat tgtacacgtc tttgtgcgga atatatccgt tatagtgctg gcccggcatc 87060
tgatcgccaa ggtgctgctc atgcttaatg gtaccctttg ttctgagttt aggaagatcc 87120
tcgtacgaaa aaaattttgt gtgctcgctg aacctcgtag aaggaaccga actatttttt 87180
gggtttttta aggaaggcaa tgaggaaggc tgggtcagac aatttttctg tgtgcccttt 87240
aagctagcca cctgcggaaa tgtttttttt tccgtacgaa caacattgcg cctaattagg 87300
ttttccgtat gggttgaaaa agcaggacga tgatttttaa aatgattaaa aagtttattt 87360
tttggaatgg agctgtacgg ctccagatct tgcgcatcgc cgtaaccaat gtttttgtgc 87420
tgagggttca gcataaaaga aaagttacgt agatcactga gttgcaatcc cttttcagcc 87480
ttttcaggac tattagtgta ttcattgtat acaggcgcgg ctccattttt gttgccgcag 87540
taccgggaat ttagtatatt atcagaatac cggttatgac gcggcaaatc gctttcccaa 87600
agaggtggat ctgacctata atcggctaac agctttgaag cataatcatg atacattgta 87660
tataaaagtt aattattata ttgagaaggc ataattactt cttgtagggg tacaagaggc 87720
tttgaatcag gcaaactgac gggttttgaa tcggccggct ttggaccggc aggtatcttt 87780
ttaggttgat cttcttctag ctcattagac acggatgggg gagaaatagg aggaataatt 87840
tcatctccgc ccttatattt gtcatggata gaagaaacaa ttacatccat gtttgattta 87900
ttataaatgt cgtttaactg gtgatttaaa acataataat gcaaaaataa tagggctaca 87960
atgcatatat atacgtaaat agccgtcttc gtttttcgtt ttttatccac cggcggatta 88020
caaattgcaa aaaatacaac taataccacc gctgtaatga ttaaggccac aatgaaagga 88080
ttttgaaagg atgttttgaa cggttcgcac gtataaattt tttctcctaa attattgata 88140
cccgcaataa aatctacatt cattttatat atttataaat tatgaaaaat ttagagttac 88200
atctccgccg gaccaatcat tgctaaaatt tgaagattct tcaaaaaggc ccgactggtt 88260
gaatgtcttc tgctcaggtt tccaaaaatt ttccaagaat ggattttgaa caataggctc 88320
atcttgattt tcttcttcaa ggatattttc tttgatatca agaacagctt ctttaaactc 88380
aggtgtatct tgattaaact caggtttatc ctgatcaatc gcaaaaatat tatcttcttc 88440
agatatatcc tgtttaatcg caagaatagt ttcttcctca ggtttatcct gatcaatcgc 88500

-continued

```
aagaatattt tcttcttcag gtttatcctg accaaactca acaatatctt tctcgctaaa  88560
tccgttttta gtgtgaagct cttggttttg aagagaatta tcaaaatcta ttttagttgt  88620
tgtcctagac cgtggcacgg gatagttatc taatggttta cttactatag tcctcgaatg  88680
tggcacggga taattgtttg gtgacttgct ggttagctct tggcttgtta atagttcttg  88740
ttttctcaat aattccatct ctactacttc tttttgatcc gctggtgtct ctttttggta  88800
ttcttcatta gaaaaatgtt cagagggtaa tgtttcaata aactttgtga gtggatagct  88860
gctctttgat gtagaagagc gttgaatttg ctgataaagg agttgaacaa gtcgccggta  88920
ttcactctgt cttttttcat attttttacg tagcgtggag agatctgcta agagcgactt  88980
gttttcagat gttaattctt caatttgatg aagaaggctg cgattgtatg aactaagtct  89040
tgcatacgtt tcttctaatt ctgtctccgg ctccacatag gcctgttttc gcagaaattt  89100
attgtatagt tccattcttt ttttgagcag aaaggtaaga ctataatctt gcatttcttt  89160
cgtaacttta tggtagtttt ctttccggtt tttgataata aagggcagca ttttttctgt  89220
tgtgataaag gtgcccagat tgctaatgta gtcgcacagt agcaattcca agatagattc  89280
tttcttttca aggcttatag attggctgta ttctttaggt atgaaagaat caacaatcgt  89340
tgttacgaag tttgaaaagt ttaatgtttt gctgttaatt tgggtaatgt tacaaaaata  89400
tttgtaaaaa ctatctagca ttttttcata aagtttttta ttttgtttaa cccctaaaat  89460
atagcccttt acttgatact gatattccgt aacaatggaa tgttttttgt atagtgcatt  89520
tttgtataaa aagttataaa aaatgttgat aaaatacgca ccaagggttt caaaaatact  89580
tataacgtgg gattcttcct gatccattat atcatatgta atattatttt aataaaaaat  89640
tactgacgaa taacatgcaa aaaaaatatg tttaaactta ttttaagcta gcacttattt  89700
aaaagtgttt taaacacgtt ttaaattgta tgttaataca cttaaaaatt aagccgaaat  89760
ttgctccaat aaggattact tttatcaatg accacctctt tactataaac ggctttacat  89820
aattttaata atgctttaga gccaaagctg aaggcagtgg gaagcggcac tgtactatgg  89880
taaaaatgtt gccgatgttc atcctcgcgg atgtacacaa gtttcctata tcctttaaac  89940
acaatatggc taatttcttc cacatactcc ttatcctgtt tggaatagcg gttgctttga  90000
cgggaaaaat tcgacataca aatagaggca tttgtaaaaa tggaaacaaa tgcgttttta  90060
cgaagattgg cgggtaaatc ggtatcatct tggcagcaaa taatcatcga aataaaacag  90120
tgacgatttt ggtaaaaaaa ctttttaaaa atttcttttg taaataatgg gtgcagttcg  90180
gccgcgcagt cgtctaatat taaaagtaaa cgaggattaa gattgatata gtttaacgta  90240
aacttttcat cctctgtaag gcataagttt ttatacatat gaatgttctg tataataatt  90300
tttttaaaa gttgctgata aagcgatgta atcttttctt cttttttttg gtccgtttgt  90360
tcagccttta agcactccac ttttgcaata tttttgtttt ccttttgctg tatatcgatc  90420
ggaagtttat gatacaatgt ttttagcata tcgatgttgt ttactcgact gtagatggag  90480
gacatcatag tttgccgctg ccagatggcc tccaaaaagc gttcagcgcc cttgttgtca  90540
ttttttttt gcttatcggc gagccacaag cggtagtgta ttagagttgg atgtacaaaa  90600
ccctcatatg aacgatttga gggttccgag ggggcaacca ctaaaatttg ttcaatatgg  90660
ggttgcagga ttttcataat atgtttaacg tacacggttt tgcctgtttt tgaggggcca  90720
tatagcacag ttgttttatc tataaaatga tgtgctttga actgtagttc aggaattagc  90780
ttccctgaat gggtcgttag ggccatctct atattattac aattctgctt ttgtatataa  90840
```

-continued

```
aatttctttt tcgagtttat tattattgtt gacccacata tctacccgta tcgtatcatc  90900
aggcacattg agcatttcaa gcgcattatc taactgtttt tttgttttta tcagctcgct  90960
ttcttcatcg ggggttaaat tttctttact aagcagttgc ttaatttttt cttcgcagtc  91020
gtctataaaa tcatactctc gagctttttt gatatttcca gatgcttttt ctaggttttt  91080
tagctcctta aaggaaagca gtcccttaat cccgctatcc gtgtgaaagg ttgaattata  91140
gatggagagc cccggagcat ccgggccagt ttcttgtata tttttgcttt ttttgtggta  91200
aatagtattt cgtaaaatct cttttcctat ctttaggtct tcctcatgac ggtccaaaat  91260
ccgtttttatt atttcattat tttgattaaa ataattgtag cgctctctgt tggccttaaa  91320
gcttcccagg agtgtccagt tgcctaattg aatggatgaa acctctgaga aaatctggtc  91380
tttatattta taataaaatt catcaacctt ttgttggttg ctgctatcca ccacatcata  91440
aataatgaag gcaaactcta ggtcgggttt ttctgggtag atgctttccg tagcggcccg  91500
caactcttcg taattatcct caatgtaata attccactta taaaaagtat cctgaggtgg  91560
aatatgctgc gaaagatatc tagtaatttt tgtgttaaag agaatgggtt taaacgccct  91620
cggattttca agcatatgtt taatgctttg gtgaagttct atattttgta atatgtgggc  91680
tgctgcccta tagccctgtg gggtttgggt gattgcatca atatcggcct gaagctcatt  91740
aggcacattt aatgtttttt gcatgatgtg taaagggatg cgctcaggat ctgctaaatc  91800
ggtgtattct gtgcttgtac aagtgcttgc acaggtatct acattggtat ctgcacacat  91860
gcttgcacag gtgtctacat tggtatctgc acacatgctt gcacaagtgt ctacattggt  91920
atctgcacaa gtatacgcac tttgagcatg aagattagga tcaaacacaa aatgttctcg  91980
taaaaagcta tcgatcgttg ttttagcttc cttgcttttc tgcgtctggg ttttgcagct  92040
atctgctata gataaaattg tatttactac cgattcagag ggaacatcat tagtttcctg  92100
tttcaaagta tcaactaacg ttattagctc actgagaaga gttttggtcg tgtgggtagg  92160
ttttgaatag gaaggcatcc attcctgcag agctttgaag acatatccaa taaagctagt  92220
cattataaga cgtcgaatat actgctcccg caaatttgta aaagagcaaa aggccaccct  92280
gctatcattt ttgaactgtt tgtaagggtt cgtcctttgg taaagctgtt taagcgtttc  92340
ttcggatatt tcagtagagg gatcctccaa tacgtttttg agaagctcat caatattaaa  92400
ttctgccata tcttagagtt tattatatac atattaaagc tttaatataa ggggggtata  92460
acaatggacg aaatcatcaa taaataccaa gctgttgaaa aactttttaa ggaaattcag  92520
caaggattgg ccgcgtatga tcaatacaag accttaatta gtgaaatgat gcactataat  92580
aatcatatca agcaggagta ttttaacttt ttaatgatta tttcacctta tcttattagg  92640
gcgcatagcg gagaaacgct gcgaaacaaa gtaaataatg aaattaaacg tcttattttg  92700
gttgaaaata tcaataccaa aatatctaaa acgctggtaa gtgttaattt tttactacag  92760
aaaaaacttt caacggacgg ggtgaaaacg aaaaacatgt ggtgcaccaa taatcccatg  92820
ctgcaggtaa aaacagccca caaccttttt aagcaactat gcgacacaca gtccaaaact  92880
caatgggtac aaactttaaa atataaggaa tgcaagtatt gtcataccga catggtgttt  92940
aacaccacgc agtttgggct gcaatgtcct aactgcggtt gtattcaaga attgatggga  93000
accatttttg atgaaacaca tttttacaac catgatgggc agaaagcaaa gtcaggtatc  93060
tttaacccta accgtcacta tcggttttgg atagaacata ttcttggtag aaatccagaa  93120
caagagttgg ggaccaaaca agatccctgc ggaaccaagg tgttgcaaca actaaaaaaa  93180
attattaagc gcgataataa atgcatcgcg cttttgacgg tcgaaaatat tcgaaaaatg  93240
```

ttaaaagaga taaaccgcac agacttaaat aattgtgttt ctcttatatt gcgtaaactt 93300
accggagtag ggccgcctca aatatcagag tcgattttac tacgaggcga atacatattt 93360
acagaggcaa ttaagatacg ggaaaaagtg tgtaaaaaag ggcgtattaa taggaattat 93420
tatccgtatt atatatataa aatttttgac gccattttgc ctccaaatga taccacgaat 93480
cgacgcattt tacaatatat tcatttgcaa ggaaatgata cgctagctaa taatgatagt 93540
gagtgggaat ctatctgtat ggagctccct gaaataaaat ggaagcccac agatcgaacc 93600
cattgtgttc attttttta aagatgaaga ttttttagat gattttttt agtttttaa 93660
aagacgaaaa aatttttaa aagatgaata ttcttaaacc ccgcaaatta cttttttta 93720
ggtactgtaa cgcagcacag ctgaaccgtt ctgaagaaga agaaagttaa tagcagatgc 93780
cgataccaca agatcagccg tagtgataga ccccacgtaa tccgtgtccc aactaatata 93840
aaattctctt gctctggata cgttaatatg accactgggt tggtattcct cccgtggctt 93900
caaagcaaag gtaatcatca tcgcacccgg atcatcgggg gttttaatcg cattgcctcc 93960
gtagtggaag ggtatgtaag agctgcagaa ctttgatgga aatttatcga taagattgat 94020
accatgagca gttacggaaa tgtttttaat aataggtaat gtgatcggat acgtaacggg 94080
gctaatatca gatatagatg aacatgcgtc tggaagagct gtatctctat cctgaaagct 94140
tatctctgcg tggtgagtgg gctgcataat ggcgttaaca acatgtccga acttgtgcca 94200
atctcggtgt tgatgaggat tttgatcgga gatgttccag gtaggtttta atcctataaa 94260
catatattca atgggccatt taagagcaga cattagtttt tcatcgtggt ggttattgtt 94320
ggtgtgggtc acctgcgttt tatggacacg tatcagcgaa aagcgaacgc gttttacaaa 94380
aaggttgtgt atttcagggg ttacaaacag gttattgatg taaagttcat tattcgtgag 94440
cgagatttca ttaatgactc ctgggataaa ccatggttta aagcgtatat tgcgtctact 94500
ggggcgtcca gctataaaac gtgactggcg tacaaaaagt ccaggaaatt cattcaccaa 94560
atccttttgc gatgcaagct ttatggtgat aaagcgctcg ccgaagggaa tggatactga 94620
gggaatagca aggttcacgt tctcattaaa ccaaaagcgc aacttaatcc agagcgcaag 94680
agggggctga tagtatttag gggtttgagg tccattacag ctgtaatgaa cattacgtct 94740
tatgtccaga tacgttgcgt ccgtgatagg agtaatatct tgtttacctg ctgtttggat 94800
attgtgagag ttctcgggaa aatgctgtga aagaaatttc gggttggtat ggctacacgt 94860
tcgctgcgta tcattttcat cggtaagaat aggtttgctt tggtgcggct tgtgcaaatc 94920
atgaatgttg cataggagag ggccactggt tccctccacc gatacctcct ggccaaccaa 94980
gtgcttatat ccagtcattt tatcccctgg gatgcaaaat ttgcgcacaa gcgttgtgac 95040
atccgaacta tattcgtcta gggaatttcc atttacatcg aatcttacgt tttcataaag 95100
tcgttctccg ggtattcgc agtagtaaac caagtttcgg tacgcattct ttgtgccggg 95160
tacaatgggt cttccaaaag gatctacaag cgtgtaaacg gcgccctcta agggtgtttg 95220
gttgtcccag tcatatccgt tgcgaggaaa cgtttgaagc tgcccatggg cccccatctg 95280
ggacgtgccc tgaatcggag catcctgcca ggatgaatga catgcaccca atatatgatg 95340
gcccaccata tcatggaaaa agtctccgta ctggggaata ccaaaggtaa gcttgtttcc 95400
caaggtgggg gtacccgtat gcgggcgtac tttattgtat tcaaacccta ctggaacata 95460
aggcttaaaa tgcgcattaa aatgcaccaa atgtgtttct tcgatttgac tcaaagtggg 95520
ttcgggatcg ggtttcccat aacttttgtt cacattttta atgttagaga tcctgctatt 95580
cagcaagtct tgggccaata taatcttgtc ggccttccca tcgttagcaa taagacaaaa 95640
agctcctcct gatgccatat ataatgttat aaaaataatt tattgttttt attaaatatg 95700
gcggtttatg cgaaggatct tgataataac aaagagttaa accaaaaatt aattaacgat 95760
cagcttaaaa ttattgacac gctcttgctg gcagaaaaaa aaaacttttt ggtgtatgaa 95820
ctacctgccc cttttgactt ttcctccggc gaccctttgg ccagtcagcg cgacatatac 95880
tatgccatca taaaaagcct cgaggagcgc gggtttactg tcaaaatatg tatgaaaggg 95940
gatcgtgccc tccttttcat cacctggaaa aaaatacaat ccattgagat aaacaaaaaa 96000
gaagaatatc tgcgcatgca cttcatacaa gacgaagaga aagcatttta ttgtaaattt 96060
ttagagtcta gatgagcttt tacgcaatgt tgtacagtgt tgtatatatg tcttgtaagc 96120
atttgttgta gagtaataag taaaagataa ataaaaatga ctattaaaat aaagcccaaa 96180
ccattaaaaa tatttttatc tgttagattt aatttaataa atggctcatg gaatgtgtgg 96240
tgcgccgctg catgaggtgt ggccgcatgg gatgtggtcg cataagatgt agctacatgg 96300
gatgtggcat ttgcttgcat gtaaggatca tgatgtgttg ggtcttcatc ccagcaataa 96360
tcgccatctt tatctagctg aattgtatac cccattatat atcacttatt attttttttt 96420
aatgtttcat gaatttcatt ataggcggtg aaagggtcct caggcccctt ctgtaaaaga 96480
ttatagagat cttcggacgc tttatgtttc gtgcgaatta aggcgggata taacaaaaga 96540
gagggcccca gttccaaaca aattttactt agcgggctca tattttgcac caagtttccc 96600
actacttgcg atgtttcata acgcatttta aagagcttta tcataaaagt gttatgcagg 96660
ccggtgtagt ctggcctata gttaaggaag gggatttctc tggtaccgtc aaacacgatc 96720
tcaagtcctc tagcaagccc gatcaaaatt tcttcagcaa tggatgagta tctaattcct 96780
acattacgaa gcgtaagcat ttctataaca tcatctattt cctgcataga ggaatctatt 96840
gtaggaattt taatatcatc tgtgctgatt tgttcattcc caagataggt aagcagcata 96900
ttaatttttt ctagctttac tagcttagtc ttacgctcat aatcatgatc tttttttataa 96960
aaagagttgg gatcaccgtt ggaccgtaga tgattaataa ggcggtctac ttgctttgta 97020
ctaggtttaa tactttttttc actatactcg ctttcagcat agtggttttt acgatctctt 97080
ttagaaatag ctgtttttttg agatgcctca gactctgcat atttttttct atgcgtagaa 97140
agagaataac cgcggtcatt acgtgaacta ctgttgcatg caaggcctcg gcgcgtctta 97200
ccgctgcgca cactgccatt gcgtatactg ccatcgcgca cactgccgct gcgtatactg 97260
ccattgcgta tactgccgct gcgtatgctg ccgctgcgta tgctgccgct acatacacta 97320
tcactacata tgctgtcagt acatacgcta tcgcggcgta tgccgccgtg taccttatcg 97380
ccgcccctac ccgagggttt tttagatata atactgtgtg gggagtcaag cgaaaattca 97440
gggtcattaa agttaatgcc caatgacttt gccaatccat taagctcttc atcaaaatga 97500
tcggtaggaa aactttgttg cttgcccatg acctgttttt caagttcctc caaattggct 97560
tgctcattta tatggagatt attcataagc gtcgtaattc cagcaagatt tgctccttct 97620
aaaaatgtgg tgtcctccat cggatatact atactattta aaagctttta aataaaaatg 97680
tgtttggaag aaatgctctc ttcaagcgtg tgtagctcag atataaatgc ctcctcagaa 97740
agctttccac catactcctt tctcatcgta taggagggcg ccggtttaat gtaggaaatc 97800
cactgggagg taaaaaaccg gtacaacata tttagcagct cgcgggcctc ccaccttttg 97860
ggctccgtat agtgcacatc aacataagag gcggcgcatg aaaagctgca aaagttgccg 97920
agaacgccca tctcaatctc tcctcgctca ttttcacgca tataggtggg cacgaatttt 97980
gggacagtct tgaaatagag atgacatgtc cagcatttaa agctagaatg ggtaacccat 98040
ttggaaacag tggtgaatac ggagggtagc ttttttcga cctcggcttc atcgtcattc 98100
gtatttaacg tatcggtggc agttttttg gattgcaagc attcttcaat ggtaatcccg 98160
gataagtata aaatattagg acaattagtt tccataattt tgatagttat ttttatacaa 98220
catggattta attaaagata aatggaggac gaaacggaac tgtgttttcg gtcaaacaag 98280
gtgacgaggc ttgaaatgtt tgtctgcaca tacgggggaa aaattaccag ccttgcatgt 98340
tcgcatatgg agttaattaa aatgttgcaa attgctgagc cggtgaaggc attgaactgc 98400
aactttggcc accagtgcct accgggctac gaatctttaa taaagactcc gaaaaaaact 98460
aaaaacatgt tgcgccgtcc gcgcaaaaca gaaggcgatg ggacttgctt caatagtgcc 98520
attgaagcct ccattttgtt taaggacaag atgtataaat taaaatgttt tcctagtacc 98580
ggggaaattc aggtcccggg cgtcattttt ccggattttg aagacggaaa aaacattata 98640
cagcagtggg tagacttctt gcaacatcaa cccattgaaa aaaaaatcca gattattgaa 98700
tttaaaacga ttatgattaa ttttaagttt caaataaacc cagtgtctcc ccgcgtcatc 98760
attcatttaa aaaaatttgc agctttgttg gaacacatcc ctactccata tcccatacgt 98820
gaaataaagc ctccattaga agactcaaaa gtatccgcaa aatttatggt cagtccggga 98880
aaaaaagtac gcattaatgt ttttcttaaa ggtaagataa atattttagg ctgcaacaca 98940
aaggaatccg cggagaccat ttatacgttt ttgaaagatc ttatcagcgt acattggcaa 99000
gaaattttgt gcgtgttacc ggtacccgat taaagaatgt tttcattaat aaggtaatcg 99060
actatgctaa aaagaataac aagaaaaata ccttgaagaa ctataccaaa gtaggtaggt 99120
tttctgcatg tcacggcatg gttaaaattg ctaataatgt agtccacaaa agcattgctc 99180
aatacgacta aaaatagtaa aaaaaggata agtgctcttt ttatatccat atactttaaa 99240
acttattttt tacactaata atttcctgcg gccgcaatat aaactgtagg tcatctataa 99300
cgcccagacc tgttaaaagt agagtactat gttttaaggg atttaaaata tccgccgcaa 99360
gaatgtgaat ataattttca aagtggttta caggaatgcg taagcgtttt tttttgcact 99420
gcggttggtt tagggtcgaa tactggcagg aggtatatat attaataaga ccgcggtcga 99480
tggtttcaat atcttcatag aattcaatgc gcggcgtcaa aagtttttta agatgttgac 99540
ataactcatc atacgtgtag gactggaggg gggaaagaag ggtgtagtca aagttaaaaa 99600 tgttttttg aagaaccttt aaagcatgtt ccgcgtccgt ggtttccaaa atatgtttta 99660
tggtatgaat gtcatttaaa tctacaaagt ctgacagctt tgtgtagaac tcggtgacgg 99720
aggttatttt ctggaaatcg gtttttgaa aaagattttc aatgtgtttg cgggttgagt 99780
tgctttgcag tccatacaag acatcaaaaa attcaatcag caaaaactta tacaaatggt 99840
taatataaaa agctttgttg gccttattct gctgaggata tggttcctct aggggatata 99900
gaatggcttg gtctatatcc ctaggatcaa tagtcaatgt tgcgatggga agcttttcca 99960
gcgtagcggg aagagtttgg gttggagcgt agtaaaagta tagcccggtt tttccctctg 100020
aaagaaagcc cacaaattct ttttttatat tttgcagcac cgctgagggt acgatttcgt 100080
actgtttata ctgtttgttg aaaagggtaa taaatttcca ggtttcttca aagcttgcaa 100140
tctgggtggg ccgcagatca aagtcgatgg gaatgtcgtc atgaatgtag gatgatagtc 100200
ttataggaaa ataaataggg cgatcggtgt ctgaatcgat aagtaaagca taacaaaagt 100260
tatgcctgtt gataagtttt ttaccaaccg tgtagccggg aatgtttttc acgtcatgga 100320
tatcccacca gttatccttg cacataaact cgctcataga ctggatgacc tccatcacag 100380
ggtcatcttc ggtaaaaata tactgggcct cactgttttt cagaaatctt ttttgctggg 100440
tgatggccat tgggtagatc ccttcgtccg tgtcaaagat aatggctatc ttcttcgatg 100500
ggctaagaat tttttgtatt gtgctggggg acacctcaaa cccgatgtcg ccctgtttat 100560
ctttaaaaaa gacacagtga aggtcgtagc atatggcaac aaggtccaga aagatgtcct 100620
gccatgtggt gtcccattga agcagttggt ttttttgttc aacaaaggtt tgtaagataa 100680
ggtttgccag ctccgcgccg ctggaaaaca tgttgccggc cccattcccc aaaatatagt 100740
actgcggtgt gttggccgcc tttgcaattt caatggcaag ggccttgggg gcaagatcca 100800
aaattcgagc aagggaataa aaaagcccgg cattgctaat tccaagcatg gtttgctcca 100860
cccccacaat gcaaaaaatg tcgggctctt ttatcgtatt taaaaacagt tcatctgcta 100920
tctggtgggg tagaaaggca atccggttca ccggtatttt ttttccatag gacaaggtat 100980
gacgcgatgt ttgtgtatta agatcctcca ggtcttgttc tacaaacgtg tgcttggtga 101040
ggcaggtatt gttaatatag aaccgctttg tgcccagcag ggccttcgtc ttttggcagc 101100
acggcagaca gtaatttagg gggtggcggc cttctagtag gcttagatga gggtagtcag 101160
gatgcgggca gctatagtag gcaggtaccc cctccgtgaa attccaatac tttactagct 101220
ccttgcgctt ggctggcggc atggacttca cctcggcctc tgagtaaatg acgggtggcc 101280
gtgggtgctg gcataggacg gagtaaaccg ttgcctgcgt gtcgtacttg cgcaggtcat 101340
acaggtcggg gtcctgttct tgaagcgcac gtagctgaga ggctcccttt ccttgttgtt 101400
tatcgtgcag ttgagagagt ttattaacca aaattttgtc aggcccggtg atcaagttat 101460
ctaaaaacac aaataggtaa acccaaagat agttaaactc ttcctgggta atgttaaaca 101520
tttctatttt gatatctgta accctatggt agatgcgaat gttgcggccg ccgtagattg 101580
tttcccaccg ggccgcaaca tttgtgtcaa agaggtacgc atacgtgttt tggagcaacg 101640
caacattgat gtccattttg cgccccggac cggaggaaat aatgatcatc cgttcgattt 101700
cgtggggatc atacgaataa atccccttt taaataaaaa attgtagacc ccggtttgct 101760
ggaggccccg cacggaaata atccctgctt gctcgtattc ccgccaacga cttttgagct 101820
cggtaaatcc cttgctagaa agcgtatagg gccaaaaggt ggacaccgac atggagctga 101880
tagaaatttg gatgtcctcg ttggagggaa ggggcagact ccctccacga ggaaacgcgg 101940
caggccccat atcattaatt gtatgaataa taggatttat gaaattattt agggtggaca 102000
ccacggagtt aaagtcgtgg cgctcgtttt ctgaccaatt gctttcgata aagtagtgcc 102060
cattattttg tatggtaaga ataaaggcct ttttattgat aaagcgtatt aaaataatag 102120
tgggtacacg gaatgtttta ttgctgaatt tttcaggctc cgtggaagtt atgtggtgtt 102180
tggaaaccac ggtgggacct gttttactat aaaagaacac caccagctga ggaatatcgg 102240
gagtagctgg aaataggtcg aaaacattgc gcacattaat ttgaatattt acgaggggtg 102300
aaattttaat cattgccgag gtgacggcca acgtgccgcg tgttagtcta ttcccctcgt 102360
acttggcaat gacttgttgt gctctggcat acgtaaagtt tattagtttt tgctctagga 102420
gaagcctctt tttaagactg gtcaaggatg gagaaagagc aggatactgt ttttccattt 102480
gtaagggaga ttgtaccaat agtttaaagg catcggggga aagaagaggc caatacttca 102540
taataaggcc gtaatagagt aagtcaaatt ggtaattatc ctctatggca atggagattt 102600
ggcgccgcat gggggccact agcgtgttga ggtctgctac aaagatgtga tgaatgtttt 102660
ttatgagctg gaagctgtcg agcgcttcca catagagctc atctttttga ctttccatag 102720
atgcgtcgat gttcacccca cccacctgtt gaaactcctt tttgtagtcg cgaatgtcta 102780
acgccacccc gctaccgctt aacaataggc gatacgttac ctgaagcgca ttgttttgaa 102840
aaaagaaaat gtgttgtcta taagggggga tccctgtggc aacgtaaatt ttttctcgaa 102900
tgtctttaaa agtgtcttca gggaaaatac tatactcgct atacatcgtc tcaatttctg 102960
gcatcatcac gtttgtctcc tcgccacgat cctccacaaa aagtttttca aactcatcta 103020
aatcatcgct atctccaccc accacgtatt gggaaagctt tttctcccaa tcctcgccgt 103080
aaaaattttg taaaatttct ttgtccttag gggttcgctg caggtctttg cggcaggcct 103140
gtaacacgtt tgcaggaacg gatcccaaaa aaataaacgt cttcgtgtac tcattttcca 103200
caggattata aagagtaact cgtagaggat ttgttaaaaa gtcattttgg aaatccatta 103260
tacccggtat agaaaataaa atttaaaata aaaaacggat gatatctatc atggaccgtt 103320
ctgagattgt tgcacgggag aacccggtga ttacccaacg agttacaaat ctcctacaaa 103380
ccaatgctcc tctactattc atgcccattg atatccatga agtacgatat ggagcctaca 103440
cacttttcat gtatggttcc ctcgaaaacg gttacaaagc agaagtaagg attgaaaaca 103500
tcccagtttt ctttgacgta cagattgagt tcaatgatac aaaccagctt tttttaaagt 103560
cgctactgac ggctgaaaat attgtgtatg aacggctgga gacgctcacc cagcgtcctg 103620
taatggggta ccgcgagaag gaaaaagagt ttgcaccata cattcgaata ttttttaaaa 103680
gcctgtatga gcgacgaaaa gccattactt acttaaataa tatgggctac aacacggccg 103740
cggacgacac aacctgttat taccgaatgg tttcccgaga attaaaacta cctcttacaa 103800
gttggataca gcttcagcac tattcctacg agcctcgcgg cttggtacac aggttttccg 103860
taaccccga ggatcttgtt tcctatcaga atgatggccc cacagaccac agcatcgtta 103920
tggcctacga tatagagacc tatagccctg ttaagggaac cgttccggac ccaaatcagg 103980
caaacgacgt ggtgttcatg atatgcatgc gcattttttg gattcactcc acagagcctc 104040
tagcgagcac gtgcatcacc atggcaccct gcaaaaagtc ctcagagtgg accaccattc 104100
tatgctcctc tgaaaaaaat ttgttgttaa gctttgctga acagtttagc cgctgggctc 104160
ctgatatatg cacagggttc aatgattctc ggtacgactg gccctttatc gttgaaaaat 104220
ctatgcagca cggtattcta gaagaaatct ttaacaaaat gagccttttc tggcaccaaa 104280
agctggatac cattctaaaa tgctattacg taaaggaaaa gagagtcaaa atctcggccg 104340
aaaaatcgat catttcctcc tttttgcata cccctggatg cctacccatt gatgtccgca 104400
acatgtgtat gcagctttac cctaaagccg aaaaaacaag cttgaaagcg tttttagaaa 104460
attgtgggtt agattcgaag gtagacctgc cgtaccatct catgtggaag tattatgaaa 104520
cacgagacag cgaaaaaata gccgacgtgg cctattactg cattatagat gcccagcgct 104580
gtcaggacct tctggtgcgc cacaatgtta tccccgatcg cagagaggta ggaattctgt 104640
catacacctc gctgtatgac tgtatctact acgcgggagg acacaaggta tgcaatatgc 104700
tcattgccta tgccatccat gatgaatacg gccgtattgc ttgcagtacc attgcccgag 104760
gtaagcggga acacggaaaa tatcccggcg cctttgtgat agaccccgtt aaagggcttg 104820
aacaggataa acccaccaca ggtctcgact ttgcgtcgct gtacccctca ctcatcatgg 104880
cctacaactt ttcgccagaa aaatttgtag cctctcggga tgaggcaaat agcctcatgg 104940
ccaagggtga atctcttcac tacgtctcct ttcactttaa caatcgtctc gtggaaggat 105000
ggtttgtgcg gcataataac gttcctgata aaatgggatt gtacccaaaa gtactcatcg 105060
atctacttaa caaacggacc gcccttaaac aagagcttaa aaaactaggt gagaaaaaag 105120
aatgtataca tgtatcccat cctgggttta aggaactaca gtttcgccat gccatggtag 105180
acgcgaagca aaaggcgttg aaaattttca tgaacacgtt ttacggcgag gcaggtaaca 105240
atttgtcgcc cttctttctg cttcctctag ccggaggagt caccagttcg ggtcaatata 105300
atcttaaact tgtctataac tttgttatca ataaaggtta cggcatcaag tacggtgaca 105360
ccgactcatt atacattaca tgcccagata gtctttatac agaggtaaca gacgcatatt 105420
taaacagcca aaaaaacgata aaacattatg agcaactctg ccacgaaaaa gtgcttctgt 105480
ctatgaaagc catgtctaca ctatgcgccg aggtgaatga atacctgcga caagataatg 105540
gcaccagtta cctacgtatg gcctacgagg aagtactctt tcctgtgtgc tttacaggca 105600
agaaaaagta ttatggtatt gctcatgtaa acacacccaa ttttaataca aaagaattat 105660
tcatccgcgg aatagatatc attaagcagg gtcaaacaaa actcaccaaa acgataggaa 105720
cgcgaattat ggaagaatcc atgaaactac gccgccctga ggaccatcgc ccccctctta 105780
ttgaaatcgt taaaacggtt ttgaaggatg ctgtggttaa catgaagcag tggaattttg 105840
aagacttcat ccaaacagat gcgtggagac cggacaaaga caacaaagca gtccaaatct 105900
ttatgtctcg catgcacgct cggcgtgagc aactaaaaaa acacggcgct gcagcatcgc 105960
aatttgctga gcccgagccg ggagaacgct tctcctacgt tatcgtggaa aaacaggtac 106020
agtttgatat ccagggccac cgcacagatt cctccagaaa gggggacaag atggaatacg 106080
tctctgaagc aaaggctaaa aatcttccta ttgatatatt gttttatatc aacaactatg 106140
ttctaggctt gtgcgcgaga ttcattaatg aaaatgaaga atttcaaccc cctgacaacg 106200
tcagcaataa ggatgaatac gctcagcgcc gagctaaatc ctacctacaa aaattcgtgc 106260
aatccattca ccctaaagac aagtctgtca ttaagcaagg caatgttcat cgacagtgct 106320
acaaatacat tcaccaagaa attaaaaaaa aaataggcat ctttgccgac ctttataagg 106380
aattttttaa caacaccaca aaccccatcg aaagctttat tcaaagcact cagtttatga 106440
tacaatactt tgatggagaa caaaaagtaa accattctat gaaaaaaatg gttgaacagc 106500
atgctacggc tagtaatcga gctggtaagc ccgctggtaa tccagccggc aatgcgctga 106560
tgcgggctat atttacgcag ctgattacgg aagaaaaaaa aattgtacaa gccttataca 106620
ataaggggga tgcaatacac gatcttctca cctatatcat taacaatata aattacaaaa 106680
ttgccacgtt tcagacgaaa cagatgttga cgttcgagtt ttccagtact catgtagaac 106740
tgctattaaa gctgaataaa acgtggctta ttttggctgg aattcatgtg gcaaaaaaac 106800
atctgcaagc ttttttggat tcatataaca atgaatcgcc gtctagaaca ttcattcagc 106860
aggctataga ggaagaatgt ggcagtatta aaccatcttg ctacgacttt atttcctaat 106920
acttcttaag aaactcttta aacaaggact tcgcatggtc aaaggttcta aacccatggc 106980
ccttatgatt cgccaaaaaa gcggtttcat caagattttc taaccctttc acggatgaag 107040
aaataaggtg ttcggcctcg tttgcccatt ttctatgatt ttttttcacc tcgggttcta 107100
gatctgtttt ctccatatac tcattgtggt catatttttt tttgggagga ggcgtgggtg 107160
gaggaatggg tggaggaagt acacccgact ttcccgcttc aaccgtttta taaaaaaata 107220
gaagcataat acaaagaata aggactatcg caaatatgat aaccagtgtc ccagtcgagg 107280
gcattttgtt atataagtaa cgtttttttt tattttttat aattcgaatg aagaaccatg 107340
ttgaatagtc ttctactcaa agacattttg ttatacggta aatgagaatt tataaaatcc 107400
gaatatcact atcatactgt ttatctgaga aggtctcact gggtcctgtg atggagaacc 107460
catactctgt aatgctgggg tttataatgt ggtcaggact gacaagcaca tttctgaact 107520
gcgagagttc taggtttaga cgcagtcgta atagtcgctg tatatttgta ataaatatta 107580
gattgcgtat gaggcgagtg tcaaagcgat cctttccaat ttgtactaag gtgggctttt 107640
gtattccaac tcccacttgt ttaacgatgg accagggtcc ttcttcccga ttttgttccg 107700
tgatataggt cagcacacta ttttctgtat atgaggtatg atgtcgcata ttaatacctg 107760
gtgccattcc aactggcggt tgtgcaattc gggctgtacc gggacccaac catcgtggag 107820
ttttataaac atatcgttct agcgtattta aaaattcctt aaggttattt acgagtagca 107880
tgaagggtgc tattaaaaca ggtggatggt ttataaccat tgtcataaac cattgcattg 107940
cttcaatatc attttgtaat gcttgacggg gaggcggggc aggtaatcca cgtatgttga 108000
ataaagcggt taattgtgca ccggctgttt ggggcgtaat attttgtatt aaatttatca 108060
tcgaattggc ttgcccggca tttcctataa gatcgattaa attggttatt tgacctcgat 108120
attgttgtac ccagttttga atggcagcga tgatctcagg ggttggattg ttttgaattt 108180
caggtgtttg tattagatta ttcacttctc ttcgtgtatc ttcaagctga gtcctaaatg 108240
catttaactc gcctataatt tggtttctat caataacatt tcttaaacct cgaactgttt 108300
cagccaatcg tatagtacgc acaatttcat gtaaggcctg gtttatgtat attgacatgg 108360
gatggcccca ccgctcacgt ccacgttgaa tacctgcggc caaactagga cctgcctcgt 108420
cataatcaaa ttgtgtagga taaaggcttc caaatagcac tttattgaaa atttggtcag 108480
aaagaaattt agggcggccc atatttagcg cgttgtcccc tctaaagatg cgtgacatgt 108540
atccggcgtt gcctttggat agtaactcat tcccatattg agtaatagag accgagacat 108600
aggggtttat aagaagtttt agcataaatt ctcgagtatt tatgggggga cgattcggaa 108660
tgtttaatac ctctgcaaca tctggttgag gagccgtggt gtccagagat cgtacttttt 108720
cagccgaaat gccgtacata agacaagcaa tttcttcaaa actatagtca tagttgtaaa 108780
tattggcaag tggtatagat cgcatcagcg catttacatt gataggtata atattcatat 108840
caaacaagtt aaatatgcgc tcgcgctctc tattagagcc aagagtgcgt gtttgacctt 108900
tcggcgacac tattttgtga atatgattga tttgctcctc ttggtaagag ctttccacga 108960
aggaaattac gtcttgcaat gttttacgaa gcgaatacac tgcattcatc cctattcccg 109020
ctgttataat gggtttatcg tctctgttct cgctaataag attaactcca ccaaaagtat 109080
tttcattgta catcatcact gttttaaaac tacggatatt tatgataaat cggagagcct 109140
gaatggcgtg ggtataaaag tgttcaaatc gcgtgggagt aatttgttcg cgagcaacta 109200
ccgtttcatt atagtttttc atgataagct gtactccggg catatctgag agctgtaccg 109260
gatcatttcc cagtaatttt cttgtgccgt atagtagttt aaactcgggg gagccgcttt 109320
caaggttcgg gtaaagaaga ggatcatata cctcattatt ttctattctt aggtcatgta 109380
aataatagag cgaaagtgaa aatggcataa gaggctcctt attgtaccgg gacatatagt 109440
tttgaatgaa gtgttcttct gtttcaagat agatgggatg atcggtaagc tcgtgcagga 109500
cctccatggc agaatctgcc agagtgtgag agcctctaat gatcccgtcg atcactgcga 109560
ccagtcgctt tcgcacaaca tcgctcgtat tattttgtgc gtctcctagg ggcataagcg 109620
taacattggg acgaaatacg ccgccaattc cccgcagggc cgcctgaccg acggatagtc 109680
ctgtcgcagg aacattgtta ttattataat aaataacgga atcattattg gctcccaaga 109740
gtgccgtcag attagggcga gctagttgga catttgtgta ttgtataaat tgttttagaa 109800
gctctccctg gctaataaga atattaaaca ttttgttaaa tagtggaaga ttggctctat 109860
aattttcttt aaggtaaatg ggaatttctg ttaaagtaga aataagatgc tgactcaggc 109920
cctggcgatt ggtatcctta ataagccgct gaagtataag tcccaaagac agaagaagca 109980
ccgactgctc tgtggggtcg cctctatgac caaagacgtt gttattgcgt gctaagtcag 110040
ggtgagcata tcccatctcc atcactgctt ggctaaagtt cccattagcg aatgcattaa 110100
taagatttag atatattttt ccgctgggag catcataaaa tcgggtaata tatgaagcta 110160
tgagctggtt aaacaccatc atcatactac gattattttg aataccatag tctgatccgt 110220
ataggcgata acgtcgaagg ttgtttgcgg catcattgac attggcatag gttctgagcg 110280
ctatgttgtc ccagtagcta agagtatttt cctcctgggc gttgttggta cgaataagat 110340
tggagagtct aaagtctcct agtgccacct gctctacacg aagtccagag ttattctcca 110400
aagcatcgta aaatacgagt ctactgaata ctcttccgta ttgttcaaag cgttcagagg 110460
attggggatt gttatttatt tgaatattag ccgcgtccct tctttgcgcc ccacctcgaa 110520
gttgcagtac attataaggc tttgtaagca aggtgtaggt tttattaatg atttggttaa 110580
ccccctccag gcccaattca ccgccaggaa gcggccttcc tccggcatcg gtaggtggtt 110640
taataagttt gtcaattaaa tgttcttcca accagtaaaa tgagccagga ttagatctat 110700
tttcatagta ttgaataatg tttttatcaa tatgcgggcg tagaagatca agaaaatact 110760
tcgtgtcggc catcaaagaa tcaattaagg aaataagacc tgtaaaatct aaatgcactt 110820
gagcggtgct ggtttcaggg aagcgaactt gaaccatttt gttaaaactg gaggtcattt 110880
cgaagatatt ggtcaacagg agctgcatga ttcgctgatt atctactaaa taccttgcgg 110940
ccaactcttg ctccggacga actcctccac cagcaggaat acccacatat ggtacaatcc 111000
aagcaaaaag agtttctgtg gttaaatttc ggtcttgggc tgctgcagcc gcttcggtag 111060
tgggatcagg gtacaccata gaaagccgca tattgatttc tttaatgact aatcctggat 111120
ttctaatctc agagatggcc ccgtgttttc ttccgagcca gtcaataaga ttggcgcggt 111180
tcacgttggc agcttgtgtc tctcgtaacc attcgataat gctttttttga atcgtatcta 111240
ggtctaaacc tttaatgtta ttacgaaagt tattaagaag tacgtaaata gcactcaata 111300
agttaagacc tgtaataacg gtttcatgaa acagaaatat tttgttaaca tctgtatctg 111360
ccagtgactc agagccttga ataagttttg aaacgatttg aattttatcg gtatgctcct 111420
ttttgagttc attgatagcc tggcgaatga gttcttggta ggaaattttg cccaattctt 111480
gttgcagact gggatcttca aacatctcac taagctgttt cctaaatttt tgtaccaaat 111540
cccactggga gttgggctgc agcattcctg tttggacatc cacagagtct atattgtata 111600
gtgccgggcg ccacttgggg gtaggctggg ttgaaggact aataaaccta tcggagggaa 111660
gtaattgtga ggattgtgta tagccatcct catcaggaag aatggagtag ttggtttgat 111720
tcatcattcc aaaatcattc atagttcgcg cttcctgaac aatgcgttga aatttttccc 111780
attcggtgcg tgtaatgaca ccgaatctgc ggtttatttc atttacaaaa tggataagcg 111840
ctttttttggt tgcttcttgt tcaccatact ctaagttaaa gtgttggtaa atgacgttta 111900
tttctttgat aagctgacga atttcggttt ctgagtagtc accaatgtta ataagctcaa 111960
taggacgcat aaagataatg cgaataagtc ctgagaagat tccttccagc tcaggaagca 112020
tcgagatctg tacattttca tctctaaagg aaaacaactt ttgataaaat tcggcgaggc 112080
ggggaaggcg gaagtaaagc tctgctgcct cgggaattac ctcgggctct agctcatcgg 112140
caccccccaa tatcatacgc gtgggtataa gtttgtacac gggctcaggc cgttcaaaca 112200
tgtcgtaaat ccctaataca ataaaaatct tggcggccat acttttcagc atgaaggtga 112260
agaagacgtc ctcggtttcc cagcgggttg atagggcgtc gttaactctc acagtagaga 112320
ggtagacccg ctgagccgct tcctcggcag tctgtgcaag cgccatcctt tgtcctccaa 112380
tttctgattg atttagattt ttaagtccca cggaaagcgc agaatgttga agatattcaa 112440
gcaaggtttt atagatttgc aggggcgaca tgggcaccat ttgccgcagc tcctctcccc 112500
caagcatgtc cccaatccgg gcaaaggcat tgatgatatt tttaagcgcc tgaaagttag 112560
aaagagagcg cccgataagg tcgcgaatgt ttttagcctg gcttgctctg acgggacgga 112620
gggtaccaac gcttcggcct tgttggattt cagccgcaac tttttcgtag tagtggcccg 112680
caggagcatt atccgtaaag acgttggagt cgttgcctgt ggaggtggga aaactttcaa 112740
agacttgtgc aagcgtgtcc cctgttgtct cggtgaacca tcgtcctata atgcgcacgc 112800
catccagcat ctgttggact gtttgaatag aatctatgtt gtttacaaac gttttggtaa 112860
tgtttttaag ataaagatct agcccttcca gagctcgata gaatcggcgt tttacatcat 112920
actccagctc gatggcgctt acggttgcct tccagtctac ttcctgggca cctccaggat 112980
ttgggcccac gtgtcctctg gcaagatcta cagccggaga attaatgcgc gcattttttt 113040
ccgtatccaa ctgcatgagg cgtcccgcaa tagcatctcc gagaatagtg gcatagtttt 113100
cctcgtagga ttgaaactcc tgtttgttat gcgttaaatt ggagtaaatc tgggccacat 113160
aatagtaata cataaaggtg ttaattgcct ggttgaggtc aacctgcgat cgcgcggcct 113220
tgctgagccc aagctcttca actgttaggg cagcaccgcc taccettgta cactcgcagt 113280 cctcctcgcc tccatacttt ttttgcacaa tatcggtata aaaatcaata atctgtagca 113340
agcgagagca ggagtcataa agatttttaa aattagggtc ggttttagat atctcctcca 113400
aaacattttt aacaagcgta agctgtgtta agaaggtttc gcgttcttct cgtgcggccg 113460
cattggtgta aaagccgata agacttagat caagtgcgat ggtgcccata tcattaatgc 113520
gcgaaagagc atctcgaagc ctcgttatgt tcggcgtcaa ggcaatttct ttaacaagtt 113580
tgatgcctat ttttttcaca ttttccaaaa agtcgttata ggcttgtgtg cttttattca 113640
aaaattccat gaggatgtgc tttctatcca gtctttgcgc ttcaatcctc ctatctagtg 113700
gcgttttctc ctcatcgccc cccttttttgg cacaactgtt ctcaaggatt ttgtggcgtt 113760
cattaaaggt ctgtcgcaac aggttcacgg ctttttcaaa ctcagcaatg ttttctgcgg 113820
agacaagacc actaaacctt ttgaggtcaa gctccttgtc aaactccgcc cagtttttgc 113880
tttgaaggta ctgttcaacc ttgagtccta ctttctggag agccttatta attttattcg 113940
caacagacgc agcaatacct agattacaaa gtgtgtacga aagtactttt ccaaaatttt 114000
tggttcccaa gacactattt gtatcattta aaagtttaat aatatccacc tcatccgtct 114060
gcagtttatc aagttccttt tgggtgggag ttaaaatatt gtcaataaaa ttcgttaaaa 114120
tgttgatttg caggttttgt tcatttaaaa gtcgacgata tactgcttca atcatggtga 114180
ctgcattaat gacttcctca ttgggggctg ctttggttac ctccgtcacc atgcgctcgt 114240
gaagttgctt aatggcgtcg tttaacagct tgatattttc aagtgtattt tctatactgc 114300
cgtgtacatc aagatactct gcgcgcagtc catgagttag ggagttaatg tacagaacta 114360
tttgtcgaca tatactggcg gccccttcgg tggtatctat aagcttatcc tgacctaaat 114420
caataaattc ctggttaatg gcgtctgcaa tcattttaca gacggtctcc tgtttttccg 114480 catttttttac aaaggtggaa ccggctcgag gatcgggcag ttgtttttttg atatctttaa 114540 gaatatcttc gatgggctgc tttgtgtcta ctttgaaccc tattttggca atcgccctga 114600
taattccttc tataatccgc agctttgctt tactcgatac ggagtctatg tgataatctt 114660
taatgtgttg tacaggattt ttgtcccccc cgccattaaa atatcctccc cctgaaaaag 114720
gacgagtttg tctttgtata tgatcctgta acttcgcata tatatttgct tctgatgaag 114780
gcagtggtct actagaggtt gaagatccac ggttacccat tataataaaa aaaaataaag 114840
atttaaaact acaaatattt tgctgtttat aaacccaatc atataagact aactaaaaca 114900
ttaaatgtag gtgagataaa agcttatttt ttttttaaaa gtttaataac catgagtctt 114960
accacctctt tttcttcttc ctttagaggg gttccataaa tggtttgaat aaaattatgt 115020
gctctaataa ccttgttaaa atcaggtgcc tttccatatt gttcaatatg ttgcacagtc 115080
ttttgtgcaa gcatatacag cttggagtct ttaggtacct ccgatgaggg ctcttgctca 115140
aacaacgttt caaaggagga tgtgcattca ttggtttcat tatcattttt ttcatgaatg 115200
ttctccgaag atgctgagga ttccgtctcc tcttcaaaca gcacatgcag aatcatattc 115260
cattcttctt gagcctgatg ttcagtatac ccttgccctg catatatacg agcagatttc 115320
acaatatcat acttaacagt actaagcaat gtttttatag cggtcgtaac aattctaccg 115380
ctattgataa tctcaacaga aaaccaatta tacaggctac ccgcatgaaa cacaacttgt 115440
gaagatgatc ttaaatccgt tttgaagatg acctccattt tcatggatat atttaaaata 115500
aaatccattc aattttaaaa ttataaaata ataagaagat gccctctaat atgaaacagt 115560
tttgcaagat ttctgtatgg ctacagcagc acgatccaga tttattagaa attatcaaca 115620
acttatgtat gcttggcaat ttatccgcgg caaagtacaa acacggagtt accttcattt 115680
accccaaaca ggcaaagatc cgcgatgaaa taaaaaaaca tgcctactcc aatgaccctt 115740
cacaagccat aaagacctta gaatcactca tccttccatt ttacattccc actccagcgg 115800
agttcaccgg ggaaatcggc tcctacaccg gagtgaaatt agaggttgaa aaaacggagg 115860
cgaataaagt tattttaaaa aatggagaag cggtcctagt accggcggcc gattttaagc 115920
cctttcctga tcgccgacta gcggtctgga tcatggagtc aggctctatg cccctggagg 115980
gtccccccta taagcggaaa aaggagggtg gggggaatga cccgccggtt cctaagcata 116040
tctcgccgta tactccgcgc acgcgtattg ccattgaggt ggaaaaggcc tttgatgact 116100
gtatgcgtca aaactggtgt agtgtcaata atccctatct tgccaagtcg gtctccttgc 116160
tgtctttctt gtcgctcaac catcccaccg agtttattaa ggtactgccg cttatagact 116220
ttgacccctt ggtgaccttt tatctacttc ttgagcccta taaaacgcat ggggatgact 116280
ttttaattcc ggaaaccatt ttattcggcc ctaccggatg gaatggtaca gatctgtatc 116340
aaagtgccat gctggagttt aaaaagtttt ttacccagat tactcgccaa acctttatgg 116400
acatagccga ttcggctact aaggaggtag atgttcccat atgttactcg gatcccgaaa 116460
ccgtacattc ctatgccaat cacgtgcgta ctgaaatttt gcatcacaat gccgtcaata 116520
aggttacaac acctaacctc gtcgtgcagg cctataatga gctcgagcaa accaatacca 116580
tacgacatta cggccctatt ttcccggaaa gtaccatcaa cgcactgcgt ttttggaaaa 116640
agctgtggca ggatgaacag cgatttgtta tccacggcct gcaccgcacg ttgatggatc 116700
aacccaccta tgaaacctct gagtttgcag agatcgttag aaatttacgg ttttcgcgtc 116760
ccggcaataa ctatataaac gagcttaata ttacaagtcc cgctatgtac ggcgacaagc 116820
ataccaccgg agatattgcg cccaatgata gatttgccat gttggtggcc tttatcaaca 116880
gtactgactt tttatacacc gcgattcccg aggaaaaggt agggggggaat gaaacccaaa 116940 ccagtagcct tacagaccta gttccaacac ggctacactc ttttttaaat cataatctaa 117000
gcaaacttaa aatcttaaac cgcgcgcagc aaacggttag aaatattctt tcaaatgatt 117060
gtcttaatca actgaaacat tatgttaaac acacgggaaa aaatgaaata ctaaagttac 117120
ttcaagaata agtatgttga tacctgtggt gtgttttacc tgtgggtttc ctattggaac 117180
ctacgcggca atttttgaca aggctcgtac cgagtatatt aaaaccaaaa tgggcggaac 117240
attgccgcaa aatatcccat tagatgcttc tctccagatt gagttaaaag acctcattac 117300
agctctggga atcccaatgc gggtgtgttg tcgcactcat ttaattacta cgttggatta 117360
tcgtaaatat tattaatatc taaaattgaa aaaatatttt taatgttact agtaaaaatg 117420
actacacaca tctttcacgc agatgatctc ctacaagcat tgcaacaagc aaaagcagaa 117480
aaaaattttt catctgtatt ttctttagat tgggataaat tacgcacagc gaagcgtaat 117540
acaacggtta aatatgttac ggtcaatgtc atagtaaaag gcaaaaaagc tccgctaatg 117600
tttaactttc aaaatgaaaa acatgtagga accattcctc ccagtaccga tgaagaggtt 117660
atacggatga atgctgaaaa tccaaagttt ttggtgaaaa aacgtgacag ggatccctgt 117720
ttgcagttca acaaatacaa aatctcgccg ccattggaag atgatggtct cactgttaaa 117780
aagaatgagc agggtgaaga aatatacccc ggcgacgaag aaaaatctaa gttgtttcaa 117840
attattgaac tgttagaaga agcctttgaa gacgctgtgc aaaaaggtcc tgaagccatg 117900
aaaacgaaac atgttataaa attaattcaa agaaaaattt ctaatagcgc ggttaaaaac 117960
gcagacaaac ctttgccgaa tcctatcgca cgcattcgta ttaaaatcaa tcccgctaca 118020
agtatactaa caccaatatt gcttgataaa aataagccca ttactttaca gaatggtaaa 118080
acaagctttg aagagttaaa agatgaagac ggcgttaagg ccaatccgga taatattcat 118140
aagcttatag aatcgcattc tatacatgat ggcatcatta atgctagatc tatttgcatc 118200
agcaatatgg gcatttcatt tccgctttgc ttggaaatgg gagttgtaaa agtttttgaa 118260
aaaaataatg ggattgatgt gaactccatt tatggctcag acgatatttc aactcttgtt 118320
aatcagattg ctattgctta aacaatttgc tcaaaacaag cttataaacg tttcttaggt 118380
atgcgatacg taaatcctaa ttctttaata agttcttttt cagtagtgat ttttagaggt 118440
actaaagttt gatttttaaa taatccatac tgatttagct tataattctt ttttttaac 118500
gcagctcgaa ttcttattaa ataagaaacg ggacccgtaa aatgaagtac tgcgtatggc 118560
ttttcctcgg ctaaggccgt aaaaagatca agttgatatg tgttttttt ccattcaata 118620
aaaagtacac actttcgttc tccgcagact tttacagaaa aagaaagatc ctttatgcga 118680
atgttgggca ggacgtgttt taaaagtttt ttttctggaa caataataag aagatccacg 118740
tcattaagca ttttctcttc gcgtcttaag ctaccaacag caacgatgtt ttttgataaa 118800
atttttataa gttgtccatt atattcaaac gcaagtcggg agcgtaagtc atttacaatt 118860
ttttttcctt gaataagcgt taacatttta tatttaatat taaaatcttt tcattttata 118920
tattatatac gcaaaatggc acttgatggt tcaagtggtg gaggctctaa tgtagaaaca 118980
ttacttatag tagcaatcat tgtggttatt atggcaatca tgctttacta tttttggtgg 119040
atgccccgcc agcaaaaaaa atgtagcaag gctgaagaat gcacatgtaa taacggaagc 119100
tgttccctaa aaacaagtta aaacatgcaa ttatatgcat gcatataaac gcatgcatat 119160
aaacgcatac atataaaatg cgtaaatact atataaaaaa ctataacata tcaatcaagg 119220
aatcaacact tttataattt tccgtaatat atttttcatc cataatgatg tcagagtaca 119280
tggtccctat gcgaggaaca gagcccataa gggtaggcgc ggcaataccg taaatgggat 119340
tcacggcgga gtcaaccgca gcatctgtca agacctggac tggagacgac aaggccattc 119400
gcaacaacac gttggaaggc tctcttgcat taagccctgc cttttctaga gaggtaacct 119460
gtcccgttct tgtcatgaga tctgcgtaca tgagtaaatg acgatggttg ggacccttgt 119520
cccccataac cgttctaatt tcactaataa tttttgccg tgccgcttct atgccgtaaa 119580
gctccatggt gtctcctata gaggacgata cgatggtgta tgggtcgatg ttatcatcaa 119640
gcattgcgcc aaaaatatta gtcccgtttg ttttgatggc gtagatattg tctagtctta 119700
ccagtttccc ctgggcatcc acacggtggc gcataagctt aacaacattc gcatttttga 119760
tgcctggtat tcctctaatc gtgctattta atagtttatc caccacattt acggcaattt 119820
tttcatccgt agccattcgg gtattggtac tgcgtctaaa ggcgctttcc cgtaggtata 119880
tgcgaataat gatgggaatc cctgaggccg tgttttccac agaatgcatg atgtaggtgt 119940
tggggtgttt agctcttaga ctattaataa tactttctag actaatgctt tttaatatca 120000
tggttgtttt gtttaattcc aagcggatac accagtttgc aatatcctct gggggctgta 120060
gtagaggatg gttttccaga aaatccgtca tccattccac atcacttgca aaatcggggt 120120
acatcacatt tttttttgtg cttgaatacg tttcgtacaa taggtgccac tgcaatatca 120180
accgttcgaa cgttataagc tctatgctgt tagcaatttc ttgcgcatat gttttatttg 120240
tttccacttc cgggttcttt agacgtaaaa gcatttcaga ggattgttca gcctctacgg 120300
gcttcgcgct aaagatctcc tggggccgca caattcccga cttgttggtt cccccggcca 120360
cggaccggtg gtgggagtcc agcatatatt gtgtcaaggg ctctgatacg gactgcgccg 120420
ccaggattcc cactgcctca ccgtagttaa taagactttg agtatattgt agccttatga 120480
ggtccaggat ggcactcatc tgctcgcagg taatgtttaa tgttttaacg gttgccagtt 120540
cgatgcgaat aagcatgcgc atcagagagg cagcccgttt aagataaacg ggtatgggcg 120600
tttgtagtcg ttcctgaatg ttgttaataa acacgtatgg aagatttttg caaaacgttt 120660
tgaccatcgc gtatttttgt agaatacttt tttcgtcgaa gggaagcacg ccactggtgg 120720
agctcagtag aatgtttttt acgatgctgg ccacgtttac cggcacctgt ctaacatctg 120780
taagcagctg actgaaatta aaattttcga cgtttaggaa gatctgtcga tatttatctc 120840
tatccttttt aaggcgtgaa aattcttctt caaacaaggg cgattgtatc ccggtgtact 120900
tgaatttgtc ttcaagttcc tggtccgaca gcatgatggt ttcaaaccgt acggtttcaa 120960
gctggcgcgc atcaaggccg tcctctccgt acaactgctg cacaagacgc gtatcgatgg 121020
aaacccgtcg gtaataatcc acaatacagg attgaaggcc aaagatggct ttacggttgg 121080
catagcctgt ggatgatgtc gataatgctt tgttgatcaa gtcgaatctt ccattcattt 121140
ccccaaagat aaattcaggg gaggtaaggc ccgcaatata gctgttgcag atgaacccgt 121200
aggcctgcgc ctccagggca aacctggggt agtacaccag ggtcctaccg aaggaaaact 121260
ggggttgaat gcgttgtgta ttaatttcaa tttggccgat gcccgccatg atgtgaatca 121320
tattggggtt tgagcccttg gcgccagtgg ccaccatctg aaaaagccca ttggtttccg 121380
gattaatgga attcataatc ggctttaaaa ttctatcggg aaatttaagc gcattcagct 121440
gcaatttttc gtagaagtca tgcgttgtca ggcctatagg cggcatgatg tctccatgaa 121500
gcagccggtt gtttatttcc tccgactcaa gcagcagttc attgataatt tcttggacct 121560
cctgatgtgc ctccggggtt aggagcatgt cggccgtgga cactgtgaat ccggcgttgc 121620
gcacgtagtt tagggcgagc tgctgggtcg caaatatcat tttcaaggcc tgctgcggcc 121680
catacctacg cgaaataagg tgatagattc caccggagga acccgctccg acggcctttt 121740
tgtcaaggac gccttcaatg agttcgccgt tgcgtatttg tgtagagatg tcctgcttgt 121800
tataatgcat gtagggtgca tacacttctg agtaccatgt gggggctcgt tgataattga 121860
tgggggtctg cctcagtagc atagatacaa ccgatttgcc atccagcagg tcagttgggg 121920
agtagttggc aaaacaaggt gggtcggttt gggttgtttg aaacaacccc atggcgtgca 121980
gcttgttcat cacatttttc cccatggggg tgttcgtgcg tgtaagcaaa aagcttccca 122040
ccgtggagtc ctgcacctgc ccattaacgg gacccgagct ctttgtggaa atgaaccagt 122100
ttcgcacaga acaaagtagt tcggcctcaa cgcggctcat gacgctccag ggaacccaga 122160
gattcatctg atccccgtca aagtccgcat tataccaggc acatgcgctg acattcattt 122220
gaaacgtaga aatttttggg ttttcaagaa cgacaatccg gtgaacccct atgctgcttc 122280
gttcgagaga aggctggcga ttaaaaaacg cgacgtcgcc agtgacgacg tcacggtaaa 122340
ggatgtctcc tacctccagc ctaaagtctt gtttgagacc ctcaatgtcg tgaacggatt 122400
gtgttatttg cttatacact cttgaacaac cagggtactg gcgctttcca tttaaaaaat 122460
agggcattaa tctattaata ttataatgtt gcactgtttc cgcaacttgc agcgttcgtg 122520
caaaggaaat gggatagcca acctcgtcca ggtgaaggtc tgagttcccg cagatggtgg 122580
accggctgat cgaccatacc tggctgccca gtagggattt acgaattctt ccctccttgc 122640
gaggaagtct tcgcatgatg gagggagcag ggcgtgcccc catgacgatc ccacgctttc 122700
ccgtgcctcc ctgggttgcg gtggtggaaa cggaatccaa caaaaagtta tagtaaagtt 122760
gctgtatggt ttgcaaattg cggtcaatat ttaaaggtat tttttggccg cgcacgattt 122820
gtaggtcctt cgggatcagc agattctttc gaaccagata ctgaatcacg ttgttaatgt 122880
cgtgaaagct ttgggggcct gacccgattc ccaatctgat gccaggtcgt atgctgatgg 122940
gggggatctg aatggcctta agcacaagtt tttcgggatg ggagtttttta cttcgcccca 123000 gttttacaac ggtgtcgtag gttacgcgcg aaaaaatctc tctgatgatc tgcgggtaca 123060
gtttgtcaat cttgccctgc tgatccgccc aaaaggtaaa ataatcttcc gagtccttaa 123120
caattttggg gtgtactgcc ttacagacgt agcactgctt tccttcggtt tggcttgaag 123180
ccgcttcaat aagacgctta ggcctaataa ggtgctcgta cctctttagg tcaacgatgg 123240
gagccccgca gttgagacat ataaccctta accatcgtcg tatttcggcg atgaagagcg 123300
gctgaagcac cggagcatgc atctgcagta tcccagggtg tcccatacat tgcttgcgct 123360
ggtgtgagca agtgatgcat ttataatggt gatcggtggt tcccattcgc gcatcataga 123420 taccccccttc ggcgggaagg gtgccctcaa ataaattaga aatggtaacc tccataacgc 123480
cttgcctctt atgatcattg tcaccggcaa tattgaactg aacggcggct atttcggcat 123540
atccagcctc catatttttg ctaaatacat aataaaactt caaatgttaa aaaaaaataa 123600
catcggttgg catatttttt tgttaaaacc aagtgttaaa tgatttctaa aacatttatc 123660
ggttcacgaa aacctaccgc acgggcctga agaggaatgc cagttttggg ggaaagctcg 123720
gcatattcca cggtaagctc ttttccataa agatgttttt taaataaggc gggcgtgagt 123780
ttttgaaaaa gagcataacg atccgcgtac gtcaaatgct taggagtgac tacaaaccgc 123840
tttttgtttg gcaattcgca aacccataaa atggcgccta agtcctttcc ctttttttccc 123900 tgagtatagt ccactaaaat aaattcagcg tctagcagcg gtttcagctt ggcaagatgc 123960
gctgagtggt agttgttgta tcccggctca tagggcccat tggcattgcg tacgatggct 124020
ccctcgtagc cctccttaat aaactgcgcc ttaagcctaa gggcctcatc cacattcttc 124080
acgctaaaat tttcaacttg gtggataaag gtaagatctt ccttctgttt aaaaatattt 124140
gttaatagct gttgtctctt gttggaaggc atttgaagct gatcactcca aaaacagtca 124200
aacacgtaaa agtgcagctc ggaggaatct gtcttcgcat tcgcctgccc cgcgatccat 124260
tgcagaggtt tgcggtgtaa ataaagctca ccatccaaat atactctcac gtctataaat 124320
aaataaagct gtttgagctc ttttttaata ttgtcaagac ctaaaaattc ctttttcgtg 124380
cgcgaataca agagaatgct accatcgccc tgctggcagg ccacagctcg aacgccatta 124440
cgcttgcgct gcacgatggg atctgtttct tcttcaaaaa atgtcttagg aattatatta 124500
aaatatttta ccagcatagg ggggataatt cctctatttg tgtgggctcc ccgcttttgt 124560
ctggcatggc gattatattt actaagggcg tccttgaatg cctgatggac taccgttgtg 124620
gcattttttt tacccaagtt ttttccctcg gtaacacgtg tcatttttga tatccgcacc 124680
gccccttctt ccacaaaaaa ttttgtgaaa atttcagcaa cggcgtcttt tacatctgtg 124740
gaaaacatct catctgtgat gggaatgatc gtgttgtgct gcaccacttg cacacaaata 124800
atccatgagg ccttttttcc gcttttcgtt tcagactcaa tcggaggaaa acaaaaaatg 124860
ttgtttgaat attgcccagg aaattgattt agcatggttt taacaataaa ataagcctat 124920
caattttttt ataatttgaa tagttattcc aaattcaata tggcttcttt agataattta 124980
gtggcacgat atcagaggtg ctttaatgac cagtctctta aaaatagtac tattgaactt 125040
gaaatacgtt ttcaacagat aaatttttta ttattcaaaa ccgtatatga ggcacttgtg 125100
gcacaagaga tccctagcac catctcccac agcatccgct gcatcaaaaa agttcaccat 125160
gaaaaccact gccgggaaaa aattttgccg tcggaaaatc tttacttcaa aaaacagcct 125220
ctcatgtttt ttaagtttte agagcctgca tctctgggct gtaaggtctc gctggccatc 125280
gagcagccca ttcgtaaatt tatcttggac tcctccattc tcgttcggct caaaaatcgt 125340
acgacctttc gggtatctga actttggaaa atagagctta ccattgtaaa gcagctgatg 125400
ggaagcgagg tctctgcaaa acttgccgct ttcaaaacgc ttctgtttga caccccagag 125460
caacaaacga caaaaaatat gatgacgtta ataaacccag atgacgaata tctttacgaa 125520
atagaaatag agtatacagg aaagcccgaa tccctaacgg cggcagatgt tataaaaatt 125580
aaaaacacgg tgttgacact tatttctcca aaccatttaa tgctaacagc ctaccaccag 125640
gccattgaat tcattgcctc ccatatactg tcctcagaaa tccttcttgc tcgtattaag 125700
agcgggaagt gggggcttaa acgcctcctc ccccaggtga aatccatgac caaagcggat 125760
tacatgaaat tttatccgcc cgttggctac tatgtaacgg acaaagcaga tggaattaga 125820
ggcatcgccg tcattcagga cacgcaaatt tatgtggttg cagaccagtt atacagccta 125880
ggtaccaccg gcattgaacc ccttaaacca accattttgg acggtgaatt tatgcctgaa 125940
aaaaaagaat tttatgggtt tgacgtcatc atgtatgagg gcaatctatt gacgcaacag 126000
gggtttgaaa caagaattga gtctttaagc aagggcatta aagtcttaca agcgtttaac 126060
ataaaagcag aaatgaagcc ctttatttcg ctaacaagtg cagatcccaa cgtgctcctc 126120
aaaaactttg aaagcatttt taagaaaaaa actcgcccat attctattga tggcatcatt 126180
ttagtagaac ctggcaattc ttatctaaat acaaacacct ttaagtggaa gcccacctgg 126240
gataacacat tagacttttt ggtgcgaaaa tgtccggaga gtttaaacgt accagagtac 126300
gcgcccaaaa aagggtttte cctgcatcta ctatttgtag gcatctccgg agagcttttt 126360
aaaaaattag cgctaaattg gtgtccagga tatacgaaac tattccccgt tacacagcgc 126420

-continued aaccaaaact actttccagt acagttccag ccatcggatt ttccattggc atttctttat 126480
taccacccag atacctcgtc attttctaat atagatggaa aggtccttga aatgcgttgt 126540
cttaagagag aaatcaatca cgtcagctgg gaaattgtaa aaatccggga ggataggcag 126600
caggatctta aaaccggcgg gtattttggc aatgatttca aaacagccga actcacatgg 126660
cttaactata tggatccctt ttcctttgag gagctggcaa agggcccttc tggaatgtac 126720
ttcgccggtg ccaaaaccgg catataccgc gctcaaacag cacttatttc ctttattaaa 126780
caagaaatca tccaaaaaat aagtcaccaa tcctgggtta tcgatcttgg aataggaaaa 126840
gggcaggacc taggacgtta cctggacgca gggataaggc atcttgttgg gatcgataag 126900
gatcaaaccg cgcttgcgga gcttgtttat cgaaaatttt cgcatgctac gacccgacag 126960
cacaagcacg ctaccaacat ttacgtgttg catcaagacc tcgcagagcc tgcgaaagaa 127020
atcagcgaaa aggtacacca aatttacggg tttcccaagg agggagcttc ttccattgtt 127080
agcaacctgt ttattcacta tcttatgaaa aacacgcagc aggtggaaaa cctggccgtt 127140
ctgtgccata agcttcttca gccgggggga atggtgtggt ttaccaccat gttgggagaa 127200
caggtcttag aattacttca tgaaaataga atagagctca atgaagtatg ggaggctcgt 127260
gaaaacgaag tggtcaaatt tgctattaaa cgtctcttta aagaggatat attacaggaa 127320
actgggcaag aaattggagt cctgttaccc ttcagcaatg gcgacttcta caatgaatat 127380
cttgtgaaca cagcgttttt aattaaaata tttaaacatc acggcttttc cctagttcaa 127440
aagcagtcct ttaaggactg gattccagaa tttcaaaact ttagtaaaag tttgtataaa 127500
attcttacag aagccgataa aacttggaca agccttttg ggtttatttg tctgcgcaaa 127560
aattaaatat tttttcataa gaagtactac ccaggtttta aagaaatagc taaaaatatc 127620
atatggatac tgccatgcag cttaaaacgt ctattggttt aattacatgt cgtatgaaca 127680
cccaaaataa ccaaatagaa actattctgg ttcaaaaacg ttacagcctt gctttttcag 127740
aatttattca ttgtcattac tctataaatg ctaatcaagg tcatctgatt aaaatgttta 127800
ataacatgac aattaatgaa cgactgcttg tcaaaacact ggattttgac cgcatgtggt 127860
atcatatttg gattgaaact ccagtctacg aactatacca caaaaaatac caaaaattta 127920
ggaaaaattg gcttctcccg gataatggga aaaagcttat ttcattaatc aaccaagcaa 127980
agggctcagg aacacttcta tgggaaatcc ctaagggtaa gccgaaggaa gacgagtcgg 128040
accttacctg tgccatacgg gagtttgaag aagaaaccgg gattacccgc gaatattacc 128100
agattctccc agagtttaaa aaatctatgt catactttga cggtaaaaca gaatataagc 128160
atatctactt ccttgcaatg ttatgtaagt cgttggagga acccaatatg aatctttctt 128220
tacaatacga aaaccgaatt gccgaaattt ctaaaatttc ttggcaaaat atggaggctg 128280
tacgttttat tagcaaacgc cagtcattaa acctggagcc tatcatcggg cctgcattta 128340
attttattaa aaactattta cgatacaagc actaggatgc cgcattaaaa tgccacataa 128400
ggtaatacac taggaatgtc gcacacgcac aagaatacaa cgtcgccgga gatttattat 128460
ctagtacacg ttttatgtat gtacaatccg ccttcattta atatattgag cggatgtact 128520
atgtatttat tttaacaaaa aacattattt ttttttaatc ttcatcatct gtttttataa 128580
actcagtaat atcaaaagta gcttgtgggg tttcagaggg ttcaccttgg ttatcctccg 128640
tgaggataac atgttcttca ggttcgtcgt cactggagaa cccatcattt aattcctctt 128700
cactcaacat ctgtaaaaaa tcttccaagc tttcgctatc gttaaaatcc tcatcatcca 128760
taagaataat ggtaccttcc tcatcgtttc ctccttgttt cgtgtctaaa taggcctgca 128820
tggcatttgc aaaagtatca aaataggctg agtcagattg ctgttccaaa atatggcctt 128880
gcgtattaaa tgtggttgca tcgttgttaa atgcttgcaa atacagtaag ggatttatat 128940
ccattattat taagcaaaaa aaatttaaat tatttttcga ccgatgttag gtaaaattaa 129000
acaattgcta taggtgttaa gcaatgttta ttgattttaa gtactcaaca accatgatgt 129060
aaatactata cagcactttt ggatttttaa tcaaatccag attaatacta acttcttttg 129120
tgatacagtt cgtaataata gtatcctgct catcgttttg taagatttct tttaatatat 129180
ttttttttac cgggatacta agcaattgat tattttcttt taaaaactcc ttttgatatt 129240
caatcgtctt attcattgaa tatttgtata taactataat tacaaatgtt caatgaattg 129300
ttattcatgt cgggagatgg ctatttaaaa atcatgtcct atttttcttt gctcaataag 129360
catccaaata ttttcatggc gttttattaa ttgttcatta ttgaacgtat cacaaagatc 129420
atttataaat tgcagatagt ttattatttc tttcaagaga gtaacaaaca ttacttcagc 129480
agaacatata ataggtaatt cagtggcgtt aaaagaattt tgatcttgtt gatacgccaa 129540
tggcgaggac ttaaggagat ttgggggtct tgcccaaaac cctaggctgc tgttcttgtt 129600
ttttagggcg tcataaagaa atgaaagcac attgcaaggc ttaagccgcg acatctcctt 129660
ccccttgggc cctttccata tttttagatc taagatctca tccgagctta tagagtaggt 129720
atagtaaagt ttttcaaaaa agcatatctg cttgaagtct tttttagaac gactttcaag 129780
aagcatttct ataatgttaa caagttttgt taggtttaag gcctgttcct gtgtaagctc 129840
ctcttgcacg tgatagactg aaaaagtgtg cttaggaatg aaaatactcc ccgtggcact 129900
ggcctgttgt ctgccaggta tatagtacac gctgctgtta gcaagctgta ccggcacaat 129960
ttgccccact tctgcaacat tattttgcga ttcggacgag ggtatgacaa tagttacggg 130020
ttcagtcaat aggctttcgc cgagaataat attactgtca tttttaataa ttttaacggc 130080
cgctattaaa tcaaaggcat ttaagtaaga aacaacagca gaaaatctta catgcatata 130140
tcctcttccg ctattattcg tacgcataat aaaacaaggg gagcgttgta taacgccagt 130200
aatattaaga ataaaactgt ttttgaaaca cttacccaca taaatgtttt caagctcctt 130260
caaaagatga gcctccacat ttgtacaaaa attggtagga tcatcaatat tcaacgttgt 130320
ctcaaaaatt ttttggtcga tcatatctat aatatattct gtctatttca atttaaataa 130380
tatacgaata aataacgaga ttattttatt aaataagcaa tggtgtatac actttgtatt 130440
tactttgaga tatactttgt gtatcacaac gtgccctaag atgtgtgcac aagtgacggc 130500
attttgtcgt taaaaaggta aaaccagcgg attccatcct gcattccatt tggttgatta 130560
cgagcctcca tttctttttg caaaaggtta ttgcgaatga gtaagcagag cttgatggca 130620
ctaatctttg taaggtttaa acttatgccc aattggtcag caattttttg ttgctcctcc 130680
cgtccgcgtg tttcgcatac ggctccccgg tttagcatgc gaatatcagt aatctcattc 130740
ttttttaaaa cctggatagg tgggcggatt ttaaatttaa gggcctttcc cttgctttcc 130800
atatagccta tgacgatgtc gttttctttt cgtttaacat taatattaag catataaagc 130860
ggaatttcat gccaggtttt atcttctcgc gaggtaataa gtcgcacgga gtcctccgtg 130920
gcatagccca ctagagtgtt gtcatcccca ggcacgtggc ttataatttt aaaaatgtcc 130980
ggaaatggct gaatatcttt ttttgaaaaa gcgatgaaaa actttttata aacctcgaca 131040
agggccccca tacctgcaag attatctata ataagtgctt ctagcatcgt atagtgaaat 131100
gaagcggggt agtggatgag tacctgctcc attggctcat cctgaaaatc cttctgaaac 131160
ttttcataca atacttgaaa gggttctttg gtctgcgagt gttcgaggta tttggtaata 131220
cggatgctgt gcatcgcggg aggctgaaaa tcccgaatat atgtttcaat atctaatacc 131280
ggttcctttt tatggttaag caccgcagcg acgtacaaat gctcaggctt tgccggcaca 131340
tgcataatgg tgcaaagacg attctgtatc cataattcct tgcactggtt ttttgagtag 131400
catagagaaa tgagcgccag cgcgaagttg tcctctgaga agagtttatt atcgatggta 131460
attccctgta tgagcttggg agtggaaaca gccttccata gctcggagta cgtccacacg 131520
gggcgtgcca taaacaaaga tataataata ttagaaattg tttttacctc ttgctccccg 131580
tatccatagg cctcaaaggt attgaggacg gtggctccga cgtttgccgg cgtgatggat 131640
ggactaaggg gcagactttc caacataggc ttatcaatct taatctggtt ggtgaaccca 131700
tcaatggcgt gctttcgcag cgccttatcc ccctcctgta ttaaaatgta ttcttttaat 131760
ttttgtgcgt acttagcgag ctctggccct ccatcgggtg ttgtcgatac gtacaaataa 131820
attgtcacgt tgcgctcact ggggggggagc tccatgtgtg aatttttttcg caccaccctc 131880 ccaaatacct gaataagccg gggaatatca aggggcaatg acataatcat ctcgtaccgc 131940
acggcctgaa agttcaaacc ctccacaatc accttggacc cgatgagaat acgcagctgg 132000
tggccttcca ggttggacga ggcgttaaaa agagccaggc ttcgttcgcg tacagcgggc 132060
tctatttcgc tgtgcagaat ggtgaaccgt actggaataa actgatggtc gctatgtgtg 132120
tgctcatcgc gaatcgcggc gcagatggag cagcgggtcg ttcccacagg ggacgaaact 132180
tcatttaaaa tgccattact ttgtaaaatt tcttgcaaga taagaacccc cgacatgcgg 132240
acccgattgt ggtaaattaa aattttcccc cggccttgcc gaataatgga aagaatgtct 132300
ttcatcattt gagtgtattt tccgctataa aaggccaatc ccgagatgtg cgttggtggc 132360
tgcagcgaca aaaagctgcc actcacatta aagggggctc tacgcgaagg ctcaataatc 132420
tgtaccccgt tttccagaag ccagtctgtg cttgccatag aaagggcggt gggggtttcc 132480
gtcgagttaa acaggccgta agccttgggt tccgtttgtt ttgaaaattt tgggttggga 132540
aacaccatgt cataaatgct gtacgcatta ctcgagattt tagggtcagg gcccagctgt 132600
ttaagcgttt caagctgata ctcagacatg gggcattcga tgaaatgtaa gtacggcaat 132660
gtttcgtctt tataggacaa catctttccg gcaaatattc tttcggggta aaaattggtg 132720
ttggtatcca acaaaaaaga tacccttccg gtgctcagtc tttccacaag agctagggcg 132780 tccttttttcc atttaacgga atgcccactg ctgtcaaaca gttgctggcg ctggaggggc 132840
tggccgttgg gcagctcatg ccgcggaacc aaaaggttta acaggtcgac gtattccatg 132900
acactcccgg ttacgggcgt tgccgacatg aagacggccc tgggggcctg gtgaggtgga 132960
aaggcatcca ggacatactg taaagcgatg ccataattat ttcgttcctg gatattgtac 133020
acgttgtgta tttcatccgc aatgagcagt cctcccctaa gttgctccat gatttttttga 133080 ttcacccgga tgaggccgtt tgtctcggcc tcgctaattt tttgcacgaa ctgagatata 133140
tcgttctcat tcaatgtatc ttctgcttcg tcagaacgat gaaacagaga aagcacatca 133200
aagtttttct cttcaccctt actcgtaata ttgaaaagct tggatgcaaa ttccttatag 133260
ccgtaaaact gaaaaaagcc tccgcggttt ctatcggtta aacggcgctt taacgtacta 133320
acgaacccat ttagatgccg tgattcgacc gacgtggtgc tgccagactg ctttgcaatg 133380
tgaagaagcc ggtgtagctc agcgacctcc ttgtaagaaa caaatcccag ctcaggacgt 133440
cttagcattt ctgtttgaat gatggcgcgt gtaaagccta ccacaaaaat ccagggcgca 133500
ttttcaataa aattcatgta gtggttcata aattgacgcg cgatggcaat cgcggcaatg 133560
ctttttcccg tcccggtctg ccagtttaat aaaagacgcg agtagggcgt gttgggattt 133620
tgaaagtttt ggacgaaaag ctgggcatta tgcaattgga gacccttgat ggaaggaaag 133680
ggcgacgcgt aggggtcaca cggaaaaaac gctcgccccc ccttctcgca gccaggccca 133740
ccgatctgga caaaatgagc ccgcagatca cgaatgagct ctttttggtc gacaggaggg 133800
gaaatcaacg atttaaactc ctttcttcgc gccaactgct gcaaaaagtc tgcggcatcc 133860
aattcgggat acgccatatt atcataaaaa aaataaacct ttttatgaaa acttttatgt 133920
gattctgtat tgcaattgtt ttttatgaat actgtaaata agcgtatcaa cttgtttttc 133980
taacgaagag gcgttattct ttttttctgg atataaaata ataataagta taataattaa 134040
gactaaacag caggcaatca ctatcaaact catattatac ttactttttt ataaaaagta 134100
ttatatctta tgaatgcgca agttcagcta attgttcgtc gcttggaatg tgggactgca 134160
gggaggtgga gtttttcctt tttctaaaga ataccgggaa atggtggtga ggctcaggtt 134220
gttgtacata gtagctagga ggaggtttag gtatgctcga cttgcagtca atagtccggt 134280
tatagtaaac gatggcaacg atgataagaa taataatgag caaaatcaaa atgcccagga 134340
gaatcgcagt tgttccggga tatttggcga ttgtatgggc taaaaggcct tgggtgcttt 134400
gtttaattcc ctcgcgggtt gacaggttat gagaaagcag tggagacgtt tcagtgtcca 134460
tttattacaa ttgaacagtt atattaatct caaataaaat ataacacaaa attaattatg 134520
gccatgcaaa agttatttac gtatatttac gagtttattg aatatcgtaa gatggtgctg 134580
ttggaagaaa aggtaccata tgataagttt gttcaaatgg tacttaatac aggatttttt 134640
cgtattaacg cggagacgct gaatcacgga atcgtatccg tgtttatctt tggagcaaat 134700
ggcaagtacg ttcaccacgg aggcgacatg agaacgcttt taacgaatac gcttaatgaa 134760
aaaaaacatt atgaagaatt aattttaatc gttgataagc ccgttttaag caaaaaaaat 134820
attttagata taatcgtcga gcagcgcgct gcaaatccca cgattgtaat aaacatatat 134880
ccctaccacc tgttctgcat taacattccc aaggtgagtg ccattcctaa acataaacta 134940
attactcagg aggaggcgca ggagttttta ggtcgcgaat atctgcaacc gcaggacctc 135000
atgcaaatta gcgcgtcaga ccccccggtg gtctggctgg gaggaagacc gggagacttt 135060
gtgcaaattg agcggccctc agagacagct atgcacgctg ttgttatccg ctttatcacc 135120
aagtccaaaa tttgagtccc gtgtttaaag atgacagaca gctaagtaag catatctgta 135180
aaattgtcga tgtcctctgt ggatagagcg ctttcctctg agcagcaaat tttttcatac 135240
atctccatgg gggatggcga ggctttaata gtatgtaggt cacgtaagaa ctgttgtatg 135300
atgggatatt tgtcttttaa aaactgggga tgtttcataa ctggaattat ttgaaagata 135360
aagaccttcc atccaaagta gccaaccaca tttggcattt cgggacacgc ggtttcataa 135420
ggcatagaat agtgaatagt gtactgatct ttttgataca gcgtttcaag tagttggcga 135480
aatgtttccg cgtcgagcgt gccaaaatct tgaggagcct cggtgtgctc ctgtgtagag 135540
cagatcgtga tgattcccca ggcaagcggg agcatggact ctggagggtg gatatccgta 135600
ttggtctcat tattcgatcc cagctgatga atgccgcaca cgcgaaacat ggcctcgacg 135660
tagatgccca tagagatagg cggcgaaagg gcaagaccgg attgtatttg cggcatatag 135720
taggagggca ccgagttttt tatttttcgg ttgaatgggg actttatttc taccagcacg 135780
gggatgcgtt tcgtggcctc atagcgtacg ttgttaaaaa ttgttttgat ttcccaggac 135840
tgttgagtgt atcccagcgt taggtgacaa aacccatcgg ggctattact atgtccgggg 135900
tatcccaaat aggtcccatc aatatgaata ttgtcaccta tgacggtggt ttggcagaac 135960
aactcaagca gatctttact aacacgctca aaaagggttc cccagctaca agcagcgcgg 136020
ttcaaattct tcttaaaaag atttgctttt tccgccaagg ttatataata gcttttgtaa 136080
gggtttaaac ctaaaacgct ggcaaggtca gagccaccca cctgagtgcg acgaatagca 136140
tgccaggcat cggagcgctg ctgaggagag tctttaaaca ggcgtacaaa ggtttccatt 136200
atacttgttt taacaggaat tcaatataaa aagtcaacac agtttgcaat ttttccaatc 136260
tcaagatata gccatacatt ttttttcca attggcgaat atgtttaagc tcatgtgttt 136320
caatattagc atccggaaat ttaaatgcat aaagatgttc aaaggcctga tttatacacg 136380
tatcaaagga tctgtggtat gttattagct tcagcatgtg tgccagatct tcaagatggt 136440
ctaaatttat acggttttcc acgtggtgga tcatgtctgc cacatcttga gcccccatcc 136500
aggggatcac aaggtactcc cccttaaaga tgattcgtcg tttttttaaa aaatcatgaa 136560
aacgttttaa agcttcaaga aaggggcagt tgggctttga ccccaaaatg ctgacgacga 136620
tatcctcggg catgatgtat tcgcagtgag gatagtagtt tacggactct aattcagcgg 136680
cccgccgttt tatttcgtat cttgcccagt tattcagaga gtactccacg cctccgacca 136740
caacagacat cctatctatt aaaaaataac aataaaaacc ttatgaaatc tatgtatagt 136800
ggccgctaaa atgtctatat tagaaaaaat tacgtcaagt ccctctgaat gcgcagagca 136860
tcttacaaac aaagatagct gtttaagtaa aaaaatacaa aaagagctca cctctttttt 136920
ggaaaaaaaa gagacactcg gttgcgattc ggagtcctgc gtaattaccc accccgccgt 136980
gaaggcctat gcgcaacaaa agggactgga cctctccaaa gaactggaga ctcggtttaa 137040
agcgccagga cccagaaaca acacgggtct tcttacaaac ttcaatattg atgaaacgct 137100
gcagaggtgg gccataaaat acaccaagtt tttcaactgt cctttttcca tgatggactt 137160
tgagagggtc cattataaat ttaatcaagt ggatatggta aaggtatata agggagaaga 137220
gctacaatat gtagaaggca aagtggtcaa gcgtccttgt aacaccttcg gatgcgtttt 137280
aaacacggac ttttcaacgg gcactggaaa acactgggta gccatctttg tggatatgcg 137340
gggcgactgc tggagcatcg aatattttaa ttcgacggga aattctcctc caggtcccgt 137400
tattcgttgg atggaacggg tcaaacagca gctattaaaa atacaccaca ccgtgaaaac 137460
gcttgcagtt accaacattc gtcaccaacg gtcgcagacc gagtgcggcc cctacagcct 137520
gttttacatc agggcacgcc tcgacaacgt gtcatacgcc cattttatat ccgctaggat 137580
taccgacgaa gacatgtata agtttagaac ccatctgttt cgcatcgcat aaactaataa 137640
agtttgaatt ctttatagga ataaaaatgg aagcgtttga aatcagcgat ttcaaagagc 137700
atgcgaagaa aaaaagcatg tgggctggcg ccctcaacaa agtcactatt tcgggtctta 137760
tgggggtctt taccgaagat gaggacctta tggcgttacc cattcacaga gaccactgcc 137820
ccgctttgtt aaaaattttt gacgagatca tcgtaaatgc cacggatcat gaaagagctt 137880
gccataacaa aacaaaaaag gtaacttaca ttaaaatttc gtttgataaa ggtgtgtttt 137940
cttgcgaaaa cgatggcccg ggaatcccca ttgcaaagca tgagcaagcc agtcttatcg 138000
ccaagcgcga tgtgtatgtt cccgaggtgg cttcatgtca ctttttagcc ggaacgaaca 138060
tcaataaggc caaggactgt atcaaggggg gaaccaacgg cgtcgggctg aagctcgcca 138120
tggtgcattc gcagtgggcc attcttacca ccgccgacgg cgcgcaaaag tatgttcaac 138180
atatcaacca acgcctagat atcattgagc ctcctaccat tacaccctcc agggaaatgt 138240

-continued ttacacgtat cgagctcatg cccgtatacc aggaactagg gtacgcggag cctctgtctg 138300
aaacagagca ggcggatctt tccgcctgga tttaccttcg cgcctgccaa tgcgcggcct 138360
acgtgggaaa aggcaccacc atttattaca atgataagcc ttgccgcacg ggctctgtga 138420
tggcgctagc caaaatgtac accctgttga gcgcgcctaa tagcacgata catacggcga 138480
ccattaaggc cgacgcaaag ccctatagcc tgcacccccct gcaggttgcg gcggtcgtgt 138540
cccccaagtt taaaaaattt gaacacgtgt ccgttatcaa cggggtaaat tgcgtaaaag 138600
gagaacatgt caccttttg aaaaagacta ttaatgaaat ggtcgttaaa aaatttcaac 138660
aaacgattaa agataaaaac cgcaaaacaa cattacgaga cagctgttca aacatcttta 138720
tcgttatagt gggttccatt ccaggaatag aatggaccgg ccagcggaag gatgaactta 138780
gcatcgcgga aaatgttttt aaaacgcatt actccattcc ttctagtttt ttaacaagta 138840
tgacaaagtc tatcgtggat attcttctgc aatccatttc taaaaaagat aaccataaac 138900
aggtcgacgt agacaaatat acgcgtgccc gcaatgcggg aggaaaaagg gcgcaggact 138960
gcatgctact cgcggcggaa ggggatagcg cactttccct gctgcgcacg ggactaaccc 139020
tgggaaagtc caacccaagc gggccctcct ttgacttctg cggcatgatc tccctgggag 139080
gagtcatcat gaatgcctgc aaaaaggtga caaacattac aacggactct ggagaaacca 139140
ttatggtgcg caacgaacag cttaccaata ataaagtgtt gcagggaatc gtgcaggtat 139200
tgggtctaga cttcaactgc cattacaaaa cacaggaaga gcgagcaaag ctgagatacg 139260
gctgcattgt tgcgtgcgtt gatcaagatc tggatgggtg tggaaaaatc cttggactgc 139320
tgctggccta ctttcacctg ttttggcctc agcttattat ccatggtttc gtaaaacgac 139380
tgcttacccc gctgatacgt gtgtatgaaa agggtaagac catgcccgtg gaattttact 139440
atgaacaaga gtttgatgcc tgggcaaaaa agcagaccag cttagccaac cataccgtaa 139500
aatattacaa gggattggcg gcgcatgaca cccatgaagt aaaaagcatg ttcaaacatt 139560
ttgacaacat ggtgtacacg tttaccctgg atgactcagc aaaggagttg tttcatattt 139620
attttggcgg ggagtcggag ttgcgaaaaa gagagctttg caccggcgtg gtgccgctca 139680
ccgaaaccca gacgcagtcc attcatagtg tccgacgaat tccttgcagc ctgcatctgc 139740
aagtagatac caaggcttac aagctggatg ccatcgagcg gcagattccc aacttcttag 139800
acgggatgac gcgggcgcgg cgcaaaattt tagccggggg ggtgaaatgc ttcgcctcca 139860
acaaccgtga acgaaaggtt tttcagttcg gggctacgt tgcagatcac atgttttatc 139920
accatggcga catgtcgtta aacacaagta ttataaaagc cgcccagtat tacccaggct 139980
cctcccacct ctatccggta ttcataggca taggaagttt tggctccagg cacctgggag 140040
gaaaggatgc aggatcccca agatacatca gtgtgcagct tgcgtctgaa tttattaaaa 140100
caatgttccc cgcggaggac tcatggcttc tcccctacgt ctttgaggac ggccagcggg 140160
cggaaccaga gtactacgtg cctgtgttgc cgcttgctat tatggagtac ggcgccaacc 140220
catcggaggg ctggaagtac accacttggg cccggcaact ggaagacatt ttggccttgg 140280
tgagggccta cgtcgacaaa gacaacccaa aacacgagct actgcactat gcaataaaac 140340
ataagattac tatactcccg ctgcggccct ccaattacaa tttcaagggc catttgaagc 140400
ggtttggcca atactactac agctacggca cgtacgtcat ctcagagcag cgaaatataa 140460
ttactattac ggagcttcct ctgcgtgttc ctacggttgc atacatcgaa agtataaaaa 140520
aatcgagtaa ccgcatgaca tttattgaag aaatcatcga ctacagtagt tcagaaacta 140580
ttgaaattct ggtgaaatta aagccaaata gtcttaaccg tatcgtggaa gaatttaagg 140640
agactgaaga gcaagattcc atagaaaatt ttctgcgcct gcgcaattgt ttacattcac 140700
atctaaactt tgtaaaacct aaaggtggca ttatcgagtt taacacgtat tatgaaattt 140760
tgtatgcgtg gctaccttac aggcgtgagc tttaccaaaa gcgtcttatg cgtgagcacg 140820
cggtgcttaa gctgcgcatt atcatggaaa ctgctattgt acgctacatc aatgagtctg 140880
cagagctaaa tctttcccat tatgaggatg aaaaggaggc aagccgcatt ctaagcgagc 140940
atggatttcc cccgctgaac cacacgctga tcatttcccc tgagtttgcc tctatagagg 141000
aactcaatca aaaagcactg cagggctgtt atacctatat actatctttg caggctcgag 141060
aattgcttat cgcagccaaa actcgtcggg tggaaaaaat aaaaaaaatg caagctcgtc 141120
ttgataaggt tgagcagctt ttgcaagagt ctccctttcc cggcgccagc gtatggctgg 141180
aggaaattga tgcggtggaa aaggctatta taaaaggaag aaatactcag tggaaatttc 141240
attaaacgct accggtttta tgatgtccaa taggtgttaa gcaatcagtt catcaacatt 141300
tttttcaaga atttgaaaag tttggataat gttctgaata ctttttttcta aaagagttat 141360
caaatcttct tgtgaggcct tatgaataat tgttaatacc atttcttgct tatggggaac 141420
acactgatac cccacaaagc taatatcagg aatcatttca taaatatatg tttttagcag 141480
atttccgatg gtatgggttt catcttttat cgtgataatg gcctttgttt tttcctcatc 141540
catggaaaac agcacaagtt ccggctgcgg ctcttcaaag ttttcataaa ttttttgaat 141600
gctttggatt cggccaataa tgatccggca ggcgtttttt aaatacgtgc gaacggcctg 141660
gttgatatgt ggcagcggca ccgctggaaa gcaaagcccc aggcggtggt gacgcgggtc 141720
tgaggtcata gagctttgct tgtaaccgct aagcgccata tattcttttt tatccgttgg 141780
gtactgttca atgtcaaggt gggaaaaatg tgttttaacg gcaagattaa aggcggcatg 141840
ctttcgtcct atgccctttt taatatagat atcctctata atcaacgatt ttccgggttg 141900
taggaagcca atctcaaagg taggattaaa aatcgggtat ttaagcttag ggcctgccac 141960
ctggatgaga tcgcggctat agatggtttt aacctcacag ctattgttta aactccgcag 142020
agcaaatacc agtgtctcgt ttttcgcata aatcggaatg aaattaatgc ggtttctaat 142080
aaattgttcc gtcataaaca ggtccgtgga atcctcgatc ttatacccac cgggcttaat 142140
atctagcata taattgggaa tttcatcttg caagacccgc gacaggccgt ggaccgcggc 142200
tctgctaatg cccttaaagt ccataacaac attgaccggg acgaggggca actgctcctc 142260
gagctgaaat agttttttgg ccgcattttt aataaagagg ttggaaaagt ctatcaaaaa 142320
cggtttgatt tccacgtttt ggaaaatttt ttccatttgt attataaata tatctatata 142380
tattcaaatt atggtagttt atgacttgct cgtttcttta agtaaggaat ccatagatgt 142440
gctacggttt gtagaggcaa accttgcggc gtttaaccag cagtatattt ttttcaatat 142500
ccaaagaaaa aactcgatca cgacacccct tctcattacg ccgcagcagg aaaaaatttc 142560
gcaaattgtt gagtttttaa tggatgaata taataagaac aatagaaggc cctccgggcc 142620
gccgcgtgag cagcccatgc acccattatt gccgtatcaa caatcctcgg acgaacagcc 142680
catgatgccg tatcaacagc ccccggggaa tgatgatcag ccatatgagc aaatatacca 142740
taaaaaacac gcgtcgcagc aagtaaatac tgaactgaac gattattatc aacatattct 142800
tgcattaggc gatgaagaca aaggtatgga cagcatgtta aaacttccag aaaaggcaaa 142860
aagggatagc gatgatgagg acgacatgtt ttctataaaa aactaacgac gtaacaatta 142920
aacaaaaaat aaaaatcatt ataaaatgaa tcttgaatac gtccaagttg ttcaaaaatt 142980
taatcaagta ctcctagaac ttaccaaaaa agtatgtacc gttgtgggcg ggagcaaacc 143040
cacctattgg tatcaccaca ttagaagggt ttgctcagaa tgtccatcca tgccgatgag 143100
tatgataggt ccgtatctga atgtctataa agcccaaatt ctaacaaggg acaagaattt 143160
ttttatgaat ttcgatcccg cgcataatga gtacaccttt atcattcaaa aactaaaaga 143220
agcagcccga aatatgccgg aagacgaatt agaacagtac tgggtaaaac ttttattttt 143280
acttaaaagc tacataaaat gtaagccctt tattaattaa agaattgatg cataactaat 143340
aaatggccgg tcgtgttaaa ataaaacaga aagagctcat agactctact gtaaaaaaca 143400
aaaatgtgat gaatctgttc catgaaatta taggctcaaa aggcaatatt aattttagcg 143460
ttgtctggcc caagtttaaa aaaatcaaac agagcgttta tgactacatt tccactcttt 143520
ctgtgctgga aaaagcaaac gttatgcaaa actttgaagc tgataagaaa ctgttggaac 143580
tttttgtaca aaagctgtgg gctgcctatg aaggctattt caaatatccc gagattgaaa 143640
aatatgaggt ggaaggccag gtaaatttca atctcgtacc tcagtgcgtc ctcgaaaagt 143700
ttagccagtt gtataggata agaatcaatt cagagcttgt cacactcatc ctaaacagct 143760
gtgcctttat gagtaaatat aacgattata ttctcaaaaa agatccctac atactaacca 143820
taacccccgg cctatgcttt tcccccattc ccaacttcga ggacctaaat tttaaacatc 143880
tttacaacag tgataaaaat tctcagcatg acaaagagtt tatcatgttt atattatata 143940
agctttatac ggctgcccta ggagtgtaca atgccatctc gattccagac atcgacgtag 144000
aagaccttga aaatatcatc ctatcctcgg tgagccagat taaaaaacaa attccgcgct 144060
gcaaagacgc cttcaacaaa attgaatctt cggtacacct gttgcgcaaa aattttaaca 144120
catattacag tgactatgtg ggctcaggct acaacccaac catcattatg gaacagtaca 144180
ttaaagacat atcacaggat tccaagaaca tatcaccacg catttcctac cagtttagaa 144240
ccatcatcaa gtattaccgc gacatgattg ccaccaggca tcaaacgatg gacccccagg 144300
tattaaacct cgtaaagcac gtcgaaaaga aattagatat gcttgataga gaaaaaaatt 144360
agtatatata gttatggtga atctttttcc tgtttttacc ttaattgtga ttattacaat 144420
tttaattacg actcgagaac tatccaccac gatgcttatt gtttctcttg taacagatta 144480
tattattatt aatacacagt atacggaaca gcagcatgaa aacaatacat ttttcatgcc 144540
gcaaaaaaat tcttttaacg aatcttataa taaagacaaa aaatctaata tacatattcc 144600
ctaccagtgg ctggcgcctg aactgaagga agctgagagc aagtactggt ggggcaatta 144660
tgatcctcat agcgagcccg ttctcgctgg cgcatcttga atatcttcat acgtggcacg 144720
tcaccatcaa aaacattgcc caacagcacg ggcttgatat aaaggtggcc attgtggtct 144780
caacatcgca tttaaataat tttttgccaa tttccggggc gcttaacatc gaatgtataa 144840
ccttccccag ttgcggcatc aaggagatag acctcctatg ggcgcgcatt aaactatttc 144900
aacattactg cgccatcggt gcccgtcttt tatggctggt aagtgctgac atcaggcccc 144960
ctgtttcagc gtggccagcc atcgccgaca gtctaaaaaa gggagcagat gcggtcgtta 145020
ttccctaccc ctcccgatgg aacaatctta tacctaccgt catcaaagaa atagttgtcc 145080
accaaaaaaa atgccttgtg gcggtggatg cacgccacct tgatacagat acccagattg 145140
taggggccgg gatgggctgc atcgtcctaa ccctaaaggc ccttatggtg cgcctaagta 145200
ttggcaaaca gcccgttaag atactgtggc ccgaccttca cggcactgcc gagggcattc 145260
ctctggaggg ggtggaggtt ggctggtttt taaacgctta tgcgcataaa ttaaatatac 145320
gctgcctagg ggctgatcat attgcgcagc acttaactta attctttatt taaaaagtcc 145380

-continued acgcatccag tggcggccta cattaagggc ctacgcacat aaatatacac tggctagaag 145440
tacgccttca tttaaaccat tgaattattt atataatggc tgcaaacatt attgcaacaa 145500
gagccgtgcc aaagatggcc agcaaaaaag agcatcaata ctgtctgcta gactcccagg 145560
aaaagcgtca tgggcattat cccttttcat ttgaattaaa gccttatggg caaacaggcg 145620
caaatatcat aggagtacag ggctcactta cccatgttat caaaatgaca gtatttccat 145680
ttatgattcc ttttccttta caaaaaactc atatagatga ttttattggt ggacgcattt 145740
atttattttt taaggaactg gacatgcaag cagtttctga tgtaaatgga atgcaatacc 145800
acttcgagtt caaggttgtt cctgtaagcc ccaaccaagt agagcttctt cctgtgaata 145860
ataaatataa atttacatat gctataccgg tagtgcaata ccttacccca atcttttatg 145920
atctttcggg accgctagat ttcccattag atactctttc ggtccatgtg gatatcctct 145980
ccaatcatat acagcttcct atccaaaacc ataacctaac aacgggtgat cgtgttttta 146040
tttctggata taaacacctg caaacgattg aattatgtaa aaataacaag atttttatca 146100
aaaatatacc gccgctttca tccgaaaaaa taaaactata tatactaaaa aatcgaatca 146160
gaattccgct atactttaaa tctttaaaaa cgtctaagta ataacatttt tatagtctac 146220
tcctagttcc gaaataggct gaatttcttt tttaagtcct ttaaaccaag gatgtgatac 146280
aagactctta aaggaaagcc gcttattttc attaattgtt aaacattccg tgataaactg 146340
ttttcccgtc tctgaaatgt tctcgggaat ataattttcc cgtttcagga tatcatttaa 146400
ataaaaattt tctgcacgaa atctaaaaag attaaccgcg accataccta tcgtccacac 146460
ggttaaagga agctggtagt aataaccata ataataaaat tctggacaca cgtattccca 146520
tgttccaaac atattatatt ggggacgggt ttcgtctaat ctaacagcgc ttccaaagtc 146580
aatgacctta atgatctttt gatttatgtc tataataagg ttctcatcct taatatcccc 146640
atggataaag cccttctcat aaatgttttg tataataaga ataagctgga atattatttt 146700
tttggcttcg gtttcctcaa gtttttttaaa gtaatgataa tgaagtagat caacactatt 146760
tggaatatat tctatgatta gtatatgata catagcattt tcggtatatt cgataagctt 146820
aataacaccg ggagtatctt gcagggcttt caacacgatg acttcatttc ctggaatttc 146880
ttttttagaa acgtacttaa atataatggg ttgccctact tgatgaccca aaaagacgtt 146940
atttctgcca ccctcaaaca tgggtctcgt cgcaatgaaa tacatgtgct gcgttgtgga 147000
gatcctttcc acctttgctg taggataaaa cgcatattgt gcctggggat tttttaacat 147060
ttttttaagc tgttgttccg gcctggacat gttttattag ctttatatat aaagggttag 147120
aaggtttaat ttcaatatat gccttaatga tgggattata ttcgtaaaag gtatagccta 147180
atcctacgtc tttgtttttt tggtaaaaaa actgtttgcc ctcgtaggat atgctatagg 147240
cttttacttc ggcttttaca agcggttggc agggattggg caaacgtaaa tcgcgttcaa 147300
agttttcatg aaaaagcaaa gcatttgtgg gctgacacat cagacagccg ctttcgccat 147360
tgaaggcaca ttcaatggcc gcccttttta gtaaatcgcg gaaagcagaa ttaagatggc 147420
tcttttcaag ccccctttcg tgaaaacgct catcaatcgt tttttgttcc tgactgcctt 147480
cgggaatact ataaaacatt ttttgattag ccaccgcgat gtacaaaaaa ggctgtacgg 147540
ttttctcctc gggcggtagc gcatcgtggc taccaatgcg tataatgcgc gccttcactt 147600
gatcctctcg ggccttatcc cagtacggct ctaggatatg aacctgccgc ccgtatttga 147660
gatccaatcc ctcagctcct gttttagaga cgagtaaaat tttaataacc tctccgtgta 147720

-continued tattcagcgg cgaattccaa agctgctgga tcatgtcgcg ctctttagat aaaatttcc 147780
ctgtaataag cgtaaatcgt gttattttgg aggacaggac taacgtatgg gtcggcccat 147840
cttccgcaaa gtttttcacc ataagatctt tcccatcctt atgaaggagg atggtgttgt 147900
gcccttcttc caatactttt aggggctgaa ggcactggta gccctctatt tctaaaaagc 147960
gggccacgac gtgaaggccc aattccacaa actgtgagta aatgagcaca gggcccggag 148020
acgttttaat atttttagc atgcgtacta ttttgggact agaattttct gtgaaggcct 148080
ctttgggcag ctgctgaaca gcctctgata atttttcatc ctcctttact gttagcattt 148140
cggacgcgaa gatgctgatc atacgggaac gcacatagta ggaggagcct gactcttgct 148200
ccgatcctgg caggcagagg gcggcggcat ttattttttc atacattcct gagctggcgt 148260
gcttttccgc gttttcaacg tctcgggcca gcagatattg cctatactgc tcgggtgaca 148320
tttcaacctt ttctataata agaggaagct ctgtggggaa tagcttgttg agctcattct 148380
ggtttccagc gtagcttatc atacccacta ggcggtttag tagtttgtcc gcgtttaaag 148440
ggctattcgt tgttttattg acataagcgg tgtagaatct ttcatagtga agaggtaata 148500
agattcgccc gcttagcata ttaaaacagg gcaccatttc aaaggggtcc ttcgaacacg 148560
gggtgcctgt taaaaacaga atacgaatat ttttagcttg cataatatta ttgtacagct 148620
ggcgggcatt tgttttatca ttggcgctat tgataattcc tctaaagagg ttgtgtgcct 148680
cgtcaacgat gagcaggcat ccatttaggg accctcccgc ctttatgatc tgctgcccca 148740
tgttgtaagc gtctagggac acaaacctga agcgccgcga gattttttgt agctctttgg 148800
agtgatccgt cgtttccgga tataaaagtt taataagctt taacaaagac tgttggaagt 148860
ttgagtgcaa cgacttgggt gcgatcagaa tcgggttgta aatatgtgaa agtgagatgg 148920
caagcgacag gctcaaaatg gttttcccca tgcccatctg gtgatagatg aggaggcccc 148980
gtgtgttttc cccctggcct atcccaaatt taggatccga aaaggcggtg taaattaaaa 149040
actggtagta tttcagggct cgtgcaaagc gggcagtgag tgaggtgtct ttgctttcct 149100
gaagctcttt atatttttca tatacctctt ttaggtatgc ttctatttgg acggggaagg 149160
aggtgttgtt gtgcacgcaa gacatgactc gttataagga tcccatatta aaacttcatt 149220
agaagaatag ggctgctgat agctagcgct gcacttaaaa atggggtagc ccttttttctt 149280
gtaaatccgg tgcctgtcgt agacctggct agaaagcggg cttagtgtat ctttaatgtc 149340
cacaacgatg cgtacctttt tttcatccga tccctgccgg gtaatacgtc ccaagatttg 149400
ctccatgttg tttctgcggg gcgttgccat gatgatcgat gtcatatgct tgaaggaaat 149460
gcctctacgc ccgtagccat aggtcagcaa gataatggaa gcgctgtgtg cctgagaaag 149520
agcggtattt gaaaccccgc cgcataggag cgccacctcc ggaacgataa tttgaacatc 149580
tttgaattct ttggaaagcg cctgataaaa aatttctaaa agtttgcgaa attccacgaa 149640
aatgatgatg ccatacggct catcggtccc ccatttgtga ggctcagcgg tatgcaggga 149700
gtaaagccgc tttgcctcat ttacgacaag ttgtatacgc gaaggatctt gaagtagttt 149760
atcaatggtg gcaatggccg atacctttc attaatatac acagggctaa cgaagtcagg 149820
atgtccctga tattcgattt ccctcacgta cccggaaaag gttgtggtgg gacttacagt 149880
cctctggggc tgtcctagat ggtgaatatat aatcttgtcc ataccatcgg gccggtccag 149940
gggtgtagcg gacagtccta atatccgact aagttgtatt ttccaaaaaa ttttgtaatt 150000
ctccggcgag tgtaattcat gtgcctcatc taacacgact agaccaaagg gctcaaagaa 150060
ctgctcaggc ttcttgcgca gggtattaat gattcccacg atgacgtcgt actctttgct 150120

-continued cgtcatgtcc tttttcttgc acgctgcatt attgtaagca gctacacgta ggtggggcag 150180
gagcaatgtt agctcgtcga tccactgtat ttgaatcgcc ttggtgggca cgatgaccag 150240
ggtagggtac aaaagttttt gaataatgct gatcgcaata cgcgttttcc ccaaaccggt 150300
atttagatgt aggtaaaagc gcccataggg ggacaggagc tttttatgaa tcttatcgac 150360
catttcttgc tggtagttaa atagtggaaa ttctgtttca acgcatggga gggcccgcag 150420
cgacacgggg cgcgtcgtgt aaaccatgtt aaacatttca aactgctttt gcagcaatat 150480
gggaaaataa atgtattccc cctgcagcgt gaaggcagtt tcctgtctta tggctatgtg 150540
ctttggctgc ccgggtaatg cccgcgccgt aacggtgagc gccttaagaa cgcgcccgaa 150600
atcatgttgt aatttacttt gtagcttctt ataatttatt cctattccag caaaggatat 150660
aatggcctcc attctcacgc tggacgggtt atatgcagag gttccaaaat tcttaccaga 150720
ggcgttacga gagggctgtg ctggcaagaa tcctctaagc ttttatattc aacaaatttt 150780
aaatttaatg ggatgtgacg gtaacgagta ccatgttctt tttaccagca gctccgagga 150840
agcaaatact catatgatca tggccgccgt gcgtcgccat ttgctgcgga cgcagcaaag 150900
gcctcatgtc attatcggag cagccgagcc ccctagcgtc accgaatgtg tgaaggcatt 150960
ggcgcaggaa aaacgctgcg tatacaccat catcccccta aaaaattttg aaatagatcc 151020
tgttgcggta tacgatgcca tacaaagcaa tacctgctta gcgtgcattt caggcactaa 151080
tgctgttgtc aaaacgttca acaaactcca ggacatcagc aacgtgttaa aaggtattcc 151140
cctgcactca gaagtgagtg atcttgttta tcaaggatgt attcaacaaa atccgcccgc 151200
tgatagtttt tcaataaata gtctctacgg cttcctggga gtcggtgttt tgggaatgaa 151260
gaaaaaggtc atgcaaggat tggggccgct catttttgga ggagggctga gaggcggaag 151320
ccctaatata cccggaattc atgccatgta taaaacgcta acccagcaaa ggccttctat 151380
gaaaaaaata aatacaatac atacgctgtt catgaaaact ttaaaaaaac atcagcatgt 151440
atatctaccc atagggggcg tgtctgcaga ggacacgtct gcagaaaaca tatctacaaa 151500
agacatgcct gttgaaggcc cgaagggact cccgggctat attttattta gcgttggccg 151560
tcgcgccgag gagctacaaa aaaaaatttt cactaaattt aatataaagg ttggccgtgt 151620
tgttgactta caagagatac tgtttcgtat caaaataccc caaaaatact gggagacatt 151680
attgttcatc caattaagag ataatttgac caaagaggac ataaaaagag ttatggttgt 151740
tttgatgcat ttagatacca tcactcctcg tggctctctt cctcctccga gccactcttc 151800
ttctttttct taatcgtttt tgtttgttct ataataaggg aaaagaactc cgtgggatct 151860
tgttccccgt acaggttatc tgcgaccata aggatgctta gaatggtaaa caggtgagaa 151920
tacataaggg tttgcgtttt aagaaaaccc tgacgttgaa tcataattga aaacaccttg 151980
caaagccgac tcatcagttg ttctgtaatg gcgttaagca ttttctggaa tttttcttgg 152040
ttttcgggtg tgattttata ttcatgtaga aagtgtttca cacctgagga gaagaatctt 152100
tcctccttcg agagcccatc tttgatgatg ggaagttcct tgatcagggc aaaccattcc 152160
tcctcttggg cttgcggatt ctgaagatac tgatggcaga tatggtttag aatggtgcac 152220
acgtagctaa taagctctga gctgattctt tggttggttt tcaaatgttg gcgaaagtag 152280
tttttcaccg aagtgcatgt aataaacgtc ttcattttct tataatatac aacagtatgt 152340
tgagtcttta atttaaaatt acaaggagtt ttctaggtct ttatgcgtat aggtgtttct 152400
ttgtcgtaaa ttttcaatag ccgacattgt ttgtgaagca gtgttctgag tagtgactgt 152460

-continued cgtgtaaggc tcagccggat gagcaggagc actcgcggcc gcaggtgcgg ccgccggccc 152520
gccagttgcc atgactagtc tgtccgtaac tgggttgtcc gtaactggtt tgtttgttgc 152580
tggtctgttt gttgccggtc tgcccgtgac tggcttgcct acacttgctg tagtcgctcc 152640
agctggttta gaggtacctg gttgtggagt gacttctacc cactgctgat cttgataagg 152700
atttataaac tgtatatctt cctcctcaat agcagcagct tttttctttc ttgaagagaa 152760
tagatagatt agaacgatga taatgatgac taagaccacg atagcaatga gaatagtata 152820
catatgtgtg gagaagaagc ttggtgtagt gactggtgac aaacactcac cataatgccg 152880
cggataaacc ggttgaaaaa attcagaatc catttaagat actattataa ataatatata 152940
aaaatgttgt ggcgcaatga aattacagaa tttatggacc aactttccaa gtattctcaa 153000
gaaatcttaa aaacgtttaa gcaattgcgt cctagtgaat ataaacaata caatgaattt 153060
ttaacacaag ttacaccgtt gctgcaaaaa acccctgaaa aaattccaga gttggttgac 153120
catatattca attacctaga caacgttgaa aaaatttgtg agctcctcgt gaatgctagc 153180
tcaattatta ttagttcaaa aatacgagaa caagtaaaac acggaatgag cttcagctat 153240
aaagccgacc tcgactcctt ggcggacatt ctctctcaaa aacagtacgt gcttatgcat 153300
ctttcaaaaa atattgcggc cgagtatttt aatacgtgtt taaaccaagg gaaatccaag 153360
ttagatctca aagctgcctc tgtattttat agtagtcgtt cccgaacggc aagctcagca 153420
gaactctata gaaaaatgct atacgcctat ggttcaccgc aggaaattaa ttattatact 153480
gaaaaagccc gaaataagac gttggatgtg gaggagagcg acagcatggc catcatcgaa 153540
cgaacggccc gacacaacct ttcccttatg cacccgctag aagccatggg gcttaccttt 153600
ggggcaacca acacggacgc cgacccggag gatctgaagg acaaaacggt gataaattta 153660
acgctcccgc aggcaacaga aagcatcacc taccatctta aatccctaat gcagctaaaa 153720
aaagtaagta cggcttcagg actaaataca aacattttga aagcatttga taatattatt 153780
tccacccctg tgaaaaaaaa taaaatggcc tccaagttgg cgcccgggat ggatgtcgtg 153840
ttcactagcg ataacggaaa aacatttttt actaaaaaca ttttaagcaa aaacatgcta 153900
gcggggccca aagagcgggt gtttgcatat aataatctca ttagtaattt aaataactcc 153960
tgtttcatac aaaatcacaa cgatttttta agacagcagg actcttggcc cttctatgac 154020
gcgcacaatt ttaccaacaa gtttttaatg cagcctattt tttcggggca gacccgtcct 154080
cggcttcagg gagccatgga ggcggcgcat gtggaaacgc atctcacggc atttttacaa 154140
agtattcagc cctctaggcc acaagatccc tctgttttgg cttcccccaa gttatctgct 154200
ctaatcttga actaaaaaca gcctttcttg gacttaaatg atggtctacc agtttttgaa 154260
ataacttaga gaactatgaa gattttcatg aaatttaaat tagagatttg caaaggttac 154320
ttgcggtcat tttctgttga attaaataat tattcgaata gtataatgtc tgaagatatt 154380
cgtcgtggtc ctggcagacc gccaaagaaa agggttgttc ccaactttga gcgcaagggc 154440
attctggaaa aaccagttcg gccacaaagc cgtctcgagt tttcctatga taacccgctg 154500
atatttaaaa atctttttat ttactttaaa aaccttaaaa gtaaaaatat tttggtgcga 154560
tgtaccccca ccgagattac cttttttca cgtgaccagt cgcaggcaag ctttgttatt 154620
gccaccatcg acggaaaaaa cgtgaaccat tattacgcca gtgatgtctt ttggctaggc 154680
atcaacagag agctcgttga aaaaatgttt aacagcattg atcgctcttt tttaaaaatt 154740
accatcgttc accgctatga caagcctgaa accctgtttt ttatctttac ggattttgac 154800
attgacaagg agtgcacgta tcagattacg gtctcggagc ccgagctcga tatggacctt 154860
atcgaaatgg aaaaaagcat cagtgaagaa agactcaaga actatcctct gcgctgggag 154920
tttacctcca agcagctcaa gaaaacattt agcgacttat caaactacac cgagctcgtg 154980
accattgaaa aactcggcgg cgatacgccg ctgcacctgt atttccaaaa gtttaactcc 155040
atctcatacc acgagatgta taaatcttcc aacaagatca acctgacctc gaccattcct 155100
aagtcgcagg tgttccagat aaatgttaaa attgctcaca tcaagtcgct ggcctcggct 155160
atggtcaccg acaagatccg cattctgtgc gaagaaaatg ggaacctaat ctttcaatcg 155220
gaaatggatg cccttatgtt aaatacgatt accttgaaca ccacgatata gttcggtaac 155280
attagatgtt ctaatattta gcatctaaat aatacgctgt agtccggtca gggttgcgtc 155340
acagttttcc catttttttg cctcgtcggc ggtggccacc gttgccctat catttacgcc 155400
cggtaagaca aagctaaagg cgttcagcgg ggcttggcaa tgcccgccca gcgtgaagga 155460
gctcggagga ttttgcgcat cccgaaatcc cttagccatg ttgtttaaca cttcggttac 155520
gtcaatcgag tgaagggatc ccttgggatc cgtgaatgta aagacgcagt ttctaaagcg 155580
catgtatgcg atggacgatt catcgggggt tttgaaggta acagtgttcc ccttgctgta 155640
cttaaagggg gaccatccgg taaaattata ccaaatgaaa gcaataataa ttaaaataac 155700
caacacaata gttatagaca acacaaagtc tgtagtgccg cccattatta aataaaaata 155760
ttttagaccg ccggcttaaa atttacttat tgctcatagc ttaagtctat tttattcata 155820
gcttaagttt attgctcatg gcttaagtct attgcttata gcttaagtct attttattca 155880
tagcttaagt ctattgttca tggcttaagt ttgttgctca tagcttaact ccattactga 155940
tagcttactg atcatgactt aaataaaaat attttgcccg cttaaaaatt gtttaggttt 156000
gaaaaaataa gagatggagg gggcaactta tcgtcattgt gtttaccccc actggaagac 156060
atcaaacggt aaataattat aagaatcaaa atgattaata taagggttaa aaaaggatga 156120
ttcatcacat taattaaaaa cgtatttata acgctgttgc agttgaaatt ttggtatagg 156180
tcggaaatat tgcccgagcc tccgtattct gcaatgttct gacatatggt gagtccgaag 156240
gggcactgct tgttggtcaa aatatttctt tgctccgttg ttttataggc atttttattt 156300
ccattacacg gagcaaacgc acattcaggc catagggtgc cggagttcac acaggcacaa 156360
tactggctat acgcatactc atcctttgag cacaatccct gtttatcgca tatgctccca 156420
ataatattgt catcctccgc cgtttgttga tttgtatgcg agcgtaaaat agcggcccag 156480
gccttgggct ccttttttttg cagctcggaa atcgaagggc ctgtacagct aaagtcgacc 156540
caaatatcat tgcatttcgt ggaaactggc atgcaagaca taattgaaat aattaataag 156600
tatatatcat ggcaacaaat ttttttattc aacctatcac cgaagaagct gaagcatact 156660
acccaccttc cgtgataacg aataaacgga aggacctggg ggtagacgta tactgttgct 156720
ccgacctagt gcttcaacct ggactaaata ttgttcgcct gcatattaaa gtagcatgcg 156780
aacacatggg caaaaaatgc ggttttaaaa tcatggcgag aagcagtatg tgcacccatg 156840
aacggctgct catccttgca aacggaattg gtttaataga cccgggttat gtgggcgagc 156900
tcatgctcaa gatcattaat cttggcgaca ccccggtcca aatatgggcc aaagaatgtt 156960
tggtgcagtt ggtggcccaa ggtgaccatg tgcctgacca tatcaacatc ctaaaaagaa 157020
accaaatatt tccgctgttt gcgcctaccc caagaggcga gggtagattt gggagcacgg 157080
gcgaggccgg gattatgaga acttaatttt attttttttc ttaacataat gggaggctct 157140
acaagcaaaa attcctttaa aaatacgacc aacattatca gcaattccat tttcaatcag 157200
atgcaaagtt gtatttccat gttggatggc aaaaattaca taggcgtatt cggtgatgga 157260
aatattttaa accacgtttt ccaggattta aacttatcat taaacacaag ttgcgtgcaa 157320
aagcacgtaa acgaggaaaa tttcattaca aatctttcga accaaattac tcaaaattta 157380
aaagaccaag aagttgcgtt aacccaatgg atggacgcag gaactcacga tcagaaaacg 157440
gatatagaag aaaatataaa ggtaaactta acaaccacac ttattcaaaa ctgcgtttca 157500
tccctgtcgg gtatgaacgt gctggtggtg aaggggaatg gcaacattgt tgaaaacgca 157560
actcagaagc agtcgcagca aatcatctct aactgcttgc aggggagcaa gcaggccata 157620
gacaccacaa ccggcatcac taacacggta aatcagtact cacactacac ctcaaaaaac 157680 tttttgact tcattgcaga cgcaatttcg gctgttttta aaaacatcat ggtcgcggct 157740
gtagttatcg ttctaatcat cgtagggttt atagccgtct tttacttttt gcattcacgg 157800
caccgccatg aggaggaaga agaagctgaa ccactcataa gcaacaaggt attaaaaaat 157860
gctgccgttt cgtaataatt taattaaaag taaaaaaaaa aggtattgtt atagtgatgg 157920
cagattttaa ttctccaatc cagtatttga aagaagattc gagggaccgg acctctatag 157980
gttctctaga atacgatgaa aatgccgaca cgatgatacc gagcttcgca gcaggcttgg 158040
aagagtttga acccattccc gactatgacc ctaccacatc aacttccctg tattcacaat 158100
tgacccacaa catggaaaaa atcgcagagg aagaggatag taattttcta cacgatacta 158160
gggagtttac ttcactggtc cccgatgagg cagacaataa accggaagat gacgaagaaa 158220
gcggtgcaaa acctaaaaag aaaaaacatt tgtttccaaa attaagctcg cataaatcga 158280
agtaaaaatt gaagcgaaaa aaagtagaaa aaaaatgttt ggagcttttg taagccaccg 158340
tttgtggtca gatagtggtt gtacgaccac ctgcatcaca aacagcattg ctaattatgt 158400
agccttcggc gaacaaattg gatttccctt taaatcagct caggtattta ttgccggccc 158460
tagaaaggct gtgataaata ttcaggaaga tgataaagtt gagcttttaa agatgattgt 158520
taagcacaat ctttgggttg ttgctcatgg aacctactta gatgtgccct ggtcccgtaa 158580
gagtgcgttt gttacacatt ttatacaaca agaactactt atatgcaagg aagtcggtat 158640
taaagggtta gttttacacc taggcgctgt ggagcctgaa cttattatgg aaggactaaa 158700
aaaaattaag ccggttgagg gggttgtcat ttacctggaa accccgcata acaaacatca 158760
tacatataaa tacagtacaa ttgagcagat caaagaattg tttttacgga tacgaaatac 158820
caggttgaaa cagattggtt tatgcattga tacggctcac atctggtctt ccggtgtcaa 158880
catctccagc tataatgacg cggggcaatg gctgcgctcg ctggaaaaca ttcattccgt 158940
gatcccacca agccacatta tgttccacct aaatgatgcc gccacagaat gcggaagcgg 159000
tatagaccga catgcaagtc tttttgaagg aatgatttgg aaatcatata gccataaaat 159060
aaagcaaagc ggtttatatt gttttgttga atacgttacg cgacaccagt gtccggctat 159120
attggagaga aacctcgggt cttccatgca attacaaacc gctttaaccg cagaatttac 159180
tacattaaaa tcgttattaa aataaggatg agttttagcg aatgtccctt agttattagt 159240
gcatgcaaaa aatttctaca aaagcgtatt acaatagaga atgaagcact tataaatgcc 159300
ttaataaccg ctttagcgca gaccagcacg ttgaatgatc tttgtttatt acctattcaa 159360
acctatttgc ttagttataa aaatgctttt gagtggatac acttcgtatg tattgcaatc 159420
accactattt tggataataa gtataactgg aaggactgta cggtagatat taattatatt 159480
tttctccatg taacctatat ttacaatatt aaaaccaagg aatacctaga ctactgttct 159540
taaactttat tttttctata tttacgccaa agagaatatt taaagttttt tttgaaaaaa 159600
aataatatat gtagataaaa ttcagttaca tgatatatgt gtaaacatgt gtggtaaaca 159660
acatatggtt atgctttata agataaatgc gcataatata tgtaaacaaa atatggttat 159720
gtgttaaatg catataaatg tattttaacg tatatcttgt gataatggat atatgcattt 159780
attaaaagag gctgtattta ttataaatct tgctaaggat gccattgtca acatatatcc 159840
catgttggac aaattgcgtt gcgatccagt tctttttttt ttgattttgt ttaatgctat 159900
ccttttttgaa gggatggttg tccaccatat ttattcgatg ttcaatgaat aggtctgctt 159960
tttcgtaagg cagtgaaggt cgttccaaga ctccttgaac gatggacgtg ttttcttgga 160020
tccacttaaa aagcacgtgg cattcaaaaa caggacagtg attggatcct tggatatgct 160080
ttggacagcc aatgcttgaa gagatgtagt cccttttctt taggacaagc ttctccacgc 160140
tggggcaaca gagatcgttc aagttctgga cggtcgcatt tggaatgttg aaacttcgta 160200
tccattcacc ctcgggtcct cccttatgaa gaaggagtat ttgctcatgg tccttagtaa 160260
tcttaaccaa atgttggaag atcatttttt tacctgcttt aaaggcctga agggtgtcag 160320
ttggcaaagc tattgaattc gggagtgggc tttcatcaag cgtgaaatgg tgaatgtgac 160380
gcgactggaa agaaaacgac cgttgattta ttttttcaaa gattgggtcg attccgccat 160440
gaaagaacag ctgcaagatt ttagaaggcg tatttttttc ccaataaaaa atgaccactt 160500
ctcgtgggat taaaatcgtc tgtgtcccat tttcattata taattggccc ataaagccat 160560
caacgtcaat caacaccaaa agcatggtat agagagcttt tagaaccgga gttcgttaaa 160620
aaaatacaaa gttcgtttaa aacgtgtaat gttactaaaa aaatgtaatg tttaaatgat 160680
aatgatacca catgcattaa tgaaaaaaac ttttaaattt ttgttttaat atttgcatga 160740
aaatggaaac atttttagtc tgtttatttc acaatgcaga tggtttacat caacagattc 160800
aggaaatttt gtatttattg cggatgcata tttacgaaac aaatctttac ttaaagcagg 160860
aactatcacg gcttatatat ccaaataggc aactttcttt tgtgttactt atgccccttt 160920
cccttctaag aaactgggat gacattgaat atttaacgga cgttgtagat gataagcaga 160980
ctctacatta cgcggcaaat ttgctgacaa actacgttct acatctatcc atgtttcaaa 161040
agctgacaaa accatacttc cttttagcgg tcaagcgggt cagcgaaaaa ctcaacaaaa 161100
agcagcgaca ttcattttac gaggtattgg taacctccga aaccttgaat aattatgaaa 161160
acctatctaa aaacatttta aatacgttga tgtttgccgt gcgctacgta tttaaaccta 161220
cgccgaacta ttcagaaatt ctcgcagagt tggaaaaaaa aaataaaatt caccatatta 161280
tttttaatat ggtaattacg gattttgcgc aaatccgtga acaacaaatg gataaacatc 161340
tgtgtgaaac aaataatgag cttcgtcagg aatgtaaaga aactattttt gatttaaagg 161400
tggtaggaaa tgtttagcca ataaactcat gcccgcattt tttacaggta caaaatatcg 161460
tggatggctc atcgagggcg cgtgtttgta cttctctgta ggtacacata cgctgcttgc 161520
agttgggaca cttataaagt tgtgacgtct tttcggcgac cttttgctgc gaacgtagag 161580
taatttctgt cttctccttt aaggcggcag aggggcaaag ctcggcgaac gtcatgctac 161640
caattgcctc cggttttagc tcgccagaaa ttagcttatt aagggcatcg ttatcctgtt 161700
gttggtgact tttttttcg cagttaataa tatgattgat cgtcccacaa cgggttgaat 161760
attcttctaa aaaggttttt tcttgttgct ggtacgtata atgataacac gaggcctcga 161820
ttttttgcgc gtattcggtg cataaatcag tatgttcctt aaaaaacata tgtttttgaa 161880
gcgttctaaa aaacatcatt tggatgatat cacgcatttc caaaataata tagggttcta 161940
gtcttttgga atctttcata actagatcgg tggtaatatt cttagtcata caatttatta 162000
aaaatggttt aatatattgt aaatattttt taggcgtgtc agcctgtaaa aaacattctt 162060
gttcaatctt atttgtaagg atagtatttt gcaaatactt atttagcaaa aatacgatag 162120
aatcgcgggc tatatgcatt ttcatataat ttttttttta aaatttaata caaaaaaaag 162180
aagtatagac tcttcttcta gtccggttag ttcgttggtt gcctcaacat ggagactcag 162240
aagttgattt ccatggttaa ggaagcctta gaaaaatatc aataccctct tactgctaaa 162300
aatattaaag tagtgataca aaaagagcac aatgtcgtct tacctacagg atctataaat 162360
agcatactgt acagtaactc agaacttttt gagaagattg ataagacaaa taccatttat 162420
cccccgcttt ggatacggaa aaactaattg taaccagtag tacatttaag gatagtttaa 162480
gcagtaaatg tagaataaca cagttaagca ataaataaca agtatatagg aatatatagg 162540
aatatataga aatatataga aatagctaag cttaatacta attcagcttt tttttaact 162600
aaaacctgaa tagatgcgaa gtagcggaca tatacatact aaaataagcc atacatttac 162660
tttcttcttg aacatgaaac cttttttct tctgttgttg gtatataaac aataggactg 162720
tttgctgagg ttgtatgatc ttctacaact gctgtctcag gatgacgatg ttttttaaa 162780
ctaaaagtgt aggatggaat gagtggaata tagttatggc tcgacttatc ctgtttcgta 162840
caggaatatt ttttacaaat agaacgcaac aagcatatga ataaaaacag aaatgatata 162900
caggagcata aaatagatat gaacactaag ggtagcagc ttttataacg ttccgtattt 162960
ttcttagcta tcaattgatt taccgtaata tttatctcgg gaaactttgt tctacaatat 163020
tttgtttggt attccagaaa ctcatgtcct ggcttattcc cgcagcttaa aaaatgatac 163080
aaaaatgtgt tattgttact aaaattaatt cttcttaaga aaaactgcgg aagacgcttt 163140
aggtacgtct gttcctgttt tagtaggaag tagtataagg gacaatttct ttttccacac 163200
attagattat tgtaatatag gtaggttggg gtgttggagc gaataagttt tctgagtatg 163260
ttataatcta tgacttgtaa atcgttatac cttaggtcca aaaacttgag ttctttacca 163320
aagccacctg caatttcaga aatatttttc atcccgcagc ggataatacg gatgtcctga 163380
aacgtcttta aaatacttgt attgtagtga atacttatgt tattttttg taaataatct 163440
atgtcatgac aagtgcatga aatgccagca gcattgcttg gtatagtatt atatgcagga 163500
agaactatac tactattgag aatagtcaca ttgtacttat accatgtatt attttctgat 163560
ataaagtatt tgcaggtgac ctgtggttta atcctacctg ttaagccact tcctaaaaaa 163620
acaaaaaata tgaaaaccct tagcatcctg tatatactat taaaaattta taaaattttc 163680
tgtttaaatt tcatttagac aaaaaaataa tatatataca tcagcaagaa attatataca 163740
gattatataa ttttctgatt ttttttgcc acaataagca tcattatatg cattaaaatc 163800
tcaatactaa acactaaaat ctaaattcta agcattaaat tctaagcatt aaattctatg 163860
cactaaactg taagcactaa aatctaagta actaaaatca acactaaatg tatgcaacct 163920
aaaatgtaaa gcattactca tcatcctcct cttcttcatc ctcatcatca taggttaaga 163980
tatatgtgtc atcctccatt tcttcacatt catcttcata agcatcactg ggtattggtg 164040
gaacattgga tgcagcattt ttaaaatatt ctatgtcttc tggtgaacac tcatctaatg 164100
attttttgac agtcctttta acttccatgg gatatgattc caaatcctct ttatataaga 164160
gtttacggta gcttttagct gcatccacat ttgctggaga atctggattt ggctcattga 164220
gcagtgaaat tacactaaga agaatggtat caatcttttg agccggagac caagtcattc 164280
cctgttcttc agcattgtct ccgtgtaaga tagagataca tagttttcca tcagagtaaa 164340
tattaggatg ccacatttca gaggtgaatg ttaatctggg tggtgcatat gggtattctg 164400
gaggaaaggc gatttttgcc ttgaataagc ctccctcata aaaagtgtca ggtgggcccc 164460
ttaagatcac atcccattca gtcatatcct tctcattcac cgaaattttg aaattctcag 164520
agggattctc tatcaggtgt ctgtactctg ctattaaaaa cctggaaacc atggttattt 164580
aatattaatt aaattccctg gtttattcct ccttaaaagt agatgaacct cttttgtttt 164640
ttattgggtt catttttact aaatttatga actggaaaaa actttaacgg cataattatc 164700
agatctagta acatagatga caccgcgcgc gataatttat cctagtttgc gcgctatatt 164760
ttgttttcta tcgcgtatta aatgtataat tgcgggactc taatcataaa aacccatctc 164820
ataaataacg tcatgcatta catgttaatt attacatgct taacgtaatt caacagaaat 164880
tatatgataa tcatcgcaag accggcaaca ggattcaatc ttaagaaact ttattgccaa 164940
atgtttgaac gatcggggaa attcgagctc ggtagcaatt cccgaggctg tagccgacga 165000
tggtgcgcca ggagagttgt tgatttacta cttgtacagc tcgtccatgc cgccggtgga 165060
gtggcggccc tcggcgcgtt cgtactgttc cacgatggtg tagtcctcgt tgtgggaggt 165120
gatgtccaac ttgatgttga cgttgtaggc gccgggcagc tgcacgggct tcttggcctt 165180
gtaggtggtc ttgacctcag cgtcgtagtg gccgccgtcc ttcagcttca gcctctgctt 165240
gatctcgccc ttcagggcgc cgtcctcggg gtacatccgc tcggaggagg cctcccagcc 165300
catggtcttc ttctgcatta cggggccgtc ggaggggaag ttggtgccgc gcagcttcac 165360
cttgtagatg aactcgccgt cctggaggga ggagtcctgg gtcacggtca ccacgccgcc 165420
gtcctcgaag ttcatcacgc gctcccactt gaagccctcg gggaaggaca gcttcaagta 165480
gtcggggatg tcggcggggt gcttcacgta ggccttggag ccgtacatga actgaggggga 165540 caggatgtcc caggcgaagg gcagggggcc acccttggtc accttcagct tggcggtctg 165600
ggtgccctcg taggggcggc cctcgccctc gccctcgatc tcgaactcgt ggccgttcac 165660
ggagccctcc atgtgcacct tgaagcgcat gaactccttg atgatggcca tgttatcctc 165720
ctcgcccttg ctcaccatat aatgttataa aaataattta ttgtttttat taaatatggc 165780
ggtttatgcg aaggatcttg ataataacaa agagttaaac caaaaattaa ttaacgatca 165840
gcttaaaatt attgacacgc tcttgctagc agaaaaaaaa aactttttgg tgtatgaatt 165900
gcctgcccct tttgactttt ctccggctaa aagattatta tattcgaatg tttgtccaat 165960
atggacaact ttgtcaccag atgttacatt tgatttggtt gttagtggct gaagcttggc 166020
acaatcaaaa ataagcccat taacactaag atatagagga gtgggttgat ctattttctc 166080
atagtttaat attccatctt tccacgtaat agcttgataa ttatccgcag caatgagttg 166140
aaattttata aatagtacag gggttttagt tgtcgttata catttaaagg gtgttttata 166200
aaaataaaaa taataattgt taaaagtatg ataataatcg ccaaaataat ttcatacatt 166260
ttttataaga attatacata gtatggtatt taaaatatta gctaaattta aaaaaacttc 166320
atgattttta aaacagggaa aaaggggatt aggttgaata aaaaaggtaa gcacttgtct 166380
atatattttt tttacaatgt tgccttgagt cgcattttta actggctggg gagtatcaga 166440
gtggaatatc actgtagtag gtctataagg tcttgttaaa atatgatcgg tcattgtttt 166500
cgtactagtg tcatttaggg tcgacctgat agctcgatat aaagttatag gggataacct 166560
atcaaataca gtcttatctg tgctgaaatg tatatcgtct tctttatcac taataatatt 166620
aggaatggct gtcattaaat aattactact tgttgttgtg ggtgaaatag ttgtactggt 166680
attattggaa atggctgtca ttaaataatt actacttgtt gttgtgggtg aaatagttgt 166740
actagtatta ttagaaatgg ctgtcgttaa ataattacta cctattacaa gtaaactaat 166800
gctaactaca tttttaacct caataaacct aaaaagccat actaaatacc taaacaacat 166860
cctgttataa tatgagcaga aaaaaaaaat aagtataatt agggaattat tcttattcgc 166920
ttactattaa gaataattca gaatcttatt tagttagaaa ctatcataaa gtgaatagga 166980
ctcatcgtcg gatgaagatt ccgtttcaga gatagtttct ttttcttcct cagaataatc 167040
tgttcctaca atagaatcgg tgtcatcctc agaaagagaa gtatttaaat atggactatc 167100
tatagcaata tcctcttcta tctcgcaatc ctcctcctcc atttccatag tgtgtaggag 167160
aatattttta tcatcatgct cacttctttt tttgttgaaa gatgaaccgt cctcaatacg 167220
gttcatgtta agttccttca tcttatgtat aatttccgta atccgtgatg tttttgacat 167280
gtaagatggt tttaaggtta tatccacaat aacaggagaa tctctatcat tttcatttga 167340
taaactttga tctttgattt cttcgtctaa aattcttgtc tttttttggg tactagatga 167400
aatagaggaa ttcatattct gaaacgatat atcaagggga gctggacgct tttttccaat 167460
taaaccgttt ttcgagatac tatgattaga tgaatgatct ttagccaagc tgtccttgga 167520
tatactatag ttagatattt tacctttaaa taatattctt ctatacaagt tattcttagg 167580
taaagaatta gtatggattc ctatattttt atctgaagga gtgtccatat cggagaacgt 167640
cctcttacga atattttgac cacgagccat ttcatccact ataggcagta ttttggctgg 167700
ctatggttct ttgttgtgac aattctatga gatttgattg caaatcaatt tttagtttta 167760
aatatattgg tacctaggac aaagaaagta tatatagcca ataattattc cactaaattg 167820
atttccagac tgatgggtat ggagccatgt tgtctctgca gacgatcgca aaaatggccg 167880
tagcaacaaa cacctactcc aagtatcact atccaatact gaaggtcttt gggctgtggt 167940
ggaaaaacaa tacgctaaat ggccctatta aaatatgtaa ccattgcaac aacataatgg 168000
taggagaata tcctatgtgt tacaatcatg gaatgagtct ggatatagct ttgattcggg 168060
cagtaaagga gcgtaatata tccttagtcc agcttttcac cgaatggggg ggaaatattg 168120
actatggggc actttgtgct aacactccat ctatgcaaag attatgtaaa agtttgggag 168180
ccaaaccacc aaagggccga atgtatatgg atgctcttat acatctttca gataccttga 168240
atgataatga tctgattagg gggtatgaga tttttgatga taatagcgtg ttggattgtg 168300
tcaatctcat acgactcaaa ataatgctta ccttgaaggc ccgtatacct ctcatggaac 168360
aactagacca aattgcctta aaacaacttc tgcagcgata ctggtatgcc atggctgtac 168420
aacacaactt aacaatcgct atccactatt ttgataatca tattcctaat ataaagccat 168480
ttagtctgcg ctgtgctttg tattttaatg atccctttaa aatccatgat gcttgcagaa 168540
ctgtaaatat ggatcctaat gagatgatga acattgcttg tcaacaggat ttaaactttc 168600
aaagcattta ctattgttat cttttagggg ctgatattaa tcaggctatg ctaatgtctt 168660
taaagtatgg tcatctttct aatatgtggt tttgcataga tttgggggcg gatgccttta 168720
aagaggcagg ggcgcttgct gagaaaaaaa ataaaagagt gttacaacac atattaggtc 168780
ttaatatctt taagcgagag ttgattcccc cctgtaaaga tcctgatcct tatcaaatcc 168840
aaattctgtt aaaaaactac attctaaaaa atgtctcaac tgtttttaca tattattgcc 168900
agtagccatt gtttatatca gaaaataacc catttgttta tctttttttg tggggcaacc 168960
attaagaccc gacgcaaaaa aagattaatc ttttatcaga tacctaaaac gttctataag 169020
ggagtctatg agatggatca tattttgatg gtcatagtaa gaagcaagct ttttggcgaa 169080
aacaacggag ttaaagaatt taacccgctc atgtttggat aggactttta acagcgagcc 169140
aaaacagtat ttaaaaattt ggcaatagtt tttttgggat gcaataaaca aacacttgat 169200
cagtgcccgc ttcactttct gatcagacat gtttgccgca taacaggcct ttttaaactt 169260
agtaatataa ttatgttccg caagcaccat taacaaggga acgatgggaa gctgcttttc 169320
ttggtgaaat ttacgtaaat attcgatggc caccgcttgg acgactgtgt aatttactaa 169380
gttagaaatg atagctttca tggttgtaaa aatatacata ggattttctt tttctgtata 169440
cagtttgaaa agcttatgat tacgtgaaat gatggccatt tttaatacaa gatggtatag 169500
tgtatcttta ggtaaaaatg ccttgcaagc cgcgatgatg tcgatgttgt ctccatgaac 169560
agcgatagaa actaatgttt ccaatctaaa tgtttttatc tgcattaata gaagaatgca 169620
gtcaatgtta ttatacttaa taatactgta atacaccgaa tcaatgaccg tcatctgaga 169680
atcaagctga cttattagta aatttaacgt ttttttggag gcatgacctt tgatcgcggc 169740
actaagtgca cacagtatag caaaattgtt aaatacattt tgatttagga gaaggagtaa 169800
tattttcctt cggttatagt acgcagcatc tgtgatgatt attggccgat aaatgttaaa 169860
atgtgttaac agctttttaa aaaaacggaa gtaatttttt tggatcgctg tttgcatcat 169920
cgaaataatg agataatcag ggtatataat gggtaggtca catgctacct ctaacaaaga 169980
atagtcgccc aatctaaagg ctgtgttgaa aagcgtacta tcatcatacg tatcgagtac 170040
ccctgctgtt acaaaccaag cgataagatg aatgtgccgt tccttgcaag ctatcgcaaa 170100
tagggagttt cctatggaat gtcgaataat gtactcccta ttttttttcca aaatgtttgg 170160
aaaattgtat agcgttgcgg catacagtag acactccatt ctggcgttat aatttttact 170220
tttacatatg aataggtgga agaactcgaa taattcttga gaacttgtta aatgcataat 170280
atggtgatat tttggtgtcg ttaaatggta tgagaaaatg cattctaata catcttttcg 170340
gttatgcttt agcgcctgag ctaaggcata ttcaggctcg acccatagga ctagtgtttc 170400
tataattgag atattcgcct gctttgccag ggcatacttt aagacgctcc ggttagaaaa 170460
aatgttgtta tgaagatgga taaccgtatc catttttacg atgggaccat tccagtatag 170520
tcctaaatgc tgtagcagat cttttgttag ttgtgaagcg ttctcgggtg tcatataaat 170580
atgttgcagg gctttttttct gtaaggagaa catttcgtcg taatcgtaca aaaaaaaatt 170640
aaaatttggg catggatgat tcaaacataa caaaatcaag attttataac agtttgcatt 170700
aacctataca tatatgcaag taaatgagat attatctatc ataacgaatc aagggatatt 170760
tgtatatatc aggagtttct gaaataaaga tatgaagatt atcatagtag tatccatcaa 170820
tcacaatgca acttccttta aggcataatt tagtaaactc agcactccca tcttctggat 170880
gctttacaac taacattaaa aactcctcag tcatattatc tgtaataaaa taagatcctc 170940
ctggagccat ttgtagcatg tctcttattc ctacaaaatc ttttttggga tggtaaaaac 171000
tcagcagttt caaactcttt tttagttttt tttcctggta tttaagccat ttgttataaa 171060
acagttttct tatgaaaatg catttgaaaa tattgggaat gtttaaccat gcttcttccg 171120
agcacatctc cagatactta ctttctttgt ttcccatgtc taatttattg ctcactaagt 171180
tagtaatgaa tctattttaa taatctactt tactaatcta tcttaataac ctatcttata 171240
atctatctta ataacctaat tataacctat ttataattgg ctaatgctgc cggcatttca 171300
tgcctatcta aacaactcct actaagcaat ctactattac atatatagat tcacttttta 171360
tatttgtaaa tcatgagaat tataaaatca ttactcattt ttattgtaaa ttagtgggta 171420
tttgtaaaaa tcttcaaacg ttttaagata gttttctaga gagaagtaat ctttgccatc 171480
aatatataat gcttttcctt taaactccag ttttgctatg tttagtgagc cgtttctaga 171540
tctttttggg caataaatag attttcattg gttgcatcgt ccgtaagcag aaaggtacca 171600
ctaggcacgt taaaaaacat acgttctatt tcatggtcgg atttttgaga atagaaaaaa 171660
tctaattttt taatccgcgt taactctttt ttatcaatct ttccagactg ttttatatat 171720
actttattgc aaatcttaca atcctctatg gcttcattat acttattttg cttatcctct 171780
attgacatgt ccgtatttga taggtaactt ccgttaaggc ggttccccat ggttttagat 171840
agatttttaa ttcagttgta tacttttatt atgaggctaa aatatagaag tttgatccta 171900
aaaaaataaa aagattttgt acatttattt atggtttata gcggtataga ggccgataaa 171960
aggtatccgg gtagtctcct atgatatcgt caattttggt ataataacag ttgttatggt 172020
agtattgtcc aaaccgagta tgtatgcgcc ggtgaagcgt ccgcccgcta atggtacagt 172080
tccaggttaa gacaatcata tcacacccaa aaagagagga aacagcatag gtgcccaaag 172140
gttcattata taacatacgc cgcatatatt ttagtttttt ttctccatgg taataatcac 172200
aggttttcat gtcctgctta ataggatgat tccccatgta tgataatata taataaattt 172260
agtttttagc tttttcaaaa aattgggcgc tcgaaactaa attttcctta tcacagcgtt 172320
tggagaaagc gtatttaaag atatatcttc ttctaacaag actgcaaaaa aaatcttacc 172380
ccttattttt ataatgttca tcatagcgtt tgaagatatc agaaggtgcc aggttttata 172440
aaaatatcct ttaggattta taacgataca agggtctata aaatatatgc gggtataatc 172500
ttataaaatc atcgattttt tcataatatt ctccgtttat acaataaaga tcataacaga 172560
tattgatgcg tagatgcatt attcgcgtgt tcgttgggca gctaaaggat atcacaacgt 172620
agtttttttt aagaaaagac gaaactacat aagtccctaa gggttcattg aatagtaaac 172680
gccatatttg ttttaaattt tgttgttcac catagtagta ttcgcacttt ttcaagtctt 172740
ttttaataag cctattcccc atgtatgctt ataaataaaa atttagaaat gtgctatatt 172800
atttgttgat gaatcatgaa cacgtcttat atgttgatat gttactttaa aaacatttgt 172860
attttcaaca gacgcgttct attcttatta agaatgatgc cgtctttatt ttaaaccttg 172920
gtttaaaatt taaagaagta tttataaact ataatcatgg gaactttttc agtaactgcc 172980
tctgcaaaaa gtgacgatgc tgtttgtaag tatttagaag aaccaataga tgaaaattac 173040
agaaacatat taagaaatga gcatgttaaa aaaaatttaa atgaggctct gaatcgacat 173100
attactacct ataatccagt agttgattgg tgtaataact attcaacatt ttcatctcag 173160
gatttcgatg aatataaaat ttatatacat agcgatctta tggatggacg acctcgtcca 173220
aaaaaaacat ggtgtgtcat catgtaatgt ttgttagttt tatataaacg caaaaatatt 173280
cttctaggag atgttgatat actacctatt gaattcaata tattaaagta catttctggc 173340
tattcccatt acggtattat tattactatt tttaagagct agatgtggat ttaagtaata 173400
ataacattct cccgttcctc ctagagacac ctcatcaaat tcccatccta tgcaaccttt 173460
atgttgtaaa cataatgatt gacagcattc atcttctttt gaccaagtcg tccaaatcct 173520
accaagatct atacgtgttt ttccaaatgg agattgaaga tcagcagtag tggcattaaa 173580
cctataaaaa ccaggtgcat aatcacatga acggatcgta ggatctaatt taatatcttt 173640
tatatcttgt tttactgctt ctagacaact tttatcagta catgttccac gtacacagtg 173700
gtgtccttta tccttacaat ccgtatctgt cttacatttt tttttcggcg gtttatgttt 173760
cagatggtaa aaacccagta ttaaaataat cacaagaata attcctataa gtacttgaac 173820
aacaggataa aacattttaa tattaaatat attttttaat taaatgaata gatttaatcc 173880
aagtagtatt aaaatttttt agaaatagtg ttctacaaat aatgaaatga atggtccaaa 173940
aaaaataagg tgtacaataa tgtaatatat tgttaggcta agtaaattta atattttaaa 174000
gtatttggaa aaatattttt taacatatga tgtctaggaa tattttttag acatttaaaa 174060
ccatatagtt actttattta ttacactgaa cttgaaaaga cttattacct aaaatattaa 174120
tagatgaagt aatattgtgt aattgagtcc ataacatggg tgggaaacaa aaatctcgta 174180
atatgaaaaa taaacatcct aaaaagagtg caattgttat aagtttatgt aactttattt 174240
taaagtaaga atataaaaat atgagtacaa gaggaatagg ggccattact aacattggct 174300
ccaacatcct gttgtctaca aaaaaaaata ttttttttag caaaaaaaaa tccatggaag 174360
gatattaata cacataatta tttgacatca cattagtgta cttaccaaat agtaatatac 174420
aaccatccta atattcacct ttatgaaatg atcccaacct atacggtaaa atagtatagg 174480
ttttaataaa gaaaaaagat attctgtggt ttttattttt gtatagtgtg tgaatacaaa 174540
ataaaatccc aaattttaac cttttctttt tttttctata caggatgtta gaaatagtat 174600
tggcaacgct gctaggcgac ctgcagcggc tccgggttct tacccctcag cagcgggcag 174660
ttgccttctt tcgagccaat actaaggagc tagaggactt cttatgctca gatgggcagt 174720
ctgaggaggt actgtctggc ccccttctta accgtctact agaaccctca ggccctcttg 174780
atattttaac cggatatcac ctatttcgtc agaatcccaa ggcaggtcag ttgcgcggcc 174840
ttgaggtcaa gatgcttgaa cggttatacg atgctaatat ttacaatata ctgtctcggc 174900
tgcggcctga aaaagttcgc aacaaggcta ttgagctata ctgggttttc cgagctatcc 174960
atatttgtca tgctccttta gttttagata ttgtacgata tgaggaaccg gactttgctg 175020
aactggcctt tatttgtgct gcttactttg gtgaacctca ggtaatgtat ttgctctaca 175080
aatatatgcc tctgacccgc gcagttctta cggatgccat ccggataagt cttgagagca 175140
acaaccaggt agggatttgc tatgcttact tgatgggagg cagcctcaag ggactagtct 175200
ccgccccact gcgtaaacgt ctgcgcgcca aactacgctc gcagcgcaaa aagaaggacg 175260
ttctttcacc ccacgacttc ttactgctgc tccagtagct ttttttgccg caggagcacc 175320
gcggatagga gctcctccac gctcgcgatc cggcgctgga agcggaaccg atcgaccgcc 175380
acctgctccc agggaccctt gcgctcgatg tcgtcggctt cccacacctc gacggctgtg 175440
gcaaaatgga catgcttcgc gtcgttcgtc cgtttttttgc gccgcctccc cattattctt 175500
cctgtaagat tagtgtttaa tacctataat aacataattt taagatttaa tataccaaaa 175560
cttaaactat ttttgtatag taactattag catgtctaca catgattgtt ctctaaaaga 175620
gaaaccggtt gatatgaacg atatatctga gaaatcagtt gtcgtggata atgcacccga 175680
gaaaccagct ggagcgaatc atatacctga gaagtcggcc cgcgaaatga catcatcaga 175740
atggattgct gaatattgga aaggtataaa acgtggaaat gacgtgccat gttgttgtcc 175800
aagaaaaatg accagtgcag acaaaaagtt ttcagtattt ggtaagggat ccctaatgcg 175860
ctccatccag aagaataatt aaaaaaaata ttttttttag caagttttta aactatttaa 175920
ataaatgtgg taaaaaaatt cacataataa ttaaagtgaa cgtgttagaa ttaatatttt 175980
tttataatcg gatataatat ccattaaatc aataaatgat agtgttgcta ccacactaaa 176040
caataacaaa cagaaacgca cgatacccttt cctcatgatt tataatagcg tgttatctaa 176100
agattttttt gaaaaaaata ttaaatttta gttgattatt tttttcagtt acaacattgc 176160

-continued tttagaaaaa atacctaatt actacatagc aaataaagcg agcgcattgt tacaaacaac 176220
atttttttgc gcctggatac tcctatatat gagaactata atacggtata ttaatcctat 176280
taccaacatt gtcaataata gtatgtaggc aatgacatac tttaaatacc aaatatccat 176340
ggttatttct aaaaatcttg aaaaaacgtt aaattttaga tcggtcacct acgacagtaa 176400
tactaatttt aataattgat gactgaaatc ataatataat gccgtgcgaa aaataattat 176460
ttttcggtta aagataccat tacataaaaa atatgccatc tactctacaa gtgcttgcta 176520
aaaaggtatt ggccttaggg gagcataaag aaaatgaaca tatatctaga gaatattatt 176580
atcatatatt aaagtgttgc ggtttatggt ggcatgaagc tccgattata ctttgttatg 176640
atgggagtga gcaaatgatg ataaagactc caatctttga agaaggcata ttacttaata 176700
ctgcattaat gaaagctgta caggagaata attatgaatt aataaagttg tttactgaat 176760
ggggagcaaa catcaattat ggattaattt ccattaatac cgagcatgcc cgggatctat 176820
gtcgaaaatt aggagctaaa gaaatgcttg aaggaaatga atttatacaa attatattca 176880
aaacattaga tgataccacc agtagtaata taattttatg tcatgaatta ttcaccaaca 176940
atcctctttt agagaatgta aatatggggg aaatgaggat gataatttat tggaggatga 177000
aaaatttaac gaacctatta ttaaataatg actctattag tgaaatatta actaaattct 177060
ggtatggtat agcagtaaaa tataatctta aggatgcgat ccaatatttt taccagagat 177120
tcatggactt caacgagtgg cgagtaacat gtgctctttc ttttaataat gtgaatgatc 177180
ttcataagat gtatataaca gagaaggttc atatgaataa tgacgaaatg atgaatctag 177240
cctgcagcat tcaagacaga aatttatcaa ccatttacta ttgttttcta ttgggggggct 177300
aacatcaatc aagcaatgtt aacctcagta ttaaattata atatttttaa cttattcttt 177360
tgtatagact taggggctga tgcctttgaa gagggtaaga ccctggcgaa acaaaagggg 177420
tataatgaaa tagtggaaat cttatcatta gatatcattt atagtccaaa tactgacttc 177480
tcatcaaaaa tagaacctga acatattagt tctttgttaa aaaactttta tccaaaaaat 177540
ctgttcgctt ttgatcgttg caaccccggt ttatattatt cttagaggac cgctacaaaa 177600
attatttttt tttcttgatc aaagctccaa aataattatt agattaaagt cgcctatagc 177660
agcagcccac tccaaaaaaa gtattttata gtacaaaaaa cacgaaaaat agtttgcggc 177720
cggcggcaaa ctatttgttg ttgtctaaaa cttaatgttt ttttaatatt tttaaatgca 177780
accatggatt gttggactat cagggagaag aactatagct acatcatatt gtcaatactg 177840
gtaatactat taatatggta tcttatactt aactattgtc gatcgaaaaa aaatgcagtt 177900
acaaacaaca tgccgccacc atacacggtg tcaagtagct gttctcaata atagggttga 177960
ttgacgctct tcgtaataat atgttgattg acgcatcata aaatgctgtg gttgattaat 178020
atgttgattg tcgcctactt tattatataa gtaatgattt ttgtataaaa tacgggtttg 178080
tgagggcttt attttttctt attagaacaa agcatgcaat ttaaggccta cagcaagagt 178140
aatttaacac ctacaacagt aattttaagg tcagtaataa tgtttaatta aggcctgacc 178200
actaaaactt aaacgatttt gtaaaaaaaa atgtctactc cactttctct acagactctt 178260
gttaaaaaag tgctggccac acagcacata tctaaagaac actactttat tttgaaatat 178320
tgtggtttat ggtggcatga agcgccgatt acgatttgca ttgatgagga tagccaaata 178380
ttgataaaat cggcaagctt caaagaaggc ttatctttag atatcgcatt aatgaaagtc 178440
gtgcaagaaa ataaccatga tttaatagag ttgtttacca agtggggtgc agatatcaac 178500
tctagcttag ttactgttaa tacggagtat acccggaacc tttgtcagaa attaggcgca 178560
aaggaagctt tgaatgaaag ggatatttta caaatatttt ataaaacacg tcatcttaaa 178620
actagcagta atattatttt atataatgaa ttgttttcta ataatctcct tttccaaaat 178680
atagagagat tgagtttaat agtttatagg ggcttgaaaa acttatcaat caactttata 178740
ttggatgata tttcatttag cgaaatgtta actagatact ggtatagtat ggcgatatta 178800
tataacctta ctgaagccat ccaatatttt tatcaacgat ataggcattt taaagattgg 178860
cggcttatat gtgggctttc ttttaacaat ttgtctgacc ttcatgaagt atataactta 178920
gagaagacgg atatagacat tgatgaaatg atgaagttga cctgtagtac gtatgatggt 178980
aattattcga ctatttatta ttgttttatg ttgggggctg acatcaatcg ggcaatgtta 179040
acctcggtaa taaactttca tattggtaac ttgttccttt gtatagattt aggagctgat 179100
gctttcgaag acagcatgga actagcaaaa caaaagaata ataatatatt agtagaaata 179160
ttatcattta aaaattatta tagttcaaat acctctcttt tatcaataaa aacgacagat 179220
ccggaaaaaa ttaatgcctt attagatgaa gaaaagtatg agtcaaaaaa tatgttaatg 179280
tatgaagaat tatctcattg atacaaaatt atttttttata acagaactct ctgatggtga 179340
caaatctccg ataggaatat atgacgtaac ataattattt ttttcgccca gaaaaaaatt 179400
ataaatgtta ttattgccag cacttttatc aactatacgt acaaaaaggt gttgaccaaa 179460
aaaataattt tttttcttga tcaaagtatg taaacgcccg cttacagcaa ggatcttaag 179520
tgagagccat taaattttat tgatagctgc ttgccaccag tagaatacgg ccaaaccacc 179580
taacaggaaa tacaaggcgg cccttcggcc aataaggtgg ataaaaatca cgcataagac 179640
ggttgtaaca tagcacttta gtgcgaatat caggaatgcc aatagcatgt agataaggca 179700
ccaaacatcg cagctataca tggctaaaga tcaaccagaa aaggtttaaa ttttaacgcc 179760
ggcccaaaac ttaaactttt tttgatattt ttaagtgcag ccatggattg gtccggccat 179820
aggatgacct atgcctacgt ggcattctca ttgatggcaa tagcaataat atggtattct 179880
acttatctat tgccgatcga aaaaaaatgt tgttacaagc ggtaatacgc tcgctttagc 179940
gccaatatcg catatgtgaa aaatgttcgc cgaaaaaaac attaaaattt agaaccgccg 180000
cggcatctca ggggcggcaa cattttttttt tatatggata ttgtcacaca ccacctcatc 180060
tatgacgcaa tatattactg ctaatatcag gttccccaat agtatgtaga gaaaccacac 180120
aagatagata ttcatggcga tttttgacga aaaaacatta agttttagct tctttgacgc 180180
ctgtgtacta ataatgttta acgcctgtag tataataatt gatacctaca gcagtaattg 180240
atacctacgg cgataatgtc tctctggccg ccccaaaaaa aagtatttac ggtagggttt 180300
attaccggcg gcgtaacacc agttatggtc aattttgtct ggcccgccgc ccagccgcaa 180360
aaaaaaatca attacaaccg caaaaaaaaa tatttccggc cgcggcgttt caaaaaataa 180420
tctttgcgaa ataattccgc atcttgtgaa atgaacgcct acagtaataa ttttaatctt 180480
tgacacctac agcagtagta ataattttaa tctttaacgc ctgcagcagt actaatattt 180540
ttaatcttta acgcctacag cagtagtaat aattttaatg tttaacgcct acagcagtag 180600
taataatttt aatctttgac gcctacagca gtagtaataa ttttaatgtt taacgcctac 180660
agcagtacaa taattttaat gtttaacgcc tgcagcagta ctaatatttt taatctttaa 180720
cgcctgcagc agtactaata tttttaatct ttaacgccta cagcagtagt aataatttta 180780
atgtttaacg cctacagcag tagtaataat tttaatcttt gacgcctaca gcagt 180835

<210> SEQ ID NO 2

<211> LENGTH: 10857
<212> TYPE: DNA
<213> ORGANISM: African swine fever virus

<400> SEQUENCE: 2
acttatacca aaattttaat acaagtgtat ttctcgtcat ttcttcttct ttttcatcta 60
aatataagat aaaacgattg taaacaaagt ctatcaatag gtgaaaatca ttgctattaa 120
agctgtcgag aatcaaaata ttgtcataat aaatttcgat cgccagtaaa acctttttc 180 gtttgacgag ataaacaaac atattataca accctacatc taaaaattct ggattggctc 240
ctagttggat acacaggtct ttagtctgct tcgttttggc acacatgatg ccaaaattaa 300
tatcagcacc ccataaaaca aataacttga ttagatcagt ctggttttcc ttcacagctt 360
ttactaaggc tctgtcaagc tcatagctgt cgacatcaga gcatgacata gagccaccgg 420
ttaccatttt acattgctta caaaaaccta tgggtccgtt ttcccaccat agtccaagct 480
gttgtagaat aaaaatatca tcctcatgat aatttgaaaa agccttggtt tctatcaaga 540
ctttttttgt aagaacctgt aaagagttca tcgtattatt atgaataaca ggagtaaacg 600
taatcaatta taaaagtgat tttttcgaaa aaaactttag atggttgaaa atgataatgt 660
acatgttcat acaaaaaata gatgcagtga tgtctaaaat caaaatttaa ttttctatgt 720
aaaaagtaca gacttactta tttgggttaa attgtttatt ttaaacttta attaaccgtt 780
tgagttagcg atgtttgatt tatcttccat actcatccgg ggggggggtc cttatagctc 840
tgacattatt gtggattatt gaatataatg aatacttcat agatgctaaa cattttaata 900
gtagttctga ggcttaattg tactctataa atttataaaa actttttgat caaaatttaa 960
tttcttataa aaagagtaca gacgtcgctt gtttaagctt catcatgttt cattcattac 1020
tttctacaat tacggggggg ggagtcccct catagcttta gtattgctat ggtttactaa 1080
ttattatgta gaatttatag aagcatatgt acctgaaagt atacctactc tataaaatta 1140
aataatttca gtatattttt tttatgaata gaacggaaat gatataaaaa taatttaata 1200
ttgcaaaaaa aattcataat gttggtatgt attataaaca taatagcatg tgtaatttat 1260
aaactgactc ctctatataa ttattagatg aggtaccaac ctacttatga tatgccgatg 1320
atagatattg tatactataa aacaaaatta ttttaaatgt attcatggat acattataac 1380
atttttaccg caaattgtct ctcagcgaag aaaatgaatg aaacgtttct gtatattcat 1440
aggttgaaat tattttacgc acttcactag gttctaatat tttcttatga agtattgaat 1500
gggggcttaa aagtcctttc ttaaaaagaa gtttcatcat aacattcttt tcttgtctaa 1560
gaagagtttc ttgtattttt tttgtataag gattggcacc caaacttata caaaaatgta 1620
cattactcca aataccataa tttgaaaaga aagttatttc cctatttact tcatgattaa 1680
tgaaacctat caacgtctct aaggccgtat tgatatttgc gcctaaggca aaacaatagt 1740
atatacccaa tttattttga gggtacatac aagcaagcga catcatgtca tttggatcta 1800
aacgtatatt ttcctgaaaa tatgcatgat ggatttcatc aacattacct aagtatacag 1860
ccgtttttaa acgccaataa tctaggtgag gaaatttctt actaagaaaa cgaataggtt 1920
ttataagatt aaactctatg gcgatcttaa accaaaattt taatacatat gtattttta 1980 tcattttttc tttttcatct aaatttaaga taaaacgatt gtaaataaag tctatcaaca 2040
cgtaaaaatc atggctatca aaactgtcga gaatcgaaat attgtcataa taaatatcta 2100
tagctaataa gacctttgt tgtttaatta gatcaacaaa catattatac aaccctacat 2160
ctaaaaattt tggatcagct cctagttgaa tacacagaac tttcgtcctt tccgtcttgg 2220

-continued

```
cacatatgat gccataatta atgttggcac cccataaaac aaataacttg attagatcag   2280
tctggttttt cttcacagcc ctcaccaagg ctctgtcaag ctcatagctg tcaacatcag   2340
aacatgacat agagccactg gttaccattt tacattgttt acaaaaacct atgggtccgt   2400
tttcccacca taatccaagc tgctgtaaaa taaaaatatc atcctcatga taatttgaaa   2460
aagccttgtt ttctatcaag actttttttg taagaacctg taaagaattc atcgtattat   2520
catgaatgaa agcagtaaat gtaatcaatt ataaaattga cttattgaag agaaatgtta   2580
aatgagtgaa atcggtgttt atgatgatgt acatgatcat acgaagaaac acgttcactg   2640
gtgtccatga tcaaaattta atgttttacg taaaaagtac agatgttaac tgtttagttt   2700
aaacataaat ttaaccttta gtttaaaccc tagttaatga tgtttaatat ttcttctata   2760
ctcattcagg gaagtgtaat gattctaata ctgttgttat ggattattaa tgaaaacttt   2820
acagatgctg gagggaataa ttttaatcat actgttttaa tgtagctata taagctttca   2880
tcaaaattta atttttttt ataaaaatac acgaattaaa ctaaagtcta aactttagtt   2940
tgactatttg agttaatgat gcttaactta tcttccatgc ttatcaaggg gggggtccta   3000
atagttttga tactattgtt gtggattgtt gaatataata aatactttat agatgctgaa   3060
atgtttgaaa ataatagtac atcaatgttg taagtttgat caaaatttaa tttctcataa   3120
aaaaggtaca catcaacatt gctcatttaa gtttcatgat gtttgattca ttacttccta   3180
caattactgg gggggggggg ggggtcttta atagctttag cattgttatg gtttgctgac   3240
tattatgtag aattcataga agcacgttta gatagtaata tcactgcagt gtagattatg   3300
aaatacatac taaactaatt tcagtatatt ttttttgttc atataagtta aggtacaaaa   3360
atgattaaac attgcaaaaa aagaaaatca caatgctatt atacatagtg atcatagtgg   3420
cttgtatcat ttctaaacta gttccaaatg aatattgggc aatacatcta tttttttatca   3480
ttatgatttt tatggtatat atgtatgaaa agttagatat acatcaaaaa tctcagttct   3540
ggaattatac catgtcaggc ttatctggac ataacgtaca ggtaacatgt aagtgttact   3600
aaatactatg aagtatctat tttttttgt tgtaaaaaaa agaacttgat agtatttttt   3660
aaaaaataaa ataattaatt gtacgtcaac ttccttattt tattctttaa aaataactcg   3720
taagtattat ttatctattt tttgaaaaaa tagatgtaat cggtttcatc atttaggtgt   3780
gtatttcttt ttagcatcta tcaagaattc attgtttagt gatatgaaaa caatgaatga   3840
tcattatctt ctatttaaca accacctaaa taaatgaacg tctttttcat cttaactgat   3900
taccaaaagt tattttgcga aaaggcatac atatgatcaa tatcagacct acaatgaata   3960
tttccataat atccctttat tgtaataatt ctatttttgc attccgatat ctcatcatct   4020
gtgctattat atgtttccat aactgtttca tcatcaaaca taaatcctgt taaataggca   4080
aaagacttta atcccggata gatttttacc attttcctga gagccgtgta tagcttgtaa   4140
taaatggcca aaaatatgca ataaagcgta gaaagagagt aatttttggc ataaaagatt   4200
ttgaaggttt gatgaatggc taaatcgcat ataatataag atacgatttt aaagcgcacc   4260
tgttcacgca gatttgttga aaaattcgtg gaaagattta acaaataaaa ggttattaat   4320
agttgctcat cattcccctt atacgacatc gtcagacgct ctaatatttt actactaggc   4380
acatctgcca catgttgaac atttaaagcc tgttcttctt ctgtgttacg gcaaaagagc   4440
cgtgcgtatt caggtgaagc tccccaggat aacaacgtcc ttgctacggc taaatttttt   4500
ttgacgatga cttttatcag aaataagtct ttatttttgc attgatcact atgcgaattt   4560
```

-continued

```
gtatagttga cgccgttgca ttgagtacat tgatataatg ttttacaatt ccagcgtagc   4620
cctaaatggt ataaaagaac tgtattttcg acataagcat gctgattaac gatgtttttg   4680
agacaacacg tcgttaagga caccatattg tctccaattt gttagataaa agtctttact   4740
aaaaaaatag atttttagtt ttaacaatcg agattttatt atttggatgc atcatcaaaa   4800
agatttataa gtataagagg ttgtataaga aaaaaaatga tgttatacta tttatgttaa   4860
aatttaattt atcatataaa aagtacagat ttaatcagtt ggttaaacta tttagttaat   4920
taaactaaat agtttaacca tttagtcaga ctacttggtt agcaatgttt gagctttctt   4980
ccattcttat ccgggggggg gtcctaatcg ttctaatact attgtggata gttgaatata   5040
atgaagactt tatagatgct ataatgatga attctagtat gcctgtataa aataattaac   5100
ctttttgatc aaaatttaat ttttttataa aaagctacag agtagtgttt tattaaacgt   5160
ggcttattta aaagttacac aatgttaaaa tctctactta ctttaattct ttgtggggtt   5220
ttattaactt tatccatatt atggcttact acttaccatg tagaacttat agaggcaata   5280
gatgatttct acgactgaaa tatagaatag tccatttttct atttgtaaaa taatgattta   5340
tattctttcc taaaaatgat actttatatg gtttgaaaac aaatattaac aacttgattt   5400
tttttctat aaataaacta taaatgaaaa tagtaaaact catagagtct tataagtgaa   5460
catcttcata atgttactca aacgttggac tattaaaaaa tattccgtgt gcattattgc   5520
ttttaatcag tatgattact ttatacgaag ccgctattaa aacgcttatc acacaccgaa   5580
aacaaatttt aaaacacccc gatagccgtg aaattttact agctttgggg ttgtactggg   5640
ataaaactca tattcttgtt aaatgtcgtg aatgtgggaa tatgagtctt accggaaaac   5700
acagtacaaa atgtattaac attaattgtc tacttattct tgccataaaa aaaaagaata   5760
agcgtattgt tgataccttg ataggaatgg gcgcggatgt aacatatata catcttttaa   5820
agaataagat aaaactgtca tacaaccagc tgtctatgct taaaagcaac tcgcagattt   5880
cattgaagga gcttcatgct atatgctatc ttttatatgg tcggcttccc aaaaaaatta   5940
aacaagggat gcgactgtgt aaaacaatgg cgggactatg tggtgaactt ttatgtgcat   6000
ttttagctcc gtaaatgata atatgtattt aaaacaaaca gatattacca aaatatattc   6060
tatgtacata atatctggga aattattttt ttttctcata cccttaaata taaaaatatt   6120
gggtttcttc actaaacttt agaggtaaaa atttttcttt gttttgcacc atcatgtatg   6180
ggtttaggct gtcccaggga ttgtttattt gaatatttcc taaataggaa cacaacgcca   6240
tgatcatata tctttcattc tggtaagctt tttgatacat cttcaaagat gccgtacctc   6300
cgagtgtgta acagcaaaca aacgtccgta cttttccatg ggtcgcagcc cattccattc   6360
cgtagctcag catcttttgc tgtatttttt tattcgcttt ataaaaaaag tttttcatcc   6420
attccacgtt ctcataaaaa caggcactta aaaagagcac taggggtagt gtagtcttat   6480
tatagaatgt aggaatgtat gttttagtta tttttttcaa cgcgtgttcc atactatgtt   6540
ttaccgccat aaaaatacaa aaccaatacc aactttttct ataaaaggtt ttgctgtaca   6600
catataaacg agcaaaatat atttcaaact ctatattctt tttataaaaa aactcgagac   6660
agtcgtttat gttacgactt tttctaaata cctcaaaaac agtaattaat tcactgtcgc   6720
tgtggaaatg ttcgtaagct aactgtttaa tgtctttagg ggtcaattct ttttttggga   6780
gcagtggttt gagattcggc aaaggtcgtc taaagtagtg agcgaacttt tcattcgctc   6840
cccaacacaa aagccgataa gccagcatgt agttatcacg ttttaccgcg taaataagca   6900
aatagtttat attgatacat gtaccatgtt gctgcccgtt tggacatatg ttgccgcatt   6960
```

-continued ctgaacactt atgaatgaga tcatagttct tacaacataa ccccaaacgg gttagtactt 7020
ctttgtcacg ttttaaaaac tcgacatgat tctttaatgt taatgctttg agcgcaatgt 7080
taaataaact ctgcatttta ttaaaatgag gttagtatca tgttttagta taaaatttag 7140
cggctgttta cataatgcta aataaactta acgttcctac taaaccaaaa aaaaatcaaa 7200
ttgactaagt catagagaat ttgacgatgt tggtaggtaa ttttttaaca tggtatatat 7260
tttttaggg tcggttatat taggtaataa aagaggacgt gccgttaaag tattttgctt 7320
aagatccttt agatccttac aaaaatatag attgttcgtc tgatgatgcc actgtgttgc 7380
agtgatggct tgatcaatat cacctcccaa gacaaaacag tagtatatcg ttaaaaagtt 7440
gtaatctttc atacaagcca actgcatcat tttatcgatg tccatatgaa cgatcttttg 7500
ctcgtatatt tcatgaaggt caaatacatt gttgaagtaa atggcgcaca tgagtcgcca 7560
catactaagg tgcccatatg tttgatagaa aaaggagata gctcttttaa gcttatattt 7620
tactgctatg gcatagcagt atttaacgaa tacgttcatg ggtacattat ctaagatata 7680
aaatatgaaa aactttaact ctcgatgaat ctcttccccc atttcctgta catttagagc 7740
ttccaacata ggatttttat caaatatttc atgacataaa ataatgttat tgctcgtttt 7800
atgacgcatt aaaccggtga aaatttcctt attatttaaa ctatctttag ctcctaactt 7860
tcgacacagc tcctgagttt gttccgtcct agcacaggtc agcccataat aaatgtttgc 7920
tccccactcg gtgaacagcc ttattacgtc atagttattt tcttttatgg ccatgattaa 7980
tgccacatca agatgaagaa gttcccccctt aaagggggtt gagcttaaaa taacgtaatt 8040
acagtagtga cataagctaa tgggcttgtt ttgccaccat aagccacaat attttaaaat 8100
ataatgatac tcctcaggca cgctctgttt ggccacagcc tttttggcca gggtttgcaa 8160
ggagagcatg ataacttctt gaaaaaaaaa ctcaaattaa gttcctactt ttttaaaata 8220
ttagtatgga cagatctacc atcatatgaa ggaattcttt catcgttaaa cactgaagag 8280
ataatacttt catcgtatag agaatatcat gtcaatccat atattgaatg ttatatatca 8340
ttaaacccat cattaatata gtgtttatgt gctatggaca ggtttttttga atgataatct 8400
tttaacatac gttttataac ttcgggatca gtttctttta aagataaaga atcattcatg 8460
ttataacaat ttaatgataa catgctggca atgaacgagt tgtctttttg atgcgctaga 8520
gtctttccct cctcaaaggc attggcgcct aagtctatac aaaagaatat gtttccgata 8580
ttatagaact gaatagaatg aaacatggcc tgattgatat cagcccctaa gacgacgcaa 8640
cagtaataaa tcgttaaata gttatagttc ttgcgacagg cccactttag catttcattc 8700
atgtctatgc gaatcctctc cttttcgtac acttcgtgaa gttcaaacac attattgtaa 8760
aaaagggcgc acataagccg ccaccgatgt agatgagcat atctctgata aaaatagcaa 8820
atcgcctcct taaggttaca ttctattgcc atcgcgtacc aatatttagt aaacatctcg 8880
cttaatatat cggtttctac cattaatccc tccagttgtt cataaatcat tccctttact 8940
tcaaaacgat ttatggtatc taaaatggga ttattagaaa atacctcatg gcagaaaatg 9000
atgttactgc tagttagatc acgtttcaat gtgtaaaaaa atcgtaaaat ttcctggtca 9060
tttaactgtt ctttggcacc tagctgcctg cacaggtctc gggtgtgctc cgtgttgaca 9120
gaaagcaaac cgtagttgat gtttgcaccc cactcggtga acaattctat tagatcgtga 9180
ttgttttcct ccacagcttt caccaaggcc gcgttaagat ttgtgccgtt cttaaaatac 9240
ggcgtccata ttttcttttg atgatacatg atagggccat tatgccacca tagaccgcag 9300

-continued

```
cacttcaaaa aatgaggatg gcatttggcc ggatactggc tggccagcac ctttttggtg   9360
agagtctgca gagagaggac catatttctt ttttttgaaa aaatcaaatt aaaaaaatca   9420
tgcttgttta gcatacatgt aatattgtta taattacgtt ataattacgt tataattacg   9480
ttataactat attataacaa tggtataaca atggtataac aatgttataa caatgttata   9540
acgatgtatc attgatgtca tcattcaact aggccaacat actttttaat ttatagtttt   9600
ttaatagatg atatattttg ttaggatctg cttcttttaa cgttaatagc gaggagtctg   9660
cactataaat gtctaatgat aaatgatgag atatcaaata gtaattccgt tgctctgcta   9720
gggcctttgc ctcttcaaag gcgtcggctc ccagatctat acaaaagaac aagttatcca   9780
tattataaaa tcgtacgcag gcaagcatag ctgaattaat attagctcct aagagaaaac   9840
aataatatat ggttaaaaaa ttgttatctt ttgtgcaggc catccgcatc atttcatcca   9900
cgtccatgcg gatcttttcc ttttcataca aattatgtag gtcaaacagc ttattaaaac   9960
aaagagcaca gattaaccac cacgtattta gatacttaaa atgttggtaa acataagaaa  10020
tggcctccct aagattatcc tgcaatgcca ctataaaaca gtatatcgtt aacatatcac  10080
catccgacat attacttaat atgtcggtgt cttctactaa ccttttcaac ttccaatata  10140
tggatgacct tatttccctt ataatgacat aggctggaaa gggattatca ttaaaaagtt  10200
taagacataa gataatatta ctgctagtag tgccagggtg tattaattta aagaacatgt  10260
gcataatctt ctttttatcc acgcggtact tggctcctaa ttcccagcaa aattctcgaa  10320
caggcggcgt attggcgcaa attaacccat agttgatgtc tgcgccccat tctgtaaaca  10380
gttttattaa ctgatagttg ttttcctttg tagccaacat tagtgccgta ttaaggtcca  10440
agccgtctgc aaagcttggc agctttatca gcatatgttt gcaatcaagg gaaattgggg  10500
ccttatacca ccatagtccg cagcgttcta agataacatg gtactcaata gatacttgct  10560
gtctggctag tacctttttg gcgaaggatt gtaaggaagg aaacatcctg tttctttttt  10620
ttttaaaaat caattatctt tgttcataat caagaaaaat ccccatattt attgagtgat  10680
aattttttaa catgcaattt attttttcag ggtccgtaac gatcgacaac agagaaataa  10740
ccggattgta atgctttaat gataaggcat gggctatcag ataattttcc ttttgttctg  10800
ccaaagcttt gccctcctca aaggcatcgg cacccaggtc tatacaaaag aacaggt     10857
```

<210> SEQ ID NO 3
<211> LENGTH: 190584
<212> TYPE: DNA
<213> ORGANISM: African swine fever virus

<400> SEQUENCE: 3

```
actgctgtag gcgtcaaaga ttaaaattat tactactgct gtaggcgtta aacattaaaa     60
ttattactac tgctgtaggc gttaaagatt aaaaatatta gtactgctgc aggcgttaaa    120
gattaaaaat attagtactg ctgcaggcgt taaacattaa aattattgta ctgctgtagg    180
cgttaaacat taaaattatt actactgctg taggcgtcaa agattaaaat tattactact    240
gctgtaggcg ttaaacatta aaattattac tactgctgta ggcgttaaag attaaaaata    300
ttagtactgc tgcaggcgtt aaagattaaa attattacta ctgctgtagg tgtcaaagat    360
taaaattatt actgtaggcg ttcatttcac aagatgcgga attatttcgc aaagattatt    420
ttttgaaacg ccgcggccgg aaatattttt ttttgcggtt gtaattgatt ttttttgcg     480
gctgggcggc gggccagaca aaattgacca taactggtgt tacgccgccg gtaataaacc    540
ctaccgtaaa tacttttttt tggggcggcc agagagacat tatcgccgta ggtatcaatt    600
```

actgctgtag gtatcaatta ttatactaca ggcgttaaac attattagta cacaggcgtc 660
aaagaagcta aaacttaatg ttttttcgtc aaaaatcgcc atgaatatct atcttgtgtg 720
gtttctctac atactattgg ggaacctgat attagcagta atatattgcg tcatagatga 780
ggtggtgtgt gacaatatcc atataaaaaa aaatgttgcc gcccctgaga tgccgcggcg 840
gttctaaatt ttaatgtttt tttcggcgaa catttttcac atatgcgata ttggcgctaa 900
agcgagcgta ttaccgcttg taacaacatt ttttttcgat cggcaataga taagtagaat 960
ataccatatt attgctattg ccatcaatga gaatgccacg taggcatagg tcatcctatg 1020
gccggaccaa tccatggctg cacttaaaaa tatcaaaaaa agtttaagtt ttgggccggc 1080
gttaaaattt aaacctttttc tggttgatct ttagccatgt atagctgcga tgtttggtgc 1140
cttatctaca tgctattggc attcctgata ttcgcactaa agtgctatgt tacaaccgtc 1200
ttatgcgtga tttttatcca ccttattggc cgaagggccg ccttgtattt cctgttaggt 1260
ggtttggccg tattctactg gtggcaagca gctatcaata aaatttaatg gctctcactt 1320
aagatccttg ctgtaagcgg gcgtttacat actttgatca agaaaaaaaa ttatttttgg 1380
accccccccc atgttttata caaaaatcat ataataaagt ggcgacaatc aacatattaa 1440
tcaaccacag cattttatga tgtgttaatc aacatatacc atattaatca accacagcat 1500
tttatgatgc gtcaatcaac atattattac ggagagcgtc aatcaatata atattgagaa 1560
cagcgacttg ataccgtgta tggtggtggc ggcggcatgt tgtttgtaac agcatttttc 1620
atcattcgaa gcttacaaaa gatatgtata agatagcata ttaatgttat taacagtaat 1680
atcaataagg cgtagctata gatcttcact ttggtagacc aataatccat ggttgcgctt 1740
aaaaatacca aaaaaaacat taagttttgg agggtaagat tggtttttca ccattggtaa 1800
agattattat tctaaatgtt taccccatag atgtgaaaca atgattcttc atatattaac 1860 atatttttttg acttatactt ttcttcatct agtaaggcgt taattttttc cggatctgtc 1920
gtttttattg ataaaagaga agagtctgga ctgtaatttt taaataataa gatatttatt 1980
aatatccaat tattcgtttg gctcgctatt tccatgctct cttcgaaagc atcagctcct 2040
aaatctatac aaaggaataa gttaccttca caaaaattca ttaccgaggt aatcattgcc 2100
cgattaatgt cagcccccaa cataaaacaa taatatatag ttgtataatt acaatcatac 2160
atacaggcca actgcatcat ttcatcaatg tctatatttg tcttctcttt gttataaatt 2220
tcatgaaggt caaagacgtt gttataagca accccacata ttaaccgcca atctttaaaa 2280
tgactatatc gttgataaaa atattggatg gcttcagtaa gcttatatag tatcgccata 2340
ctataccaat acctagttag catttcgttg aatgaaatat tatccaatgt aaagttaatt 2400
gataatgtat ctagttcacc aaaaattctt aatttcagtt gagcattatt taggaaaagg 2460
ggattatcag ataataattc atggcataga ataatattac tgctagtttt aacatactgt 2520
acattataaa atatttctaa aattttattt tcactcaaag ctttcctcgc acctaacttt 2580
tggcataggt cctggtgcac tccatattga cagtaaccaa cccaaagctg atgtctgcac 2640
cccattcggt aaacagctct attaaaccat gattgttttc ctgtacagcc ttcattaatg 2700
caacatttaa tgttaaacca tgtttaaaac ttgctgtttt tattaatatt tgttcatcta 2760
tacaagtatg ataaatcgta attggggctt catgccacca caaaccacaa cgctctaaaa 2820
tacaataatc atcttttaac acaggctgtg tagctagtac ttttttagta agtgcttgta 2880
aagtagatgg catcttctat ctgcaaaata attatttccg aaaaaaaaat caaattaaaa 2940

-continued

```
tactaaattc tatttttttt tttaataaag cctgtaaatt atataataaa tctcgcccac   3000
cgtattattt ccggacacaa ctttttatac ctcattatat ttttagatct atagtttttt   3060
aacaaggcat taatttttttc tggatctgtc gtttttaaag ataaaagaga gacgtttgaa   3120
ctataataat ctttaaatga taatatttct actaatatat catgattctt ttgttttgct   3180
aattctaagc tctcttcgaa agcattagct cctaaatcta tacaaaagaa caagttattc   3240
atataaaagt tttttaccga ggtaaccatt gcccgattga tgtcagcccc caatacaaaa   3300
caatagtaaa tggttaaaaa attgctatct ctcatacagg ccagatatat catttcatca   3360
atattcatat caaccttttt tatatgatac atttcatgaa gatcagacac gttattaaaa   3420
gaaagcccac atattagccg ccaatcttta aaatgactat atcgttgata aaaatattgg   3480
atggcttcag taagcttaca tagtatcgct atactatacc aatatctagt tagcatttcg   3540
ttgaatgtta tttcattcaa tataaagttg atcgatatct tctctagaaa acaacaaatt   3600
attactttta attcctctat attctggaaa aggggattat tagataacaa tttatggcat   3660
aaaataatat tactactagt tttaatacga tgtattttat aaaatatttg tacaatatcc   3720
atttcattca aaatttttgc gcctaactcc cggcagaaat tccaagtatg ctccgtattg   3780
acagtgacta agctagagtt gatgtctgca ccccattcag taaacaactc tattagatca   3840
tagttgtttt cctgcacagt tttcattaat gcgagattta actctaaacc atctttaaaa   3900
attgctgatt ttatcatcaa ttgattatcc tcattagtag aaagcataat tggagctcca   3960
tgccaccaca aaccacaata tttcaaaata aagtagtgtt ctttagatat gtgctgtgtg   4020
gccagtattt ttttagcaag agcctgcaga gaaattggag tagacatatt tttttttgca   4080
aaatggttta agtttttcaa gaatacagat tggataaatt aggttgttga cttagttaca   4140
ggaggtatta aatattatgt agacataaaa atgagatcct ccaaaaaaat aaacaacaaa   4200
aaaaaatatg tttaatatta aaatgacaat ttctacattg cttattgctc ttattatact   4260
acttattatt attttagtag tgtttttata ctataagaaa caacaaccac cgaaaaaggt   4320
ctgtaaagta gataaagatt gtggtagtgg agagcattgt gttcgtggat catgtagctc   4380
attgagctgc ttagatgccg taaaaatgga caaacgaaat attaagatag attctaagat   4440
ttcctcatgc gaattcactc ccaattttta ccgttttacg gatactgctg ctgatgagca   4500
gcaagaattt ggaaaaacac ggcatcctat aaaaataact ccatctccaa gtgaatccca   4560
tagcccccaa gaggtgtgtg aaaaatattg ttcatgggga accgatgact gtacaggttg   4620
ggaatatgtt ggtgatgaaa aggagggaac atgttatgta tataataatc cacatcaccc   4680
ggttcttaaa tatggtaagg atcacatcat agccttacct agaaatcata aacatgcata   4740
aataaataca ttaggctcat cgtatctttt taaaatccat aaatattcgt ttgatatatg   4800
ctgaaatttt tataaaaaaa aataactatt tcctataaat catctagaaa tagtcctcgt   4860
tttgatcggt ttatatctta taatattgtg catcgatgca caactgcttt ttttggtcct   4920
tctggaacat cattatattt tctttcatta atataccatt cagatgtaaa cgttgaataa   4980
tttttatggc aacaatctac cattgaatta tatttagtaa catctaatac atcgtttgtt   5040
ttatcaggct cagctctata atcttgataa tttttgttat cagcttctaa agctccatca   5100
ttatttttca aagaagtatc cataattatg tttggtaaaa atactttaag ttttaatgtg   5160
atatttaaaa tggttgttat ataaatttac cgcttacagg taatctttat tcagtgtcat   5220
aaactatact tttgatgatt cagtattttg tgaatcagta catttattat cattaatatt   5280
tttaggctgt ttttccaatg ttttattgtt gcaatgagcc tgctcctcct ttgacgagga   5340
```

agtgtctgtt ggagtcatct gtttaggaag agtatcatcc atatctatta tgaagaaaat 5400
atataaatat tgatatacaa tcaaaaatat ttttgatcac gtctttgtta tctatcgata 5460
ttgttgataa cgtcttgaat aacctacatc attttttac ataaaaaaat agatataatt 5520
tttattatat ctcaattatt ttaaagataa ttatcaatac agcaaatatc ataagctaac 5580
atatttttcg aataatagtt ttttagtaaa gtattaatct tttcaggatt ggtttctttt 5640
gataataaga taggattcgc tttataaatt tttaaagata atatattcac aatgatagaa 5700
taaccgtata tatctgctaa tgtcttactg tgttcaataa cattagcccc taaatccata 5760
caaaagaaca tattttcaat acaaaagttt tttaccgaga ttaacattgc tcgattagcg 5820
ttggctccca atgcaaaaca gtagtaaatg gtcaaaaaat tattatcgcg catacaggcc 5880
agctccatca ttttattaat actcatatga attttcgttg tgttacatat ttcatgaagg 5940
tcaaacacat tgttgaaaga aagtgcacaa attaatcgcc attcatcaaa atgcctgtat 6000
tcttgacaaa aatattgaat agcttcttta agattatatt ttaccgctat gccataccaa 6060
tatttggtta gcatctcact aaatgagatc tcatttaaca tagaatttgt tgttaaatcc 6120
ttcaactccc aataaatgat catccttaaa tccaccatgt ttacattttg taaaaaaggg 6180
ttattagaaa ataattcatg acacaaaatg acattactac ttgttatttt acactttgtt 6240
tcaaagaaaa atcgtaaaat ttcacttgtc tcaagctctt ctttagctcc caattttcgg 6300
cataggtttc gagtatgctc gttattaata aaaagtaacc cataattaat atttgcaccc 6360
cattcagtaa acaacatgat tagatcatca ttgttttcct taactgccaa taccaatgca 6420
gtattaagcc ttataccctc tttaaagcat aatgtcctta tcattatttg attatcatca 6480
tctatataca ttgagatagg agcttcatgc caccataaac cataacgctc taaaatataa 6540
taatcatctt tagatacgtg ttgcgtggcc aatgcccttt tagcaagtgc ttgtaaagtc 6600
gatggctgca tgtttattct gttaaaaaaa aatcaaatta tcgggtaaac ataaggatca 6660
acccgtagtt aatatttgca gtagtatttt ttaacaatga attataataa aaaaataatt 6720
cattactatc tattataaaa cccatcttta actttaaaga agaactagat catctttttt 6780
tttgttgtgt cagaacttct tcaatttatt acccacattt tatctaaaaa aaataaaaac 6840
tacatcatat cttgtttctt catcaaatta tcataccatt tatagggtgt aggttgggaa 6900
cattccatca tgtggtaatc agggtattta tatatttttt gatagtaaca tctatttggc 6960
agatgtattg tccaacaatc atgtctaata aaatcatttt cacctatggg ggaatcatct 7020
taaaaacctt attcctacag attccatttt gacagtccca gcaaaagtca caatattttc 7080
catgagtaca ccaatgttca agctctcttt cgggaggaat gctgccaatt ttatgttttt 7140
tagcttctaa ctctctgtac aacatcagtt gggaaagcag aaagaagatt accaggagaa 7200
ccattaaata tataatagtc tgcaaactac gtttgcgaat gtaatttgca actaaaacac 7260
aacccacaag gtaaaatcca taagttaata acttttgcca ttttcgtatg acagcctcgt 7320
gccattcatg gttgtgttgt gggcattctg ttcggtaaac ttcatgaggc tttatagaag 7380
ttacatagta ggtacagaat tcattgtgac gaaaaacact gcagttagct atgtagtcat 7440
tttcaagaat gggagaatgg ttttcaaaga ccttattctt acagatgcca tcttgacagt 7500
cccaacagaa cctacaatga tttgcatagg tgcaccagta ttcaagctcc ttttcaggag 7560
gggttcttgt tagatccagg agctctagct catatgtata aagaagagtt ggaatggata 7620
gtaaagtaaa tatttgcaga ccaagcatgg ctacttgtga acaagtggct gctcgtcaac 7680

-continued

```
aaatagctgt ttatcagcaa atagctgttt atcagcaaca actaattatc agcaaatgct   7740
gcttgtgggt aagccaataa ataggccata cccttgaaag gagaattcag tttgataaaa   7800
aaaataacga gttttctaat aacccggtca agcatttaat aaatgaatag catcacacgt   7860
ctgcatcgtg cattctgcct ggaaaatggg cccatctcta atatatttac actgacggtg   7920
aatcatacag tgttccatgg gatagctatg ctcctgtaca ggaggcatat cttttagaac   7980
tttattctta caaagaccat cttgacaagc ccagcaaaac cgacaatttt tcacatattg   8040
acaccagtat ctaagctcct cttccagggg attgtcggtc gaaaacccct gtagactagc   8100
taggccagct agcagcaagc cgaggtaact aaagaacctc attgtagtgt tatattacga   8160
aaaaacatgt taaaatttgg aaaaaaaagc ccttttttata gatctggaaa aaaattttca   8220
caaatctaat taaaagcctt acagatcatc cttttcataa attttcatta acaattggtg   8280
ggggcggttg tgaggtactg gatcagaaca atccataaca tggtaatgtc catttccttc   8340
accatatgta cactggttat accagcgaga aacctcacaa gatgtcaaat aactgttctc   8400
aacaatcaat ggcatgctct tattcacctt gttcttgcaa attccatgtg cacattccca   8460
gcaaaacttg cagttttcca tgtaagtaca ccagtatcca agttcttctt gtggaggatt   8520
atccgttgaa cgaagatgcc ctcctgcctg agtaggtagt cctaagacct gattggccag   8580
caggccaaga atttccaaga agatcaccaa cattgctacg gctggctgaa cagctggcag   8640
atagctagct aattagcaaa ccaagtgact cgccctctct actcttaata tgagaattta   8700
agattcggtc cggctttttt cccatgtttt acagggaaaa ggtattttta gcctatgaat   8760
gtacatggtt ccgcacatta aaaaaaaata aaagaaatta tttaatattg gctgttattt   8820
tctttcaact agcaacaagc caggtaacta aagaacttca ttgtagtttt atattacgga   8880
aaaggttaaa ttttggacaa aaaaaatcat atctaattaa aaatcctcac agatctttct   8940
tttcataaat tttcattaac aattggtagg ggcggttgtg aggtactgga tcagaacaat   9000
ccataacatg gtaatgccca tttccttcac catatgtaca ctggttatac cagcgagaaa   9060
cctcacatgt tgtcaagtag ctgttttcaa taatcaatgg catgctatta ttcaccttgt   9120
tcttgcaaat tccatgtgca cattcccagc aaaacttgca cctttccatg taagtgcacc   9180
agtatccaag ttcttcttgt ggaggattat ccgttgaacg aagatgccct cctgcctgag   9240
taggtagtcc tacgacctga ttggccagca ggccaagaat tcccaagaag actaccaaca   9300
ttgctacggc tggctgaaca gctggcagat agctagctaa ttagcaaacc aagtgactca   9360
ccctctctac tcttaatatg agaatttaag atccggtccg acatttttcc gatattttac   9420
aagaaaaaga tatttttagc tacaaataca cttcatatat ccctaaaaaa aacaaaaatt   9480
tatttaattt taactattat tttctttcca ctctctcttt aagattttgt aaggattcca   9540
gggctttggt tcagaacagg ccattacatg gtgaatcccc tgtcctagat catacataca   9600
tttatttagc cagcgggaaa ctatacatga ttgcacatac tcattttcaa gaattgttgt   9660
attctccaat ttgccctcac aaaggccatt ttgacaattc cagcaaaact tgcagttttc   9720
tgtataagtg caccagtatt caagttcttc ttgtggagga ttatccgttg gatgaagttg   9780
tccagctggt tgattaggta gccctaagac ctggttgcaa ttcatggtat ggtagatacc   9840
cttatctaaa tcatacatac atttatccag ccaacgggaa accagacatg atttcacata   9900
ctcattcttg taaattactg acccatctat tttgtttata caagtgccgt cttggcagtc   9960
ccagcaaaat tggcaacttt ccatgtaggc acaccagtat tcgagttctt cctctggagg  10020
ctcctctgtt ggacgaagtt gtccaacgag ctgacttgaa acctggctgg ccagaaggcc  10080
```

-continued

```
aagaattccc aagaagatca ccaacattgc tacggctggc tgaacagctg actgaatagc  10140
tagccaatta gcaatccact gtacttttca taagatcatt taagattcgg tcggcatttt  10200
ttcaatagtt tgctaggaaa aaatttttaa ttttatagat tcacactact tcattctcat  10260
gcttaggaaa aaaacaaact aaatcttaca atgtatctgg atctaatgag aagctagaat  10320
tcatcttttt tcaaatcctt tctgggatgt tcattctttt tccactcctt ccttgcaatt  10380
ttataaggat tccagggctt tgggtcagaa cagttcatgc tatggtaaat gtgctcctcc  10440
acatcatatc tacataggtc accccagcgg gaaacctcac aatattttac atagtcattc  10500
tcaataatac ttgtggagtt gtttccccaa accctgctgg tacaaatccc atcttcacaa  10560
tcccagcaga accgacagct ttccacataa gtgcaccagt atccaagttc attctctggg  10620
ggttcaaatg ttagaggaag atgtccacct acccgagtag aagtggagga tgaaaccagg  10680
ttgctactgg ccagcaggcc aataattccc aggataatca ccagcattgt gctcaaccag  10740
caacggctag caacgactag caactgacta gcaatagcta gaaatggcta gcaatcagta  10800
gtagctaacg ctctactctt tataagaaaa tttaaaattc gatcagattt ttttagaatt  10860
gagaatgagt aaaacgctta tattcttttt ctagctagaa aaaataagct agtttaagat  10920
aggatttccc ttactaacgg tttaattttt agcaaaggta taggtaaaat acacttgtac  10980
ttagctgcaa aaaaataagc ttatggcgta taagccgcca taagtttatt taattaaaat  11040
gttaaactct gtgataagac tggaatctta ggcaggtttg atgtggagaa cagcatgaaa  11100
tacaagagtg cctgttacac gaataagttc tctcaaaccg gggatggtca tactcacatc  11160
tatgaaatcc tggtctagga gattcatttg atgcatgatg gccgcaccca cacttatgag  11220
acactgaaga actaaagggt ttaattttga tctgaatggt actatatagg atgatggcaa  11280
tccatatcaa gattagagca atcaaaatca cctcctcaag aagcatgatg tagccttaaa  11340
tcttagactg ctttaaacct taggccctca ctatctttaa tgaaggagtt taaattttga  11400
tcccttttc aagacccatt tagaagaaaa aaataaagtt tatatcaatc taattcataa  11460
gtcatctctt tcataaatct tcatgtattc tctatgtgga taagtatggg atgttggatt  11520
tgcgcagtcc atttgatgat ctgtatggtt tttgggtcct tcataataac tacatatacc  11580
attccagcgg gaaaccgtgc aatttataat ccagtcattt tgatgaataa ctggccaatc  11640
tgtttgaatc ctgtttcggc agataccgtg gacgcattcc cagcaaaagt cacattggtt  11700
tgcgtaagtg caccaataaa ctagctcatg ttcaggagga taacgggttg gtagtaaatc  11760
ttctaattta cgtataggag cggcttgaag gacaaccacc cccagtagta ctagaatcag  11820
tacctttata gtggccaccc tacactagac ctctaagttg aagacaaaga actaaaattt  11880
agagccgttt aattactact aataattata tttttattg tctacaatag gattctatta  11940
aaaaataatg atttttacca agaaatattt ttataaaaaa ttaatatatt ttgtaataaa  12000
ctttatttcc aatgactgtt aaaataagga aactatcctt agttagtcga ggaagatggt  12060
taggttattt cgcaatccga taaaatgttt attttatcgt aggtctcgta aaatccagga  12120
aaaaaaatta cggaagagtt taaaaaagct aaatttttac caccctccag aagattgttg  12180
tcaaatatat cgtttgctag aaaatgttcc tggaggaact tactttatta cagaaaatat  12240
gacgaatgat ttaattatgg tcgtaaagga ttcggtggat aaaaaaatta aaagcattaa  12300
attatatctt catggaagtt atattaagat tcatcagcac tattatatta atatttatat  12360
gtatcttatg agatataccc aaatttataa atatccctta atttgtttta acaaatatta  12420
```

taacatctaa gtaaatattc ttggaatgga ttttcttata gaatggttac aggatatgtc 12480
agcgacaggc ttaataacaa atttgttaat atttttttgt taaataaatg aacaggccac 12540
catttaatat tacccgttgc aaaataagaa aaaaaaaaca aacttatagt tacaaatcat 12600
cttgattaat cacatgtcgt tttaactcaa tgaaccattc taaatctttg ggttgtgaac 12660
aattcatgtt atgttgatag tgtatcctaa agtgagcttc atacatacac cggtcatgcc 12720
accgggaaac tgtacaatta acaatataat catttttgcgt aataataggg tggtcactaa 12780
acactttatt tttacacatt ccatctttac aggtccagca gaagtcacag tgttttgcat 12840
aggtgcacca gaacttgaga tccctttcag gaggcctacg catttgcatc ggattatctg 12900
tggaaagagg taggttcatt attatgttcg tcatcaaaat tcctaaaaga acatagaagc 12960
caagaaagat aagcagtctt gtagcggctt gcattcgcat tcgtgagtat tgtttgcgaa 13020
catagcttat gagagcaatg gtagctatca tacaaagaca agtatgtttg atattctcag 13080
tgtcaatgac cctatcctcc tttatttgca ttaactcatc aaaccaatca taatatgtgg 13140
gatttgtaca gctcatgatg tgaaagcggc gtatcctaga gtctgtaaag tagctacatc 13200
tttcattata gcgagaaacc ctacatattt gtatgtaatc atttttttg atgagagggt 13260
gtttttcaaa aaccttattt ttacaaaccc cgtgtcgaca attccagcag aagtcacacg 13320
attttgcata ggtgcaccaa tactcaagct ctctctttgg aggtctccgg gtcattggta 13380
actctcctgt tcctggaaaa gattggcttt gaatgaccgg ctgcatgacc gccagtacca 13440
aaaggaacac aatcaccttc atggctgcaa cttataagtt gcaacttatg ggttgcaata 13500
ctgcaacgta taggttgcac cttatagatc gcgactcaaa aggtatgaaa accttaccct 13560
caatacagaa tttaagtttt aatcctgata atgtatctgt ttatgaaaaa aaattttttt 13620
tactcatgta tgaattctta tacgaatcat aatatgtagg ctgagaataa taattcatat 13680
acggtgttgc gggctcaata aaaattttgt taccacaaaa aataaatgct ggatttttaa 13740
gatatatatc tattaatgac taaacccttt atacgctgta ggctgaaaac aatccatata 13800
atgaatatac ggtgatttgg gtttaataaa atacatacaa cggtcaaaat agcgggcaat 13860
actacattga ctaatataat cattttgttt aataagaggc atatcatccc acactttatt 13920
tttacaaata ccgttcctac attcccagca gaaatcacag tgttttccat acgtgcacca 13980
gtattcaagc tctcttatag gaggcgtata agtccttggt aaattttgtt tcatataaaa 14040
gatggaaagg ggtcgattta aacccggctg agatagccaa atcaaaatac ataaaagagc 14100
aagtagtttc atagtggtat ttagatgtaa atttttatag tatgcaaata caatgtaacc 14160
tacaaataca atactaaata caaggtaaaa acaacaatgt cttataatga ttggccaata 14220
atcacccccc ccccccatt tttccatgaa tatttcattt cctgtatagg gtctaggatg 14280
tgaacactcc atgttatgat gattaggcat tttaactgat atttcataaa aacaccccca 14340
ggaattgcga ttaactatac agtttacaat cgaattcatc gaattagact catttgttat 14400
cttattttta caaatgccat tttgacaatc ccagcagaag tcacaattct ttacatacgt 14460
acaccaatat ggaagctcct ccttaggagg atgctgggtt cttggtaatt ctggtaattc 14520
atgtgcaaga atgaggactg agtagcccaa caaaagtcct agaaccttca tgttgtgtcc 14580
aaatggcacc tgtcatttta aaaaagattt aaattttgct accgcaaaaa aaaatccagt 14640
atgtattttt ttaatacata taattattga agtcttataa gataaagccg agaacactat 14700
attttgtata gatgatgtat ccggtattca aactctctta taagtacatg taggaaatgg 14760
tcaattattc aagattggct gagataacaa caaaaccaaa atactcaaaa gcataagtaa 14820
tttcatggtt gtactcagtc gtagattttt gcagatcgca aatgcaacgc aaccagcaaa 14880
tacaaagcta aatacaaggt aaaaacaata ataccttata atgattggcc aattcttatc 14940
cctccatttt tccatgaaca tttcatgttc ataaagtcta ggatacgaac aacatttcat 15000
gctatgatga ttaggtattt taagtgatat ttcataaaaa caccacgggg ttgttggtga 15060
ttgataggta agaataagga tggttgaata acctagtaaa agtcctagaa aaaccttcat 15120
attgcgttca taccacagat gttatttaaa aaaaatataa attttacagt atgtgatata 15180
cacataccac aaaaatgttc ttatattaac taaaatatgt gggcagagag caattcatat 15240
aatgaatata tggtatttta ggctcaataa agtacataca acgatcaata aaacgggtaa 15300
tactacattt actgatgtaa tcattttgaa caataagagg catatcatcc aaaaccttat 15360
ttttacaaat accattctta caatcccagc agaaatcaca gtgtttttcca tacgtacacc 15420
aatattcaag ttctctcata ggaggcgtat aggtccttgg taaaatttgt ttcgtataaa 15480
agatggaaag gggtcgattt aaaactggct gtgctaacca aaccaaaata ctcaaaagaa 15540
cgaaaagttt catggttgta ctcagacgca gattcttaca aagcgcacat acaaagcagc 15600
ctgtatatgc aataccaatg atgaaataga gacagtattg ctttatagat aattgttgat 15660
ggtcaccccc cccccccccc ccatgtttgc atgaatattt catttcctgt atagggtcta 15720
ggatgtaaac attccatgct aaagtgatta ggcattttag atgaaatttc atataaacag 15780
gattgagtct tggaatcacg gaaaactcta cagtttacaa tagaatgatt ggagtcaatg 15840
aaacgagatt ccgttatctt atttttgcaa atgccatctt gacagtccca acagaaatcg 15900
cattgtggta catacgtaca ccaatatgaa agctcactct tgggaggatg ctgggttctt 15960
ggtaagtctg gtaattcatg tgcgagaatg aggactgagt agcccaacaa aagtcccaga 16020
agaaccttca tgttgcgtct aaatgacacc tgcacttaca aaaaaaaatt taaattttga 16080
atataacaca aaaaaaccac cttaaaattt cttatattat ttcttggatc tgccccgacg 16140
tcatacaatg tattaaaatt atagaccaat catctttttg tatataggct aatcatcttt 16200
atatatagat tttagatgtt tgcttgttgt atcaacttaa ctgctagcga agaaaatgga 16260
taaaaacttt ctgtattttt ataggttgaa atcattttat gcacatcgct aggatctaat 16320
attttatttt gaagaaccga atgtgggctt aaaatttttt tcttagaaaa aagtagaatc 16380
ataatattgc tatgtttttg tttaatgatt tcttgtatct tttttgtata cgggttggca 16440
cccaaaccta tacaaaaata tacattactc aaataactac cttctataca taatcttttt 16500
tccccacgta ttttcctatt tatttcccta tttatggaat taaaggatat caatctctct 16560
aaggcacggt caaggtctgc gcctaaggca aaacaataat atatacctaa tttattccca 16620
gggcgtgcac aggcaagaaa catcatgacg tttagcccta aacgtatatt ttcctgaaaa 16680
tacgcatgat gaacttcatc aatattacct aagtatatgg ccgtttgtaa acgccaaaga 16740
tctaaatgag gaaatttttt actaagataa tgaataggtt ttgtgagatt aaaatctatg 16800
gcgaacttat accaaaattt taatacaagt gtatttctcg tcatttcttc ttctttttca 16860
tctaaatata agataaaacg attgtaaaca aagtctatca ataggtgaaa atcattgcta 16920
ttaaagctgt cgagaatcaa aatattgtca taataaattt cgatcgccag taaaaccttt 16980
tttcgtttga cgagataaac aaacatatta tacaacccta catctaaaaa ttctggattg 17040
gctcctagtt ggatacacag gtctttagtc tgcttcgttt tggcacacat gatgccaaaa 17100
ttaatatcag caccccataa aacaaataac ttgattagat cagtctggtt ttccttcaca 17160

-continued

```
gcttttacta aggctctgtc aagctcatag ctgtcgacat cagagcatga catagagcca  17220
ccggttacca ttttacattg cttacaaaaa cctatgggtc cgttttccca ccatagtcca  17280
agctgttgta gaataaaaat atcatcctca tgataatttg aaaaagcctt ggtttctatc  17340
aagacttttt ttgtaagaac ctgtaaagag ttcatcgtat tattatgaat aacaggagta  17400
aacgtaatca attataaaag tgattttttc gaaaaaaact ttagatggtt gaaaatgata  17460
atgtacatgt tcatacaaaa aatagatgca gtgatgtcta aaatcaaaat ttaattttct  17520
atgtaaaaag tacagactta cttatttggg ttaaattgtt tattttaaac tttaattaac  17580
cgtttgagtt agcgatgttt gatttatctt ccatactcat ccgggggggg ggtccttata  17640
gctctgacat tattgtggat tattgaatat aatgaatact tcatagatgc taaacatttt  17700
aatagtagtt ctgaggctta attgtactct ataaatttat aaaaactttt tgatcaaaat  17760
ttaatttctt ataaaaagag tacagacgtc gcttgtttaa gcttcatcat gtttcattca  17820
ttactttcta caattacggg ggggggagtc ccctcatagc tttagtattg ctatggttta  17880
ctaattatta tgtagaattt atagaagcat atgtacctga aagtatacct actctataaa  17940
attaaataat ttcagtatat tttttttatg aatagaacgg aaatgatata aaaataattt  18000
aatattgcaa aaaaaattca taatgttggt atgtattata aacataatag catgtgtaat  18060
ttataaactg actcctctat ataattatta gatgaggtac caacctactt atgatatgcc  18120
gatgatagat attgtatact ataaaacaaa attattttaa atgtattcat ggatacatta  18180
taacattttt accgcaaatt gtctctcagc gaagaaaatg aatgaaacgt ttctgtatat  18240
tcataggttg aaattatttt acgcacttca ctaggttcta atattttctt atgaagtatt  18300
gaatgggggc ttaaaagtcc tttcttaaaa agaagtttca tcataacatt cttttcttgt  18360
ctaagaagag tttcttgtat tttttttgta taaggattgg cacccaaact tatacaaaaa  18420
tgtacattac tccaaatacc ataatttgaa aagaaagtta tttccctatt tacttcatga  18480
ttaatgaaac ctatcaacgt ctctaaggcc gtattgatat ttgcgcctaa ggcaaaacaa  18540
tagtatatac ccaatttatt ttgagggtac atacaagcaa gcgacatcat gtcatttgga  18600
tctaaacgta tattttcctg aaaatatgca tgatggattt catcaacatt acctaagtat  18660
acagccgttt ttaaacgcca ataatctagg tgaggaaatt tcttactaag aaaacgaata  18720
ggttttataa gattaaactc tatggcgatc ttaaaccaaa attttaatac atatgtattt  18780
tttatcattt tttctttttc atctaaattt aagataaaac gattgtaaat aaagtctatc  18840
aacacgtaaa aatcatggct atcaaaactg tcgagaatcg aaatattgtc ataataaata  18900
tctatagcta ataagacctt ttgttgttta attagatcaa caaacatatt atacaaccct  18960
acatctaaaa attttggatc agctcctagt tgaatacaca gaactttcgt cctttccgtc  19020
ttggcacata tgatgccata attaatgttg gcaccccata aaacaaataa cttgattaga  19080
tcagtctggt tttcttcac agccctcacc aaggctctgt caagctcata gctgtcaaca  19140
tcagaacatg acatagagcc actggttacc attttacatt gtttacaaaa acctatgggt  19200
ccgttttccc accataatcc aagctgctgt aaaataaaaa tatcatcctc atgataattt  19260
gaaaaagcct tgttttctat caagactttt tttgtaagaa cctgtaaaga attcatcgta  19320
ttatcatgaa tgaaagcagt aaatgtaatc aattataaaa ttgacttatt gaagagaaat  19380
gttaaatgag tgaaatcggt gtttatgatg atgtacatga tcatacgaag aaacacgttc  19440
actggtgtcc atgatcaaaa tttaatgttt tacgtaaaaa gtacagatgt taactgttta  19500
gtttaaacat aaatttaacc tttagtttaa accctagtta atgatgttta atatttcttc  19560
```

tatactcatt cagggaagtg taatgattct aatactgttg ttatggatta ttaatgaaaa 19620
ctttacagat gctggaggga ataattttaa tcatactgtt ttaatgtagc tatataagct 19680
ttcatcaaaa tttaattttt ttttataaaa atacacgaat taaactaaag tctaaacttt 19740
agtttgacta tttgagttaa tgatgcttaa cttatcttcc atgcttatca agggggggt 19800
cctaatagtt ttgatactat tgttgtggat tgttgaatat aataaatact ttatagatgc 19860
tgaaatgttt gaaaataata gtacatcaat gttgtaagtt tgatcaaaat ttaatttctc 19920
ataaaaaagg tacacatcaa cattgctcat ttaagtttca tgatgtttga ttcattactt 19980
cctacaatta ctgggggggg ggggggggtc tttaatagct ttagcattgt tatggtttgc 20040
tgactattat gtagaattca tagaagcacg tttagatagt aatatcactg cagtgtagat 20100
tatgaaatac atactaaact aatttcagta tatttttttt gttcatataa gttaaggtac 20160
aaaaatgatt aaacattgca aaaaaagaaa atcacaatgc tattatacat agtgatcata 20220
gtggcttgta tcatttctaa actagttcca aatgaatatt gggcaataca tctattttt 20280
atcattatga tttttatggt atatatgtat gaaaagttag atatacatca aaaatctcag 20340
ttctggaatt ataccatgtc aggcttatct ggacataacg tacaggtaac atgtaagtgt 20400
tactaaatac tatgaagtat ctattttttt ttgttgtaaa aaaaagaact tgatagtatt 20460
ttttaaaaaa taaaataatt aattgtacgt caacttcctt attttattct ttaaaaataa 20520
ctcgtaagta ttatttatct attttttgaa aaaatagatg taatcggttt catcatttag 20580
gtgtgtattt ctttttagca tctatcaaga attcattgtt tagtgatatg aaaacaatga 20640
atgatcatta tcttctattt aacaaccacc taaataaatg aacgtctttt tcatcttaac 20700
tgattaccaa aagttatttt gcgaaaaggc atacatatga tcaatatcag acctacaatg 20760
aatatttcca taatatccct ttattgtaat aattctattt ttgcattccg atatctcatc 20820
atctgtgcta ttatatgttt ccataactgt ttcatcatca aacataaatc ctgttaaata 20880
ggcaaaagac tttaatcccg gatagatttt taccattttc ctgagagccg tgtatagctt 20940
gtaataaatg gccaaaaata tgcaataaag cgtagaaaga gagtaatttt tggcataaaa 21000
gattttgaag gtttgatgaa tggctaaatc gcatataata taagatacga ttttaaagcg 21060
cacctgttca cgcagatttg ttgaaaaatt cgtggaaaga tttaacaaat aaaaggttat 21120
taatagttgc tcatcattcc ccttatacga catcgtcaga cgctctaata ttttactact 21180
aggcacatct gccacatgtt gaacatttaa agcctgttct tcttctgtgt tacggcaaaa 21240
gagccgtgcg tattcaggtg aagctcccca ggataacaac gtccttgcta cggctaaatt 21300
ttttttgacg atgactttta tcagaaataa gtctttattt ttgcattgat cactatgcga 21360
atttgtatag ttgacgccgt tgcattgagt acattgatat aatgttttac aattccagcg 21420
tagccctaaa tggtataaaa gaactgtatt ttcgacataa gcatgctgat taacgatgtt 21480
tttgagacaa cacgtcgtta aggacaccat attgtctcca atttgttaga taaaagtctt 21540
tactaaaaaa atagattttt agttttaaca atcgagattt tattatttgg atgcatcatc 21600
aaaaagattt ataagtataa gaggttgtat aagaaaaaaa atgatgttat actatttatg 21660
ttaaaattta atttatcata taaaaagtac agatttaatc agttggttaa actatttagt 21720
taattaaact aaatagttta accatttagt cagactactt ggttagcaat gtttgagctt 21780
tcttccattc ttatccgggg gggggtccta atcgttctaa tactattgtg gatagttgaa 21840
tataatgaag actttataga tgctataatg atgaattcta gtatgcctgt ataaaataat 21900

-continued

```
taacctttttt gatcaaaatt taattttttt ataaaaagct acagagtagt gttttattaa  21960
acgtggctta tttaaaagtt acacaatgtt aaaatctcta cttactttaa ttctttgtgg  22020
ggttttatta actttatcca tattatggct tactacttac catgtagaac ttatagaggc  22080
aatagatgat ttctacgact gaaatataga atagtccatt ttctatttgt aaaataatga  22140
tttatattct ttcctaaaaa tgatacttta tatggtttga aaacaaatat taacaacttg  22200
atttttttt ctataaataa actataaatg aaaatagtaa aactcataga gtcttataag  22260
tgaacatctt cataatgtta ctcaaacgtt ggactattaa aaaatattcc gtgtgcatta  22320
ttgcttttaa tcagtatgat tactttatac gaagccgcta ttaaaacgct tatcacacac  22380
cgaaaacaaa ttttaaaaca ccccgatagc cgtgaaattt tactagcttt ggggttgtac  22440
tgggataaaa ctcatattct tgttaaatgt cgtgaatgtg ggaatatgag tcttaccgga  22500
aaacacagta caaaatgtat taacattaat tgtctactta ttcttgccat aaaaaaaaag  22560
aataagcgta ttgttgatac cttgatagga atgggcgcgg atgtaacata tatacatctt  22620
ttaaagaata agataaaact gtcatacaac cagctgtcta tgcttaaaag caactcgcag  22680
atttcattga aggagcttca tgctatatgc tatcttttat atggtcggct tcccaaaaaa  22740
attaaacaag ggatgcgact gtgtaaaaca atggcgggac tatgtggtga acttttatgt  22800
gcatttttag ctccgtaaat gataatatgt atttaaaaca aacagatatt accaaaatat  22860
attctatgta cataatatct gggaaattat tttttttct catacccta aatataaaaa  22920
tattgggttt cttcactaaa ctttagaggt aaaaattttt ctttgttttg caccatcatg  22980
tatgggttta ggctgtccca gggattgttt atttgaatat ttcctaaata ggaacacaac  23040
gccatgatca tatatctttc attctggtaa gctttttgat acatcttcaa agatgccgta  23100
cctccgagtg tgtaacagca aacaaacgtc cgtacttttc catgggtcgc agcccattcc  23160
attccgtagc tcagcatctt ttgctgtatt tttttattcg ctttataaaa aaagtttttc  23220
atccattcca cgttctcata aaaacaggca cttaaaaaga gcactagggg tagtgtagtc  23280
ttattataga atgtaggaat gtatgtttta gttatttttt tcaacgcgtg ttccatacta  23340
tgttttaccg ccataaaaat acaaaaccaa taccaacttt ttctataaaa ggtttttgctg  23400
tacacatata aacgagcaaa atatatttca aactctatat tctttttata aaaaaactcg  23460
agacagtcgt ttatgttacg actttttcta aatacctcaa aaacagtaat taattcactg  23520
tcgctgtgga aatgttcgta agctaactgt ttaatgtctt taggggtcaa ttcttttttt  23580
gggagcagtg gtttgagatt cggcaaaggt cgtctaaagt agtgagcgaa cttttcattc  23640
gctccccaac acaaaagccg ataagccagc atgtagttat cacgttttac cgcgtaaata  23700
agcaaatagt ttatattgat acatgtacca tgttgctgcc cgtttggaca tatgttgccg  23760
cattctgaac acttatgaat gagatcatag ttcttacaac ataaccccaa acgggttagt  23820
acttctttgt cacgttttaa aaactcgaca tgattcttta atgttaatgc tttgagcgca  23880
atgttaaata aactctgcat tttattaaaa tgaggttagt atcatgtttt agtataaaat  23940
ttagcggctg tttacataat gctaaataaa cttaacgttc ctactaaacc aaaaaaaaat  24000
caaattgact aagtcataga gaatttgacg atgttggtag gtaatttttt aacatggtat  24060
atattttttt agggtcggtt atattaggta ataaaagagg acgtgccgtt aaagtatttt  24120
gcttaagatc ctttagatcc ttacaaaaat atagattgtt cgtctgatga tgccactgtg  24180
ttgcagtgat ggcttgatca atatcacctc ccaagacaaa acagtagtat atcgttaaaa  24240
agttgtaatc tttcatacaa gccaactgca tcattttatc gatgtccata tgaacgatct  24300
```

```
tttgctcgta tatttcatga aggtcaaata cattgttgaa gtaaatggcg cacatgagtc  24360
gccacatact aaggtgccca tatgtttgat agaaaaagga gatagctctt ttaagcttat  24420
attttactgc tatggcatag cagtatttaa cgaatacgtt catgggtaca ttatctaaga  24480
tataaaatat gaaaaacttt aactctcgat gaatctcttc ccccatttcc tgtacattta  24540
gagcttccaa cataggattt ttatcaaata tttcatgaca taaaataatg ttattgctcg  24600
ttttatgacg cattaaaccg gtgaaaattt ccttattatt taaactatct ttagctccta  24660
actttcgaca cagctcctga gtttgttccg tcctagcaca ggtcagccca taataaatgt  24720
ttgctcccca ctcggtgaac agccttatta cgtcatagtt attttctttt atggccatga  24780
ttaatgccac atcaagatga agaagttccc ccttaaaggg ggttgagctt aaaataacgt  24840
aattacagta gtgacataag ctaatgggct tgttttgcca ccataagcca caatatttta  24900
aaatataatg atactcctca ggcacgctct gtttggccac agccttttttg gccagggttt  24960
gcaaggagag catgataact tcttgaaaaa aaaactcaaa ttaagttcct acttttttaa  25020
aatattagta tggacagatc taccatcata tgaaggaatt ctttcatcgt taaacactga  25080
agagataata ctttcatcgt atagagaata tcatgtcaat ccatatattg aatgttatat  25140
atcattaaac ccatcattaa tatagtgttt atgtgctatg gacaggtttt ttgaatgata  25200
atcttttaac atacgtttta taacttcggg atcagtttct tttaaagata aagaatcatt  25260
catgttataa caatttaatg ataacatgct ggcaatgaac gagttgtctt tttgatgcgc  25320
tagagtcttt ccctcctcaa aggcattggc gcctaagtct atacaaaaga atatgtttcc  25380
gatattatag aactgaatag aatgaaacat ggcctgattg atatcagccc ctaagacgac  25440
gcaacagtaa taaatcgtta aatagttata gttcttgcga caggcccact ttagcatttc  25500
attcatgtct atgcgaatcc tctccttttc gtacacttcg tgaagttcaa acacattatt  25560
gtaaaaaagg gcgcacataa gccgccaccg atgtagatga gcatatctct gataaaaata  25620
gcaaatcgcc tccttaaggt tacattctat tgccatcgcg taccaatatt tagtaaacat  25680
ctcgcttaat atatcggttt ctaccattaa tccctccagt tgttcataaa tcattccctt  25740
tacttcaaaa cgatttatgg tatctaaaat gggattatta gaaaatacct catggcagaa  25800
aatgatgtta ctgctagtta gatcacgttt caatgtgtaa aaaaatcgta aaatttcctg  25860
gtcatttaac tgttctttgg cacctagctg cctgcacagg tctcgggtgt gctccgtgtt  25920
gacagaaagc aaaccgtagt tgatgtttgc accccactcg gtgaacaatt ctattagatc  25980
gtgattgttt tcctccacag ctttcaccaa ggccgcgtta agatttgtgc cgttcttaaa  26040
atacggcgtc catattttct tttgatgata catgataggg ccattatgcc accatagacc  26100
gcagcacttc aaaaaatgag gatggcattt ggccggatac tggctggcca gcaccttttt  26160
ggtgagagtc tgcagagaga ggaccatatt tctttttttt gaaaaaatca aattaaaaaa  26220
atcatgcttg tttagcatac atgtaatatt gttataatta cgttataatt acgttataat  26280
tacgttataa ctatattata acaatggtat aacaatggta taacaatgtt ataacaatgt  26340
tataacgatg tatcattgat gtcatcattc aactaggcca acatactttt taatttatag  26400
ttttttaata gatgatatat tttgttagga tctgcttctt ttaacgttaa tagcgaggag  26460
tctgcactat aaatgtctaa tgataaatga tgagatatca aatagtaatt ccgttgctct  26520
gctagggcct ttgcctcttc aaaggcgtcg gctcccagat ctatacaaaa gaacaagtta  26580
tccatattat aaaatcgtac gcaggcaagc atagctgaat taatattagc tcctaagaga  26640
```

-continued

```
aaacaataat atatggttaa aaaattgtta tcttttgtgc aggccatccg catcatttca  26700
tccacgtcca tgcggatctt ttccttttca tacaaattat gtaggtcaaa cagcttatta  26760
aaacaaagag cacagattaa ccaccacgta tttagatact taaaatgttg gtaaacataa  26820
gaaatggcct ccctaagatt atcctgcaat gccactataa aacagtatat cgttaacata  26880
tcaccatccg acatattact taatatgtcg gtgtcttcta ctaacctttt caacttccaa  26940
tatatggatg accttatttc ccttataatg acataggctg gaaagggatt atcattaaaa  27000
agtttaagac ataagataat attactgcta gtagtgccag ggtgtattaa tttaaagaac  27060
atgtgcataa tcttcttttt atccacgcgg tacttggctc ctaattccca gcaaaattct  27120
cgaacaggcg gcgtattggc gcaaattaac ccatagttga tgtctgcgcc ccattctgta  27180
aacagtttta ttaactgata gttgttttcc tttgtagcca acattagtgc cgtattaagg  27240
tccaagccgt ctgcaaagct tggcagcttt atcagcatat gtttgcaatc aagggaaatt  27300
ggggccttat accaccatag tccgcagcgt tctaagataa catggtactc aatagatact  27360
tgctgtctgg ctagtacctt tttggcgaag gattgtaagg aaggaaacat cctgtttctt  27420
tttttttaa aaatcaatta tctttgttca taatcaagaa aaatccccat atttattgag  27480
tgataatttt ttaacatgca atttattttt tcagggtccg taacgatcga caacagagaa  27540
ataaccggat tgtaatgctt taatgataag gcatgggcta tcagataatt ttccttttgt  27600
tctgccaaag ctttgccctc ctcaaaggca tcggcaccca ggtctataca aaagaacagg  27660
tttccaagat tatagttttg tatggaaaca agcatggctt gattgatgtt ggctcccatg  27720
ataaaacagt agtaaatggc cgaatagcta taatcttgga tgcaggctat gtgcatcatt  27780
tcatcaatat ccatgcggac cctttctatt tcgtacagct cgtgaaggtc gaacacgttg  27840
ttgtaaaaaa gggcgcacat gagccgccac ctatgtagac gcgggtattt ctggtaaaag  27900
tagcggatag catctttgag gtcatagtcc accgctatcg cgtaccagta tttggttaaa  27960
acagtgctaa agctatcatc atggtccagc atgaaggtta tctccatgag ccctcttaac  28020
tcccacatga tttcccccct cagatccaga ttatctataa tccttaaatt ggggttattg  28080
gaaaacacct cgtggcaaaa gataatattg ctactggttt tatcgcgcgt tgtatcaaag  28140
aaaattttta aaatatactc tctttctaaa tattctttgg ctcccagctc tttgcacaga  28200
tcacgggtat tttccgtgag agcacaaatc attccatagt taatatctgc accccattca  28260
gtaaacagct ttatcaagtc atgattattc tccttcacgg ctttcatcag tcctatgttt  28320
aactcgatac cttgactaaa acaggttgac cttataaata atttattgcg tcgaatatga  28380
agcataatgg ggccattatg ccaccacagg ccacaacact tcaggacatg atattgatct  28440
accggtatac actgcccggc cagtactttc ttcgtgaggg attgcaggga aggcaacatg  28500
cctttccatc ctttgacgga aatcaaatta tctactaata actatcagtg tttatattaa  28560
gtatttagat attatcccgg gctggatacg tagtatcgct attcacatgt acttccaact  28620
ctagccggag cctgcagggt catttatttt taatattgat tctttttgt atttaatcat  28680
ttagagaagg tcatcatagg agccagatgt tctctctcca gaacttatgt cgaaaaacat  28740
tacctaaccg taaacttcct gaatttttg acgaatatat attacaactg ctgggattat  28800
actgggaaaa ccatggaact attcaacgag caggaaacaa ctgtgtgctt atacagcaac  28860
ataccctcat tcccgtaaat gaagccctga gaacagcagc atctgaagaa aattatgaga  28920
tcgtgagcct tttattagcg tgggagggga acctttacta tgctattata ggggctctag  28980
agggcaaccg ccacgactta attcgtaaat atgatgacca aatcaaggac catcatgaaa  29040
```

-continued

```
ttctgccatt cattgacgat ccagtcatat ttcacaaatg ccatatcatg cggcaatgct  29100
tttttgattg tattttatat caagctgtaa aatatagtaa gtttcgcgtt cttctttact  29160
ttaaacatag attagaggat gatttgccct tcactcattt acttattgaa aaggcatgta  29220
aagatcataa ttatgaagtt attaaatgga tatatgaaaa cctacatatc tacaatatga  29280
tagatacctt tgaatgtgct attgcccata aggatctaca tctatattgt ttggggtata  29340
gatttatata taacagaatc gtacccgata agtatcatca tttagatatt cgcatgcttt  29400
caagcctaca actcctacat aaggtggcag ccaaaggata cttagatttt atcctagaaa  29460
ccttaaagta tgatcataat aaagataata taaatattat tctaacacaa gctgcaacct  29520
ataaccatag aaaaatttta atctatttca ttcctcaatc aacccacgca cagatagaac  29580
aatgtttact agtggcgata aaagcaaaat cttccaggaa aaccttgaac ttactactgt  29640
ctcacctaaa cctttccatc aacctcatca aaaaaataag ccattatgtt gccacttaca  29700
attcaacaaa tataataggc attctgagta tgcggcggaa aaagaagata tatttagata  29760
tcatattgac aaaatttgta aaaaaagcta tttttaataa gtttgtcgtt cgatgtatgg  29820
atacattttc tataaacccg gaaagaatcc ttaaaatagc cgcgcgaata aataggatga  29880
tgttagtgaa aaaaatatct gaacatgttt ggaaaaatca tgcggttaga cttaaatacc  29940
ttaaacatgc ggtacacacg atgaagcata aagatgggaa aaatagactc atgaacttta  30000
tctatgatcg ctgttattac catatgcaag gggaagaaat ctttagcctc gcaagatttt  30060
atgcaatcca tcatgcacca aagttgtttg acgtttttta tgattgttgt atcctagata  30120
cgatacgatt caaaagcctt cttttagatt gttcacatat cataggtaaa aacgctcatg  30180
atgctaccaa tatcaacatc gtgaacaagt atatcggcaa cctgtttgtt atgggagttc  30240
ttagcaaaaa agaaatctta caggactatc catccattta ttctaaacaa tacatgcctt  30300
agtttatttt ttttgcggcc gaaacattat tcttacccta gaaaacgctt atagtcatct  30360
taaatcatag gtaaggaaga tcatcatatt ttttgaaacg taattttta acgcatgatc  30420
tatgatttca gggtccgtgc ttttaggcaa cggggtggtg gccggactat aaatctttag  30480
ggataaaatg ttctttataa gctcataccc ttcccctaaa gctgtagtac cctcttcgaa  30540
aacatcagcc cccagatcta tacaaaagaa catgttttct atattatagt actgtattga  30600
gctaagcatg gcttgattga tgttggcgcc caggacatag cagtagtaca tggttgaaag  30660
gttgtggtct ttgatgcagg cgatccgcat catctcttct atgtccatat ggatcttgtc  30720
cttttcatac gcctcatgaa ggtcaaacac attattaaaa caaagagcac atgttaaccg  30780
ccacgtattc aggtgtgtat atttttggta aaaatactgt atggcctctt tcaggttata  30840
gcgtatggct atagcgtacc agtatttgag tagtaatgta ctgagcgaaa actcattatt  30900
tagcagatcg gtttttacta ttaactccct taactcccag aaaatttcta tcctcatttt  30960
tatattattt actttttgta atatcggatt gttggaaaac acctcatggc ataaaataat  31020
gttactacta gttttatgaa actttagatc tataaaaatt tgtaaaattt cttcttcatt  31080
caaggtttcc ttggcaccta gctctcgaca gaggtcccag gtgtgctccg tgttgacaga  31140
taccagcccg tagttgatgt ccgccccccca ctctgcaaac agttttataa ggttgtagtt  31200
gttttccctt acagccttca ctaacgccgt atttaggttt aagccctctt taatacctgc  31260
tgattttatg agccttaggt tatgatcaaa cgtgatcgga gcatcatgcc accataggtc  31320
ataacacttt aaaagataat gttggttcgt gggcacgcat tgtccagcca acaccttttt  31380
```

-continued

```
ggtcagagat tgcagggaag gcaacatgtc tcttcatctt ttaaaaaaaa atcaaattaa  31440
ttagccgaat aaatttttct ttcgagggct ttttaaaaga gctctttaag agctctttaa  31500
gagcttttta agagattaaa aaattattct tgctggcatt ctgccaagta tgcggcattc  31560
ctatcatcta tagtatatta tgagaatatt cccaaatgat ggataagttt tttgatttat  31620
aatcttttaa taaactgctt atttcttcgg ggtcctttaa gtttagtggc aaggaagcat  31680
ctgagctgta aatatccaaa gccaaactat ggctcagaaa attataacct ttttgttccg  31740
ctatggcacg accctcttca aaggcattac cacccaaatc tatacagaaa aatatattac  31800
cgatgttata atattgtact gaagtaagca tagcttggtt gatgttgccc cccagcgcgt  31860
aacagtaata tattgttaat ggattgttat ccttggtaga agccagacat atcatgtcat  31920
ggacgtctat ttggatgttt tccttgtggt acatctcatg aagctcatat attttgttat  31980
aatacaggag acattttaat cgccattcat taagatccgt atatttctca tctagaaaac  32040
aaatggcgtc cttacaatcg tattgtactg ctttggcgta ccaatacttc actagtaaac  32100
catttaactc gtccgttctt tttatttcta tgagccccca tagtctttta taaattaagc  32160
cccttaattg tataacaaat ttgttttcta aaataggatt attcataaaa atttcatggc  32220
acaaaataat actgccgctg gttttattgt gcattatcct ggtaaaaata cggaaaatat  32280
cgttgtcctc tagagtttct ttggcgccta gctgtctaca caactctcgg atgtgcttcg  32340
tattgataga aagcaaacca tagttgatat ttgcgcccca ctctgtaaag agctttatca  32400
gactatagtt gttttcctta acagctatta ttaatgccac acgaaggtct atatcttctc  32460
ctaaaaatcc tgattttatt tgtattcggc cacgatccat acaaagcttg agaggagcat  32520
catgccacca taggccacaa tatttcaaaa tgcagtgttc atctattgac aaacactggc  32580
tggctatcgt ctttttgacg agggtctgca gagagagcgg caacgacatg tttctttttc  32640
accaaaaaaa aatcaaatgt tctcgtcttt aaaggttaat tcatgttctt aaaatgttca  32700
tttcatgata gtgattaata atatggttta ataacgctag aaggcttgtt tataagacag  32760
tcataagcag tctataagac agtctataag cagtctataa gacagtctat gacttagtct  32820
ataactataa tttctggatg ggctgtaaga tactcttcgg ctcgtttcag attttttgaa  32880
gtatatgtct ttagcatatc atatatttcc tggggttcgg ttacatctaa taccaaggtc  32940
acatcacggc tgaaaagctg ctttactaag aaaatgttgc tcaagttata catataagct  33000
ttgtgcgcaa tgagttgtgc cctatcaaaa tcggcagccc ccaaatcaat acagaaaaac  33060
atgtttaaag tattattgtt atagatagaa agattcatgc cataatcgag actagccccc  33120
aacctatgac agtaataaat ggccgcgtaa ttttttttccc gcaagcaagc aaatttcatc  33180
atcagattag ggctgatgca aatctctttt tcacgacaca actcgtgtat gtcaaaaatg  33240
ttattaaaat aaaggctaca agctacccgc caatagaggt gatttttatg ccttttatag  33300
aaatagtgaa tagcctttgt aaaattatgt cgtaatgcca gggcaaacca aaactttgtt  33360
aataggtggt gcgccgtatc ccccgtcaac ggaatgtttg aacaggtgta cgtaactgtg  33420
tctaaagtgg ttctagttac ggtttccaag agtggattat gacaaaacat gtcataaccc  33480
agcagaactc ctgcacagga ttttagcctg gccacttctt ttaaaatttc cagaagacgg  33540
ggttcggata caggcgttaa gcctcccagt tccgcacaca gccgctttag atacacggca  33600
ggaacacgta taagcccata ttcaggattt gcgccccaat ccacaaataa acgtataagt  33660
tcaagattat cgctcttcac ggcctttact agcgccgctt cgagacaaag atcatcctca  33720
gaaaaacact gtaaatgttt atacgaaaaa acttgcttac aattgttaca taggtgaata  33780
```

ggacctaaat cccaccacaa accaaaacgc tgcaacgtat aatcatagtc acttgaaaga 33840
taattgcatg ccacaacttt tttggccaac gtttgtaaag acaacatact aagtttaaaa 33900
catcttaaat ctaagctagc taactttcaa gaaaaccctc tatccctaag aatatatctt 33960
ataactagac ttatagcagt aaaaatcaac tttggttatt ctttttaata taaaacgtct 34020
aattacttgc aaaggactat aaagcccatt ttcctcagct agaattttta ttttttaatg 34080
aagtaggggg atatgttttc ccttcaagac ctttgccgaa agcatctttt tattcttccc 34140
gatgtttttg gcgagcatgt actacaacga ttaggactgt attggagatg tcacggctcc 34200
cttcaacgca taggagacga ccacatactc atacgacggg atctcatcct ttccaccaac 34260
gaggccttaa gaatggcggg agaggaagga aacaatgaag tagtaaagct cttgttactg 34320
tggaagggaa atcttcatta cgccgtcata ggagccttgc agggtgatca atatgacctg 34380
atccataagt atgaaaacca aatcggcgac tttcatttta tcttaccatt gattcaagac 34440
gcgaatacgt ttgaaaaatg ccacgcttta gaacgttttt gtggtgtttc atgtctgcta 34500
aaacatgcta caaaatacaa catgctccct attctccaaa aataccaaga agagctgtct 34560
atgagagcgt atcttcacga aaccctattt gaactagcat gcctatggca gaggtatgat 34620
gtccttaaat ggatagagca aaccatacat gtttacgacc taaagattat gtttaatatt 34680
gccatctcca agagggatct gactatgtac tccttaggat atattttcct ttttgataga 34740
gggaacaccg aagctacgtt gctaacgcaa catctcaaga agacagcggc caaagggctc 34800
ctccactttg tgctagaaac gttaaaatac ggcggcaaca tagataccgt cctgacccaa 34860
gccgtaaagt acaatcatag aaaactttta gattattttc tgcgtcaact acctcgtaaa 34920
catattgaaa aacttttgtt gctggccgtg caggaaaagg cttctaaaaa aacattgaac 34980
ttactgttgt cacatttaaa ctactccgtg aaacgcatca aaaaactacc gcgctatgtg 35040
atagagtacg agtccacctt ggtgataaag attttattaa aaaaaagagt gaacctgata 35100
gatgccatgt tggaaaagat ggtaagatat ttttctgcga cgaaagtgag gacgatcatg 35160
gatgagcttt cgattagtcc ggaaagagtc attaagatgg ctatacagaa aatgagaacg 35220
gatatcgtaa tccatacttc ttatgtttgg gaggatgatc tagaacgtct tactcgtctt 35280
aaaaatatgg tatacaccat aaagtacgaa catgggaaaa aaatgttaat taaagtcatg 35340
cacggcatat acaaaaactt attatacggc gaaagggaaa aagtcatgtt ttatttagcc 35400
aagctctatg ttgctcaaaa cgcggccacc caattcagag acatttgtaa ggactgttac 35460
aaactggatg tggcacggtt taaaccgcgg tttaagcaac taatattaga ctgtttagaa 35520
attattacta aaaaatcttg ctatagtatc ctggaaatct tagaaaaaca tattatttcc 35580
ctgtttacta tgaaagttat gactgaagaa gaaaaaaacc tatgtttaga aatattatat 35640
aaagtaattc attataaaac aatacaatgt taaaattcaa tagatatcca tcattaatat 35700
tgattatatt ttcgaatatt atcttctatg gtgcaagata atcatctagc gcgtgaaaca 35760
tgtcctcttc tcttcaggaa ctttgtcgaa aaaagctgcc tgactgcata cttccagagt 35820
tttttgacga ctatgtattg caactgttag gactgcactg gcaagatcat ggttcccttc 35880
agcgtatcga gaagaaccag atacttgttc aacaggaacc catccatatc aatgaagcac 35940
tcaaagtagc agcatcggaa gggaactatg aaatcgtaga gctgttgttg tcatgggagg 36000
cagatccccg ctacgccgtc gtaggagccc tagaaagcaa atactatgac ctggtttaca 36060
aatactatga ccaagttaaa gactgccatg atatcttgcc gctgattcaa aatccggaaa 36120

```
cattcgaaag atgtcatgag ttaaacagca cctgttcact gaaatgctta ttcaagcatg  36180
ctgtgataaa tgacatgctg ccgattcttc aaaaatatac agactatctg gataggtggg  36240
agtattgcag ccagatgctg ttcgaactgg catgtagtaa aaaaaaatat gagatggttg  36300
tgtggataga gggagttcta ggcgtcggca aagttacatc tcttttcacc attgcgatta  36360
gcaacagaga cctacagctg tattctctgg gctactcaat tatccttgag aatttgtact  36420
cctgtggaca ggaccccaag tttttactaa atcatttcct gcgagacgtt tcaataaaag  36480
ggcttctacc ctttgtaatc aaaaccatag aatatggtgg aagcaaggag atagccataa  36540
ctctggctaa aaaatatcag cataaacata ttttgaaata cttcgaaacc tgggaaagct  36600
aggttcagta tggtgtactc actattgtag tgaatcgtat cctgtaaatt ttgtaaaaaa  36660
gcttaaactt ttgaccacat catattgttt tagaaatctc aaaccagtga acaacagtct  36720
tatcatacat taaaattcca gtaaaattta tatttttttt ggtaaacaaa tgttttctct  36780
tcaagacatc tgtcggaaac atctttttca acttcctgac gcttttgatg aatatatatt  36840
acaagcgcta ggactatact gggaaaaaca cggatctctt caacgaataa gaaaggacgc  36900
tgtgtttgta cagcgaaaca tcgtcctttc taccaatgag gccctgagaa tcgcagcctc  36960
agagggaaac gaaagggtaa taaaacttct gttatcatgg gagggaaatt ttcattatgt  37020
gatcatagga gctctagagg gtgaccaata tgacctaatt cataagtatg atagtcaaat  37080
taaagactac cacatgattt tatcattgat ccaaaatgca aataccttg aaaagtgtca  37140
tcagttatcc aatagtaata tgtggtgtct tatacagaat gctataaaat ataatatgct  37200
ccctattctc caaaaacaca gaaatattct gacacatgag ggagagaatc aggaattgtt  37260
tgagatggca tgtgaggaac agaaatatga catagtttta tggataggac aaaccctaat  37320
gttaaatgag ccggagttta tttttgatat cgccttcgaa cggatagatt tttctttatt  37380
aacaatgggt tatagccttc tttttgataa caagatgagt agtatagaca ttcatgatga  37440
agaagatctt acttcattac caacagaaca cctcgaaaaa gcagccacta agggatgttt  37500
cttctttatg ctagaaactt taaaacatgg tggaaatgta aatatggcag tcttatctaa  37560
agctgttgag tataatcata gaaaaatttt agaccatttt attcggcggc aaaaatgttt  37620
atcacgtgaa gagattgaaa acctattatt aaccgccata accaattgtg catccataaa  37680
aacgttaaac ttactcttgt cttacctaaa ctattccgta aaaaatatca ttggaaaaat  37740
agtacaacat gtcataaaag atggtgatta taccatcata ttacttttaa aaaaaaagaa  37800
aataaaccta gtggaacctg ttttaacagg ttttatagat tattactata gctattgttt  37860
tataaaacat tttatccaag agtttgctat tcgtccggaa aaactgatta aaatggccgc  37920
gcgaaaaggt aaactaaata tgattatcga attccttaac gaaaaatatg ttcataaaga  37980
tgatcttgga actatattta aatatctcaa aaccctagta tgtaccatga aacataaaaa  38040
aggaaaagag acattaattg ttcttattca taaaatatat caagatattc atctggagac  38100
taaagaaaaa tttaaattat taagatttta tgtcatgcat gatgcaacta tccaatttct  38160
atctatgtgc aaagactgtt ttaatttagc cggttttaaa ccatttgttt tagaatgttt  38220
ggatattgct attaaaaaaa attaccctga tatgatacaa tatatagaaa ttctatcgaa  38280
atctgagtaa aatttatttt tttgatcaga gtaagaaaat gttctccctc caggagatct  38340
gtcgaaagaa catctacttt ctacctgact ggctcggtga gcatgtgatt cagcgactag  38400
gtctgtactg ggaaaaacat ggttctcttc agcgaatcgg agacaactat gtacttatac  38460
aacaggacct catcatcccc atcaatgaag ccctaagaat ggcaggggag gaggggaatg  38520
```

```
atgaggtggt acaactccta ttactatggg agggaaacat tcattatgcc atcataggag  38580
ctttggagag tgaccattat agcctaatac gtaagctcta tgaccaaatc gaagactgtc  38640
acgacatcct tcccttgatt caagacccaa aactctttga aaaatgccat gaattagata  38700
aatcttgtaa cattttatgt ctcgtattac acgccgtaaa aaacgatatg ctttgcattc  38760
ttcaagagta taaaatgcat ctaagtggag aggatattca agtggtgttt gaaacagcat  38820
gccgttcaca aaaaaacgat attgtgtcat ggatgggaca aaatattgca atatacaacc  38880
ccgaagttat ttttgatatt gcctttgata agatgaatgt gtccttatta tctatagggt  38940
atacgcttct tttcaatcat catataaata atacgaacga aaatattaat tctttattga  39000
cacaacatct tgaatgggct gccggcatgg gccttcttca ttttatgctg gaaactttaa  39060
agtatggcgg ggatgtaacg ataatagtct tgtctgaggc cgtaaaatat gaccacagaa  39120
agattttaga ttattttctc cgtcgaaaaa acttgtacca agaagatctt gaagaactat  39180
tattgttggc gatacgtgca gattgttcta aaaagacctt aaacttgtta ttatcttact  39240
taaactattc cataaacaat atccgtaaaa aaatattaca atgtgtaaaa gaatatgaaa  39300
cgaccgttat tataaaaatt ttacggaaaa gaaagataaa tctgatagag cccattttgg  39360
cagactttat aggatatcat agctatacct atatggtaga ttttatgcgt gagttttcca  39420
tccatccgga aaaaatgatc aaaatggctg cacgagaatc gagggaggac ttgatcataa  39480
aattttccaa aaaagtttgc aaagagccta aagatagact tcactatctc aaaagcttag  39540
tgtatactat gcgacataaa gaaggcaaac aactgttaat ttatacaatc cataacttat  39600
acaaagcttg tcatctagag agtaaagaaa tgtttaattt ggcacgattt tatgcacggc  39660
ataatgcagt gatccagttc aaatcgattt gccacgatct ctccaagctc aatattaata  39720
tcaaaaactt gttgttagaa tgtttaggta ttgctattaa aaaaaattac tttcaactta  39780
tcaaaacaat agaaacggat atgcgttatg agtaacattt ttagatgagg gaagattcta  39840
ccaaactaac taagaccttt cgctagaatg tatcttattg ttaatataga tgagatatgt  39900
cattgtgaaa aaatagatta ggtaggttgt gaaaaacaga ttaaacttaa aattatgtgt  39960
attatgtaaa attttagaaa taaaaattta ttttttttta ttgagggtac ggaaaatgtt  40020
ctccctacag gacctctgtc ggaagaacat tttcttcctt ccaaatgatt ttagcaagca  40080
taccctacaa tggctgggat tatattggaa agagcatgga tccgtccatc gagcagaaaa  40140
agacagcata atgatacaga atgaattggt tctttctatc aatgatgctt tacagcttgc  40200
aggagaggag ggggacacag atgtagtaca gctcttgtta ttatgggagg gaaatctgca  40260
ttatgccatc ataggagcct tgaagactga aaaatataac ctaatatgtg agtatcatag  40320
ccaaattcag gactggcata ttctcctacc catgattcaa gatccagaaa cattcgaaaa  40380
atgtcatgat ttaagccttg gatgtgactt tatttgcctt ctccaacatg ctgtaaaata  40440
caacatgctt tctattcttg tcaaatataa ggaggatcta ctaaatgcaa ggattaggca  40500
tcgtatccaa tccctgtttg ttttggcatg cgaaaaatcgg agaattgaaa ttattgattg  40560
gataggccaa aatctgccaa ttcctgaacc tgatgccatt tttagcattg ctgttgctac  40620
aagagattta gaactgtttt ccttagggta caagattatt tttgattaca tgcaaagaca  40680
gggaatcatt caattaacca atggagttcg catggttgtg ctaaatcgtc acattagcat  40740
ggcaatagat aatggtcttt taccttttgt tctggaaact ttaaaacatg gtgggaatat  40800
acatagagcc ttatcttatg cagtaacaca caatagaaga aaaattctgg attatcttat  40860
```

tcgccagaaa aatatagccc ctaatacaat tgaaagactt ttatatctgg ccgtgaaaaa 40920
tcaatcttcc aggaaaactt tgaacttgtt gctatcttac ataaattaca aggtgaaaaa 40980
tgttaaaaag ctggtagagc atgtagtaaa tgagaaatcc actcttgtgt taaaaatttt 41040
attagaaaaa aaggaaaatc tagtggatgc tgttttaaca agacttgtaa aacattctac 41100
atatttccag gtgagagaat ttatccagga gttttccatc agcccagaaa aattcattaa 41160
aatagctgtg cgggaaaaga aaaatgtgtt aatcgaggct atttctgaag atatttggga 41220
aaatcccaca gaaagaatta cttatctcaa acagatagtg cacaccataa aatatgaaag 41280
tggaaggcga tttttggtag acatcattca cagcatttac caaagttact cactaaaaca 41340
cgaagatatt cttaaactgg caacatttta tgtcaaacac aatgcaatca cccattttaa 41400
agacctctgc aaatatcttt ggctgaacag aggaacagaa agtaagaaac tgtttttaga 41460
gtgtttagaa attgctgatg agaaggagtt tcctgatatt aaaagtattg tgagtgaata 41520
tattaactac ttgtttactg caggagctat taccaaggaa gaaatcatgc aagcctatga 41580
tgctttagag tagccatgta ttaacattct gaaagtagaa taaaatatac tatatactaa 41640
aaaccaaatt agccattttt aactatcttc ttcttaaaaa ctctggataa aaatttattt 41700
ttttttaatt tgggtaggga aaatgttctc ccttcaggac ctctgtcgga agaacacctt 41760
cttccttcca agtgatttta gcaagcatac cctgcatttg ctggggttat actggaaggg 41820
gcatggatct atccaaagga taaagaatga tggtgtgctt atagagcatg atcttactct 41880
ttccatcaat gaagccttaa ttcttgcagg agaagaggga aacaatgaag tagtaaagct 41940
cttgttacta tgggaaggaa atcttcatta tgccatcata ggagctttga ggactgagaa 42000
ctataaccta gtatgtgagt accatagtca aattcaggac tggcatgttc tcctcccttt 42060
gattcaagat ccagaaacat tcgaaaaatg tcatgattta agccttgaat gtgatctttc 42120
atgccttctc caacatgctg taaaatataa catgctttcg attcttgtta aatataaaga 42180
ggatctacta aatgtactat ttaggcaaca aattcaagga ctatttattt tagcatgtga 42240
aaatcggaag cttgagattc ttacgtggat gggtcaaaat ctgccaattc ctgatcctga 42300
gcctattttt agcattgctg ttgtcacaaa agatttagaa atgttttcct tagggtacaa 42360
gattgttttt gaatacatgg aaaaccaagg acttcattta acccaggtag ttcgtatggt 42420
tatgctaaat catcactttg gcatggtaat aaataaagga cttttaccct ttgtgctgga 42480
aattttaaat tatggtggga atgtaaatag agccttatct tatgctgtca cacaaaataa 42540
aagaaagatt ttagaccatg ttgttcgcca aaagaatata ccccataaaa ccattgaaag 42600
aatgttgcat ctggctgtaa aaaagcatgc tcccaggaaa actctgaact tgttactatc 42660
ttacataaat tacaaggtga aaaatgttaa aaagttgtta gaacatgtag tgaaatacaa 42720
ctctactctt gtgataagac tcttgttaga aaaaaagaaa aacctgctgg atgctacttt 42780
gacaagatat gtcaaagatt ctacatactt tcaggtgaaa gaatttatgc aagacttctc 42840
catcagccca gaaaaattca ttaaaatagc tgtgcgggaa aagagaaatg tgttgatcaa 42900
gggtatttct gaagatattt gggaaaatcc cgcggaaaga atcaggaatc ttaagcagat 42960
agtgtgtacc ataaaatatg aaagtggaag acaattcctg ataaatatca ttcacaccat 43020
ttaccagagt tattctttga aacctgaaga aattcttaaa ttggcaacat tttatgtcaa 43080
acacaatgca accacccatt ttaaagatct ctgcaaatat ctttggctga acagaagaac 43140
agaaagtaag aaactgtttt tagagtgctt ggaaattgct gataagaagg agtttcctga 43200
tattaaaagt attgtgagtg aatacattaa ctatttgttt actgcaggag ctattaccaa 43260
ggaagaaatc atgcaagcct atgctttgga gtatgccatg tattaaattt ctgaatcagt 43320
aagcaataga tagattttag aatatgctgt attaagttag tttctgaata agtaattaat 43380
agatagattt tagtttatgt aaaaatgtta acatttgttc ataagtttta gataccattt 43440
tagagttact tttttagata ttactatttt agccattatt atcttaaata atcactattt 43500
tagataggtc cccgtattaa aaaccaaatt aaccattatc tatgttttta ataatacttt 43560
ttaaaaaccc tccataaaaa tttatttttt tttcataaaa gtagagaaaa tgttctccct 43620
acaggatctc tgtcggaaga accttttttct tccacttgag cccttaggca agcatgtggt 43680
tcaacggctg ggattatact gggaaggcca tggttcagtt aaacgagtgg gtgattgctt 43740
tatatgtgta gaccagattt ggatgctatc aatccataag gctatacaaa ttgcagcctc 43800
ggaaggaaat gagaacattg tcaagctttt cttactatgg aaggggagtc tacaatatgc 43860
catcatagga gccttagagg gcaggcaata tgatctgatt caaaaatatt acaaccaaat 43920
tggggactgc catcagattc taccactgat tcaagatcca gaaatttacg aaagatgtca 43980
tgaattaaat gttacatgta cctttcaatg cttatttcaa catgctataa gagataacat 44040
gctgcccatt ttccaaaaat atggagaaga tctgaatgga aacaggagaa tggttcaact 44100
tctgtatgag atggcatgcc gattacaaaa ttatgatatc atcaaatgga taggatctaa 44160
cctgcatgtt tataacttgg aagccatttt tagcattgct tttgttagaa aggatttaac 44220
tttgtattct ttaggctaca tgcttcttct gggtagaatg agtactgaag atagaaactt 44280
tatctcaatc ataacacgcc atcttgaata cgcatcaaaa aagggacttt ttgactttgt 44340
actagaatct ttgaaatatg gaggtcaagt ggatacagtg ttgtttcagg ctgtaaaata 44400
caaccatagg aaaattttgg cccattttat tcatgaaatt ccccgtgaaa cggttgaaaa 44460
gctgatactc catgctgtgg agtcacgggc ctccagaaaa acattcaacc tgcttttatc 44520
ttccataaac tactgtgtga acccttttgt caaaaaacta ctgcacgctg tggtgaaaca 44580
caagtacatg cttatcataa agcttttgct cgagcggccc aaaaagaaga taaacctggt 44640
agatgctgct ctattcaaac ttgtaaaata ctctacttat acagaaatag taaaatacat 44700
gggtgagttt tctgtggacc caaaaagggt ggtcaaaatg gcagcacgac tcatgagagt 44760
ggacctgatt aaaaagattt ctaatgatgc atgggaagat aaactagaga gaatcaagca 44820
ccttaaacag atggtaaata ccatgaacca cagaaatgga aaaaatctat tgatgtacaa 44880
tattcacaat attactggat atacctatct gaacaccaaa gaagcattta acttaacaag 44940
attttatgct gtccacaatg caacatgttt gtttaaagaa atgtgtaaaa gctgttttgt 45000
acatgataaa atacagctca gagaattgct tgaagattgt ttacatattg ctaataggca 45060
tgattatatc cagattgcag aaaccgcaga tgaatgtatc aaatatatag atcttattac 45120
atttaagtaa accatgtata tatcaagtaa atccagatta aatcaggcta attgtaaata 45180
gttgtagata ccatataatg aatgttttat taggatagta gttcagttaa gatagtagtt 45240
tagttaagat agtagtttag ttaagatagt agttatgtta agatagtagt tctgttaaga 45300
taatagttta gttaaaacta gttcatgtta agttaatagt tttgttaaga caatagttca 45360
tttaagtcaa tagttcagtt aagtcaatag ttttgttaag tcaatagttt agttaagtca 45420
atagtttagt taagtcaata gtttagttaa gtcaatagtt atattaagac attagttctg 45480
ctaatacatt agttttgtta agataataaa aatttatttt tttttcatca gggtagagaa 45540
aatgttctcc ctacaggagc tctgccggaa gaacatttac attcttcctt acccccttggc 45600 taagcatgta cttcaacaac tagggctgta ctggaaggga catggatctc ttcaacgaat 45660
cggagatgac catgtactct tacagcagga cctgatcttt tccatcaacg aggccttaag 45720
aatggcagga gaggaaggaa acaatgaagt agtaaagctc ttgttactat gggagggaaa 45780
ccttcattat gccatcatag gagctttaga gggcgaccga tatgacctta tccataaata 45840
ttatgatcaa attggggact gccacaagat tcttccttta atccaagacc cgcaaatctt 45900
tgaaaaatgc catgaattga gtaactcctg taatattcga tgccttttag aacatgcagt 45960
aaaacacgac atgctttcta ttcttcaaaa acacaaggag caaataagat tacacatggc 46020
attaacccaa atactatttg aattggcgtg tcatgaacgt aaaaatgaca tcattagatg 46080
gatcggttat tccctgcaca tacaccatct agagactatt tttgatgttg cattcgccca 46140
taaaaattta tccttatacg ttttagggta tgaacttctc atgcacaaag taaatacaga 46200
ggctgcatat atagaattac ccaatttgct atcatatcac cttcgaactg cggcggcagg 46260
aggtcttctt aactttatgt tagaaacaat aaagcatggt ggatatctgg ataaaacggt 46320
tttatccgcg gctatcaggt acaagcatag gaaaattgtg gctcatttta ttcatcaggt 46380
tccccgtaaa accgttaaaa aactgttact ctatgctgtg caggctcggg cccccaaaaa 46440
aacactgaac ctacttttat cttccttaaa ctactccgtg cacaccatca ccaaacaact 46500
cgtacacaat gtcgtcatct acagttccac gcttatcgta aagcttttac tcatgcggcg 46560
aaaaaacaag ttaaacctag tagatgccgt tttagccaga cttgtaaaat attccaccta 46620
tacagacatt gtacaattca tgggtgagtt ttctgtgagc ccagaaaggg tgatcaaaat 46680
ggctgcacgg gaatccagga cctttctgat tgaaatgatc tccaaagctg cttggggaaa 46740
tcacccacag acgttgattc atcatctcaa acaactaacc aataccatga agcctcaatc 46800
tggaaaagac cacatcatat ataccatcca ctatatttat ctaaactcta atatgctggt 46860
agcggaggag gaaaaaaata tttttaaatt agcaaaattt tatgcgaatc ataatgcggt 46920
aaacaggttt aaacaaattt gtgaagacta ttatatatta gatgcacgat ttaaaacact 46980
tattttagaa tgttttgaaa ttgccgtcca gaaaaactat cctagaattg caaatattgt 47040
ggatgactat attcgattcc ttttttacag gggaaatata accgaggaag aaattcgtga 47100
agcctattct ttaaaagatg ctgaggttta tgtagattta aaatggttac aacaaggaga 47160
aatggtttaa accaaatccg gtttaaacta aatccaattt aaactacatt tggtttatca 47220
ttagtcattg aaaccatcga aaaaaaagct atttgtttat ccccataaac tcatcttttt 47280
tttgtctcaa agtttgacac taaaattcag tgttttatag tgtttataat taagtgtttt 47340
gcatgcattg cagaaatttt catctttttt aattggttca ataccacatg tcatacaata 47400
tgttgtttga ttatcaagat taactttatg aaaggaaagt aagtgagccg caaatttaaa 47460
agtaaaatat ctttcattta aaatgatctt atgaatgtat tttcgataag gaggaatgaa 47520
agcatttgcc aaaataaatc gcataaaagg cttggaaaaa cccatatctt ctaatctttt 47580
gtgggtataa accctatttt ggtgttttac aaaaacttca ttgttataat agtcgttata 47640
gctatcaatc attttttttaa gtcctataat gcccaaggtt gcacgcataa agccacagtt 47700
tctgctccaa aaagcatgca cctgtaaagg gtgcttttca tataaccaat tacaaaattt 47760
cattccgcaa cagtagcatg ttatttcagt gggggatgta tagaataatc cggcattcga 47820
aaatttttca taattttttta tgtcatggat tgcgaagctt tgatttcgtg catctatgga 47880
gctatagcct acatatttag gttttacttc aaataatcgc aaagagatgt atggatctat 47940
cgtatttatt ttaggaaaca tttcataatt ttaaattctt atatataata taaaaaaaat 48000
tacaaacatt tgtaatgatc atcctcaatt gaaggctgag ttgtaggctt tatttttcta 48060
attatacgaa gaaggtaggt tctcataaag ccttcaagat gactattgat gtttccaata 48120
cattttctca atgagttcat aaacccagac attttgctaa tggcttggca aagtgccaac 48180
aagttgtcca caaagtactg gtagattgcc actagctata gctagctata gtgagccaac 48240
ctctctgtat gtattttata tatttcattt tttaatagat ttaatatttt tataaaaaaa 48300
tatttagttt tttatacaag aatgtcgaca aaaaaaaagc ccacaattac caagcaagag 48360
ctttactcct tagtagcggc agatacccag ttaaataaag cattgattga aagaatcttt 48420
acaagtcagc aaaaaataat acaaaatgct ttaaagcaca atcaagaagt tattatacca 48480
cccggaatca agttcaccgt cgttacggtg aaagctaaac ctgctcgcca gggccataat 48540
cccgccacag gagagcctat tcaaattaaa gctaaacctg aacataaagc cgtaaagata 48600
cgagcattga aacctgtcca tgatatgtta aactaaacta taaagtcata ttcttcttta 48660
tcgttattat cttcaatata tttttgccaa tcgaaatcga ataaattcag atcctggaca 48720
tttaaatact tatcatcgta cattttaata taatttaaac atgagttgtt gtcaaaaact 48780
tttagcgttt ttgttaaaat tatcatatga ataatttcct tattaagagt tgccggaata 48840
atacaaaacc tatttttagg tacatcatcc atgataatag taaaattagt aaaaattgtt 48900
tcttgttttt cttttgtttc aaataaacgt tgtaaggtta aaggtttctc gttcaatggt 48960
ttctttgaag ataaaaagaa tgtataatct ggtttaaagg tatttttggt ttcaatcgtg 49020
attccatctg cttgagcata tactaaacca gaccaaatat aacggtccac tattacaata 49080
taatttagct taagtagcac tgcaatttct gcgataaatt cactacgatg ttttgtaaat 49140
aatttatgta attgttccga tgacatttct atggttttat ttaacacctg caatataaga 49200
tcaccggtgg tcgtgtctgg attaggaaaa tgtatacata tagcattata atccatgcat 49260
tccaatgttt cttttaattt cattgcctgt gtgctttttc ccacaccatt gattccctcg 49320
atggcaatga gtattccacg catgattaat aaaaggaaaa aaagaattca gtttttaaca 49380
tttcttacaa atcttttttt atacaacatt gtacaacact gcattagcgg tatatgatgt 49440
tatagcttca ttaaatattt gcttttatat aatctttacc aacctatatt tggtagatca 49500
ctgcagatgg tcataaatag gccataacta agataaaaat tatttcagac gctactacgg 49560
tagtattatt aaaatcatgt gtggcaatgt atgacgtctt aatagataaa acatttaagg 49620
aaaacaaatt tgaataaaaa aaataattgt tatgatggcg ttgttacaca aagaaaagct 49680
tatagagtgc atctatcatg agctagaaaa tggcgggaca atattgcttc taacaaaaaa 49740
tattgttgtg tcagaaattt catacattgg caatacttat aaatatttta cctttaatga 49800
caatcatgat ctgataagca aagaagatct taaaggagca acatccaaaa acattgctaa 49860
aatgatttat aattggatta taaaaaatcc tcaaaataat aagatttgga gtggtgagcc 49920
gcgtactcaa atttattttg aaaatgattt atatcataca aattacaatc ataaatgtat 49980
aaaagatttt tggaatgttt caacttcagt cggtcctcat atctttaatg atcgtagcat 50040
ttggtgtact aaatgcacat ccttttaccc atttaccaac attatgtcgc ccaatatatt 50100
ccaataaatt agatatcttt gctattaaaa tagttaaaaa ccttatagga taattaggta 50160
ctttattacg ataaattatg atattttata attagttact ttattataat taatctcttt 50220
attaatgaat tatcataaga taactaatta ttttttttcca tatatcagat aataaatctg 50280
atatgggcta aaagtatgtt tcaaactatt tacaatagaa tttctgttaa gaaaacatac 50340

-continued

```
ataatttgaa taaaattttt ttaaatatca ccgaaacaat caacatggtg ttaatagagt  50400
ttttaacagg tttcttctat ttatatggaa agagactgtt ttccattagt aaagtcatgg  50460
acatgatatg tctagactat tataccatta ttcctgctcc tctggcgatg atgttagcgg  50520
caagactaaa aaactatgac ctcatgaaac gactgcacga atgggaaatc tctattgact  50580
acgctctact tgtagtagat gatgtgccgt ctattgacta ttgcttaagt cttggcgcta  50640
gatccccgac tagagcacaa aaaagagaac tgctgaggga caacacgttt aatcccgtgt  50700
ataagtatct tatgaactgt tccggcttcc caacaaagag agaaaaaaac attccttgtg  50760
atgttcaatg cgaaagactg caaaaaaaca ttataaaaga actggtattt aactgctctg  50820
tactgcttga aatggtactg cacacagaaa gagaatatgc atacgcccta cactgtgctg  50880
caaaacataa ccaattgccc atcctcatgt attgttggca acaatccaca gacgcggaat  50940
ctattttgtt gaaaacctgc tgttctgata agaacatcaa ttgttttaac tattgtattc  51000
tatatggcgg cgcccaaaat ttggatgctg caatggtgga agcggcaaag cacgatgccc  51060
ggatgctgat aaactactgt gtcatgcttg gtggaagatc cttaaacgaa gcaaaagaaa  51120
cggctgccat gtttggacac attgaatgcg cacaacactg ttttaaactg cagtcttacg  51180
tcgtggacac atcgaataca gacgacactg attaaagcga caatcttacg tcatgaacga  51240
ctgtcttttg agtatctata cttacattat atttttttat gaaaaaaata taaaggttgt  51300
atacaaacct ttgtatacaa gaaatttgga tcattaaaca ataattaatt tggacacagg  51360
aaacgatcta gatcgatcaa aaagctattt tttttgcaca cagaacattt agataattga  51420
gagattactt tccatacttg ttaagctttt ttacacacag gaactttgga ttctgttcag  51480
gaagtttttc atagacatta tgtttacagc cagtaataat aattttgggc tttttcttaa  51540
accaccggtg gaaaacatcc agcttgtaaa gagggaaatg catgtagaga ggttttggta  51600
gtcatggtta agagatttga ctaactccat gtttcctgta aagactgccc agtcccaagc  51660
agtaaaacct ctatgatagt ctttttgagt cggatctgct ccaaatttta tgagagaaag  51720
catatttaaa gaacggcccc gtattgcggc cttcatcaca ggagtcatcc cattaaaatt  51780
cggtaaacaa attctggtcc catttttttcc gaaatagccc aacacccctt ccaggattaa  51840
atgatttttt ttctcagcta aataatgtaa agcagagttt ccatctttat ccctcctatg  51900
agggttaatt atttctccag gataagattc ttgttcaaaa agaaatttta aaaagtctat  51960
acgtccgtag atgcatatcc acatgaatac cgaggatcca tttttatcgc atctattgac  52020
aatccacgga tctgttttaa aaaattcctc aaatagtgta agattcccat ttctaatatg  52080
ttttttaatc catttaacaa acaagttttc tatctccctt tctggaaaca tgtgttccat  52140
tttgaatgtc gcccctactc cactatatga ttttactcct ttaattttta atgtcctttt  52200
ttttcggact tctttggata agctgtttat taccatcttt aaatgcctta tagcggggag  52260
gagccaggcc cttttcccat atgtgcggta attcttggtg tttatgcttg cctttggcat  52320
aaccaggcca gtatttttcg atatattcag ggtttgtttt tacgtattct ttaaaggtcc  52380
gataggcttc ttgaatacag gtaggctcac cggtataatt tccatgttca tcttccttta  52440
aaaagccatt aaccctgtcc tttctccact taagattgtg ctttccaaaa atgcgatcaa  52500
gatcttgcgc ctgctggggt ggaatcataa atccctttt aggtcgaagc tttttatttt  52560
ttccatagct tcggccatcg cgttgcgaaa cagtggttag gacgcctgat agtctttcca  52620
tgggcgtcgc atctaatcct atccatccac cctgatgaat atcaatggca acaagctctc  52680
ctttattttg ggcaagccaa gtttccaaga atgccatgct ttcttcccag ggataaggcc  52740
```

```
cgccaacacc acgggttgtc caatcttgca aggactccag gtccgacacc tggtaaggct  52800
ctaaagaaga cggttccttg tttttgtact gcaaataaga tttaatgacc catttatacc  52860
atgtgtcgaa ccgcagcgtg gcgcctccaa agtgaaagcc gtcgttgatt ttaggatatc  52920
tgcaacatat ttcaaccgta cgtttgagtt ctgcaaaagc ggccttccaa ggaagtcttt  52980
cgctgcgggt aagacggtct attttgccct gcgtgccata gcgtatggca tgtcgtgcca  53040
attgcaacaa ttctgacacc gatccgtggg ccccgatcca gtttatcgga taggcaacct  53100
ccgaagggtt taaaagatgc tcgtaaaagc gtggatcttc agatgccaag gcgtctgcaa  53160
aggggataat gctagaaaac ctgtctagac atacgttttc tgtgtttact tctaaaggta  53220
gaaaaatggt tgcgtgaggc ttttgaacct gcttgttcag cggtctgcat atgctttgaa  53280
taatgtctct aggactatgt cgcggcgctg caaaaaatac cgcgtttagt tctggaacct  53340
ctacgccctc ttgaaagagt cgacagttta ataaaataac gggttccttt gaggaacaaa  53400
attctgtaaa tgttttgagg ataacctgtc gcggcagggt tgagtgagct atcagggcat  53460
agacccccttg gtctaccaac gccgcgtata gctccttggc ctgtttaata tcacgggtaa  53520
ataccagcat tttaggagcc ggtatattgg tttttaaata ggctaaggcc attataattt  53580
gctttactat gatctgtttc gtggtctcct ctttggtact cggttggtgg gccaatttag  53640
gcgcggctac catctgcaat tcaaaatcat ttacatagcc ggcctctatg ccttctcgca  53700
gatagtagcg aaaggcaacg ccgccaaaaa gttcacgatt tttcatggaa agcggggtgt  53760
cgtacctggg cgttgccgtt aaaaaaagtc ggtgcccttt tttaaagttg agcaacacgt  53820
gggtaaaggg ccgtgtctcc cattcgccgc aaatccggtg acattcatcg ctaataataa  53880
gatcgaaatc atccaccagt agcgtggagg attggtaggt ggcaatcaca agaagagaag  53940
gggcctcccg tatccgtttt gcaataaaga caggattggt ggtcatttct atattgtcgt  54000
gatttagcac aatgcgggtc tggtcagacc ccacaagcaa aacgttcttc aaagaaattc  54060
catactgata gagtttttcc agagtctgcc gtagtaggga caggcccggc accaggtaca  54120
aaacttttcc ttgaagataa ttggagagga taagataggc gacgcgagtt ttgccgcatc  54180
ggcaggccat ctgcagaatg gccctcccac ttcgccgcag ctcctgatag cccatattgg  54240
ccgcctcctt ctgataaagt cgatcctcga ttgcagtccg tgtctcatct gtagaaaaaa  54300
ataatacgtc atctgcgaaa tgttcatctt ccacaggagt tatcaccagg tgtctcagtt  54360
tctccttgct tatcagcgga tcagagggca aagatggctc aaccactatc gtggaatcat  54420
tcatctcata ggcgggagaa tcacacaaag tatagcttat gtccagacag tttgcaacat  54480
cctcagccaa ttgttttatt ttttcgggta aaagacatac gagttctttg tttttgacgc  54540
gaaaaaactg tgcacaatat aacacccctg cttcaatttt ttgcgcatcc ttctttgtag  54600
atgtttccaa tgtgaaacaa tacttccatt catccgtaaa acaggttgta taagatccat  54660
catgaagcct agcggccaag tttcctgtgt gcccaacttt atgtaaggat tgggcctcca  54720
gccagggatg aaccgccacg taaaatcctg cgcacatgct atatcaaatt gcagtttctt  54780
aataactgta cacaggatct gaaaaacatg tgattacaaa atttagataa gaaatattta  54840
atattaaaaa tcacagaata catgtcactg tgtagagaga aagccaaaaa ctcctcttga  54900
ccgccgtggg aaatcatcca gggtagtagg ttgtgtttca taaagttgta tgccgtagtg  54960
atcaccgtgg actccagatg gttattggca tctttgcaat actttgccat cttggcagaa  55020
aagacgataa atccacaaat tctaccccag ttgataagat ccttaaacag ctcagtcaca  55080
```

accccagtaa actgggtttt aatttcttga acactcgtaa gagaaaaggt aattgtaacc 55140
tgtttgttca aacactcatc ataataggtt aaaatttttt ttatttgttg ttgatatggg 55200
ctaagctcat gctctgaaat atcattaatg taatatttaa tatatcccac tagtatttca 55260
ttaatgatat tatgatatat taactcttct ccctccatag cggcacccta tattttttta 55320
tttaggtttc aatgttatca caattgcgat acaattgtga tacaattgtg acacaactgt 55380
gttgtataca acaaatgtta ggccacgtat agcaacctat atgttaagaa atatttttat 55440
cccaacatta gttggaaacg agcagccgca aagaagtcat ttaaaataag ccatttaaag 55500
atttagaatt tatatgtata caactgtaca atggaagcag ttcttaccaa actcgaccag 55560
gaggaaaaaa aggctctcca aaattttcat cgttgtgctt gggaagaaac taaaaatatt 55620
ataaacgatt ttcttgaaat ccctgaggaa cgatgcacct ataaattcaa ctcatacaca 55680
aaaaaaatgg agcttttatt taccccctgaa ttccacaccg cctggcatga agttcctgag 55740
tgcagagagt tcatattaaa ctttttgaga ctcatttcgg gacatcgagt ggtattaaaa 55800
ggccctacat ttgtttttac aaaagagatc aagaatctgg gcattcctag taccatcaat 55860
gttgactttc aggccaacat tgaaaatatg gatgatctac agaagggaaa tctcatcggc 55920
aagatgaata tcaaagaagg ctaaataaaa caactaacat caaaaaacat taaaggctat 55980
gttgtggacg atgcctttgt ctcaatagtt tcgaggtcat ccaataactc atgtaacgta 56040
aaaaagttgg tccatttttt tgaaaacatt aaaagacgtt cgtcttcata aataaaaaag 56100
tcattcgaag gaaaaatgat atactcaata ccatagtctt gtaatatttt ttttaggtct 56160
ctcagggtcc agggatttac caggcttcta cgcgaagtga gcatcataaa aatatctaat 56220
attttttgcg ccataagcca gcgcggattc tcattggccc acaaatcaac aataattctc 56280
ttatcaaccg tgagcattcc tacttgattc gaagaaatga ttagatgccc agcagtccac 56340
cccatgagta gataacgcag cgttgtagaa atgtcacata tggaaggcat tcctccacaa 56400
catgaaccca aattaggatg cgtgtgaaac acaaacatag caggcttgtt ggccaccctg 56460
ctataaatat cagcaggcat catagcctcg ctgccaaaat aaatgttctc tcctgcccta 56520
taggggcttg gaatgatttc cactatctcg ggtacaccgt ttatcatatt aatgcggccg 56580
caccattcac ggtcatcgtc caaaaatttt ttgatggcac cccgaacatt gtcccagtta 56640
agcaacagag tattcacaat ctcattacgc tccgcccagt attccttaaa acttctttta 56700
gacttgctga gctgttccca ggattcgaac tcagtccaat gttttttttc ttttggggaa 56760
gacttccctt ttgaaacatt ttttgcggct ccaccatcta cactatgatt ttccaaaata 56820
atctccttca tcgtttgagt tatatgggca ttgctaagca ccttagtggt aacctgttta 56880
cctatgtgat ttagcagaaa accaagtttg tccatttgtg tctcaaccat ttattcttaa 56940
caaaacaaaa aaaaattaaa aatcatcgtc gtttaaaaag agtttgaagg caaacgcatc 57000
atccttaaca cagttctgat actgcgtagg tcttaactcg aaaaagttgg tttttttctac 57060
ttcattaaga aagaatttag tcatctgagg aaaagggttt cccaccttat aaatgctttt 57120
gcactgcatc atgaagcaca aattatctgt aaagtagcgt atatattgaa atagcatttc 57180
ttttgaaaaa ccgggaactc ttcctcttgc cttgtcaaag gcatagttaa taaactcatc 57240
caccaactcc acagcctcct tcaaaatttt gtgaatgatc ttttcctcgg gaatgttata 57300
cacgtaattt gagataagaa aacacgcaaa actacagtgc atcccttcat cacgtgagat 57360
aaactcatta tagcttacaa gccccggcat aatattctgt tccttaagaa actggatcgc 57420
cacaaagtgg ttttgaaata aaatgccttc tacggcggcg aagcccacca gccgctcacc 57480
tagagtgttc ctgtcggggt ccatccactg ccgcacccac tgcgccattt tttttatgat 57540
agggtgtttt tcaatgccgc taaagatgcg ctgttgttcc ttctcatccg ggatcagcgt 57600
ttttacctgt attgagtagg cttcgctatg aacgcactct tgggcagcct gcattgtata 57660
aaagtataac acttccttta ctttaatttc gcgcataaaa ttggttaaaa ggttttcgat 57720
aacaatttcg tcggcaacaa caaagaaggc taaaatttgt ttataaaatt cgcgctgtgg 57780
ctttggcatg gcttcccaat catcaatgtc cttacacatg tccacctcct gcgccgtcca 57840
cgtcaaactt tctaattttt tataccagtt ccaacattcg gggtgctgaa taggaaaaat 57900
agtgaaacgt tgggaatttt caattagtaa ttcctccata tttgaaataa atattaacat 57960
cttcaaattt attggctgcc atggagacgt tttttattga gacgttggca tctgatgtgt 58020
atggaaaggc gttaaatgtt gatttagata gactatcgca ggcgcaggtt aaatataccc 58080
ttcaagagct tatttcctac tgcagcgctc taaccatttt acattatgac tattcaaccc 58140
ttgcggcgcg tctttcggtg taccagctgc accagtcaac ggcctcctcc ttctcaaagg 58200
cggtgaggct gcaggccgca caatcctgct cacgcctgtc cccccagttt gtggacgtcg 58260
tttacaagta caaagccatt tttgacagct acattgacta tagcagagat tacaagctgt 58320
ccctcctggg gatagaaacc atgaaaaatt cttatttgtt aaaaaataaa gatggggtca 58380
tcatggaacg cccgcaggat gcttatatgc gggttgccat catgatctat gggatgggaa 58440
gagtggtcaa tatgaaaatg attctgctaa cctatgacct gctttcccag cacgtcatca 58500
cacacgcgtc gcccaccatg ttcaatgcag gcaccaaaaa gccacaactc tccagctgtt 58560
tcctgctaaa tgtaaatgat aatttagaaa atttatatga tatggtcaaa acggccggca 58620
tcatttcagg cggcggcggt ggaatagggc tgtgcttgtc aggaatacgg gcaaagaata 58680
gttttatttc tggtagtggt cttaaaagta acggcataca gaattatatt gtgctgcaaa 58740
atgcttcaca atgctacgcg aaccagggag gcctacgtcc cggagcctac gccgtctact 58800
tagagctgtg gcaccaagac atctttacat ttttacaaat gcctcgccta aaaggacaaa 58860
tggctgaaca acggcttaat gcccctaatc tcaagtacgg cctatgggtc cccgacctat 58920
tcatggaaat acttgaagac caaatacaca acagaggcga cggcaaatgg tacctctttt 58980
cgccggatca ggccccccaat ctacataagg tctttgattt ggaacggtcg cagcacgaaa 59040
acgcacaccg cgaatttaaa aagctttact atcagtatgt tgctgaaaaa aggtacaccg 59100
gcgtcacaac ggccaaagag attatcaaag agtggttcaa aacagttgtt caagtaggga 59160
atccctatat cgggtttaaa gatgccataa atcgtaaaag taatctttca catgtaggca 59220
ctatcacgaa ctccaatctt tgtattgaag tcacaatccc ctgctgggag ggtgataagg 59280
ctgaacaagg tgtttgtaat ctggccgcag taaatctagc cgcctttata cgtgaaaatg 59340
gctacgacta ccgtgggctc atagaagcat caggcaatgt cacagaaaat ttagataata 59400
ttatagataa tggctactac cccacagaag ccacgcggag aagcaatatg cgtcaccgac 59460
ctattggcat cggggtcttt ggcctagccg acgtgtttgc gtctttaaaa atgaaatttg 59520
gttcacccga ggccattgcc atggatgagg ccatccatgc ggccctatac tacggggcca 59580
tgcgacgatc catagaactt gcaaaagaaa aaggaagtca tcccagcttt ccggggtctg 59640
cggcctcaaa gggtctactg cagcccgacc tatgggttcg ctgtggtgat ttagtttcct 59700
cctgggaaga acgcgtggca cagacgacgc agggtgtgtt gacgccgaaa aggtggtcgc 59760
agctacgcct ggcggctatg cagggacttc gaaatggata tgtcacagct cttatgccca 59820

```
ccgcaacctc ctcaaattct acaggaaaaa acgaatgttt tgagcccttt acatccaatc  59880
tatatacacg tagaacgtta agcggggagt ttattgtttt aaataagtat ttaatagacg  59940
atttaaaaga aattaatctt tggacagaag ccattcaaca gcagctacta aatgcgggag  60000
gtagcattca gcacattttg gatataccgg ccgagatccg cgatcggtat aaaacctcca  60060
gggaaatgaa tcaaaaaatt ttaacaaaac acgcggccgc acgaaacccc tttgtatccc  60120
aaagtatgtc cttgaactat tacttttatg aacctgaact aagccaggta cttacagtgc  60180
tcgtcctagg ctggaaaaaa ggtttaacta ccggttccta ttactgtcat tttagccctg  60240
gagcgggtac ccaaaaaaag attataagaa actctgagaa agcgtgtaat gcggactgcg  60300
aggcgtgtct tctgtaggtg tctcgcggta aaagagcagc ggggaccata tggtaaaccc  60360
caacaagagg ataatgaata aaaaaagtaa acaggcatcc attagttcca tattaaattt  60420
ttttttcttc tatataatgg aatattttgt tgcggtagac aatgaaacct ccttgggggt  60480
ttttacttct atagagcaat gtgaagaaac gatgaaacaa taccccggcc tccattatgt  60540
cgtttttaag tatatgtgtc cggcggatgc agaaaataca gatgttgtat atttaatacc  60600
ctcgttaacc ttgcataccc ccatgtttgt agaccactgt ccaaatcgta ccaaacaagc  60660
acgacacgta ttgaaaaaaa taaacttagt gttcgaggaa gagtctattg aaaattggaa  60720
ggtttcagta aatactgtgt tcccccatgt tcacaacaga ttatctgcgc cgaaactttc  60780
catcgacgag gctaatgaag ccgtagaaaa gtttttgata caagcaggac gactcatgtc  60840
tctgtaaatg tctcttcctt tatgggtgac gtctcttcct ttgccgagga agtctctgtt  60900
atgggcaaga ggtttgaaac aacgcaagga ctctgcttaa tctgctgtct cacaaaggga  60960
atcaaactac ctgctttcgt atttttaatg tagtaattac ccttgttgtg atgaatttta  61020
agaccatagc gtagtcccag tactttatta atgaatttta aaattgtttg agggtccgtt  61080
ttattgggct ttttaagctt aaactcaaag ctgatcgcgc ttaaatcata ctgaacaaat  61140
tcatcaacga gtttcgtcat taattgttca ttggtcaata tattagggtc ctgaacgcat  61200
ttaaagccgc acttagttaa tagcataata gcgtacatat gagattgaaa actataatta  61260
aattgtagat catgatgctc tgcgtgttgc atggcccatt gatgaaagtt taattcctga  61320
gtttgtaaca tagtgagcga ctcgtatact gtctttccgc ggcttatttg gacacggcca  61380
gtatagttct gttttgtcat aaaactattg tattgttcaa caaatttggg agtaatttta  61440
tgaccgtgcc atgcataaaa ttcgagtagt ttatactttt catacgcaaa taggtcttgc  61500
tggtctactg tgatgccttc ctttaagttt tgtttaattt gtaaagcttt attggcatca  61560
atggtttcag ccgaggcaat gtttacatag tcctggtgtt taatttccat tttaatgctt  61620
gtatattgtt tgactgtctc cagcttttca cccgtcagta taaacacctt agcgccggtg  61680
tcggcgatct ggttaataaa tcgggttata aagtgatttt ttgatagatg ttgtatccgc  61740
attgtttcga gccatagatg gtagtatgga gttttataat atatcggcct acctgtttcc  61800
ttactatacg tgaaggaaag ctggtgattg cttatggtct gaaaaagggt gtcacgtttt  61860
tgtaacgtaa acatttcaat gtcttcgatg gtttctggat agtaattttg tttcccctgt  61920
aagcagattt tataacactt actttttaat tcacgcacgc ggcccaacat ttggcaacat  61980
gtttctacgt cacacgacat attgttaaaa aagccgtata aaacatcaaa tctcttatct  62040
tcgtatgaaa cacccgctga aatcgtgggc gtatagataa ggatatcaac gagcccccaa  62100
taatacgata cattattaaa atgggattcc cgttcatgag cagtgctttt agaactataa  62160
aacccaattt ttttttccgg aaactttttt tggataaatg attgcaacag ccgggcctcc  62220
```

attaatgaat ttgtagggat aacaattttt ttgtcttcta gcaaatcctt taaaaggtta 62280
tttaaccaag tttctcgtga agaggtaaaa taatacgtgt catgctgggc ccttttatat 62340
tgattccagt gaaagaagat agggacatcc ccgcgaaaac gctgtagaat attatacgtt 62400
cgatttccta ggtttgcgtc caagcatata acataatttg ccgtttcgag catccacatg 62460
aaaatggcaa aagagggagc aaagtatttg tgcaggccgc tattgaattg attaaaaatc 62520
gattctacct catccaaaat aagtaggtct acaggctcgg ctgtggaggt tagccggaaa 62580
agtgattcta cctgaatgat gactctttcg tagctgtcca aatctccagt tacttcgctg 62640
tacaatgtga aattcggtag ccgggattgt atatttttg agaagatctg tcgaaacgtc 62700
acaaaccgta tggtttgttg ttttgaaata gaattattgc cgtagtattt ttgcaaatag 62760
ttgcgcagtt ggacggtttt acctattttc atttgagcct ttacaacaag cgtagggact 62820
cgttcatatt ctcgcatact actttcatca tagatgtgtt tttgagtatc aggcagttct 62880
tcaaagagaa tggactcatg aacctctatg ctctttgtca tcacttggtc cacatatgtt 62940
tccacaaaat tatttgtgcc ggaaaggctg cccatgagaa ggctatgttt attgtcatgg 63000
cgacagtgtt gatacacttt gtttcccgtg actcttaaaa ttagggtatt gtccttatca 63060
tgcatacgct tacatatttc gcagtaactt ggacttgtac gtttaaacaa tactaaattt 63120
ttatgaacac ggaggaagca atgattttta catagtgttc ctgcaaattt taatacctct 63180
tcaagttcac tttgttggat agtatcgcag gaactcggtg ttgtttcttt tacatttgtg 63240
aagatacaag gtaaacacgt cgtttcaaag gggggttgcta taagggtatc actcttttc 63300
gtggttgtac tggtctcaaa cacctctgca agctcctcat taaacatttt aacacgcatg 63360
ctaccttttt tatgagaccc tatgatgcga aaattttgaa tacttttgtt gacctggggg 63420
tcaacaaaag gataaacgtg tttgggaaga ttttctaaca ctttggatgt aaagactttg 63480
gcctcattat tgtttaatac tgagtatgta taaagtatga tatgaaagga gtatttaagt 63540
tctcgctttt tatttaatcc gatagaatct gttagcaaaa tttgttcacg cgttagattg 63600
atgttataag gtaaagaata tgtctcgtaa aatacatcca tgatgacgtt aattatcatg 63660
tcaaggatgt catagacatt gtcttcgaca ttatcattgt catcaacatt gtcatcagag 63720
tatgacttat ttaccggaaa gtcgatgtca aattttaagc gctgaggcaa aaacccaaat 63780
accacttcgt ggaaacactt ctgctcaaag ggctgagccg cctcccactc ccaaaagtca 63840
tcacgacttg aaaaaactct aaaaagatta ttatattcat ctcgcaccac gaagtgattc 63900
tttaaggttt cgagagaata tttatcctct acggcttctc cttgggagtt acagcgaaga 63960
aacttgaatg tttcttgcat tttgatattt aaaattaaat caattatgat gcggccgcta 64020
atgcggcggt tgacgcggcc gcgccgctga cgcagccatc atacataaag cggcatggcc 64080
gttttataac gactagtcgg ccgttatatg acgaactata taaaaatgaa ttcttttaat 64140
tagagttaag tattgttgat tgtataatcc atcatggttg agccacgcga acagtttttt 64200
caagatctgc tttcagcagt ggatcaacaa atggacactg taaaaaatga cataaaagac 64260
attatgaaag aaaaaacgtc ttttatggta tcattcgaaa actttataga acgttacgat 64320
accatggaaa aaaatattca agaccttcag aataagtacg aagaaatggc ggccaacctt 64380
atgaccgtca tgacggatac aaaaaattcag cttggagcca ttatcgccca acttgagatt 64440
ctaatgataa atggcactcc acttccggca aaaaagacaa caattaagga ggctatgccc 64500
ttaccttcat caaacacgaa taatgaacaa acgagtcctc ccgcctcagg caaaacaagt 64560

```
gaaacaccta aaaaaaatcc cacgaatgcg atgttcttca cgcgtagcga atgggcatcc  64620
tcgaatactt ttcgagaaaa gtttttaaca ccagaaattc aagccatatt ggatgagcag  64680
tttgcaaaca agaccgggat cgaaagattg catgccgagg gtctttacat gtggagaacc  64740
caattctctg acgaacagaa gaaaatggtc aaagagatga tgaagaagta atatttttgg  64800
taaaaatatt tttatcaaaa ttttttttacc aaataataaa aaatattttt tacttttttt  64860
tcttcataat atacatagaa tgcctacaaa agctggcaca aaaagtaccg caaataaaaa  64920
aacaacgaag ggctcctcca aatctggttc ttccagaggc cacaccggca aaacccatgc  64980
ttcttcgtcc atgcattccg ggatgctcta taaagatatg gtaaatattg ctagatctag  65040
aggcattccg atttaccaga atggatcgcg tcttactaaa agtgaattgg agaaaaaaat  65100
taaacggtca aaatgaatat aatcaggaaa cttaagcctg gaacaattag ccttgtgctg  65160
ggacccatgt ttgccggcaa aactacgttt cttattcatt gcatttacat gctcgaacgt  65220
ttggaaaaaa aagtagtctt cataaaatct accaaaaaca cccgagacaa aactattaaa  65280
acacactccg gtatacagct acgacccaaa caatgtaaaa tcatagaaag cacacagtta  65340
tctgacgtgg gttctctcac cgatatccat gcagttgtcg tagatgaagc gcattttttt  65400
gacgatttaa tcacatgccg cacttgggca gaggaagaaa aaattattat tcttgcggga  65460
ctcaatgctt ccttcgagca gaaaatgttt ccgcccatcg ttcgtatttt tccttactgc  65520
agctgggtta agtatattgg ccgcacctgt atgaaatgta accaacataa tgcatgcttt  65580
aatgtgcgta agaacgcaga caagacgctt atccttgcgg gaggaagtga actgtacgta  65640
acatgttgta acaactgtct aaaaaataca tttattaagc agttgcaacc tattaaatat  65700
taaaaatctt atacaataat ggatcattat cttaaaaaat tacaagatat ttatacgaag  65760
ctcgagggtc atccctttct ttttagcccg tcgaaaacca atgaaaaaga gtttattact  65820
ctgctaaacc aggccttggc ctcaacgcag ctttaccgca gcatacaaca gctgttttta  65880
acgatgtata agctagatcc cattgggttt attaactata ttaaaacgag taaacaagag  65940
tatttatgcc tgttaattaa tcctaaactc gttactaagt ttttaaaaat aacgagcttt  66000
aaaatttaca ttaatttcag gctgaaaact ttttatataa gtcctaataa gtataataat  66060
ttttacaccg ctccctctga agaaaagact aaccatcttc taaaagaaga aaaaacttgg  66120
gcaaagattg ttgaagaagg aggagaagaa tcctaagtcg cttacatttt tttttgctat  66180
ttttatagaa tgtacacgca tgttgatgtt gtcggaatag ctgaagcctc agcggccctc  66240
tacgtgcaaa aagataggga tcgctactta gacgtgctaa caaccattga aaactttatt  66300
taccaacaca aatgcatcat aacaggggaa agcgcccacc tactcttttt aaaaaaaaat  66360
atttatcttt acgaatttta ctccaacaat gtggcggagc acagcaaggc tttggcgacc  66420
ctgctttata aacttgatcc ggaatacctc actcgttaca cagtactcat taccaaaatt  66480
cccaaccatt ggtatgtgat taacgtagat cagcgagaat ttgtgcgcct atatgccatc  66540
ccggcagtta aacaacactt accgattccc attttaccct tctattgcac cagcgcactc  66600
acccagcaag aattgttttg tttaggacct gaactgcagt taatacaaat atattccaag  66660
ctctgtaacc ccaactttgt cgaggaatgg cctacgttgc tcgactacga aaaaagcatg  66720
cggatgttat ttttagaaca gtttccgcaa agattggaaa tgacgggcgg gaagaaggag  66780
gagaaggaaa agcatgaaag tatcattaaa aaaataatac tagaaatggt ctctacccgt  66840
cagcgaatcg ttgttgggggg ttacatacaa aaaaacctgt acaaccatgt actcaagaat  66900
agaaatcgtt tacagcttat tacgagctta aatatttatg aagaaaaaga tatcatccag  66960
```

```
caattttgtg attcaaatgg actgaagatc aaaatacgta tcaacaatcc gctcttgcct  67020
acaaatccgg aattacggcg tttgactatt tattttaatc ataataatga tgatgatcag  67080
tcatatctaa tagtagatat gtacaacacg ggaagctatg agctagtgcc tacaaatcag  67140
ataaacacgc ttgatggcag ctttttaata ggaacaccct tcgtgcaagc gcgatttttg  67200
ttggtagaga tctgggtgct tatgcttatt gcgcagcaaa ctaaaaagga caccaaaaaa  67260
ataatacaat tttttataaa tcaatatgaa atgcttatga atagtccttg gcccagtatg  67320
gaggcccttt ttccctcaag cagtaaaaga tatttaggca actatgtaga ccctaacgcg  67380
ctcataaagt gggcacaact caaattaaaa agaataccgc ctttttatcc tggaaagccg  67440
gatgaagaat catgttaagc cgattaaaaa atcatgttaa gctggttgaa aaatcatgtt  67500
aagctggttg aaaaactctt ggtgaaagca cggatgtaat attaacattg gccgctcgca  67560
tttcgtgttg aaatacgatg gaagagcgac ggctatctac catgccgata tcggcctgga  67620
catcacagtt catgcacttg tagatgggat gactcgcgtt atagatggca ggctcgccac  67680
agtttctaca gatgtaggag atgcagccat ccgagtcgtc gtgcgatttt tctatgatgg  67740
tttgcatggc gccctgcgcc gtaagcaccc aatgctccat ttctcccaga cgaagacctc  67800
cgtgcgatcg tttgccgtcc aacggctggc ctgtgagggc atccgtgggc ccatagcttg  67860
caacggcgta tcggtcatcc agcacaaatt tttgcaggcg ctggtgatag gtcggtccta  67920
tgaagatggc cgcatcaaag tactcgccgg tctggccgtt gaacattttt tggcatccat  67980
tgaagcgtag accttcttgc gccagtcttt ctgaaagaag ctgcacatta ataggcagga  68040
atgcggtgcc gtctgttacc accccctgta gggcatttgc tagaccaacc gtggtttcta  68100
tcatttgacc gttggtcatt cgggagggat gtgagtgggg gtttacaatg aggtcgggct  68160
gcaatccgtc ctctgtgaag ggcatgtctg aagtgggcag ggccagcgcc gcaatgccct  68220
tgttcccgct gcgagaactc attttgtcgc ctatattgag atttctttca tagcgcaggc  68280
gcatgaggcc aaagatctcg tcattaggcc catggggacg catcacagca tccacgacgg  68340
ccggctcatc gaagccgtac atgacagacc ggtcgatgta tttgttgagt tcgtcttttt  68400
cgccccgtat tttggccact tttcctataa tgatgtcgcc ctttttgacc accgttccta  68460
cgggcacgaa tccatctaca agcttttcgt aattagcacc aggcttaaga tttttggtga  68520
ttaaagggtc gggcttccca aacgactcta tatcgctttc taattctact ttttcttctc  68580
ggtagaaggt gccggcaaag ccgcccctgt caataaagga ctgcgacacg atcacagagt  68640
cctcctgatt gtagccgccg tagatcatat aagccacaat ggtattaagc ccgttgggta  68700
tgacatagtt atgtgctatg gtctttacaa gcggcatttc attgtaaaac tggaagaagc  68760
ggttcatgtc gacacgatat ggccagctaa agcaatacca gccccccgtt tgccggcctt  68820
ggtttgtttc ataggtaaca cgcgcaggtt gggtacagtt tgcgtagggg gacactaggg  68880
cggcaaggcc caaaatagct tggggcacgt ccacgtgtgt gaaacgacgc gttacatcat  68940
gtttatgttt gcgtagctcg atgatggaga aggcaacaag acagttttcc gcctcctcgg  69000
gggtaatgaa ctcacagatg ccctgtgcta cgagatcttc aagtgtaagc gttccggcta  69060
aaatgtcttt tgccatttga ggcgtaaatc gcgtattttg aatgaaaggg attttatgtt  69120
tttcccagtc tttatcgcct ttttttctgg cctctgcggc cttgtagcag gcttgattgt  69180
atttttcaat attattatct acaatgagta gggggcgggt cagcctaccg acgtccaacc  69240
aaaattctac ttcgtctacc atgctatccc agtagatggt ggtatgggga tgcacaacct  69300
```

tgccctcacg gcgaagcatt ctataccgct gagcaagctc aaaggcattg gtgcagcagc 69360
cgatccattc tccgttgata aatacgcgcg ctaggccctt tcgtacaatg tccttgttgg 69420
aaacatcggc taactgttga atggccggat ctgatagaag gcgttgtttt aacgaaagta 69480
cttctccggc ggtgcagaca ttggcagtga tggctaactg tttagacatg cctacttttt 69540
caccagtatc ggctgactgg gctacgcaga tgtatccagg ataggatgcg tgcacgcgac 69600
gcatcatgtc agccctttct gtttgtttgg atgcgttggt ggtgttatga gtatttaccg 69660
tacgcaatgc tgaaatggta tttaataaat tttttctttc caaactttga gtagatactc 69720
tgtttacaat ggggcgctgt cgcaccatga tggttttatt tcctgaaatg atagactgtt 69780
ccatactgcg attaagatcg gaggcggtat tttttgataa agcggcagaa aatgcctcga 69840
taatgtttcg ctgagtaagc tcctcaaagg ctgtttgttt aagaagttct ttgaacccat 69900
tgatgatggg tgctatcacg gaagtattaa aaatagcctt aaaggccttg gcgagtgaga 69960
cccctgagcc gtgcacccgc ttggtgcggt agctatcacg gtccgtgggt ggaaacacat 70020
tcataatgac aagaagtatt ttatgaataa gcaggcctaa aaagcgcagc tttcgtacac 70080
gtgtatctgc ggtttggccc atgtgtggca gcaatatttt gtctaaaata gtaagttgtc 70140
tttcatttaa gtattgtacc gcattttcat cgcttttgta agcagatggg tttgagacaa 70200
atttggaaac cttctcggat aaaaaactgga taattttttc tcggttcagc tcgtgttgga 70260
ccggttgaaa tatggggtct aaaacatgaa tggatttttc cagaatttct atcatgaagg 70320
tattcacaag ggagttggat tctagatcaa ataccacttg ctcaatgatg ctgtcatcgc 70380
ctgtcattcc aaacatgcga aagatgagat accaaggtat gcgaagtttt gagaacttgg 70440
tgctattgat ttcaatggta atggcgccgg tggtcatgta gcgtataata atttgagagc 70500
tattttcgaa ggcacctccc ggttgggaga taaactcgcc gcgaatgatt tcattattcc 70560
cttgttgcat ggtatggtaa tggatgtgaa gcgtgttaaa gcggatgttt tctaagaggt 70620
ctacgaccca ttccccgcct cgggctataa agtagccgcc gggttcatta gggtcttctc 70680
ctatttcttt ttttgcggtt tttgataggt gatgagtgtg gcagcggttg ctgccccgca 70740
tgatgggaaa tgtagatacc tgaaaaggag gaatacttgc tcgttttacc tcctgccgac 70800
cattgctgta gtgcgccgtt aaaataacct cggcggctag attaaccggg cccgaatagg 70860
aaaggccaca caggcgtgcc ttattgggta gtaaatttat cttgtttccc tgtgaatagt 70920
ttcgatgttg cgggcgttca atgttcacat ctgtaaagtt aaattggatc tgaactgatt 70980
cccgaagctt atctatttca gtatggtcgc gttggtcttt ataagtaata tccacgttaa 71040
acatttgttt tacaatttgc ggaattccat tgtccataag atcgtcgaag cttttgatgt 71100
tataccctat caatcctgta gagtttactg cagcggagat aaagctcagc atatcagcct 71160
ctgtaagctc ctcattatcc acggtttcaa tggggccgta ggttatttgc ggccgcaagg 71220
gttccatgat tatgaagtac tacattaata ttcagttatt ctttaaaata aatctttatt 71280
tataaatctt atttataata taagaatgcc ttatgcaaga gacatcacaa agtttattac 71340
ggcaacggaa ccagaggtgg gtcttcccct gttggcgctg cagcgctcca aatccatcat 71400
aggggttatt cttcttgtaa taagtttgtt atttattttc attggcatta ttatattatc 71460
agtgagtagt ggtcatacca cagcagcctc tatatttatc gtattgagtc ttatcctagg 71520
tggcggtggt ttttttctta tttataaaga taattcttaa cccacataaa atttgaaaaa 71580
atatagagta agaaaatgtc caattactat tattactatg gcggggggag atatgattgg 71640
ttaaaaacag tagaacccac taattttta aaaatcgggt tgccttacca ggcacaccca 71700
ttacatcttc aacatcaggc aactactccc ccatctatct tagaaaaatt taaacgagca 71760
gacattcttc ttaatgaggt gaaggccgaa atggacccac tcatgttaca accagaaacc 71820
gaaaaaaaac tattccagat attgagtagt attgatatgt tcaaaggtct gcgaaaaaaa 71880
gtagaattca cgtacaatgc tcaaattgtt acgaatgctt ggcttaaaat gtatgagctg 71940
ctaaatacca tgaattttaa taatacatct caggcatttt gcaattgtga gcttccagga 72000
gggtttataa gtgcaattaa ccattttaat tatacaatga tgcattaccc tacttttaac 72060
tgggtagctt cctcccttta ccccagttcg gaaacagatg ccctggaaga tcactatggt 72120
ctttatcagt gcaatccgga taactggttg atgcaatctc ctttactgaa aaaaaatata 72180
gattataata acggggacgt aaccatcgct agcaatgtaa aaaacctagc gcttagagcc 72240
acacaaaggc tgacgcccat ccatctatat acggctgatg gggtattaa tgtaggacat 72300 gactacaata aacaggaaga attaaatctt aagcttcact ttggtcaagc ccttacgggt 72360
ttgttgagtc ttagcaaagg cggaaacatg atactcaaac actatacctt aaatcatgca 72420
tttactcttt ctttaatatg tgtattttct cactttttg aggaactata cattaccaaa 72480
cctacctcct ctcggcccac aaactctgaa acctatattg tgggtaaaaa cagattacgc 72540
ttatttaccc ccaaggaaga acaagtcctt ctaaaacggc tagaattttt taatgatacg 72600
cccctcgtag acctaagtct ttaccaaaat ttacttgaaa gcgtttactt tgccgtagaa 72660
acaatacatc taaaacaaca aatagaattt ctaaacttcg gaatgaaatg ttatcgacat 72720
ttttataaca agattaaact acttaacgat tatttagctc cgaaaaaaaa gatttttcag 72780
gataggtggc gtgtgcttaa taagctttat gttcttgaaa aaaagcataa acttaagctt 72840
tgtgcctcct agggatctgt tgcttaattt aacagatgca atcttaacag atgtaaacta 72900
aaaagtgtgt tcatacaagg attgtattta tgaatattta ttaacatata aggttgtgat 72960
gtaacactgt ataacctata taactacact atgaagcacg gcgtataata atttatattg 73020
aacacgatgt tgactcattt atttgcaaac aaatatttgt ttgcaagacg tttgcatgca 73080
tttactaata tgttgttgac tagtttattt gcaaactaga tgtttgattg caaactagat 73140
gtttgcacgt atttatttga actaatatac actccttgtt ttatttgtta tatacacagc 73200
atacataagt gtatattgtt tacacttatg tttataactc gacgtaataa cattttacac 73260
gctttttttt tgcaaatctt aataatattg tatgataaat caaacaatgt cttatatatg 73320
tggtttatta ttttaggcgc cgcaagatgt actccattct cattgcatgc ttggtgttat 73380
tactctgtct agttatatat gtcggtcatc gtgccgatca tgcacgaaaa tatttagaag 73440
gaatgtggca tggagatccg gtttttctaa aacagtcggg gctacaatcc ttttatctct 73500
acatacaacc tgaccataca tgttttttta gcattgtgaa taaaaatggt gaaaagctga 73560
tggaaaccaa aataccttgt acgataacaa ataaaatata tatgtttttt aaacctattt 73620
ttgaatttca tgttgtgatg gaagacatac atagctactt ccctaagcag tttaactttc 73680
tgttagatag tacagaaggt aaacttattt tagaaaacaa tcacgttatt tatgctgtat 73740
tgtataagga taatttcgcc accgcactag gaaaaacggt tgaaaaatat ataacacaaa 73800
attaatcatg ttttctaaca aaaagtacat cggtcttatc aataagaagg agggtttgaa 73860
aaaaaaaata gatgattata gtatattaat aattggaata ttaattggaa ctaacatctt 73920
aagccttatt ataaatataa taggagagat taataaacca atatgttacc aaaatgatga 73980
taagatattt tattgcccta aagattgggt tggatataat aatgtttgtt attattttgg 74040

```
caatgaagaa aaaaattata ataatgcaag taattattgt aagcaattaa atagtacgct  74100
tactaataat aatactattt tagtaaatct tactaaaaca ttaaatctta ctaaaacata  74160
taatcacgaa tctaattatt gggttaatta ttctttaatt aaaaatgagt cagtactatt  74220
acgtgatagt ggatattaca aaaaacaaaa acatgtaagt ttattatata tttgtagtaa  74280
ataatatttt taattactta aaatttttat atataagttt ttgatactat attataaaac  74340
atatgttcat aaaatgataa tacttatttt tttaatattt tctaacatag ttttaagtat  74400
tgattattgg gttagtttta ataaaacaat aattttagat agtaatatta ctaatgataa  74460
taatgatata aatggagtat catggaattt ttttaataat tcttttaata cactagctac  74520
atgtggaaaa gcaggtaact tttgtgaatg ttctaattat agtacatcaa tatataatat  74580
aacaaataat tgtagcttaa ctatttttcc tcataatgat gtatttgata caacatatca  74640
agtagtatgg aatcaaataa ttaattatac aataaaatta ttaacacctg ctactccccc  74700
aaatatcaca tataattgta ctaatttttt aataacatgt aaaaaaaata atggaacaaa  74760
cactaatata tatttaaata taaatgatac ttttgttaaa tatactaatg aaagtatact  74820
tgaatataac tggaataata gtaacattaa caattttaca gctacatgta taattaataa  74880
tacaattagt acatctaatg aaacaacact tataaattgt acttatttaa cattgtcatc  74940
taactatttt tatacttttt ttaaattata ttatattcca ttaagcatca taattgggat  75000
aacaataagt attcttctta tatccatcat aactttttta tctttacgaa aaagaaaaaa  75060
acatgttgaa gaaatagaaa gtccaccacc tgaatctaat gaagaagaac aatgtcagca  75120
tgatgacacc acttccatac atgaaccatc tcccagagaa ccattacttc ctaagcctta  75180
cagtcgttat cagtataata cacctattta ctacatgcgt ccctcaacac aaccactcaa  75240
cccatttccc ttacctaaac cgtgtcctcc acccaaacca tgtccgccac ccaaaccatg  75300
tcctccacct aaaccatgtc cttcagctga atcctattct ccacccaaac cactacctag  75360
tatcccgcta ctacccaata tcccgccatt atctacccaa aatatttcgc ttattcacgt  75420
agatagaatt atttaatatg tactatatat taattattta acctttcaag ctggtcttca  75480
tttaaattta aaatccacta ataaaatgta ttttctagta gcagatcatc gagaacatca  75540
tgtgattcct tttcttaaaa ccgatttcca tcacatgcat caaaatccta tacaaaaaaa  75600
tcaagctctc ctagaaatca aacagctttt tactggagat tatctcatct gcaaaagccc  75660
ttctaccatt ctggcctgta ttgaacgaaa aacctacaaa gactttgcgg cttctttgaa  75720
agatggacgt tataaaaatc gccaaaaaat gctgtcgctg cgagaacaaa ccaactgtca  75780
actttatttt tttgtagaag gcccggcatt tcctaaccct caaaaaaaaa ttaatcacgt  75840
tgcctatgca agcattatta ctgctatgac gcatcttatg gttagagatc atatttttgt  75900
cattcaaacg aaaaatgagg cccacagttc ccaaaagctt gtgcagcttt tttatgcctt  75960
ttctaaggaa atggtgtgcg tcgttcccac ctccctcacc cccacggatg aagagctatg  76020
catcaagcta tggtcttctc tttctggtat ttcaggcgtg ataggtaaaa tcttggcaaa  76080
cacttgttcc gtagctcatt tggttcatgg aaagctttca tcgcagaata ttgatcagtt  76140
aaaaactccc tccaaccgac cattccccaa aaaagtaaaa cgtatgctta taagcattag  76200
caaaggaaat aaggagttag aaataaaatt gctctcgggg gttcccaata tcgggaaaaa  76260
attagctgcc gaaattttaa aagatcatgc gcttcttttt tttctaaatc agcccgtaga  76320
atgcttggca aatatacaaa tcgttcaaaa aacccgtacg attaagttgg gaatgaagcg  76380
agccgaagcg attcattatt ttttaaactg gtgtggctct gcccatgtaa ccgatgatag  76440
```

```
ccaaaatatc acagaggcgt cgcggtccac aatgcaggtc gcgacgcagt ccgccgcaat  76500
acagcccgct gcaacgcagc cattgcacga agtatcagat gatgcatcat cagatgcttc  76560
atcacccgta gggtatcaaa cattatctaa agaaatgtta ttgaacacag cctgatgtta  76620
ataattcact acatctaaag aaatgttaac ctcgatacta aaaagtcatt gaacacaact  76680
actggggcgc taagttgtcc aacacatcta aagaaatgtc aacatcctcg atgctaaaag  76740
ggtcatcgag ccggtcaata atgtcttccc caaaaagtcc gggagaactg taggccgaga  76800
tgtcgtccat ggagctatct tccccagagc acacaaagtc ctctccaaaa atcataaagt  76860
taaatgcacc gggcttactt aacagctttt cgctttgaat aatagtgttg agttctgtca  76920
gcgcaaactc tctcacaata ttcacaaccc aggagggctc tttaatttca tacagcgtta  76980
agaaacttat acataaaaat tctatagagt aaagcaaggc gctggcagga tctgttaccc  77040
gtaggtgttt aaatgtagtg tgatattcat tcacaacgtt aggcagcacc ttttccaaat  77100
cctccttttc ctcgtacgac aggtgcttta caagcctttc aacatgtata ggaggcttgt  77160
taaatgtact aacgtgccgc aaacagttat aattatataa gaaaatacgt acggcagagt  77220
cgaccgccat gagccttgga tcatccattg aggtaggtgg tggcggggca ccctggcctt  77280
ccctgatgtc tgcgtaggag cgccccctcca tggcccctat ggcctctatc acagcaggac  77340
tgatatccaa aatcttggcc gtcttgatta tttttccgta atcgaaagtc catggctcct  77400
gtggaggctt gggttgtgtt tcggtggagg gcgtggtcat atctttcttt atttgaatag  77460
aacggatcga catcttttcc ttatcgtact ggtctttata attattataa tagtcatgaa  77520
ctaattcggg ttgagaaaga tgatcgtata taatataggt aaaaagtccg cacttgacac  77580
atttttatc ctggaagtcg tgtaatcctc ccttggggca gcgtgactcg tagaaggcat  77640
aaaaggtgtt aaattctaag ctcgccttta gggctgtttg gaccttttt atgtttaatt  77700
gccccacctc atgttgtagc acgtggcata cagaacagcg tagatcggca agtgcataat  77760
ggttgtcaat tttttttatg acgtctttgc gtgttacttc aatctcggcg ggtttctgcg  77820
aactgtctac ggccttgtaa acgtaaatgg tccacttatg aggaagcccc ctttcatcgt  77880
atagggttga aatgggaagc cttttatact caaacagccg agtccgttgg tcggctcttc  77940
ctgtgttagg atcaaatatg ttataaaatc cttgctgagc aagcagggcc ttttgctcgc  78000
cataagcatt ttcgtacgtt ttgaattctg caagttcgga gttaaaatta ggtgcatttt  78060
gtaaatactt aagaaataat tcataggctc taaggtaaat gagagttgag gttttttcct  78120
catcccgtcc tccccaccac acccgcaggc tttcttcttg aaaatagatg tcattcagac  78180
gcgtcaactg cgtaaaatca ggccgatatt tagaggtata aattttatca taaaattctt  78240
tttgcgataa tagctcggcc ggggtacgtc ctatcacggt tttaaactca tattcagcct  78300
ccttgggagt ccgtggtttg tgcataggga tgctgccgtc aatacgggcc actgtggcag  78360
cataatcata catggggtcc agcagaatct ctgtcaaaag taccttggtg tcgtcctgca  78420
cgctaagccc ttgtagccca ttttggtgga taattttttt gaaagcctcc cgaaaattat  78480
tagcaatcca ctgatccgta atctcagata gctgatttat tataccgcta tattgctgca  78540
tcattttctc caaaagaaag gtcacgtatg cattcaaaga gctatccgcc ttcattccat  78600
gaatggtaat cgtaagaaat tctttatttt tttgcgagct ataaatgaga ttcaaaatat  78660
aggcatagat gtagatcaca gcatacagct gcgttaaagg atcgtaatcc tcttcctttt  78720
taatattttc gatgctatac acgagcggca ggcagacatt tacggctata ttggcaaact  78780
```

gtttcacgtc tacaagcttt ccaaagtgga taaacgtgca ggccttcatg gtttcctgcc 78840
aaataaaaac acggagctta ctattaagat cgccgatgat gcccacatct gccgtacgat 78900
cctcttgaat aaaatgggcc agctcttcgc cacaaatttt gcaaaagtag gagtaaataa 78960
gcccctggtt gttttctttc tccttgttta ttcctgaaaa tttcattagc ttggttcgca 79020
tggtgtcgta ggacgcttct gccgcttgaa gctgtataag catgtccaca tggggacaaa 79080
gcagcttaaa cccgcaggct ttgcatagat tccaattggt ggtattgttt ttttccttgt 79140
agagtacacg aatactttct aatactttta ataactccgc gtattgaaga cccgaacgca 79200
actgttttac cagcttgaga tgagcacatg catttttttc ttggagttcc cactgttttt 79260
taatgtttag gtattctgtt gtaataagtt ctgcctcctg tttcccacag gctttaatga 79320
cttcttgaag gatgctgtta gggtcatcca ctttaccctc cattgtaaga atttcacgta 79380
tagcatccga ctgcacccta cctatttttt cttccataat tttaaaatac tgtctcgcct 79440
gggtaatgac ctctgtgagc ttcatgtcca cctgctgcag aatcatttgc tccttttcac 79500
gctgttcagc atgttgtaaa aacttttgtt ctacagggtt ccaaagcacc tccaaatagc 79560
ctgctctata taggtcataa agcaagggca tgtatcccga tgtaaaaacc ggggacaccg 79620
agtacatcgt agacaactct tttaaaaaaa atatcacgcg cttaatgttc tcctccggtt 79680
caatctcctc ggtttcaacg atattagata tatgactgcc ctgatcctca cggtctagct 79740
ttcggtgtac catctcctct gctagccgat taatgagcca gctatgcccg ccgctccgca 79800
aaaacttata aagttcgata tactggtgcg taaactggat gatgttttcc ttggtggtta 79860
cgacaacccc ttctccgttt tttttccagg tttcttgatc cacgcatttc ataaatactc 79920
gaataaaatt ggtcaaattg gctcctgagg cgacgtagcc caaggtttca ggcgagaagg 79980
agcctatctc agccatacgc ataaaacact gcggggaaaa agtttttagc cgcaacttaa 80040
gtccatagat ttcaatgggg gcttctgcgg gaacggccag gtgcgtccca ttaattaaaa 80100
aaatttcttt gcgtgtgcta gggcgaacac gtaattcctt tttttttca ctcacgatgg 80160
ggaccacatc ggggtctacc agcagttgac gtatgtaggc ctctatgggc atggatagat 80220
cgggcagctt tgactgctcg gcgcgaacat ggttcacaaa atcttttaga gtgaaaagaa 80280
agtctattaa acgtatgttt tttatatcat tagacccttt aagggtagag tagatttcat 80340
ccactagtgc ctcgatttcc tcattattga gcgataagat atctgtgcca cggtggacta 80400
tttgcgcgat cgtaattact tcctccatta gatagaaact gaatattata tttaaaataa 80460
atacaaaatg tcaaatgaaa gttttcccga aacgttggaa aacttacttt caatgttaca 80520
gaccaaacag caaaacgcaa ttcagtcaga ggtgattgaa tggctgcaca gcttttgtga 80580
aacctttcac ttaaaaatac actgccataa acagtttatt cctagcgggg aaaaaaaacg 80640
agctaaaata cccgctcaag aaacacaggg aaacacgcag ccctcccacc atgtgtaccg 80700
ggttgttctc tccagagcac agccagtcaa agcacaggaa tctctgctaa caaccatgtg 80760
caacggactg gtgctagatg caaacacatg gacatgccta gccattcctc cgcctgcgcc 80820
ctttcaacag gcgacccgcc aggtccaaca cttttaccgt aacaatttct acgaagtggt 80880
tcccatccag gatggcaccc ttctcacaat ctaccactgg gatgaccctg aatatggccc 80940
ctcctggtgc ctagcaagta cccacggata tgatgtgagt aactactgtt ggataggcga 81000
caaaaccttc gccgagcttg tatacgaatt gctgcagcag cactctacct gcgacgtcac 81060
cctggaaaaa aataaaacgc ggggaacgcg tcttttcttt gataacttaa atcccgatta 81120
ctgctatacg attggaatcc ggcaccataa tttacagccg ctcatctatg accctcaaaa 81180

```
tatttgggcg attcaatcta caaacctaaa aacgcttaaa acggtatatc cagaatacta  81240
cggctatata ggcattccag gaattcagag tcaagttcct gagcttcccc agtatgattt  81300
accttatcta atacgatctt ataaaactgc tatgaatcaa gccaaaaatg ctataaaaaa  81360
tggcaaaaaa gacaagggat actttaatta tggctattta ctcatttcgc gagcgcctgc  81420
cattactaaa agtacttcta atgttttgtt aaaatcgcct ctgctggtat ttttacaaaa  81480
aagtgtgtac cagaaaaaac acaatatctc taacagccag cgactagaat ttattatact  81540
gcaaaactac ttgatgcagc attttcgaga tcatttcatt gctctatttc cgcagtacat  81600
atcctattat acgaaatacc aaaacatgtt gaatatgatt atccatagta ttgcaactaa  81660
agataaagat catccctttg caggagccgt ggtaaaaaaa gtgttggaag atattgaaaa  81720
cgccgaaaac attattgatc atacaaccat tcaaaactat gcccatcaaa gcaagtacgc  81780
catgctttac ttgtcaatta tttcccattt ttaatctaat acggccaaag ccgcgggttt  81840
tttaataaac taacatttaa aaaaactgtt ttattaaaaa ttataatact tttattatat  81900
atggaacatc catctacaaa ctatactccc gaacagcaac acgaaaaatt aaaacattat  81960
gttttaatcc ctaaacacct ttggtcttat attaaatacg gaacgcatgt ccggtactac  82020
accacacaaa atgttttccg agtcggtggc tttgtgcttc aaaatcccta cgaagccgtt  82080
ataaaaaatg aggtaaaaac agcaataaga ctgcaaaata gttttaacac aaaagcgaaa  82140
gggcatgtaa cgtgggccgt cccatatgat aatattagca agctatatgc caaaccagat  82200
gcaattatgc ttaccataca agaaaatgtt gaaaaagctc ttcatgcttt aaaccaaaac  82260
gtactgacgc tcgcatcaaa aatacgttaa atataatttt tgtagaggat aaaaagctat  82320
tttagctaaa aaataattca tatacgttta tgcagaggaa gaacggtggc tttcaaattc  82380
agattgcatc cacgtagacc gtagcgtttt ttttgcttct ggtttatatc gtaaaccgta  82440
ataaacatca tcatttgtat ccgttggatc tttttcccac tccggataaa aaatcggttt  82500
tctttttttt tggtcgtttt ttgcagtaag ctgtaaatta agggaatata gcttatcgaa  82560
aagttgttcc tgatccatat aaatagcagc atatattaaa aaaaaataaa aaaagacgct  82620
tcaacgagtc agtaccactg cttgccaacg atttacgttg gttggtgcat tatggtgata  82680
tagtaatgag tgcctgcaca agtgcttgca caagtgcctg cacaagtgct tgcacaagtg  82740
cttgcacaag tgcttacaca agtgcttgca caagtgcctg tacacattac tgcatcgcca  82800
aagcacctgc aatgcctact tcctcaacag agtacgataa ctaaatgctt ttaagcaccg  82860
cttgcgtcga tgtgtccttc ggggcaatcg ggttcaattg gatccaatat tattagtcat  82920
aattacctaa tacttattca attttatctt ttttaccttg taagatttaa acagcgtttt  82980
agcttgttta aagcaacgtt taaaacaagc taaaatgctg tttaaaacaa cgttttaaac  83040
aagttaaaac aaataagctt ataaatatac catgacaaaa ttagcccaat ggatgtttga  83100
gcagtatgtc aaagatttaa acctaaaaaa tcgagggtcc ccctcgttcc gcaaatggct  83160
cacattgcaa ccctcactgc tgcgctattc gggtgtgatg cgtgctaacg cctttgacat  83220
cctaaaatat ggctatccta tgcagcagtc aggttatacg gttgctacgc ttgaaatcca  83280
ctttaaaaat attaggtctt cctttgccaa catttactgg aaccgtgata gcgaggagcc  83340
tgagtacgtc tgctgttgtg ccacctatca atcgcacgat ggcgaatacc ggtatcgatt  83400
tgtttggtac caacccttca tagaggctta taatgccata gaggcggccc tggatcccct  83460
ggaaaccatt atcctgaacc tcattgcggc acgagatcta gacttcgttg ttcacatatt  83520
```

tccttataat aagggccatg aagactattt ggcctccacg caacttattc tcaaaatctt 83580
tattgcgacg cttttaatgg acattttaag aattaaagac aacacgttgg acgttcactt 83640
aaattccgac tatattattg tgatggagcg gctttggcct cacataaagg atgccataga 83700
acactttttt gaagcccata aggacttact agggtactta attgcctttc gcaatggggg 83760
gaactttgca ggaagtctta gaccctcctg tgggcaaaag attgttcccc taacgattcg 83820
agaggtccta caaatgaatg atattaattt agccgtatgg cgggaggtgt ttattatgca 83880
ggaatgttcc gacttagtca tcaatgggat agcgccctgt ttccccattt ttaacacgtg 83940
gacgtatttg caaggtatta accagatttt ttttgaaaac acgtctttgc aggagaaatt 84000
taaaaaagat tttattgccc gagagctttc caaagaaatt atcaagggcc aaaaaacgtt 84060
gaatgacaag gagtttaaaa agttaagcct acatcaaatc cagtacatgg aatcctttct 84120
acttatgtcg gatgttgcca ttatgattac cacagagtat gttggctata cccttcaatc 84180
cctgccgggt attatttcgc gatccagcta tttatccccc atcgtgaaaa acattttgat 84240
ggacgaagac tcttttatgt ccctactatt tgacctatgc tatggcgcct acgtgttgca 84300
taaaaaagaa aatgtgattc acgcggattt gcacctgaat aacatgacct actaccattt 84360
caacccaacc agttttacag atcgcaacaa accaggaaaa tacaccttaa aggtcaagaa 84420
tcctgtgatt gcctttataa ccgggcccaa agtcgaaacc gaaacgtacg tgttcaagca 84480
catagatggg ttcggctgca tcattgactt tagcagagcc attatggggc caaaccatgc 84540
aatcaagctt gagcggcagt acggcctcgc ttttgtaaac accttttacc gcaatcaaag 84600
tgagcatatt ttaaaggtat tacggtacta ttttcctgaa atgctaacca atcgcgaaaa 84660
cgaaatacag gggtgattt tatcaaactt taatttcttt ttcaatagca ttactgccat 84720
tgatttttac gccattgcta gaaacctacg tagtatgctt tctttggact atttacacac 84780
ctctgaggtg aaacgaaacg tagaaatttc gcaaacattt ttggatacat gtcaattttt 84840
ggaggaaaag gccgtggaat ttttgtttaa aaatcttcat actgtcttat ctggcaagcc 84900
ggtcgaaaaa acggccgggg atgtgctttt acccatcgta tttaaaaaat ttttataccc 84960
aaatattcct aaaaatatat tacggtcttt taccgtaata gatgtataca attataataa 85020
tataaagcgt tattctggga aagctataca aacgtttcca ccctgggctc aaaccaaaga 85080
aatcttgacg cacgccgagg gtcgtacatt tgaagatatt tttcctagag gagaattagt 85140
ttttaaaaag gcttacgcag aaaacaacca tttggacaaa attttacagc gtattcgtga 85200
gcagcttgct aatgaaaatt tgtaaggctt gcagttcttg tatggtcaga acctatgtcg 85260
atggaaacat tatttttcgc tgcagctgcg gcgaaagcgt tcaaggggat agtcagaact 85320
tgctcgtctc tagcaaggtg taccacaccg gggaaatgga agataagtac aagattttta 85380
ttaaaaatgc accctttgac ccccacgaatt gccaaataaa aaaggattgc ccaaattgtc 85440
atttagacta tttgacacaa atctgtattg gaagccaaaa aatcattata ttggtgtgcc 85500
gctgtggcta tatgagcaac agaggataaa ccatatcatc ccaccgaatt atgacattcc 85560
tttaaaaccg tccgcctaaa tagttttcac acctttggtg gcagactatt ttataaaaag 85620
taatgttggt tcatgaagat aaagtgtgcc aaagaaactt ttataaacaa atgattaatg 85680
taggtgctag tcgtgtgtac ttaaacaggg tattctatag ccaagtattt tctatagcca 85740
agtattttct atagccagta ttagtcaagt atttagatgt cagggtattt ttatagccag 85800
tatttttcta tatgtacaaa ctattccagt aaacatatgt gtgttcttta ttgagcagca 85860
tcatggcatt aacaagttta ttaaactgct ctaatgggca ttaaatgaca actcggtgct 85920
tagcaaaagt gcctatacct tttaacaatt agggccggga ggcattccca gctttttct 85980
ataatcagcc atacagtacc cctgagcctc atacacggga ataaggtcct tccattcctt 86040
gttgggatcg gcgggccagc tctcaaatga ggtgtgaatg taagggtcct gttcttttc 86100
cttaatgaag cgtttaatct ccatttgatg ttgtttactt ttttgtttgc ggcggagcgt 86160
gttccgcacc aatacgtaaa aaataccaag aatcacacat aaaagaatta ttaaaaaaaa 86220
tatcatcatc gcggggttta aaaaacgatc ccatgcaaca ggaatcgttc ttaaaacctt 86280
gtctggcagg gctgtaaaca tgaagtctcc tcctataatc ggggtgggac tgtagcctaa 86340
cagttcaagg tcctgtcgtt ctagatactt attggcgaac tgcccaccct ttgccccgt 86400
tttttatta atcaagcagc gctgcatttt ccaccattct aaatcttcag gagaaagctc 86460
aatgccatat atcaacttta acgttattgc atctttttca atatccttat caatttggct 86520
gagcttttga gctttaagcg ggtctagtgt gtacttccat ttaaacttag tgtcctgtag 86580
tttggctaca tgaaatacgg aacatttcgg cggggccttt gtgacgccct tacactgcgg 86640
aagtttatca ttaggacagg cgcatagatg agactgcgcc acagcatcgc gaactacatc 86700
gcagacggag tacattttcc tcctatgtta aacaataaat tttttcata gctgaaattt 86760
gtgggcctat cttttccctt gcccggataa taattataag ggagtgttga aacatctggg 86820
agagaattgc ttaaaaaatg ggtttttggg aggggtaact gcgactgttg tacgtcgttg 86880
gccagggaga ttctatatgc cgggctaaag gtgcaacgtt cctgtgaaca acttagtacg 86940
cgcgttgtta atacaaatgg actggtatta gcaaacctcg taaactcttc cggacttgtt 87000
tgtttttgta tgatgtttag cagggagtct gccttttcga gaatccaaag cgtcgcattg 87060
tagtaaaata aaaatagcga cttatcggca ggcgttgcaa aagcgccgta tagaaaataa 87120
agcagtaagt actggggaga caccacaata aggttatctt gaatgataga tatcgctagc 87180
tctttaaaca tagtgctaaa aaaatgtatg tcgttcgtct tgaatatagg gggactatag 87240
tccatgtagg gctcacatat ctcagtcagg tgaaggccca tttcttttat gacttcttcc 87300
gggttgtacg tcgctaacac cagcgcggga taggctttgg gcatatccac ggtaagtgtt 87360
atgtttttat cattcttatg gtaggagtaa gatggttgtg gaaattctgt tttccactcc 87420
gggactttgc aggtaattct cagctcattt agagtctggt acaggagggc gtatgccgca 87480
aagccgtgta tggccacttg tttaaaggga attgaaaacg ttttactttc gtatgtcgac 87540
ttcacaggaa caacgggaat ggggtaatat ttttctatga ggttataccg ctgcaaatcc 87600
tttttaaacc tgctaaaaac atcttccctt ggtgggttat caaaaggaaa gcaaaatgct 87660
aggtgtagcc cggcccgctg gtaatcgggg tgaatgattt taaggttttt atacgttaat 87720
gtgggtatgg tgttaaagat attgggggc atatatgaaa gatcagcaac ccacacaaag 87780
tccgtgcgca cccgcatggt ctgcacatgg atggcgcgca ccgtgcccac ctgcttgaag 87840
cccttttcat acaaaatgtc agcaagttcg taggcgtcct caacgtggtt gggggaaaac 87900
atatcaaagt cgggtctttc tccctcggga taaattgagc tgcctttaag atgcagggca 87960
taatcaatgg caatcccccc gtacaaaata agctttttct ttatgataaa ttcgcggacc 88020
acctccaaag ccgcctcaat ctccacggca tttgcctcac gtttttgagc aatgagccgg 88080
tacttagaaa cattaaaatc agtctttagt aaagacgtca taaatagtgt ttaatatata 88140
ttaaaggttt gaataaaata ctaaatagta aaaatggatg ccctattaaa ggaaatagaa 88200
aagttatcgc agccatcctt gcagaaagaa aacaatgatg tatgcgatct ctgttttatg 88260

```
caaatgaaaa aaatttctaa ctatcagctt ttatgcgaag agtgcggtca gctgaaggac  88320
tggtttgaac ctgaatataa tgaaaaattc acggtatatt ctcgtctaaa gatcgtgggt  88380
gccaatagtt cctatcacca gcgcgatttg gacaaggcca actcaagtga ctatagctcc  88440
ttgcaatttc atcacatttt agaggagctc aaatccctaa atgttaagta tatggatgcg  88500
gggcaaaagc cctttcctat tcaggtgtta aaagaaactg ctcacagtta taaccaagta  88560
caacaacatc gggtcatacg cagcattaca aagcttcaga tcttagccag tattctacgt  88620
agcatttgtt taaaattaaa cattgcttgt acggtggcag acgccgcgag gtttactcaa  88680
cttaatacca aagggatctc aaggggcatg gatcttctgc gctccctatt tgtagacaat  88740
aaaattactt taaacgttga tttaaaccct atagacagct ttattaatag tacctacagt  88800
gccttacaaa ttaaacaaat ccaccaagaa ctgcaggagg aaaatgttta taatttaaaa  88860
gaaattgtta agagctttat attatacgcg gatgagaaga acatcggcgt cgatcttaac  88920
aggagaaccg ttgtgattgc tacgatgtat aatgttttac gccgtgccta ctaccccata  88980
gaaattgata cggtggtgta tcaatgtaaa atacgaaaaa atacaattac acgtgctctt  89040
aaaatgtatg aggattacta ctcccacttt aagtctcttt atgagcagta tcatttaaac  89100
gcggcaaaaa aattaattta aactaaacgt ttaaactaaa tgtttaaact aaacgttaaa  89160
actaaacatt tcgactaaag tttaaaacct agtctaacag cgggatgccc atttccctgg  89220
ggttccatat ttcaacaatt ttttgacctt cgggtgttac cttgatgcag cgcatgacga  89280
gcagtggaat tttcctatta aagagttctt gcttagctat atcaatagga ctgctatatt  89340
tttttttaag cattgtagat ccattaattg ccaattgttg cgctctaacg gcgaccaacc  89400
ttgtggcctc aaaggtggtt aaaacgttgg aggtaatgcg ctcgttatcg ggtataatga  89460
ccaatgtttg cgacgaggcc tgcacaaagc cctcgcagat ggacggagac tccacgatct  89520
cgtccttgtc ctcggactcc tcctcactgt cgacgaggtt ctcctcttcc gtttccacat  89580
attcctccac gaggtcatcc atgataagat cctcgttgtc attatcagcc atattacact  89640
gttatcaaat gtactgttta atacgcaaat ggatttacta cgttttaatt gtatgtcttc  89700
atgtgcaggc tctagtggaa agtaattttc tcacaatttt tggcaccgtt acacttgtgc  89760
ccacaaaaac ccgcgatttt tttattttat attacttttg gaagtacgag tttaaccagt  89820
cgctttcaaa ccttatgcgt ctatctcgcc aaaaaacgct cacagcggtg ttggatatta  89880
cctttaaaaa aataacatta atttttacca cagagggcgt attgcgtatg gattctacga  89940
ataagccagg cgtgccactc gatatagacc cccagttcat tgaccttgat agtattttaa  90000
tggaactgga tcattaggac ctctcccgcc catttaaatt tttagtttct acaataataa  90060
aatgcgcgag gaatcatggg aagaccacga taccattcag ctcaccgctc agcgcaaata  90120
cctcgccgag gtgcaagctc tagagaccct tttgactcga gagctttcag tctttctcac  90180
agagccaggc agcaaaaaaa caaatattat taatagaatc acaggaaaaa cctacgcact  90240
tcccagcaca gagctactaa gactctacga gcatctcgag caatgtcgca agcaaggcgc  90300
cctcatgtat tttttggaaa gacaggggac ctactcgggt ctcatgttgg actatgacct  90360
taaactcaat acaaatgctg ttccccccgct ggaacccccc gcgctatcac ggctttgcca  90420
tcgaatattt gtgcatataa aaaacagcag tgtgctgcct gagggcagcc ataaaatcca  90480
cttctttttt acattaaaac ctgaagtggt tcagggcaaa tatgggttcc atgtgctcat  90540
tcctggtctc aagctggcgg cttctaccaa aaaaagcatt ataggatccc tacagcacga  90600
tgccaccgta caaaaaattc tacacgagca gggcgttaca aatcctgagt cctgtctgga  90660
```

```
cccccactcc gcctccgttc cctcgctcct ctacggctcc tccaaactaa accacaagcc  90720
ctaccaactg aaaaccggct ttgagttagt ctttgatagc tctgatcccg actacattcc  90780
cattcatcaa ataaaaaatt tagaatctta taatttagtt tctgagttga gccttacgaa  90840
tgaacaggga agccttgtaa gacctgtcta ttgcgcggca gacattgccg ctgagaagga  90900
ggaagagatc ccgaccgagg atcactcgct ctccatatta atgctacatg atcccgaagc  90960
ccggtattta cataaaattt taaatctgct tcctccggag tattatgtag agtacccccct  91020
atggagcaac gtcgtattcg ctttggccaa tacatccgct aactatcggc ccctcgccga  91080
atggttttcg caaaaatgcc ctgaaaaatg gaatacggga ggaaaagaga aactagaaaa  91140
actttggaat gatgcctcgc accacactga aaagaaaatc accaagcggt ccattatgta  91200
ctgggcccac aaacatgccc cccagcaata caaagaaatt gtagaacaag gctacttttc  91260
cattctcgct gaatatgtgt atagctataa cggcatgctt gagcactaca tgatcgccaa  91320
agtcatctat gctatgatgg gcaacaagtt tgtagtggac gtggattcaa acgggaagta  91380
cgtttggttc gaatttgtgc taccgggcca gccaatgaat cagggagaaa tatggaagtg  91440
gcgcaaggag gtaaacccgg atgagctgca catctatatt tccgaaaact tttcaagggt  91500
gatggaccga atcacggagc acatcaaata ccacctcagt caaccccatg aaagcaatat  91560
tttaaattat tataaaaaac tattaaaagc ctttgaacgc tctaaaagta aaatctttaa  91620
tgacagcttt aaaaagggag ttatcaggca agctgagttt ttatttcgcc aaagaagctt  91680
tattcaaact ctggatacca atccccacct actgggggtt ggcaacgggg ttctctccat  91740
tgagaccatc ccggctaagc tcattaatca ttttcacgag catcccattc atcagtacac  91800
acacatatgt tatgtgccct ttaatcccga aaacccctgg acaaaactat tattgaatgc  91860
actccaagac atcatcccag aacttgatgc taggctgtgg atcatgttct acctaagcac  91920
ggccatattt cgcggcctga aggaggctct gatgcttttg tggcttggag gcggctgcaa  91980
tggaaaaact tttctaatgc gacttgtggc catggtattg ggcgatcact atgcctccaa  92040
gctcaacatc agccttctta caagctgcag agaaaccgcg gaaaaaccca acagtgcctt  92100
tatgcggctt aaggggcggg gatatgggta ctttgaggaa accaacaaaa gcgaggttct  92160
aaatacgtcg cggctgaagg aaatggtaaa tccgggcgat gtcaccgctc gagagcttaa  92220
tcaaaaacag gaaagctttc agatgacggc caccatggtc gccgcgtcca actataactt  92280
catcattgac acgacggacc acggcacatg gagaagactg cggcattatc ggtcaaaggt  92340
gaaattctgc cataaccccg accccagtaa cccctacgag aaaaaggaag atcctcgctt  92400
tattcacgag tacatcatgg atccagactg ccaaaacgca ttcttcagca tactcgtcta  92460
tttttgggag aagctacaga aggaatacaa cgggcagatt aaaaaagtgt tttgtcccac  92520
cattgagagc gaaacggagg cgtacagaaa gtcacaagat acgctacata ggtttatcac  92580
agaaagagtc gtggagtcgc cctccgcaga aactgtgtac aacctatccg aggtcgtgac  92640
ggcctacgcg gaatggtaca acaccaacat taacgtaaag cgccatattg ccctcgagct  92700
atcccaggag ttagaaaact ctgtgctaga aaaatacctt cagtggtctc ccaacaaaac  92760
gcgaattcta aagggttgcc gtattttgca taaatttgaa acgctgcagc ccggcgaatc  92820
ctacattggg gtgtccacgg ccggcacact cctaaacaca cccatatgcg agccaaaaaa  92880
taaatggtgg gaatggtccc ctaatccctc tgcccctcct gagaaagaag cgtctgcacc  92940
aactccttag ggaatatcct tagaagcatg tctttcggca gagccattac cggtagcaaa  93000
```

aaagcaacat tgagtatatt atatgcctta gcctgctcat aagcgtcctt ttttttcatg 93060
gtattttatg tttttaaata tttttaatta ttttttaaat acgatgaaca gttcgtgctc 93120
cgaaggctgt ttactaaaaa tcggtgtgaa tccgcattct ttaaatatgg tttcccattc 93180
ggggatggta tggaaatcca tgtctctacg aatagtatgg tgcccaagtg cgtcctgcag 93240
gctgtgaagc cagaaggcct cctgaccttg atgaaggtcg tacatgataa gaaaaccatc 93300
aggtttcaac agatggtaaa gcttgttaaa atcgtttatc gtaagatgat gcgccgccat 93360
aggtaaccct atgagctcca cagagttttc atgctggaca tcgtccatat cggtataaaa 93420
cgtttcacag taaatgagac gcttaaacga gtatcgatga caaacattta tttccaagta 93480
ggtttgcact acgtttttag gtatatcggg aatcatgttg attaaggttg tttcgggaaa 93540
cttaatcatc tgactaggct tcattttcaa ctctttaaag gatttcccgg agaagtgaaa 93600
atgggtcttt acgtatttat gtaaaaatac ctgaatgggc agagggggct cctcctcttc 93660
gttctcgacg cctcccaaaa tatttggaat ttcctgacgt ggcaaaagaa agtttatgtc 93720
cacgtttacg aatccatcga ggacggacac aaagcttggc tctaatctcc attccatata 93780
ctgtttagaa acgggagata gcataatcct aggcgtcaca atgcacgaag ggtttttaat 93840
caccgcatcg tggtaagaaa agtgtattcc atttcttcca gtataaagaa gcctatgttc 93900
gtcgtagcag aaacaattaa ggcggtatgc ctcatacata cactgtttca aagtacaaac 93960
acgttttaaa aaggtttctg cattggcgga ggccaagcgg ttttgccatt ggtggaaggg 94020
gttcaatcct acaatggcca gctcgtttaa aatatcttcg cggcgcgcta aaatctgcac 94080
catagaagaa tactttagca tttttttttc gcaccattcg cgaagatgtt tagctacatt 94140
attaacctta ttattgataa agtatacgat ggcatgttgg aagccttcaa aaataaagag 94200
cccctccaaa agatcatctg ccaatagaag atggatgttg gtgtaagcat tgtcaatatt 94260
ttgtagaaac ggcggaatgc ctgccaaaac cgcttcagca agcatagctc cgttccgttg 94320
tttactgtcc aatagattcg taagtttttt gtccgcaaca gacacgacgg ctaggatggt 94380
tgcaatgtca gaaatggcgg cttgccagaa ataacccgaa aagcacatgc gcgcttcttc 94440
tatagataaa aacgaaaagc gagaggcaat gtctccgagc tgcgtgagtt gaagaccttt 94500
ttctcctctg gttaaaaggc ctgccacaat ggcccgctca atggctgatg ccagcgcatc 94560
cgtgggggga ggatccagca tatcaatctc ctctgcctta aacacgcctt ccttattttt 94620
tttaatcgtt tctacgacaa tgctaagaaa aatggcccca gggccttccg taatgatttc 94680
aggatactgc tgcactggta tttgctcaaa gacgtgtttt gtgtaaagcg ggtaaaagtg 94740
cccaggaaat actctcccta cacgcccctt tctttgctcg atacggcttt gagccgcggg 94800
gcgcgtaata agccctcccg cccattcggg atagtaggtt tcaatgcttc tgttccaccc 94860
gggatctatg acgtacttca gcgtttcaat ggtaaggccc gtttccgcaa caaccgtgga 94920
aacaatgacc cttcttaaag gtttttccac tttagcggtt aagggatttt tcacccacag 94980
attcttaatt tccgctttca ggccaaggta ggcctcattt tcctgcgcaa tcgcctcact 95040
atcgatcggc aaaatcaaca ttaacggcag cttttctttg gcaaggtcca tatttgcatt 95100
attcagcaac atcgaaagga agcgtatttc agccataccg ggcatgaaaa ttaaaatatc 95160
tgcttccgtg ggacgatcat gaatgttttc tttatgaata gtgagagccg tttcgcaggc 95220
ggtcttaatg tagttgttgg tgttatacag cggccagtgg gtttccacac cgtactgtcg 95280
tccttccacc aaaataatgt tttcttttcc gataccaaaa taggttgagt atttatgggt 95340
atcaatggtg gcggaggtta aaattacaaa gggaatacgc agcgccccta tgcttcctct 95400
ttgcaacatg cgctgaagca tacttttaat atacatgagc ataaggtcga tgcctagggc 95460
tcgctcatgg gcctcatcta taatcataaa ggcatagcgg gaagctatct catcatccgt 95520
cattgtatgt agctgcgcca acagaacccc cgcggttgca taaataaggc cccgattggg 95580
tttttccgtc agaggcttcg tttggtagcc cactgtttgg cctaatatca tgtcggggta 95640
gtgggttgag gcgccgatgt ctttggcgag ggtcaccgcg gttaggactc ttggctgggt 95700
acaaataacc gagcgtccca agtatttttg gaaagaatgc gtgttttcat ttctcagaat 95760
tctgaacacg tgtacgggta aggccgtgga ttttccggaa ccagtgcgtg actttataat 95820
gagcacccgg tctgcgaggg aggttggaat ggcccctcca aactccggga gacgttgttt 95880
tatccaagtg atgatgtaat gaataggaac atcattcttg tgctcagcgg gcacgttata 95940
gagatgacca ggctccaata aagtcggttt tcccatattc tattgtttta aggattgatt 96000
gttcataaat atttttatac tctgaccaag aaattatttt tttattaagc cggttattta 96060
cgttgttatg gaacgcgaag gtccagtact gaaagtcctc cgagttgttt aatgtcaagg 96120
gattttttgt aagatacgaa aaggcgtggt gctggcacct ggtgcatggc agagactcga 96180
taaagttcag tatccattgg atggcttcat atttttcttt ccagctagga gcgtctgaaa 96240
aaaagatagc atatagatgc aaggatcgcc agtatttagg tccccaatgc aacatttata 96300
accttttgaa aaatctcatt ccatatagag gtaaatattt tttttccatg gagaattttt 96360
ttgcactctt gaagggattg cgccacatcg tcaaatgttt tttgttttcc atgtattttg 96420
gcgtaattcc agccagtatc tgtgtcatgg tccttaatgt catccgctaa ctgaaaggca 96480
tgtccaaaac aatgggcagc cctttcaatc atcccaatgt cttcaacgga tccagttcct 96540
aaaacccagc ccataataaa cgcgatctta aaaaagggaa tggtttttttc tggagtgtct 96600
actaactgac cggaacccgc gctgtttaga gagtggctta caaaggtaca cagcagcgct 96660
cccagttggt tgggatccgg aaaccttgga cagtgttcct taatccagtc gatttgccgg 96720
caaatatttt gaaatccttg catggttagc gccagagcgc tcatctgcgc cttggctacg 96780
ccaaagcggg cccacactgt atctttattt cgccgcttca catcgttgtc aaaggagggc 96840
atatcatcga taatcaaaga agctacgtga aagtactccg ctgctagggc ggcctctgcc 96900
ggataaatag gcgccccaaa ggaatgttgc aactgacagg cccgaacaat ttccatcagg 96960
ataatgggac ggatatactt cccacctctt agagcgtaag agcaaggctc tgttagttgt 97020
cccttaaagt ccccatcttc aatagcatta tttaagatgg tctcaaactc ttcactaaag 97080
gttttataat ttttaggatt cagtggatgt attccatgaa aaagcgcgac actacgcggt 97140
gctgtgattc taaaatactt aggtttgcgc gtataggata ttaaaataat aataagaact 97200
acaatgatgg agatatagat gagatgcaac atgctgagtt gtctccccgc agggaatggt 97260
ccttttccgc gcttgttaac ggtaccgagg aggcgttgaa atctttagga aaggtgctgt 97320
ctagtttgga atctccaatt cctcccgtat atttaggtat ataattattg tgtctagaaa 97380
ttgtttgctt tgaggtatca aaatattcag cctgaccgct atttctttta gaataattcg 97440
gtatagggct tgagtagttg gcaatactct taaaccgggg caccaaggta acaatatttt 97500
ccatataatg ggtttgatac gctttgttta aaaatgggct taccggcttt atgcttgtta 97560
gttgtgcatt gagtaccggt atgtcttcta ggatttgtgg ctttatagaa tgattagcaa 97620
acacagaatg tagtatatta gatacttgta gcatatgtct atttgcggaa aattcctggt 97680
attctctgcc gtgttgcgaa tctttgggcg gaaggggacc aagcatcggc acgtccgtgt 97740
aggtactggt ggattttatg agttcctgct ctatgttcgg tttgacatgt ggatttccta 97800
aaggaatacc tctacctgca atccc ttttt ctaccgacgc aggtagattg tgcgctaaac 97860
acaaaatatt gtacacgtct ttgtgcggaa tatatccgtt atagtgctgg cccggcatct 97920
gatcgccaag gtgctgctca tgcttaatgg taccctttgt tctgagttta ggaagatcct 97980
cgtacgaaaa aaattttgtg tgctcgctga acctcgtaga aggaaccgaa ctatttttttg 98040
ggttttttaa ggaaggcaat gaggaaggct gggtcagaca atttttctgt gtgcccttta 98100
agctagccac ctgcggaaat gttttttttt ccgtacgaac aacattgcgc ctaattaggt 98160
tttccgtatg ggttgaaaaa gcaggacgat gatttttaaa atgattaaaa agtttatttt 98220
ttggaatgga gctgtacggc tccagatctt gcgcatcgcc gtaaccaatg tttttgtgct 98280
gagggttcag cataaaagaa aagttacgta gatcactgag ttgcaatccc ttttcagcct 98340
tttcaggact attagtgtat tcattgtata caggcgcagc tccatttttg ttgccgcagt 98400
accgggaatt tagtatatta tcagaatacc ggttatgacg cggcaaatcg ctttcccaaa 98460
gaggtggatc tgacctataa tcggctaaca gctttgaagc ataatcatga tacattgtat 98520
ataaaagtta attattatat tgagaaggca taattacttc ttgtaggggt acaagaggct 98580
ttgaatcagg caaactgacg ggttttgaat cggccggctt tggaccggca ggtatctttt 98640
taggttgatc ttcttctagc tcattagaca cggatggggg agaaatagga ggaataattt 98700
catctccgcc cttatatttg tcatggatag aagaaacaat tacatccatg tttgatttat 98760
tataaatgtc gtttaactgg tgatttaaaa cataataatg caaaaataat agggctacaa 98820
tgcatatata tacgtaaata gccgtcttcg tttttcgttt tttatccacc ggcggattac 98880
aaattgcaaa aaatacaact aataccaccg ctgtaatgat taaggccaca atgaaaggat 98940
tttgaaagga tgttttgaac ggttcgcacg tataaatttt ttctcctaaa ttattgatac 99000
ccgcaataaa atctacattc attttatata tttataaatt atgaaaaatt tagagttaca 99060
tctccgccgg accaatcatt gctaaaattt gaagattctt caaaaaggcc cgactggttg 99120
aatgtcttct gctcaggttt ccaaaaattt tccaagaatg gattttgaac aataggctca 99180
tcttgatttt cttcttcaag gatattttct ttgatatcaa gaacagcttc tttaaactca 99240
ggtgtatctt gattaaactc aggtttatcc tgatcaatcg caaaaatatt atcttcttca 99300
gatatatcct gtttaatcgc aagaatagtt tcttcctcag gtttatcctg atcaatcgca 99360
agaatatttt cttcttcagg tttatcctga ccaaactcaa caatatcttt ctcgctaaat 99420
ccgtttttag tgtgaagctc ttggttttga agagaattat caaaatctat tttagttgtt 99480
gtcctagacc gtggcacggg atagttatct aatggtttac ttactatagt cctcgaatgt 99540
ggcacgggat aattgtttgg tgacttgctg gttagctctt ggcttgttaa tagttcttgt 99600
tttctcaata attccatctc tactacttct ttttgatccg ctggtgtctc tttttggtat 99660
tcttcattag aaaaatgttc agagggtaat gtttcaataa actttgtgag tggatagctg 99720
ctctttgatg tagaagagcg ttgaatttgc tgataaagga gttgaacaag tcgccggtat 99780
tcactctgtc tttttcata tttttacgt agcgtggaga gatctgctaa gagcgacttg 99840
ttttcagatg ttaattcttc aatttgatga agaaggctgc gattgtatga actaagtctt 99900
gcatacgttt cttctaattc tgtctccggc tccacatagg cctgttttcg cagaaattta 99960
ttgtatagtt ccattctttt tttgagcaga aaggtaagac tataatcttg catttctttc 100020
gtaactttat ggtagtttc tttccggttt ttgataataa agggcagcat tttttctgtt 100080
gtgataaagg tgcccagatt gctaatgtag tcgcacagta gcaattccaa gatagattct 100140
ttcttttcaa ggcttataga ttggctgtat tctttaggta tgaaagaatc aacaatcgtt 100200
gttacgaagt ttgaaaagtt taatgttttg ctgttaattt gggtaatgtt acaaaaatat 100260
ttgtaaaaac tatctagcat tttttcataa agttttttat tttgtttaac ccctaaaata 100320 tagccccttta cttgatactg atattccgta acaatggaat gtttttttgta tagtgcattt 100380 ttgtataaaa agttataaaa aatgttgata aaatacgcac caagggtttc aaaaatactt 100440
ataacgtggg attcttcctg atccattata tcatatgtaa tattatttta ataaaaaatt 100500
actgacgaat aacatgcaaa aaaaatatgt ttaaacttat tttaagctag cacttattta 100560
aaagtgtttt aaacacgttt taaattgtat gttaatacac ttaaaaatta agccgaaatt 100620
tgctccaata aggattactt ttatcaatga ccacctcttt actataaacg gctttacata 100680
attttaataa tgctttagag ccaaagctga aggcagtggg aagcggcact gtactatggt 100740
aaaaatgttg ccgatgttca tcctcgcgga tgtacacaag tttcctatat cctttaaaca 100800
caatatggct aatttcttcc acatactcct tatcctgttt ggaatagcgg ttgctttgac 100860
gggaaaaatt cgacatacaa atagaggcat ttgtaaaaat ggaaacaaat gcgtttttac 100920
gaagattggc gggtaaatcg gtatcatctt ggcagcaaat aatcatcgaa ataaaacagt 100980
gacgattttg gtaaaaaaac tttttaaaaa tttcttttgt aaataatggg tgcagttcgg 101040
ccgcgcagtc gtctaatatt aaaagtaaac gaggattaag attgatatag tttaacgtaa 101100
acttttcatc ctctgtaagg cataagtttt tatacatatg aatgttctgt ataataattt 101160
tttttaaaag ttgctgataa agcgatgtaa tcttttcttc ttttttttgg tccgtttgtt 101220
cagcctttaa gcactccact tttgcaatat ttttgttttc cttttgctgt atatcgatcg 101280
gaagtttatg atacaatgtt tttagcatat cgatgttgtt tactcgactg tagatggagg 101340
acatcatagt ttgccgctgc cagatggcct ccaaaaagcg ttcagcgccc ttgttgtcat 101400
tttttttttg cttatcggcg agccacaagc ggtagtgtat tagagttgga tgtacaaaac 101460
cctcatatga acgatttgag ggttccgagg gggcaaccac taaaatttgt tcaatatggg 101520
gttgcaggat tttcataata tgtttaacgt acacggtttt gcctgttttt gaggggccat 101580
atagcacagt tgttttatct ataaaatgat gtgctttgaa ctgtagttca ggaattagct 101640
tccctgaatg ggtcgttagg gccatctcta tattattaca attctgcttt tgtatataaa 101700
atttcttttt cgagtttatt attattgttg acccacatat ctacccgtat cgtatcatca 101760
ggcacattga gcatttcaag cgcattatct aactgttttt ttgtttttat cagctcgctt 101820
tcttcatcgg gggttaaatt ttctttacta agcagttgct taattttttc ttcgcagtcg 101880
tctataaaat catactctcg agctttttttg atatttccag atgctttttc taggtttttt 101940
agctccttaa aggaaagcag tcccttaatc ccgctatccg tgtgaaaggt tgaattatag 102000
atggagagcc ccggagcatc cgggccagtt tcttgtatat tttttgcttt tttgtggtaa 102060
atagtatttc gtaaaatctc ttttcctatc tttaggtctt cctcatgacg gtccaaaatc 102120
cgttttatta tttcattatt ttgattaaaa taattgtagc gctctctgtt ggccttaaag 102180
cttcccagga gtgtccagtt gcctaattga atggatgaaa cctctgagaa aatctggtct 102240
ttatatttat aataaaattc atcaaccttt tgttggttgc tgctatccac cacatcataa 102300
ataatgaagg caaactctag gtcgggtttt tctgggtaga tgctttccgt agcggcccgc 102360
aactcttcgt aattatcctc aatgtaataa ttccacttat aaaaagtatc ctgaggtgga 102420
atatgctgcg aaagatatct agtaattttt gtgttaaaga gaatgggttt aaacgccctc 102480
ggattttcaa gcatatgttt aatgctttgg tgaagttcta tattttgtaa tatgtgggct 102540
gctgccctat agccctgtgg ggtttgggtg attgcatcaa tatcggcctg aagctcatta 102600
ggcacattta atgtttttg catgatgtgt aaagggatgc gctcaggatc tgctaaatcg 102660
gtgtattctg tgcttgtaca agtgcttgca caggtatcta cattggtatc tgcacacatg 102720
cttgcacagg tgtctacatt ggtatctgca cacatgcttg cacaagtgtc tacattggta 102780
tctgcacaag tatacgcact ttgagcatga agattaggat caaacacaaa atgttctcgt 102840
aaaaagctat cgatcgttgt tttagcttcc ttgcttttct gcgtctgggt tttgcagcta 102900
tctgctatag ataaaattgt atttactacc gattcagagg gaacatcatt agtttcctgt 102960
ttcaaagtat caactaacgt tattagctca ctgagaagag ttttggtcgt gtgggtaggt 103020
tttgaatagg aaggcatcca ttcctgcaga gctttgaaga catatccaat aaagctagtc 103080
attataagac gtcgaatata ctgctcccgc aaatttgtaa aagagcaaaa ggccaccctg 103140
ctatcatttt tgaactgttt gtaagggttc gtcctttggt aaagctgttt aagcgtttct 103200
tcggatattt cagtagaggg atcctccaat acgtttttga gaagctcatc aatattaaat 103260
tctgccatat cttagagttt attatataca tattaaagct ttaatataag gggggtataa 103320
caatggacga aatcatcaat aaataccaag ctgttgaaaa actttttaag gaaattcagc 103380
aaggattggc cgcgtatgat caatacaaga ccttaattag tgaaatgatg cactataata 103440
atcatatcaa gcaggagtat tttaactttt taatgattat ttcaccttat cttattaggg 103500
cgcatagcgg agaaacgctg cgaaacaaag taaataatga aattaaacgt cttattttgg 103560
ttgaaaatat caataccaaa atatctaaaa cgctggtaag tgttaatttt ttactacaga 103620
aaaaactttc aacggacggg gtgaaaacga aaaacatgtg gtgcaccaat aatcccatgc 103680
tgcaggtaaa aacagcccac aacctttta agcaactatg cgacacacag tccaaaactc 103740
aatgggtaca aactttaaaa tataaggaat gcaagtattg tcataccgac atggtgttta 103800
acaccacgca gtttgggctg caatgtccta actgcggttg tattcaagaa ttgatgggaa 103860
ccatttttga tgaaacacat ttttacaacc atgatgggca gaaagcaaag tcaggtatct 103920
ttaaccctaa ccgtcactat cggttttgga tagaacatat tcttggtaga aatccagaac 103980
aagagttggg gaccaaacaa gatccctgcg gaaccaaggt gttgcaacaa ctaaaaaaaa 104040
ttattaagcg cgataataaa tgcatcgcgc ttttgacggt cgaaaatatt cgaaaaatgt 104100
taaaagagat aaaccgcaca gacttaaata attgtgtttc tcttatattg cgtaaactta 104160
ccggagtagg gccgcctcaa atatcagagt cgattttact acgaggcgaa tacatattta 104220
cagaggcaat taagatacgg gaaaaagtgt gtaaaaaagg gcgtattaat aggaattatt 104280
atccgtatta tatatataaa atttttgacg ccattttgcc tccaaatgat accacgaatc 104340
gacgcatttt acaatatatt catttgcaag gaaatgatac gctagctaat aatgatagtg 104400
agtgggaatc tatctgtatg gagctccctg aaataaaatg gaagcccaca gatcgaaccc 104460
attgtgttca tttttttaa agatgaagat tttttagatg attttttta gtttttaaa 104520
agacgaaaaa attttttaaa agatgaatat tcttaaaccc cgcaaattac ttttttttag 104580
gtactgtaac gcagcacagc tgaaccgttc tgaagaagaa gaaagttaat agcagatgcc 104640
gataccacaa gatcagccgt agtgatagac cccacgtaat ccgtgtccca actaatataa 104700
aattctcttg ctctggatac gttaatatga ccactgggtt ggtattcctc ccgtggcttc 104760
aaagcaaagg taatcatcat cgcacccgga tcatcggggg ttttaatcgc attgcctccg 104820
tagtggaagg gtatgtaaga gctgcagaac tttgatggaa atttatcgat aagattgata 104880
ccatgagcag ttacggaaat gtttttaata ataggtaatg tgatcggata cgtaacgggg 104940
ctaatatcag atatagatga acatgcgtct ggaagagctg tatctctatc ctgaaagctt 105000
atctctgcgt ggtgagtggg ctgcataatg gcgttaacaa catgtccgaa cttgtgccaa 105060
tctcggtgtt gatgaggatt ttgatcggag atgttccagg taggttttaa tcctataaac 105120
atatattcaa tgggccattt aagagcagac attagttttt catcgtggtg gttattgttg 105180
gtgtgggtca cctgcgtttt atggacacgt atcagcgaaa agcgaacgcg ttttacaaaa 105240
aggttgtgta tttcaggggt tacaaacagg ttattgatgt aaagttcatt attcgtgagc 105300
gagatttcat taatgactcc tgggataaac catggtttaa agcgtatatt gcgtctactg 105360
gggcgtccag ctataaaacg tgactggcgt acaaaaagtc caggaaattc attcaccaaa 105420
tccttttgcg atgcaagctt tatggtgata aagcgctcgc cgaagggaat ggatactgag 105480
ggaatagcaa ggttcacgtt ctcattaaac caaaagcgca acttaatcca gagcgcaaga 105540
gggggctgat agtatttagg ggtttgaggt ccattacagc tgtaatgaac attacgtctt 105600
atgtccagat acgttgcgtc cgtgatagga gtaatatctt gtttacctgc tgtttggata 105660
ttgtgagagt tctcgggaaa atgctgtgaa agaaatttcg ggttggtatg gctacacgtt 105720
cgctgcgtat cattttcatc ggtaagaata ggtttgcttt ggtgcggctt gtgcaaatca 105780
tgaatgttgc ataggagagg gccactggtt ccctccaccg atacctcctg gccaaccaag 105840
tgcttatatc cagtcatttt atcccctggg atgcaaaatt tgcgcacaag cgttgtgaca 105900
tccgaactat attcgtctag ggaatttcca tttacatcga atcttacgtt ttcataaagt 105960
cgttctccgg ggtattcgca gtagtaaacc aagtttcggt acgcattctt tgtgccgggt 106020
acaatgggtc ttccaaaagg atctacaagc gtgtaaacgg cgccctctaa gggtgtttgg 106080
ttgtcccagt catatccgtt gcgaggaaac gtttgaagct gcccatgggc ccccatctgg 106140
gacgtgccct gaatcggagc atcctgccag gatgaatgac atgcacccaa tatatgatgg 106200
cccaccatat catggaaaaa gtctccgtac tggggaatac caaaggtaag cttgtttccc 106260
aaggtggggg tacccgtatg cgggcgtact ttattgtatt caaaccctac tggaacataa 106320
ggcttaaaat gcgcattaaa atgcaccaaa tgtgtttctt cgatttgact caaagtgggt 106380
tcgggatcgg gtttcccata acttttgttc acatttttaa tgttagagat cctgctattc 106440
agcaagtctt gggccaatat aatcttgtcg gccttcccat cgttagcaat aagacaaaaa 106500
gctcctcctg atgccatata taatgttata aaaataattt attgttttta ttaaatatgg 106560
cggtttatgc gaaggatctt gataataaca aagagttaaa ccaaaaatta attaacgatc 106620
agcttaaaat tattgacacg ctcttgctgg cagaaaaaaa aaactttttg gtgtatgaac 106680
tacctgcccc ttttgacttt tcctccggcg accctttggc cagtcagcgc gacatatact 106740
atgccatcat aaaaagcctc gaggagcgcg ggtttactgt caaaatatgt atgaaagggg 106800
atcgtgccct ccttttcatc acctggaaaa aaatacaatc cattgagata aacaaaaaag 106860
aagaatatct gcgcatgcac ttcatacaag acgaagagaa agcattttat tgtaaatttt 106920
tagagtctag atgagctttt acgcaatgtt gtacagtgtt gtatatatgt cttgtaagca 106980
tttgttgtag agtaataagt aaaagataaa taaaaatgac tattaaaata aagcccaaac 107040
cattaaaaat atttttatct gttagattta atttaataaa tggctcatgg aatgtgtggt 107100
gcgccgctgc atgaggtgtg gccgcatggg atgtggtcgc ataagatgta gctacatggg 107160
atgtggcatt tgcttgcatg taaggatcat gatgtgttgg gtcttcatcc cagcaataat 107220
cgccatcttt atctagctga attgtatacc ccattatata tcacttatta ttttttttta 107280
atgtttcatg aatttcatta taggcggtga aagggtcctc aggccccttc tgtaaaagat 107340
tatagagatc ttcggacgct ttatgtttcg tgcgaattaa ggcgggatat aacaaaagag 107400
agggccccag ttccaaacaa attttactta gcgggctcat attttgcacc aagtttccca 107460
ctacttgcga tgtttcataa cgcattttaa agagctttat cataaaagtg ttatgcaggc 107520
cggtgtagtc tggcctatag ttaaggaagg ggatttctct ggtaccgtca aacacgatct 107580
caagtcctct agcaagcccg atcaaaattt cttcagcaat ggatgagtat ctaattccta 107640
cattacgaag cgtaagcatt tctataacat catctatttc ctgcatagag gaatctattg 107700
taggaatttt aatatcatct gtgctgattt gttcattccc aagataggta agcagcatat 107760 taatttttc tagctttact agcttagtct tacgctcata atcatgatct tttttataaa 107820
aagagttggg atcaccgttg gaccgtagat gattaataag gcggtctact tgctttgtac 107880
taggtttaat acttttttca ctatactcgc tttcagcata gtggttttta cgatctcttt 107940
tagaaatagc tgttttttga gatgcctcag actctgcata tttttttcta tgcgtagaaa 108000
gagaataacc gcggtcatta cgtgaactac tgttgcatgc aaggcctcgg cgcgtcttac 108060
cgctgcgcac actgccattg cgtatactgc catcgcgcac actgccgctg cgtatactgc 108120
cattgcgtat actgccgctg cgtatgctgc cgctgcgtat gctgccgcta catacactat 108180
cactacatat gctgtcagta catacgctat cgcggcgtat gccgccgtgt accttatcgc 108240
cgcccctacc cgagggtttt ttagatataa tactgtgtgg ggagtcaagc gaaaattcag 108300
ggtcattaaa gttaatgccc aatgactttg ccaatccatt aagctcttca tcaaaatgat 108360
cggtaggaaa actttgttgc ttgcccatga cctgtttttc aagttcctcc aaattggctt 108420
gctcatttat atggagatta ttcataagcg tcgtaattcc agcaagattt gctccttcta 108480
aaaatgtggt gtcctccatc ggatatacta tactatttaa aagcttttaa ataaaaatgt 108540
gtttggaaga aatgctctct tcaagcgtgt gtagctcaga tataaatgcc tcctcagaaa 108600
gctttccacc atactccttt ctcatcgtat aggagggcgc cggtttaatg taggaaatcc 108660
actgggaggt aaaaaaccgg tacaacatat ttagcagctc gcgggcctcc caccttttgg 108720
gctccgtata gtgcacatca acataagagg cggcgcatga aaagctgcaa aagttgccga 108780
gaacgcccat ctcaatctct cctcgctcat tttcacgcat ataggtgggc acgaattttg 108840
ggacagtctt gaaatagaga tgacatgtcc agcatttaaa gctagaatgg gtaacccatt 108900
tggaaacagt ggtgaatacg gagggtagct ttttttcgac ctcggcttca tcgtcattcg 108960
tatttaacgt atcggtggca gttttttttgg attgcaagca ttcttcaatg gtaatcccgg 109020
ataagtataa aatattagga caattagttt ccataatttt gatagttatt tttatacaac 109080
atggatttaa ttaaagataa atggaggacg aaacggaact gtgttttcgg tcaaacaagg 109140
tgacgaggct tgaaatgttt gtctgcacat acgggggaaa aattaccagc cttgcatgtt 109200
cgcatatgga gttaattaaa atgttgcaaa ttgctgagcc ggtgaaggca ttgaactgca 109260
actttggcca ccagtgccta ccgggctacg aatctttaat aaagactccg aaaaaaacta 109320
aaaacatgtt gcgccgtccg cgcaaaacag aaggcgatgg gacttgcttc aatagtgcca 109380
ttgaagcctc cattttgttt aaggacaaga tgtataaatt aaaatgtttt cctagtaccg 109440
gggaaattca ggtcccgggc gtcatttttc cggattttga agacggaaaa aacattatac 109500
agcagtgggt agacttcttg caacatcaac ccattgaaaa aaaaatccag attattgaat 109560
ttaaaacgat tatgattaat tttaagtttc aaataaaccc agtgtctccc cgcgtcatca 109620
ttcatttaaa aaaatttgca gctttgttgg aacacatccc tactccatat cccatacgtg 109680
aaataaagcc tccattagaa gactcaaaag tatccgcaaa atttatggtc agtccgggaa 109740
aaaaagtacg cattaatgtt tttcttaaag gtaagataaa tattttaggc tgcaacacaa 109800
aggaatccgc ggagaccatt tatacgtttt tgaaagatct tatcagcgta cattggcaag 109860
aaattttgtg cgtgttaccg gtacccgatt aaagaatgtt ttcattaata aggtaatcga 109920
ctatgctaaa aagaataaca agaaaaatac cttgaagaac tataccaaag taggtaggtt 109980
ttctgcatgt cacggcatgg ttaaaattgc taataatgta gtccacaaaa gcattgctca 110040
atacgactaa aaatagtaaa aaaaggataa gtgctctttt tatatccata tactttaaaa 110100
cttatttttt acactaataa tttcctgcgg ccgcaatata aactgtaggt catctataac 110160
gcccagacct gttaaaagta gagtactatg ttttaaggga tttaaaatat ccgccgcaag 110220
aatgtgaata taattttcaa agtggtttac aggaatgcgt aagcgttttt ttttgcactg 110280
cggttggttt agggtcgaat actggcagga ggtatatata ttaataagac cgcggtcgat 110340
ggtttcaata tcttcataga attcaatgcg cggcgtcaaa agttttttaa gatgttgaca 110400
taactcatca tacgtgtagg actggagggg ggaaagaagg gtgtagtcaa agttaaaaat 110460
gtttttttga agaaccttta aagcatgttc cgcgtccgtg gtttccaaaa tatgttttat 110520
ggtatgaatg tcatttaaat ctacaaagtc tgacagcttt gtgtagaact cggtgacgga 110580
ggttattttc tggaaatcgg ttttttgaaa aagattttca atgtgtttgc gggttgagtt 110640
gctttgcagt ccatacaaga catcaaaaaa ttcaatcagc aaaaacttat acaaatggtt 110700
aatataaaaa gctttgttgg ccttattctg ctgaggatat ggttcctcta ggggatatag 110760
aatggcttgg tctatatccc taggatcaat agtcaatgtt gcgatgggaa gcttttccag 110820
cgtagcggga agagtttggg ttggagcgta gtaaaagtat agcccggttt ttccctctga 110880
aagaaagccc acaaattctt tttttatatt ttgcagcacc gctgagggta cgatttcgta 110940
ctgtttatac tgtttgttga aaagggtaat aaatttccag gtttcttcaa agcttgcaat 111000
ctgggtgggc cgcagatcaa agtcgatggg aatgtcgtca tgaatgtagg atgatagtct 111060
tataggaaaa taaatagggc gatcggtgtc tgaatcgata agtaaagcat aacaaaagtt 111120
atgcctgttg ataagttttt taccaaccgt gtagccggga atgtttttca cgtcatggat 111180
atcccaccag ttatccttgc acataaactc gctcatagac tggatgacct ccatcacagg 111240
gtcatcttcg gtaaaaatat actgggcctc actgtttttc agaaatcttt tttgctgggt 111300
gatggccatt gggtagatcc cttcgtccgt gtcaaagata atggctatct tcttcgatgg 111360
gctaagaatt ttttgtattg tgctggggga cacctcaaac ccgatgtcgc cctgtttatc 111420
tttaaaaaag acacagtgaa ggtcgtagca tatggcaaca aggtccagaa agatgtcctg 111480
ccatgtggtg tcccattgaa gcagttggtt tttttgttca acaaaggttt gtaagataag 111540
gtttgccagc tccgcgccgc tggaaaacat gttgccggcc ccattcccca aaatatagta 111600
ctgcggtgtg ttggccgcct ttgcaatttc aatggcaagg gccttggggg caagatccaa 111660
aattcgagca agggaataaa aaagcccggc attgctaatt ccaagcatgg tttgctccac 111720
ccccacaatg caaaaaatgt cggggctcttt tatcgtattt aaaaaacagtt catctgctat 111780
ctggtggggt agaaaggcaa tccggttcac cggtattttt tttccatagg acaaggtatg 111840
acgcgatgtt tgtgtattaa gatcctccag gtcttgttct acaaacgtgt gcttggtgag 111900
gcaggtattg ttaatataga accgctttgt gcccagcagg gccttcgtct tttggcagca 111960
cggcagacag taatttaggg ggtggcggcc ttctagtagg cttagatgag ggtagtcagg 112020
atgcgggcag ctatagtagg caggtacccc ctccgtgaaa ttccaatact ttactagctc 112080
cttgcgcttg gctggcggca tggacttcac ctcggcctct gagtaaatga cgggtggccg 112140
tgggtgctgg cataggacgg agtaaaccgt tgcctgcgtg tcgtacttgc gcaggtcata 112200
caggtcgggg tcctgttctt gaagcgcacg tagctgagag gctccctttc cttgttgttt 112260
atcgtgcagt tgagagagtt tattaaccaa aattttgtca ggcccggtga tcaagttatc 112320
taaaaacaca aataggtaaa cccaaagata gttaaactct tcctgggtaa tgttaaacat 112380
ttctattttg atatctgtaa ccctatggta gatgcgaatg ttgcggccgc cgtagattgt 112440
ttcccaccgg gccgcaacat ttgtgtcaaa gaggtacgca tacgtgtttt ggagcaacgc 112500
aacattgatg tccattttgc gccccggacc ggaggaaata atgatcatcc gttcgatttc 112560
gtggggatca tacgaataaa tccccttttt aaataaaaaa ttgtagaccc cggtttgctg 112620
gaggccccgc acggaaataa tccctgcttg ctcgtattcc cgccaacgac ttttgagctc 112680
ggtaaatccc ttgctagaaa gcgtataggg ccaaaaggtg gacaccgaca tggagctgat 112740
agaaatttgg atgtcctcgt tggagggaag gggcagactc cctccacgag gaaacgcggc 112800
aggccccata tcattaattg tatgaataat aggatttatg aaattattta gggtggacac 112860
cacggagtta aagtcgtggc gctcgttttc tgaccaattg ctttcgataa agtagtgccc 112920
attattttgt atggtaagaa taaaggcctt tttattgata aagcgtatta aaataatagt 112980
gggtacacgg aatgttttat tgctgaattt ttcaggctcc gtggaagtta tgtggtgttt 113040
ggaaaccacg gtgggacctg ttttactata aaagaacacc accagctgag gaatatcggg 113100
agtagctgga aataggtcga aaacattgcg cacattaatt tgaatattta cgaggggtga 113160
aattttaatc attgccgagg tgacggccaa cgtgccgcgt gttagtctat tcccctcgta 113220
cttggcaatg acttgttgtg ctctggcata cgtaaagttt attagttttt gctctaggag 113280
aagcctcttt ttaagactgg tcaaggatgg agaaagagca ggatactgtt tttccatttg 113340
taagggagat tgtaccaata gtttaaaggc atcgggggaa agaagaggcc aatacttcat 113400
aataaggccg taatagagta agtcaaattg gtaattatcc tctatggcaa tggagatttg 113460
gcgccgcatg gggccacta gcgtgttgag gtctgctaca aagatgtgat gaatgttttt 113520
tatgagctgg aagctgtcga gcgcttccac atagagctca tctttttgac tttccataga 113580
tgcgtcgatg ttcaccccac ccacctgttg aaactccttt ttgtagtcgc gaatgtctaa 113640
cgccaccccg ctaccgctta acaataggcg atacgttacc tgaagcgcat tgttttgaaa 113700
aaagaaaatg tgttgtctat aagggggat ccctgtggca acgtaaattt tttctcgaat 113760
gtctttaaaa gtgtcttcag ggaaaatact atactcgcta tacatcgtct caatttctgg 113820
catcatcacg tttgtctcct cgccacgatc ctccacaaaa agtttttcaa actcatctaa 113880
atcatcgcta tctccaccca ccacgtattg ggaaagcttt ttctcccaat cctcgccgta 113940
aaaattttgt aaaatttctt tgtccttagg ggttcgctgc aggtctttgc ggcaggcctg 114000
taacacgttt gcaggaacgg atcccaaaaa aataaacgtc ttcgtgtact cattttccac 114060
aggattataa agagtaactc gtagaggatt tgttaaaaag tcattttgga aatccattat 114120
acccggtata gaaaataaaa tttaaaataa aaaacggatg atatctatca tggaccgttc 114180
tgagattgtt gcacgggaga acccggtgat tacccaacga gttacaaatc tcctacaaac 114240
caatgctcct ctactattca tgcccattga tatccatgaa gtacgatatg gagcctacac 114300
acttttcatg tatggttccc tcgaaaacgg ttacaaagca gaagtaagga ttgaaaacat 114360
cccagttttc tttgacgtac agattgagtt caatgataca aaccagcttt ttttaaagtc 114420
gctactgacg gctgaaaata ttgtgtatga acggctggag acgctcaccc agcgtcctgt 114480
aatggggtac cgcgagaagg aaaaagagtt tgcaccatac attcgaatat tttttaaaag 114540
cctgtatgag cgacgaaaag ccattactta cttaaataat atgggctaca acacggccgc 114600
ggacgacaca acctgttatt accgaatggt ttcccgagaa ttaaaactac ctcttacaag 114660
ttggatacag cttcagcact attcctacga gcctcgcggc ttggtacaca ggttttccgt 114720
aacccccgag gatcttgttt cctatcagaa tgatggcccc acagaccaca gcatcgttat 114780
ggcctacgat atagagacct atagccctgt taagggaacc gttccggacc caaatcaggc 114840
aaacgacgtg gtgttcatga tatgcatgcg catttttttgg attcactcca cagagcctct 114900
agcgagcacg tgcatcacca tggcaccctg caaaaagtcc tcagagtgga ccaccattct 114960
atgctcctct gaaaaaaatt tgttgttaag ctttgctgaa cagtttagcc gctgggctcc 115020
tgatatatgc acagggttca atgattctcg gtacgactgg ccctttatcg ttgaaaaatc 115080
tatgcagcac ggtattctag aagaaatctt taacaaaatg agccttttct ggcaccaaaa 115140
gctggatacc attctaaaat gctattacgt aaaggaaaag agagtcaaaa tctcggccga 115200
aaaatcgatc atttcctcct ttttgcatac ccctggatgc ctacccattg atgtccgcaa 115260
catgtgtatg cagctttacc ctaaagccga aaaaacaagc ttgaaagcgt ttttagaaaa 115320
ttgtgggtta gattcgaagg tagacctgcc gtaccatctc atgtggaagt attatgaaac 115380
acgagacagc gaaaaaatag ccgacgtggc ctattactgc attatagatg cccagcgctg 115440
tcaggacctt ctggtgcgcc acaatgttat ccccgatcgc agagaggtag gaattctgtc 115500
atacacctcg ctgtatgact gtatctacta cgcgggagga cacaaggtat gcaatatgct 115560
cattgcctat gccatccatg atgaatacgg ccgtattgct tgcagtacca ttgcccgagg 115620
taagcgggaa cacggaaaat atcccggcgc ctttgtgata gaccccgtta aagggcttga 115680
acaggataaa cccaccacag gtctcgactt tgcgtcgctg tacccctcac tcatcatggc 115740
ctacaacttt tcgccagaaa aatttgtagc ctctcgggat gaggcaaata gcctcatggc 115800
caagggtgaa tctcttcact acgtctcctt tcactttaac aatcgtctcg tggaaggatg 115860
gtttgtgcgg cataataacg ttcctgataa aatgggattg tacccaaaag tactcatcga 115920
tctacttaac aaacggaccg cccttaaaca agagcttaaa aaactaggtg agaaaaaaga 115980
atgtatccat gaatcccatc ctgggtttaa ggaactacag tttcgccatg ccatggtaga 116040
cgcgaagcaa aaggcgttga aaattttcat gaacacgttt tacggcgagg caggtaacaa 116100
tttgtcgccc ttctttctgc ttcctctagc cggaggagtc accagttcgg gtcaatataa 116160
tcttaaactt gtctataact ttgttatcaa taaaggttac ggcatcaagt acggtgacac 116220
cgactcatta tacattacat gcccagatag tctttataca gaggtaacag acgcatattt 116280
aaacagccaa aaaacgataa aacattatga gcaactctgc cacgaaaaag tgcttctgtc 116340
tatgaaagcc atgtctacac tatgcgccga ggtgaatgaa tacctgcgac aagataatgg 116400
caccagttac ctacgtatgg cctacgagga agtactcttt cctgtgtgct ttacaggcaa 116460
gaaaaagtat tatggtattg ctcatgtaaa cacacccaat tttaatacaa aagaattatt 116520
catccgcgga atagatatca ttaagcaggg tcaaacaaaa ctcaccaaaa cgataggaac 116580
gcgaattatg gaagaatcca tgaaactacg ccgccctgag gaccatcgcc cccctcttat 116640
tgaaatcgtt aaaacggttt tgaaggatgc tgtggttaac atgaagcagt ggaattttga 116700
agacttcatc caaacagatg cgtggagacc ggacaaagac aacaaagcag tccaaatctt 116760
tatgtctcgc atgcacgctc ggcgtgagca actaaaaaaa cacggcgctg cagcatcgca 116820
atttgctgag cccgagccgg gagaacgctt ctcctacgtt atcgtggaaa aacaggtaca 116880
gtttgatatc cagggccacc gcacagattc ctccagaaag ggggacaaga tggaatacgt 116940
ctctgaagca aaggctaaaa atcttcctat tgatatattg ttttatatca acaactatgt 117000
tctaggcttg tgcgcgagat tcattaatga aaatgaagaa tttcaacccc ctgacaacgt 117060
cagcaataag gatgaatacg ctcagcgccg agctaaatcc tacctacaaa aattcgtgca 117120
atccattcac cctaaagaca agtctgtcat taagcaaggc aatgttcatc gacagtgcta 117180
caaatacatt caccaagaaa ttaaaaaaaa aataggcatc tttgccgacc tttataagga 117240
attttttaac aacaccacaa accccatcga aagctttatt caaagcactc agtttatgat 117300
acaatacttt gatggagaac aaaaagtaaa ccattctatg aaaaaaatgg ttgaacagca 117360
tgctacggct agtaatcgag ctggtaagcc cgctggtaat ccagccggca atgcgctgat 117420
gcgggctata tttacgcagc tgattacgga agaaaaaaaa attgtacaag ccttatacaa 117480
taagggggat gcaatacacg atcttctcac ctatatcatt aacaatataa attacaaaat 117540
tgccacgttt cagacgaaac agatgttgac gttcgagttt tccagtactc atgtagaact 117600
gctattaaag ctgaataaaa cgtggcttat tttggctgga attcatgtgg caaaaaaaca 117660
tctgcaagct tttttggatt catataacaa tgaatcgccg tctagaacat tcattcagca 117720
ggctatagag gaagaatgtg gcagtattaa accatcttgc tacgacttta tttcctaata 117780
cttcttaaga aactctttaa acaaggactt cgcatggtca aaggttctaa acccatggcc 117840
cttatgattc gccaaaaaag cggtttcatc aagattttct aaccctttca cggatgaaga 117900
aataaggtgt tcggcctcgt ttgcccattt tctatgattt tttttcacct cgggttctag 117960
atctgttttc tccatatact cattgtggtc atattttttt ttgggaggag gcgtgggtgg 118020
aggaatgggt ggaggaagta cacccgactt tcccgcttca accgttttat aaaaaaatag 118080
aagcataata caaagaataa ggactatcgc aaatatgata accagtgtcc cagtcgaggg 118140
cattttgtta tataagtaac gttttttttt attttttata attcgaatga agaaccatgt 118200
tgaatagtct tctactcaaa gacattttgt tatacggtaa atgagaattt ataaaatccg 118260
aatatcacta tcatactgtt tatctgagaa ggtctcactg ggtcctgtga tggagaaccc 118320
atactctgta atgctggggt ttataatgtg gtcaggactg acaagcacat ttctgaactg 118380
cgagagttct aggtttagac gcagtcgtaa tagtcgctgt atatttgtaa taaatattag 118440
attgcgtatg aggcgagtgt caaagcgatc ctttccaatt tgtactaagg tgggcttttg 118500
tattccaact cccacttgtt taacgatgga ccagggtcct tcttcccgat tttgttccgt 118560
gatataggtc agcacactat tttctgtata tgaggtatga tgtcgcatat taatacctgg 118620
tgccattcca actggcggtt gtgcaattcg ggctgtaccg ggacccaacc atcgtggagt 118680
tttataaaca tatcgttcta gcgtatttaa aaattcctta aggttattta cgagtagcat 118740
gaagggtgct attaaaacag gtggatggtt tataaccatt gtcataaacc attgcattgc 118800
ttcaatatca ttttgtaatg cttgacgggg aggcggggca ggtaatccac gtatgttgaa 118860
taaagcggtt aattgtgcac cggctgtttg gggcgtaata ttttgtatta aatttatcat 118920
cgaattggct tgcccggcat ttcctataag atcgattaaa ttggttattt gacctcgata 118980
ttgttgtacc cagttttgaa tggcagcgat gatctcaggg gttggattgt tttgaatttc 119040
aggtgtttgt attagattat tcacttctct tcgtgtatct tcaagctgag tcctaaatgc 119100
atttaactcg cctataattt ggtttctatc aataacattt cttaaacctc gaactgtttc 119160
agccaatcgt atagtacgca caatttcatg taaggcctgg tttatgtata ttgacatggg 119220
atggccccac cgctcacgtc cacgttgaat acctgcggcc aaactaggac ctgcctcgtc 119280
ataatcaaat tgtgtaggat aaaggcttcc aaatagcact ttattgaaaa tttggtcaga 119340
aagaaattta gggcggccca tatttagcgc gttgtcccct ctaaagatgc gtgacatgta 119400
tccggcgttg cctttggata gtaactcatt cccatattga gtaatagaga ccgagacata 119460
ggggtttata agaagtttta gcataaattc tcgagtattt atggggggac gattcggaat 119520
gtttaatacc tctgcaacat ctggttgagg agccgtggtg tccagagatc gtactttttc 119580
agccgaaatg ccgtacataa gacaagcaat ttcttcaaaa ctatagtcat agttgtaaat 119640
attggcaagt ggtatagatc gcatcagcgc atttacattg ataggtataa tattcatatc 119700
aaacaagtta aatatgcgct cgcgctctct attagagcca agagtgcgtg tttgaccttt 119760
cggcgacact attttgtgaa tatgattgat ttgctcctct tggtaagagc tttccacgaa 119820
ggaaattacg tcttgcaatg ttttacgaag cgaatacact gcattcatcc ctattcccgc 119880
tgttataatg ggtttatcgt ctctgttctc gctaataaga ttaactccac caaaagtatt 119940
ttcattgtac atcatcactg ttttaaaact acggatattt atgataaatc ggagagcctg 120000
aatggcgtgg gtataaaagt gttcaaatcg cgtgggagta atttgttcgc gagcaactac 120060
cgtttcatta tagtttttca tgataagctg tactccgggc atatctgaga gctgtaccgg 120120
atcatttccc agtaattttc ttgtgccgta tagtagttta aactcggggg agccgctttc 120180
aaggttcggg taaagaagag gatcatatac ctcattattt tctattctta ggtcatgtaa 120240
ataatagagc gaaagtgaaa atggcataag aggctcctta ttgtaccggg acatatagtt 120300
ttgaatgaag tgttcttctg tttcaagata gatgggatga tcggtaagct cgtgcaggac 120360
ctccatggca gaatctgcca gagtgtgaga gcctctaatg atcccgtcga tcactgcgac 120420
cagtcgcttt cgcacaacat cgctcgtatt attttgtgcg tctcctaggg gcataagcgt 120480
aacattggga cgaaatacgc cgccaattcc ccgcagggcc gcctgaccga cggatagtcc 120540
tgtcgcagga acattgttat tattataata aataacggaa tcattattgg ctcccaagag 120600
tgccgtcaga ttagggcgag ctagttggac atttgtgtat tgtataaatt gttttagaag 120660
ctctccctgg ctaataagaa tattaaacat tttgttaaat agtggaagat tggctctata 120720
attttcttta aggtaaatgg gaatttctgt taaagtagaa ataagatgct gactcaggcc 120780
ctggcgattg gtatccttaa taagccgctg aagtataagt cccaaagaca gaagaagcac 120840
cgactgctct gtggggtcgc ctctatgacc aaagacgttg ttattgcgtg ctaagtcagg 120900
gtgagcatat cccatctcca tcactgcttg gctaaagttc ccattagcga atgcattaat 120960
aagatttaga tatattttc cgctgggagc atcataaaat cgggtaatat atgaagctat 121020
gagctggtta aacaccatca tcatactacg attattttga ataccatagt ctgatccgta 121080
taggcgataa cgtcgaaggt tgtttgcggc atcattgaca ttggcatagg ttctgagcgc 121140
tatgttgtcc cagtagctaa gagtattttc ctcctgggcg ttgttggtac gaataagatt 121200
ggagagtcta aagtctccta gtgccacctg ctctacacga agtccagagt tattctccaa 121260
agcatcgtaa aatacgagtc tactgaatac tcttccgtat tgttcaaagc gttcagagga 121320
ttggggattg ttatttattt gaatattagc cgcgtccctt ctttgcgccc cacctcgaag 121380
ttgcagtaca ttataaggct ttgtaagcaa ggtgtaggtt ttattaatga tttggttaac 121440

```
ccccctccagg cccaattcac cgccaggaag cggccttcct ccggcatcgg taggtggttt 121500
aataagtttg tcaattaaat gttcttccaa ccagtaaaat gagccaggat tagatctatt 121560
ttcatagtat tgaataatgt ttttatcaat atgcgggcgt agaagatcaa gaaaatactt 121620
cgtgtcggcc atcaaagaat caattaagga aataagacct gtaaaatcta aatgcacttg 121680
agcggtgctg gtttcaggga agcgaacttg aaccattttg ttaaaactgg aggtcatttc 121740
gaagatattg gtcaacagga gctgcatgat tcgctgatta tctactaaat accttgcggc 121800
caactcttgc tccggacgaa ctcctccacc agcaggaata cccacatatg gtacaatcca 121860
agcaaaaaga gtttctgtgg ttaaatttcg gtcttgggct gctgcagccg cttcggtagt 121920
gggatcaggg tacaccatag aaagccgcat attgatttct ttaatgacta atcctggatt 121980
tctaatctca gagatggccc cgtgttttct tccgagccag tcaataagat tggcgcggtt 122040
cacgttggca gcttgtgtct ctcgtaacca ttcgataatg ctttttttgaa tcgtatctag 122100
gtctaaacct ttaatgttat tacgaaagtt attaagaagt acgtaaatag cactcaataa 122160
gttaagacct gtaataacgg tttcatgaaa cagaaatatt ttgttaacat ctgtatctgc 122220
cagtgactca gagccttgaa taagttttga aacgatttga attttatcgg tatgctcctt 122280
tttgagttca ttgatagcct ggcgaatgag ttcttggtag gaaattttgc ccaattcttg 122340
ttgcagactg ggatcttcaa acatctcact aagctgtttc ctaaattttt gtaccaaatc 122400
ccactgggag ttgggctgca gcattcctgt ttggacatcc acagagtcta tattgtatag 122460
tgccgggcgc cacttggggg taggctgggt tgaaggacta ataaacctat cggagggaag 122520
taattgtgag gattgtgtat agccatcctc atcaggaaga atggagtagt tggtttgatt 122580
catcattcca aaatcattca tagttcgcgc ttcctgaaca atgcgttgaa atttttccca 122640
ttcggtgcgt gtaatgacac cgaatctgcg gtttatttca tttacaaaat ggataagcgc 122700
ttttttggtt gcttcttgtt caccatactc taagttaaag tgttggtaaa tgacgtttat 122760
ttctttgata agctgacgaa tttcggtttc tgagtagtca ccaatgttaa taagctcaat 122820
aggacgcata aagataatgc gaataagtcc tgagaagatt ccttccagct caggaagcat 122880
cgagatctgt acattttcat ctctaaagga aaacaacttt tgataaaatt cggcgaggcg 122940
gggaaggcgg aagtaaagct ctgctgcctc gggaattacc tcgggctcta gctcatcggc 123000
accccccaat atcatacgcg tgggtataag tttgtacacg ggctcaggcc gttcaaacat 123060
gtcgtaaatc cctaatacaa taaaaatctt ggcggccata cttttcagca tgaaggtgaa 123120
gaagacgtcc tcggtttccc agcgggttga tagggcgtcg ttaactctca cagtagagag 123180
gtagacccgc tgagccgctt cctcggcagt ctgtgcaagc gccatccttt gtcctccaat 123240
ttctgattga tttagatttt taagtcccac ggaaagcgca gaatgttgaa gatattcaag 123300
caaggtttta tagatttgca ggggcgacat gggcaccatt tgccgcagct cctctccccc 123360
aagcatgtcc ccaatccggg caaaggcatt gatgatattt ttaagcgcct gaaagttaga 123420
aagagagcgc ccgataaggt cgcgaatgtt tttagcctgg cttgctctga cgggacggag 123480
ggtaccaacg cttcggcctt gttggatttc agccgcaact ttttcgtagt agtggcccgc 123540
aggagcatta tccgtaaaga cgttggagtc gttgcctgtg gaggtgggaa aactttcaaa 123600
gacttgtgca agcgtgtccc ctgttgtctc ggtgaaccat cgtcctataa tgcgcacgcc 123660
atccagcatc tgttggactg tttgaataga atctatgttg tttacaaacg ttttggtaat 123720
gtttttaaga taaagatcta gcccttccag agctcgatag aatcggcgtt ttacatcata 123780
ctccagctcg atggcgctta cggttgcctt ccagtctact tcctgggcac ctccaggatt 123840
```

tgggcccacg tgtcctctgg caagatctac agccggagaa ttaatgcgcg catttttttc 123900
cgtatccaac tgcatgaggc gtcccgcaat agcatctccg agaatagtgg catagttttc 123960
ctcgtaggat tgaaactcct gtttgttatg cgttaaattg gagtaaatct gggccacata 124020
atagtaatac ataaaggtgt taattgcctg gttgaggtca acctgcgatc gcgcggcctt 124080
gctgagccca agctcttcaa ctgttagggc agcaccgcct acccttgtac actcgcagtc 124140
ctcctcgcct ccatactttt tttgcacaat atcggtataa aaatcaataa tctgtagcaa 124200
gcgagagcag gagtcataaa gatttttaaa attagggtcg gttttagata tctcctccaa 124260
aacattttta acaagcgtaa gctgtgttaa gaaggtttcg cgttcttctc gtgcggccgc 124320
attggtgtaa aagccgataa gacttagatc aagtgcgatg gtgcccatat cattaatgcg 124380
cgaaagagca tctcgaagcc tcgttatgtt cggcgtcaag gcaatttctt taacaagttt 124440
gatgcctatt tttttcacat tttccaaaaa gtcgttatag gcttgtgtgc ttttattcaa 124500
aaattccatg aggatgtgct ttctatccag tctttgcgct tcaatcctcc tatctagtgg 124560
cgttttctcc tcatcgcccc cctttttggc acaactgttc tcaaggattt tgtggcgttc 124620
attaaaggtc tgtcgcaaca ggttcacggc tttttcaaac tcagcaatgt tttctgcgga 124680
gacaagacca ctaaaccttt tgaggtcaag ctccttgtca aactccgccc agtttttgct 124740
ttgaaggtac tgttcaacct tgagtcctac tttctggaga gccttattaa ttttattcgc 124800
aacagacgca gcaataccta gattacaaag tgtgtacgaa agtacttttc caaaattttt 124860
ggttcccaag acactatttg tatcatttaa aagtttaata atatccacct catccgtctg 124920
cagtttatca agttcctttt gggtgggagt taaaatattg tcaataaaat tcgttaaaat 124980
gttgatttgc aggttttgtt catttaaaag tcgacgatat actgcttcaa tcatggtgac 125040
tgcattaatg acttcctcat tgggggctgc tttggttacc tccgtcacca tgcgctcgtg 125100
aagttgctta atggcgtcgt ttaacagctt gatattttca agtgtatttt ctatactgcc 125160
gtgtacatca agatactctg cgcgcagtcc atgagttagg gagttaatgt acagaactat 125220
ttgtcgacat atactggcgg ccccttcggt ggtatctata agcttatcct gacctaaatc 125280
aataaattcc tggttaatgg cgtctgcaat cattttacag acggtctcct gtttttccgc 125340
attttttaca aaggtggaac cggctcgagg atcgggcagt tgtttttttga tatctttaag 125400
aatatcttcg atgggctgct ttgtgtctac tttgaaccct attttggcaa tcgccctgat 125460
aattccttct ataatccgca gctttgcttt actcgatacg gagtctatgt gataatcttt 125520
aatgtgttgt acaggatttt tgtccccccc gccattaaaa tatcctcccc ctgaaaaagg 125580
acgagtttgt ctttgtatat gatcctgtaa cttcgcatat atatttgctt ctgatgaagg 125640
cagtggtcta ctagaggttg aagatccacg gttacccatt ataataaaaa aaaataaaga 125700
tttaaaacta caaatatttt gctgtttata aacccaatca tataagacta actaaaacat 125760
taaatgtagg tgagataaaa gcttattttt tttttaaaag tttaataacc atgagtctta 125820
ccacctcttt ttcttcttcc tttagagggg ttccataaat ggtttgaata aaattatgtg 125880
ctctaataac cttgttaaaa tcaggtgcct ttccatattg ttcaatatgt tgcacagtct 125940
tttgtgcaag catatacagc ttggagtctt taggtacctc cgatgagggc tcttgctcaa 126000
acaacgtttc aaaggaggat gtgcattcat tggtttcatt atcatttttt tcatgaatgt 126060
tctccgaaga tgctgaggat tccgtctcct cttcaaacag cacatgcaga atcatattcc 126120
attcttcttg agcctgatgt tcagtatacc cttgccctgc atatatacga gcagatttca 126180
caatatcata cttaacagta ctaagcaatg tttttatagc ggtcgtaaca attctaccgc 126240
tattgataat ctcaacagaa aaccaattat acaggctacc cgcatgaaac acaacttgtg 126300
aagatgatct taaatccgtt ttgaagatga cctccatttt catggatata tttaaaataa 126360
aatccattca attttaaaat tataaaataa taagaagatg ccctctaata tgaaacagtt 126420
ttgcaagatt tctgtatggc tacagcagca cgatccagat ttattagaaa ttatcaacaa 126480
cttatgtatg cttggcaatt tatccgcggc aaagtacaaa cacggagtta ccttcattta 126540
ccccaaacag gcaaagatcc gcgatgaaat aaaaaaacat gcctactcca atgacccttc 126600
acaagccata aagaccttag aatcactcat ccttccattt tacattccca ctccagcgga 126660
gttcaccggg gaaatcggct cctacaccgg agtgaaatta gaggttgaaa aaacggaggc 126720
gaataaagtt attttaaaaa atggagaagc ggtcctagta ccggcggccg attttaagcc 126780
ctttcctgat cgccgactag cggtctggat catggagtca ggctctatgc cctggaggg 126840 tccccccctat aagcggaaaa aggagggtgg ggggaatgac ccgccggttc ctaagcatat 126900
ctcgccgtat actccgcgca cgcgtattgc cattgaggtg gaaaaggcct ttgatgactg 126960
tatgcgtcaa aactggtgta gtgtcaataa tccctatctt gccaagtcgg tctccttgct 127020
gtctttcttg tcgctcaacc atcccaccga gtttattaag gtactgccgc ttatagactt 127080
tgaccccttg gtgacctttt atctacttct tgagccctat aaaacgcatg ggatgactt 127140 tttaattccg gaaaccattt tattcggccc taccggatgg aatggtacag atctgtatca 127200
aagtgccatg ctggagttta aaaagttttt tacccagatt actcgccaaa cctttatgga 127260
catagccgat tcggctacta aggaggtaga tgttcccata tgttactcgg atcccgaaac 127320
cgtacattcc tatgccaatc acgtgcgtac tgaaattttg catcacaatg ccgtcaataa 127380
ggttacaaca cctaacctcg tcgtgcaggc ctataatgag ctcgagcaaa ccaataccat 127440
acgacattac ggccctattt tcccggaaag taccatcaac gcactgcgtt tttggaaaaa 127500
gctgtggcag gatgaacagc gatttgttat ccacggcctg caccgcacgt tgatggatca 127560
acccacctat gaaacctctg agtttgcaga gatcgttaga aatttacggt tttcgcgtcc 127620
cggcaataac tatataaacg agcttaatat tacaagtccc gctatgtacg gcgacaagca 127680
taccaccgga gatattgcgc ccaatgatag atttgccatg ttggtggcct ttatcaacag 127740
tactgacttt ttatacaccg cgattcccga ggaaaaggta gggggggaatg aaacccaaac 127800 cagtagcctt acagacctag ttccaacacg gctacactct tttttaaatc ataatctaag 127860
caaacttaaa atcttaaacc gcgcgcagca aacggttaga aatattcttt caaatgattg 127920
tcttaatcaa ctgaaacatt atgttaaaca cacgggaaaa aatgaaatac taaagttact 127980
tcaagaataa gtatgttgat acctgtggtg tgttttacct gtgggtttcc tattggaacc 128040
tacgcggcaa tttttgacaa ggctcgtacc gagtatatta aaaccaaaat gggcggaaca 128100
ttgccgcaaa atatcccatt agatgcttct ctccagattg agttaaaaga cctcattaca 128160
gctctgggaa tcccaatgcg ggtgtgttgt cgcactcatt taattactac gttggattat 128220
cgtaaatatt attaatatct aaaattgaaa aaatattttt aatgttacta gtaaaaatga 128280
ctacacacat ctttcacgca gatgatctcc tacaagcatt gcaacaagca aaagcagaaa 128340
aaaatttttc atctgtattt tctttagatt gggataaatt acgcacagcg aagcgtaata 128400
caacggttaa atatgttacg gtcaatgtca tagtaaaagg caaaaaagct ccgctaatgt 128460
ttaactttca aaatgaaaaa catgtaggaa ccattcctcc cagtaccgat gaagaggtta 128520
tacggatgaa tgctgaaaat ccaaagtttt tggtgaaaaa acgtgacagg gatccctgtt 128580

-continued tgcagttcaa caaatacaaa atctcgccgc cattggaaga tgatggtctc actgttaaaa 128640
agaatgagca gggtgaagaa atataccccg gcgacgaaga aaaatctaag ttgtttcaaa 128700
ttattgaact gttagaagaa gcctttgaag acgctgtgca aaaaggtcct gaagccatga 128760
aaacgaaaca tgttataaaa ttaattcaaa gaaaaatttc taatagcgcg gttaaaaacg 128820
cagacaaacc tttgccgaat cctatcgcac gcattcgtat taaaatcaat cccgctacaa 128880
gtatactaac accaatattg cttgataaaa ataagcccat tactttacag aatggtaaaa 128940
caagctttga agagttaaaa gatgaagacg gcgttaaggc caatccggat aatattcata 129000
agcttataga atcgcattct atacatgatg gcatcattaa tgctagatct atttgcatca 129060
gcaatatggg catttcattt ccgctttgct tggaaatggg agttgtaaaa gtttttgaaa 129120
aaaataatgg gattgatgtg aactccattt atggctcaga cgatatttca actcttgtta 129180
atcagattgc tattgcttaa acaatttgct caaaacaagc ttataaacgt ttcttaggta 129240
tgcgatacgt aaatcctaat tctttaataa gttctttttc agtagtgatt tttagaggta 129300
ctaaagtttg atttttaaat aatccatact gatttagctt ataattcttt ttttttaacg 129360
cagctcgaat tcttattaaa taagaaacgg gacccgtaaa atgaagtact gcgtatggct 129420
tttcctcggc taaggccgta aaaagatcaa gttgatatgt gtttttttc cattcaataa 129480 aaagtacaca ctttcgttct ccgcagactt ttacagaaaa agaaagatcc tttatgcgaa 129540
tgttgggcag gacgtgtttt aaaagttttt tttctggaac aataataaga agatccacgt 129600
cattaagcat tttctcttcg cgtcttaagc taccaacagc aacgatgttt tttgataaaa 129660
tttttataag ttgtccatta tattcaaacg caagtcggga gcgtaagtca tttacaattt 129720
tttttccttg aataagcgtt aacattttat atttaatatt aaaatctttt cattttatat 129780
attatatacg caaaatggca cttgatggtt caagtggtgg aggctctaat gtagaaacat 129840
tacttatagt agcaatcatt gtggttatta tggcaatcat gctttactat ttttggtgga 129900
tgccccgcca gcaaaaaaaa tgtagcaagg ctgaagaatg cacatgtaat aacggaagct 129960
gttccctaaa aacaagttaa aacatgcaat tatatgcatg catataaacg catgcatata 130020
aacgcataca tataaaatgc gtaaatacta tataaaaaac tataacatat caatcaagga 130080
atcaacactt ttataatttt ccgtaatata tttttcatcc ataatgatgt cagagtacat 130140
ggtccctatg cgaggaacag agcccataag ggtaggcgcg gcaataccgt aaatgggatt 130200
cacggcggag tcaaccgcag catctgtcaa gacctggact ggagacgaca aggccattcg 130260
caacaacacg ttggaaggct ctcttgcatt aagccctgcc ttttctagag aggtaacctg 130320
tcccgttctt gtcatgagat ctgcgtacat gagtaaatga cgatggttgg gacccttgtc 130380
ccccataacc gttctaattt cactaataat tttttgccgt gccgcttcta tgccgtaaag 130440
ctccatggtg tctcctatag aggacgatac gatggtgtat gggtcgatgt tatcatcaag 130500
cattgcgcca aaaatattag tcccgtttgt tttgatggcg tagatattgt ctagtcttac 130560
cagtttcccc tgggcatcca cacggtggcg cataagctta acaacattcg catttttgat 130620
gcctggtatt cctctaatcg tgctatttaa tagtttatcc accacattta cggcaatttt 130680
ttcatccgta gccattcggg tattggtact gcgtctaaag gcgctttccc gtaggtatat 130740
gcgaataatg atgggaatcc ctgaggccgt gttttccaca gaatgcatga tgtaggtgtt 130800
ggggtgttta gctcttagac tattaataat actttctaga ctaatgcttt ttaatatcat 130860
ggttgttttg tttaattcca agcggataca ccagtttgca atatcctctg ggggctgtag 130920

-continued tagaggatgg ttttccagaa aatccgtcat ccattccaca tcacttgcaa aatcggggta 130980
catcacattt ttttttgtgc ttgaatacgt ttcgtacaat aggtgccact gcaatatcaa 131040
ccgttcgaac gttataagct ctatgctgtt agcaatttct tgcgcatatg ttttatttgt 131100
ttccacttcc gggttcttta gacgtaaaag catttcagag gattgttcag cctctacggg 131160
cttcgcgcta aagatctcct ggggccgcac aattcccgac ttgttggttc ccccggccac 131220
ggaccggtgg tgggagtcca gcatatattg tgtcaagggc tctgatacgg actgcgccgc 131280
caggattccc actgcctcac cgtagttaat aagactttga gtatattgta gccttatgag 131340
gtccaggatg gcactcatct gctcgcaggt aatgtttaat gttttaacgg ttgccagttc 131400
gatgcgaata agcatgcgca tcagagaggc agcccgttta agataaacgg gtatgggcgt 131460
ttgtagtcgt tcctgaatgt tgttaataaa cacgtatgga agatttttgc aaaacgtttt 131520
gaccatcgcg tatttttgta gaatactttt ttcgtcgaag ggaagcacgc cactggtgga 131580
gctcagtaga atgtttttta cgatgctggc cacgtttacc ggcacctgtc taacatctgt 131640
aagcagctga ctgaaattaa aattttcgac gtttaggaag atctgtcgat atttatctct 131700
atccttttta aggcgtgaaa attcttcttc aaacaagggc gattgtatcc cggtgtactt 131760
gaatttgtct tcaagttcct ggtccgacag catgatggtt tcaaaccgta cggtttcaag 131820
ctggcgcgca tcaaggccgt cctctccgta caactgctgc acaagacgcg tatcgatgga 131880
aacccgtcgg taataatcca caatacagga ttgaaggcca aagatggctt tacggttggc 131940
atagcctgtg gatgatgtcg ataatgcttt gttgatcaag tcgaatcttc cattcatttc 132000
cccaaagata aattcagggg aggtaaggcc cgcaatatag ctgttgcaga tgaacccgta 132060
ggcctgcgcc tccagggcaa acctggggta gtacaccagg gtcctaccga aggaaaactg 132120
gggttgaatg cgttgtgtat taatttcaat ttggccgatg cccgccatga tgtgaatcat 132180
attggggttt gagcccttgg cgccagtggc caccatctga aaaagcccat tggtttccgg 132240
attaatggaa ttcataatcg gctttaaaat tctatcggga aatttaagcg cattcagctg 132300
caatttttcg tagaagtcat gcgttgtcag gcctataggc ggcatgatgt ctccatgaag 132360
cagccggttg tttatttcct ccgactcaag cagcagttca ttgataattt cttggacctc 132420
ctgatgtgcc tccggggtta ggagcatgtc ggccgtggac actgtgaatc cggcgttgcg 132480
cacgtagttt agggcgagct gctgggtcgc aaatatcatt ttcaaggcct gctgcggccc 132540
atacctacgc gaaataaggt gatagattcc accggaggaa cccgctccga cggccttttt 132600
gtcaaggacg ccttcaatga gttcgccgtt gcgtatttgt gtagagatgt cctgcttgtt 132660
ataatgcatg tagggtgcat acacttctga gtaccatgtg ggggctcgtt gataattgat 132720
gggggtctgc ctcagtagca tagatacaac cgatttgcca tccagcaggt cagttgggga 132780
gtagttggca aaacaaggtg ggtcggtttg ggttgtttga aacaacccca tggcgtgcag 132840
cttgttcatc acatttttcc ccatgggggt gttcgtgcgt gtaagcaaaa agcttcccac 132900
cgtggagtcc tgcacctgcc cattaacggg acccgagctc tttgtggaaa tgaaccagtt 132960
tcgcacagaa caaagtagtt cggcctcaac gcggctcatg acgctccagg gaacccagag 133020
attcatctga tccccgtcaa agtccgcatt ataccaggca catgcgctga cattcatttg 133080
aaacgtagaa atttttgggt tttcaagaac gacaatccgg tgaaccccta tgctgcttcg 133140
ttcgagagaa ggctggcgat taaaaaaacgc gacgtcgcca gtgacgacgt cacggtaaag 133200
gatgtctcct acctccagcc taaagtcttg tttgagaccc tcaatgtcgt gaacggattg 133260
tgttatttgc ttatacactc ttgaacaacc agggtactgg cgctttccat ttaaaaaata 133320

-continued

```
gggcattaat ctattaatat tataatgttg cactgtttcc gcaacttgca gcgttcgtgc 133380
aaaggaaatg ggatagccaa cctcgtccag gtgaaggtct gagttcccgc agatggtgga 133440
ccggctgatc gaccatacct ggctgcccag tagggattta cgaattcttc cctccttgcg 133500
aggaagtctt cgcatgatgg agggagcagg gcgtgccccc atgacgatcc cacgctttcc 133560
cgtgcctccc tgggttgcgg tggtggaaac ggaatccaac aaaaagttat agtaaagttg 133620
ctgtatggtt tgcaaattgc ggtcaatatt taaaggtatt ttttggccgc gcacgatttg 133680
taggtccttc gggatcagca gattctttcg aaccagatac tgaatcacgt tgttaatgtc 133740
gtgaaagctt tgggggcctg acccgattcc caatctgatg ccaggtcgta tgctgatggg 133800
ggggatctga atggccttaa gcacaagttt ttcgggatgg gagtttttac ttcgccccag 133860
ttttacaacg gtgtcgtagg ttacgcgcga aaaaatctct ctgatgatct gcgggtacag 133920
tttgtcaatc ttgccctgct gatccgccca aaaggtaaaa taatcttccg agtccttaac 133980
aattttgggg tgtactgcct tacagacgta gcactgcttt ccttcggttt ggcttgaagc 134040
cgcttcaata agacgcttag gcctaataag gtgctcgtac ctctttaggt caacgatggg 134100
agccccgcag ttgagacata taacccttaa ccatcgtcgt atttcggcga tgaagagcgg 134160
ctgaagcacc ggagcatgca tctgcagtat cccagggtgt cccatacatt gcttgcgctg 134220
gtgtgagcaa gtgatgcatt tataatggtg atcggtggtt cccattcgcg catcatagat 134280
accccccttcg gcgggaaggg tgccctcaaa taaattagaa atggtaacct ccataacgcc 134340
ttgcctctta tgatcattgt caccggcaat attgaactga acggcggcta tttcggcata 134400
tccagcctcc atatttttgc taaatacata ataaaacttc aaatgttaaa aaaaaataac 134460
atcggttggc atattttttt gttaaaacca agtgttaaat gatttctaaa acatttatcg 134520
gttcacgaaa acctaccgca cggccctgaa gaggaatgcc agttttgggg gaaagctcgg 134580
catattccac ggtaagctct tttccataaa gatgtttttt aaataaggcg ggcgtgagtt 134640
tttgaaaaag agcataacga tccgcgtacg tcaaatgctt aggagtgact acaaaccgct 134700
ttttgtttgg caattcgcaa acccataaaa tggcgcctaa gtcctttccc ttttttccct 134760
gagtatagtc cactaaaata aattcagcgt ctagcagcgg tttcagcttg gcaagatgcg 134820
ctgagtggta gttgttgtat cccggctcat agggcccatt ggcattgcgt acgatggctc 134880
cctcgtagcc ctccttaata aactgcgcct taagcctaag ggcctcatcc acattcttca 134940
cgctaaaatt ttcaacttgg tggataaagg taagatcttc cttctgttta aaaatatttg 135000
ttaatagctg ttgtctcttg ttggaaggca tttgaagctg atcactccaa aaacagtcaa 135060
acacgtaaaa gtgcagctcg gaggaatctg tcttcgcatt cgcctgcccc gcgatccatt 135120
gcagaggttt gcggtgtaaa taaagctcac catccaaata tactctcacg tctataaata 135180
aataaagctg tttgagctct tttttaatat tgtcaagacc taaaaattcc tttttcgtgc 135240
gcgaatacaa gagaatgcta ccatcgccct gctggcaggc cacagctcga acgccattac 135300
gcttgcgctg cacgatggga tctgtttctt cttcaaaaaa tgtcttagga attatattaa 135360
aatattttac cagcataggg gggataattc ctctatttgt gtgggctccc cgcttttgtc 135420
tggcatggcg attatattta ctaagggcgt ccttgaatgc ctgatggact accgttgtgg 135480
catttttttt acccaagttt tttccctcgg taacacgtgt catttttgat atccgcaccg 135540
ccccttcttc cacaaaaaat tttgtgaaaa tttcagcaac ggcgtctttt acatctgtgg 135600
aaaacatctc atctgtgatg ggaatgatcg tgttgtgctg caccacttgc acacaaataa 135660
```

tccatgaggc ctttttccg cttttcgttt cagactcaat cggaggaaaa caaaaaatgt 135720
tgtttgaata ttgcccagga aattgattta gcatggtttt aacaataaaa taagcctatc 135780
aatttttta taatttgaat agttattcca aattcaatat ggcttcttta gataatttag 135840
tggcacgata tcagaggtgc tttaatgacc agtctcttaa aaatagtact attgaacttg 135900
aaatacgttt tcaacagata aattttttat tattcaaaac cgtatatgag gcacttgtgg 135960
cacaagagat ccctagcacc atctcccaca gcatccgctg catcaaaaaa gttcaccatg 136020
aaaaccactg ccgggaaaaa attttgccgt cggaaaatct ttacttcaaa aaacagcctc 136080
tcatgttttt taagttttca gagcctgcat ctctgggctg taaggtctcg ctggccatcg 136140
agcagcccat tcgtaaattt atcttggact cctccattct cgttcggctc aaaaatcgta 136200
cgacctttcg ggtatctgaa ctttggaaaa tagagcttac cattgtaaag cagctgatgg 136260
gaagcgaggt ctctgcaaaa cttgccgctt tcaaaacgct tctgtttgac accccagagc 136320
aacaaacgac aaaaaatatg atgacgttaa taaacccaga tgacgaatat ctttacgaaa 136380
tagaaataga gtatacagga aagcccgaat ccctaacggc ggcagatgtt ataaaaatta 136440
aaaacacggt gttgacactt atttctccaa accatttaat gctaacagcc taccaccagg 136500
ccattgaatt cattgcctcc catatactgt cctcagaaat ccttcttgct cgtattaaga 136560
gcgggaagtg gggcttaaa cgcctcctcc cccaggtgaa atccatgacc aaagcggatt 136620
acatgaaatt ttatccgccc gttggctact atgtaacgga caaagcagat ggaattagag 136680
gcatcgccgt cattcaggac acgcaaattt atgtggttgc agaccagtta tacagcctag 136740
gtaccaccgg cattgaaccc cttaaaccaa ccattttgga cggtgaattt atgcctgaaa 136800
aaaaagaatt ttatgggttt gacgtcatca tgtatgaggg caatctattg acgcaacagg 136860
ggtttgaaac aagaattgag tctttaagca agggcattaa agtcttacaa gcgtttaaca 136920
taaaagcaga aatgaagccc tttatttcgc taacaagtgc agatcccaac gtgctcctca 136980
aaaactttga aagcattttt aagaaaaaaa ctcgcccata ttctattgat ggcatcattt 137040
tagtagaacc tggcaattct tatctaaata caaacacctt taagtggaag cccacctggg 137100
ataacacatt agacttttg gtgcgaaaat gtccggagag tttaaacgta ccagagtacg 137160
cgcccaaaaa agggttttcc ctgcatctac tatttgtagg catctccgga gagcttttta 137220
aaaaattagc gctaaattgg tgtccaggat atacgaaact attccccgtt acacagcgca 137280
accaaaacta ctttccagta cagttccagc catcggattt tccattggca tttctttatt 137340
accacccaga tacctcgtca ttttctaata tagatggaaa ggtccttgaa atgcgttgtc 137400
ttaagagaga aatcaatcac gtcagctggg aaattgtaaa aatccgggag gataggcagc 137460
aggatcttaa aaccggcggg tattttggca atgatttcaa aacagccgaa ctcacatggc 137520
ttaactatat ggatcccttt tcctttgagg agctggcaaa gggcccttct ggaatgtact 137580
tcgccggtgc caaaaccggc atataccgcg ctcaaacagc acttatttcc tttattaaac 137640
aagaaatcat ccaaaaaata agtcaccaat cctgggttat cgatcttgga atagaaaaag 137700
ggcaggacct aggacgttac ctggacgcag ggataaggca tcttgttggg atcgataagg 137760
atcaaaccgc gcttgcggag cttgtttatc gaaaattttc gcatgctacg acccgacagc 137820
acaagcacgc taccaacatt tacgtgttgc atcaagacct cgcagagcct gcgaaagaaa 137880
tcagcgaaaa ggtacaccaa atttacgggt ttcccaagga gggagcttct tccattgtta 137940
gcaacctgtt tattcactat cttatgaaaa acacgcagca ggtggaaaac ctggccgttc 138000
tgtgccataa gcttcttcag ccggggggaa tggtgtggtt taccaccatg ttgggagaac 138060
aggtcttaga attacttcat gaaaatagaa tagagctcaa tgaagtatgg gaggctcgtg 138120
aaaacgaagt ggtcaaattt gctattaaac gtctctttaa agaggatata ttacaggaaa 138180
ctgggcaaga aattggagtc ctgttaccct tcagcaatgg cgacttctac aatgaatatc 138240
ttgtgaacac agcgttttta attaaaatat ttaaacatca cggcttttcc ctagttcaaa 138300
agcagtcctt taaggactgg attccagaat ttcaaaactt tagtaaaagt ttgtataaaa 138360
ttcttacaga agccgataaa acttggacaa gcctttttgg gtttatttgt ctgcgcaaaa 138420
attaaatatt ttttcataag aagtactacc caggttttaa agaaatagct aaaaatatca 138480
tatggatact gccatgcagc ttaaaacgtc tattggttta attacatgtc gtatgaacac 138540
ccaaaataac caaatagaaa ctattctggt tcaaaaacgt tacagccttg ctttttcaga 138600
atttattcat tgtcattact ctataaatgc taatcaaggt catctgatta aaatgtttaa 138660
taacatgaca attaatgaac gactgcttgt caaaacactg gattttgacc gcatgtggta 138720
tcatatttgg attgaaactc cagtctacga actataccac aaaaaatacc aaaaatttag 138780
gaaaaattgg cttctcccgg ataatgggaa aaagcttatt tcattaatca accaagcaaa 138840
gggctcagga acacttctat gggaaatccc taagggtaag ccgaaggaag acgagtcgga 138900
ccttacctgt gccatacggg agtttgaaga agaaaccggg attacccgcg aatattacca 138960
gattctccca gagtttaaaa aatctatgtc atactttgac ggtaaaacag aatataagca 139020
tatctacttc cttgcaatgt tatgtaagtc gttggaggaa cccaatatga atctttcttt 139080
acaatacgaa aaccgaattg ccgaaatttc taaaatttct tggcaaaata tggaggctgt 139140
acgttttatt agcaaacgcc agtcattaaa cctggagcct atcatcgggc ctgcatttaa 139200
ttttattaaa aactatttac gatacaagca ctaggatgcc gcattaaaat gccacataag 139260
gtaatacact aggaatgtcg cacacgcaca agaatacaac gtcgccggag atttattatc 139320
tagtacacgt tttatgtatg tacaatccgc cttcatttaa tatattgagc ggatgtacta 139380
tgtatttatt ttaacaaaaa acattatttt tttttaatct tcatcatctg tttttataaa 139440
ctcagtaata tcaaaagtag cttgtggggt ttcagagggt tcaccttggt tatcctccgt 139500
gaggataaca tgttcttcag gttcgtcgtc actggagaac ccatcattta attcctcttc 139560
actcaacatc tgtaaaaaat cttccaagct ttcgctatcg ttaaaatcct catcatccat 139620
aagaataatg gtaccttcct catcgtttcc tccttgtttc gtgtctaaat aggcctgcat 139680
ggcatttgca aaagtatcaa aataggctga gtcagattgc tgttccaaaa tatggccttg 139740
cgtattaaat gtggttgcat cgttgttaaa tgcttgcaaa tacagtaagg gatttatatc 139800
cattattatt aagcaaaaaa aatttaaatt atttttcgac cgatgttagg taaaattaaa 139860
caattgctat aggtgttaag caatgtttat tgattttaag tactcaacaa ccatgatgta 139920
aatactatac agcacttttg gatttttaat caaatccaga ttaatactaa cttcttttgt 139980
gatacagttc gtaataatag tatcctgctc atcgttttgt aagatttctt ttaatatatt 140040
tttttttacc gggatactaa gcaattgatt attttctttt aaaaactcct tttgatattc 140100
aatcgtctta ttcattgaat atttgtatat aactataatt acaaatgttc aatgaattgt 140160
tattcatgtc gggagatggc tatttaaaaa tcatgtccta tttttctttg ctcaataagc 140220
atccaaatat tttcatggcg ttttattaat tgttcattat tgaacgtatc acaaagatca 140280
tttataaatt gcagatagtt tattatttct ttcaagagag taacaaacat tacttcagca 140340
gaacatataa taggtaattc agtggcgtta aaagaatttt gatcttgttg atacgccaat 140400
ggcgaggact taaggagatt tgggggtctt gcccaaaacc ctaggctgct gttcttgttt 140460
tttagggcgt cataaagaaa tgaaagcaca ttgcaaggct taagccgcga catctccttc 140520
cccttgggcc ctttccatat ttttagatct aagatctcat ccgagcttat agagtaggta 140580
tagtaaagtt tttcaaaaaa gcatatctgc ttgaagtctt ttttagaacg actttcaaga 140640
agcatttcta taatgttaac aagttttgtt aggtttaagg cctgttcctg tgtaagctcc 140700
tcttgcacgt gatagactga aaaagtgtgc ttaggaatga aaatactccc cgtggcactg 140760
gcctgttgtc tgccaggtat atagtacacg ctgctgttag caagctgtac cggcacaatt 140820
tgccccactt ctgcaacatt attttgcgat tcggacgagg gtatgacaat agttacgggt 140880
tcagtcaata ggctttcgcc gagaataata ttactgtcat ttttaataat tttaacggcc 140940
gctattaaat caaaggcatt taagtaagaa acaacagcag aaaatcttac atgcatatat 141000
cctcttccgc tattattcgt acgcataata aaacaagggg agcgttgtat aacgccagta 141060
atattaagaa taaaactgtt tttgaaacac ttacccacat aaatgttttc aagctccttc 141120
aaaagatgag cctccacatt tgtacaaaaa ttggtaggat catcaatatt caacgttgtc 141180
tcaaaaattt tttggtcgat catatctata atatattctg tctatttcaa tttaaataat 141240
atacgaataa ataacgagat tattttatta aataagcaat ggtgtataca ctttgtattt 141300
actttgagat atactttgtg tatcacaacg tgccctaaga tgtgtgcaca agtgacggca 141360
ttttgtcgtt aaaaaggtaa aaccagcgga ttccatcctg cattccattt ggttgattac 141420
gagcctccat ttctttttgc aaaaggttat tgcgaatgag taagcagagc ttgatggcac 141480
taatctttgt aaggtttaaa cttatgccca attggtcagc aatttttttgt tgctcctccc 141540
gtccgcgtgt ttcgcatacg gctccccggt ttagcatgcg aatatcagta atctcattct 141600
tttttaaaac ctggataggt gggcggattt taaatttaag ggcctttccc ttgctttcca 141660
tatagcctat gacgatgtcg ttttcttttc gtttaacatt aatattaagc atataaagcg 141720
gaatttcatg ccaggtttta tcttctcgcg aggtaataag tcgcacggag tcctccgtgg 141780
catagcccac tagagtgttg tcatccccag gcacgtggct tataatttta aaaatgtccg 141840
gaaatggctg aatatctttt tttgaaaaag cgatgaaaaa ctttttataa acctcgacaa 141900
gggcccccat acctgcaaga ttatctataa taagtgcttc tagcatcgta tagtgaaatg 141960
aagcggggta gtggatgagt acctgctcca ttggctcatc ctgaaaatcc ttctgaaact 142020
tttcatacaa tacttgaaag ggttctttgg tctgcgagtg ttcgaggtat ttggtaatac 142080
ggatgctgtg catcgcggga ggctgaaaat cccgaatata tgtttcaata tctaataccg 142140
gttccttttt atggttaagc accgcagcga cgtacaaatg ctcaggcttt gccggcacat 142200
gcataatggt gcaaagacga ttctgtatcc ataattcctt gcactggttt tttgagtagc 142260
atagagaaat gagcgccagc gcgaagttgt cctctgagaa gagtttatta tcgatggtaa 142320
ttccctgtat gagcttggga gtggaaacag ccttccatag ctcggagtac gtccacacgg 142380
ggcgtgccat aaacaaagat ataataatat tagaaattgt ttttacctct tgctccccgt 142440
atccataggc ctcaaaggta ttgaggacgg tggctccgac gtttgccggc gtgatggatg 142500
gactaagggg cagactttcc aacataggct tatcaatctt aatctggttg gtgaacccat 142560
caatggcgtg ctttcgcagc gccttatccc cctcctgtat taaaatgtat tcttttaatt 142620
tttgtgcgta cttagcgagc tctggccctc catcgggtgt tgtcgatacg tacaaataaa 142680
ttgtcacgtt gcgctcactg ggggggagct ccatgtgtga attttttcgc accaccctcc 142740
caaatacctg aataagccgg ggaatatcaa ggggcaatga cataatcatc tcgtaccgca 142800
cggcctgaaa gttcaaaccc tccacaatca ccttggaccc gatgagaata cgcagctggt 142860
ggccttccag gttggacgag gcgttaaaaa gagccaggct tcgttcgcgt acagcgggct 142920
ctatttcgct gtgcagaatg gtgaaccgta ctggaataaa ctgatggtcg ctatgtgtgt 142980
gctcatcgcg aatcgcggcg cagatggagc agcgggtcgt tcccacaggg gacgaaactt 143040
catttaaaat gccattactt tgtaaaattt cttgcaagat aagaaccccc gacatgcgga 143100
cccgattgtg gtaaattaaa attttccccc ggccttgccg aataatggaa agaatgtctt 143160
tcatcatttg agtgtatttt ccgctataaa aggccaatcc cgagatgtgc gttggtggct 143220
gcagcgacaa aaagctgcca ctcacattaa agggggctct acgcgaaggc tcaataatct 143280
gtaccccgtt ttccagaagc cagtctgtgc ttgccataga aagggcggtg ggggtttccg 143340
tcgagttaaa caggccgtaa gccttgggtt ccgtttgttt tgaaaatttt gggttgggaa 143400
acaccatgtc ataaatgctg tacgcattac tcgagatttt agggtcaggg cccagctgtt 143460
taagcgtttc aagctgatac tcagacatgg ggcattcgat gaaatgtaag tacggcaatg 143520
tttcgtcttt ataggacaac atctttccgg caaatattct ttcggggtaa aaattggtgt 143580
tggtatccaa caaaaaagat acccttccgg tgctcagtct ttccacaaga gctagggcgt 143640 ccttttttcca tttaacggaa tgcccactgc tgtcaaacag ttgctggcgc tggaggggct 143700
ggccgttggg cagctcatgc cgcggaacca aaaggtttaa caggtcgacg tattccatga 143760
cactcccggt tacgggcgtt gccgacatga agacggccct gggggcctgg tgaggtggaa 143820
aggcatccag gacatactgt aaagcgatgc cataattatt tcgttcctgg atattgtaca 143880
cgttgtgtat ttcatccgca atgagcagtc ctcccctaag ttgctccatg atttttttgat 143940 tcacccggat gaggccgttt gtctcggcct cgctaatttt ttgcacgaac tgagatatat 144000
cgttctcatt caatgtatct tctgcttcgt cagaacgatg aaacagagaa agcacatcaa 144060
agtttttctc ttcaccctta ctcgtaatat tgaaaagctt ggatgcaaat tccttatagc 144120
cgtaaaactg aaaaaagcct ccgcggtttc tatcggttaa acggcgcttt aacgtactaa 144180
cgaacccatt tagatgccgt gattcgaccg acgtggtgct gccagactgc tttgcaatgt 144240
gaagaagccg gtgtagctca gcgacctcct tgtaagaaac aaatcccagc tcaggacgtc 144300
ttagcatttc tgtttgaatg atggcgcgtg taaagcctac cacaaaaatc cagggcgcat 144360
tttcaataaa attcatgtag tggttcataa attgacgcgc gatggcaatc gcggcaatgc 144420
tttttcccgt cccggtctgc cagtttaata aaagacgcga gtagggcgtg ttgggatttt 144480
gaaagttttg gacgaaaagc tggcattat gcaattggag acccttgatg gaaggaaagg 144540
gcgacgcgta ggggtcacac ggaaaaaacg ctcgcccccc cttctcgcag ccaggcccac 144600
cgatctggac aaaatgagcc cgcagatcac gaatgagctc tttttggtcg acaggagggg 144660
aaatcaacga tttaaactcc tttcttcgcg ccaactgctg caaaaagtct gcggcatcca 144720
attcgggata cgccatatta tcataaaaaa aataaacctt tttatgaaaa cttttatgtg 144780
attctgtatt gcaattgttt tttatgaata ctgtaaataa gcgtatcaac ttgtttttct 144840
aacgaagagg cgttattctt tttttctgga tataaaataa taataagtat aataattaag 144900
actaaacagc aggcaatcac tatcaaactc atattatact tacttttttta taaaaagtat 144960 tatatcttat gaatgcgcaa gttcagctaa ttgttcgtcg cttggaatgt gggactgcag 145020
ggaggtggag tttttccttt ttctaaagaa taccgggaaa tggtggtgag gctcaggttg 145080
ttgtacatag tagctaggag gaggtttagg tatgctcgac ttgcagtcaa tagtccggtt 145140
atagtaaacg atggcaacga tgataagaat aataatgagc aaaatcaaaa tgcccaggag 145200
aatcgcagtt gttccgggat atttggcgat tgtatgggct aaaaggcctt gggtgctttg 145260
tttaattccc tcgcgggttg acaggttatg agaaagcagt ggagacgttt cagtgtccat 145320
ttattacaat tgaacagtta tattaatctc aaataaaata taacacaaaa ttaattatgg 145380
ccatgcaaaa gttatttacg tatatttacg agtttattga atatcgtaag atggtgctgt 145440
tggaagaaaa ggtaccatat gataagtttg ttcaaatggt acttaataca ggattttttc 145500
gtattaacgc ggagacgctg aatcacggaa tcgtatccgt gtttatcttt ggagcaaatg 145560
gcaagtacgt tcaccacgga ggcgacatga gaacgctttt aacgaatacg cttaatgaaa 145620
aaaaacatta tgaagaatta attttaatcg ttgataagcc cgttttaagc aaaaaaaata 145680
ttttagatat aatcgtcgag cagcgcgctg caaatcccac gattgtaata aacatatatc 145740
cctaccacct gttctgcatt aacattccca aggtgagtgc cattcctaaa cataaactaa 145800
ttactcagga ggaggcgcag gagtttttag gtcgcgaata tctgcaaccg caggacctca 145860
tgcaaattag cgcgtcagac cccccggtgg tctggctggg aggaagaccg ggagactttg 145920
tgcaaattga gcggccctca gagacagcta tgcacgctgt tgttatccgc tttatcacca 145980
agtccaaaat ttgagtcccg tgtttaaaga tgacagacag ctaagtaagc atatctgtaa 146040
aattgtcgat gtcctctgtg gatagagcgc tttcctctga gcagcaaatt ttttcataca 146100
tctccatggg ggatggcgag gctttaatag tatgtaggtc acgtaagaac tgttgtatga 146160
tgggatattt gtcttttaaa aactggggat gtttcataac tggaattatt tgaaagataa 146220
agaccttcca tccaaagtag ccaaccacat ttggcatttc gggacacgcg gtttcataag 146280
gcatagaata gtgaatagtg tactgatctt tttgatacag cgtttcaagt agttggcgaa 146340
atgtttccgc gtcgagcgtg ccaaaatctt gaggagcctc ggtgtgctcc tgtgtagagc 146400
agatcgtgat gattccccag gcaagcggga gcatggactc tggagggtgg atatccgtat 146460
tggtctcatt attcgatccc agctgatgaa tgccgcacac gcgaaacatg gcctcgacgt 146520
agatgcccat agagataggc ggcgaaaggg caagaccgga ttgtatttgc ggcatatagt 146580
aggagggcac cgagtttttt atttttcggt tgaatgggga ctttatttct accagcacgg 146640
ggatgcgttt cgtggcctca tagcgtacgt tgttaaaaat tgttttgatt tcccaggact 146700
gttgagtgta tcccagcgtt aggtgacaaa acccatcggg gctattacta tgtccggggt 146760
atcccaaata ggtcccatca atatgaatat tgtcacctat gacggtggtt tggcagaaca 146820
actcaagcag atctttacta acacgctcaa aaagggttcc ccagctacaa gcagcgcggt 146880
tcaaattctt cttaaaaaga tttgcttttt ccgccaaggt tatataatag cttttgtaag 146940
ggtttaaacc taaaacgctg gcaaggtcag agccacccac ctgagtgcga cgaatagcat 147000
gccaggcatc ggagcgctgc tgaggagagt ctttaaacag gcgtacaaag gtttccatta 147060
tacttgtttt aacaggaatt caatataaaa agtcaacaca gtttgcaatt tttccaatct 147120
caagatatag ccatacattt ttttttccaa ttggcgaata tgtttaagct catgtgtttc 147180
aatattagca tccggaaatt taaatgcata aagatgttca aaggcctgat ttatacacgt 147240
atcaaaggat ctgtggtatg ttattagctt cagcatgtgt gccagatctt caagatggtc 147300
taaatttata cggttttcca cgtggtggat catgtctgcc acatcttgag cccccatcca 147360
ggggatcaca aggtactccc ccttaaagat gattcgtcgt ttttttaaaa aatcatgaaa 147420
acgttttaaa gcttcaagaa aggggcagtt gggctttgac cccaaaatgc tgacgacgat 147480
atcctcgggc atgatgtatt cgcagtgagg atagtagttt acggactcta attcagcggc 147540
ccgccgtttt atttcgtatc ttgcccagtt attcagagag tactccacgc ctccgaccac 147600
aacagacatc ctatctatta aaaaataaca ataaaaacct tatgaaatct atgtatagtg 147660
gccgctaaaa tgtctatatt agaaaaaatt acgtcaagtc cctctgaatg cgcagagcat 147720
cttacaaaca aagatagctg tttaagtaaa aaaatacaaa aagagctcac ctcttttttg 147780
gaaaaaaaag agacactcgg ttgcgattcg gagtcctgcg taattaccca ccccgccgtg 147840
aaggcctatg cgcaacaaaa gggactggac ctctccaaag aactggagac tcggtttaaa 147900
gcgccaggac ccagaaacaa cacgggtctt cttacaaact tcaatattga tgaaacgctg 147960
cagaggtggg ccataaaata caccaagttt ttcaactgtc ctttttccat gatggacttt 148020
gagagggtcc attataaatt taatcaagtg gatatggtaa aggtatataa gggagaagag 148080
ctacaatatg tagaaggcaa agtggtcaag cgtccttgta acaccttcgg atgcgtttta 148140
aacacggact tttcaacggg cactggaaaa cactgggtag ccatctttgt ggatatgcgg 148200
ggcgactgct ggagcatcga atattttaat tcgacgggaa attctcctcc aggtcccgtt 148260
attcgttgga tggaacgggt caaacagcag ctattaaaaa tacaccacac cgtgaaaacg 148320
cttgcagtta ccaacattcg tcaccaacgg tcgcagaccg agtgcggccc ctacagcctg 148380
ttttacatca gggcacgcct cgacaacgtg tcatacgccc atttatatc cgctaggatt 148440
accgacgaag acatgtataa gtttagaacc catctgtttc gcatcgcata aactaataaa 148500
gtttgaattc tttataggaa taaaaatgga agcgtttgaa atcagcgatt tcaaagagca 148560
tgcgaagaaa aaaagcatgt gggctggcgc cctcaacaaa gtcactattt cgggtcttat 148620
gggggtcttt accgaagatg aggaccttat ggcgttaccc attcacagag accactgccc 148680
cgctttgtta aaaatttttg acgagatcat cgtaaatgcc acggatcatg aaagagcttg 148740
ccataacaaa acaaaaaagg taacttacat taaaatttcg tttgataaag gtgtgttttc 148800
ttgcgaaaac gatggcccgg gaatccccat tgcaaagcat gagcaagcca gtcttatcgc 148860
caagcgcgat gtgtatgttc ccgaggtggc ttcatgtcac tttttagccg gaacgaacat 148920
caataaggcc aaggactgta tcaagggggg aaccaacggc gtcgggctga agctcgccat 148980
ggtgcattcg cagtgggcca ttcttaccac cgccgacggc gcgcaaaagt atgttcaaca 149040
tatcaaccaa cgcctagata tcattgagcc tcctaccatt acaccctcca gggaaatgtt 149100
tacacgtatc gagctcatgc ccgtatacca ggaactaggg tacgcggagc ctctgtctga 149160
aacagagcag gcggatcttt ccgcctggat ttaccttcgc gcctgccaat gcgcggccta 149220
cgtgggaaaa ggcaccacca tttattacaa tgataagcct tgccgcacgg gctctgtgat 149280
ggcgctagcc aaaatgtaca ccctgttgag cgcgcctaat agcacgatac atacggcgac 149340
cattaaggcc gacgcaaagc cctatagcct gcacccccctg caggttgcgg cggtcgtgtc 149400
ccccaagttt aaaaaatttg aacacgtgtc cgttatcaac ggggtaaatt gcgtaaaagg 149460
agaacatgtc accttttga aaaagactat taatgaaatg gtcgttaaaa aatttcaaca 149520
aacgattaaa gataaaaacc gcaaaacaac attacgagac agctgttcaa acatctttat 149580
cgttatagtg ggttccattc caggaataga atggaccggc cagcggaagg atgaacttag 149640
catcgcggaa aatgttttta aaacgcatta ctccattcct tctagttttt taacaagtat 149700
gacaaagtct atcgtggata ttcttctgca atccatttct aaaaaagata accataaaca 149760
ggtcgacgta gacaaatata cgcgtgcccg caatgcggga ggaaaaaggg cgcaggactg 149820
catgctactc gcggcggaag gggatagcgc actttccctg ctgcgcacgg gactaaccct 149880
gggaaagtcc aacccaagcg ggccctcctt tgacttctgc ggcatgatct ccctgggagg 149940
agtcatcatg aatgcctgca aaaaggtgac aaacattaca acggactctg gagaaaccat 150000
tatggtgcgc aacgaacagc ttaccaataa taaagtgttg cagggaatcg tgcaggtatt 150060
gggtctagac ttcaactgcc attacaaaac acaggaagag cgagcaaagc tgagatacgg 150120
ctgcattgtt gcgtgcgttg atcaagatct ggatgggtgt ggaaaaatcc ttggactgct 150180
gctggcctac tttcacctgt tttggcctca gcttattatc catggtttcg taaaacgact 150240
gcttaccccg ctgatacgtg tgtatgaaaa gggtaagacc atgcccgtgg aattttacta 150300
tgaacaagag tttgatgcct gggcaaaaaa gcagaccagc ttagccaacc ataccgtaaa 150360
atattacaag ggattggcgg cgcatgacac ccatgaagta aaaagcatgt tcaaacattt 150420
tgacaacatg gtgtacacgt ttaccctgga tgactcagca aaggagttgt ttcatattta 150480
ttttggcggg gagtcggagt tgcgaaaaag agagctttgc accggcgtgg tgccgctcac 150540
cgaaacccag acgcagtcca ttcatagtgt ccgacgaatt ccttgcagcc tgcatctgca 150600
agtagatacc aaggcttaca agctggatgc catcgagcgg cagattccca acttcttaga 150660
cgggatgacg cgggcgcggc gcaaaatttt agccgggggg gtgaaatgct tcgcctccaa 150720
caaccgtgaa cgaaaggttt ttcagttcgg gggctacgtt gcagatcaca tgttttatca 150780
ccatggcgac atgtcgttaa acacaagtat tataaaagcc gcccagtatt acccaggctc 150840
ctcccacctc tatccggtat tcataggcat aggaagtttt ggctccaggc acctgggagg 150900
aaaggatgca ggatccccaa gatacatcag tgtgcagctt gcgtctgaat ttattaaaac 150960
aatgttcccc gcggaggact catggcttct cccctacgtc tttgaggacg gccagcgggc 151020
ggaaccagag tactacgtgc ctgtgttgcc gcttgctatt atggagtacg gcgccaaccc 151080
atcggagggc tggaagtaca ccacttgggc ccggcaactg gaagacattt tggccttggt 151140
gagggcctac gtcgacaaag acaacccaaa acacgagcta ctgcactatg caataaaaca 151200
taagattact atactcccgc tgcggccctc caattacaat ttcaagggcc atttgaagcg 151260
gtttggccaa tactactaca gctacggcac gtacgtcatc tcagagcagc gaaatataat 151320
tactattacg gagcttcctc tgcgtgttcc tacggttgca tacatcgaaa gtataaaaaa 151380
atcgagtaac cgcatgacat ttattgaaga aatcatcgac tacagtagtt cagaaactat 151440
tgaaattctg gtgaaattaa agccaaatag tcttaaccgt atcgtggaag aatttaagga 151500
gactgaagag caagattcca tagaaaattt tctgcgcctg cgcaattgtt tacattcaca 151560
tctaaacttt gtaaaaccta aaggtggcat tatcgagttt aacacgtatt atgaaatttt 151620
gtatgcgtgg ctaccttaca ggcgtgagct ttaccaaaag cgtcttatgc gtgagcacgc 151680
ggtgcttaag ctgcgcatta tcatggaaac tgctattgta cgctacatca atgagtctgc 151740
agagctaaat ctttcccatt atgaggatga aaaggaggca agccgcattc taagcgagca 151800
tggatttccc ccgctgaacc acacgctgat catttcccct gagtttgcct ctatagagga 151860
actcaatcaa aaagcactgc agggctgtta tacctatata ctatctttgc aggctcgaga 151920
attgcttatc gcagccaaaa ctcgtcgggt ggaaaaaata aaaaaaatgc aagctcgtct 151980
tgataaggtt gagcagcttt tgcaagagtc tccctttccc ggcgccagcg tatggctgga 152040
ggaaattgat gcggtggaaa aggctattat aaaaggaaga aatactcagt ggaaatttca 152100
ttaaacgcta ccggttttat gatgtccaat aggtgttaag caatcagttc atcaacattt 152160
ttttcaagaa tttgaaaagt ttggataatg ttctgaatac ttttttctaa aagagttatc 152220
aaatcttctt gtgaggcctt atgaataatt gttaatacca tttcttgctt atggggaaca 152280
cactgatacc ccacaaagct aatatcagga atcatttcat aaatatatgt ttttagcaga 152340
tttccgatgg tatgggtttc atcttttatc gtgataatgg cctttgtttt ttcctcatcc 152400
atggaaaaca gcacaagttc cggctgcggc tcttcaaagt tttcataaat tttttgaatg 152460
ctttggattc ggccaataat gatccggcag gcgtttttta aatacgtgcg aacggcctgg 152520
ttgatatgtg gcagcggcac cgctggaaag caaagcccca ggcggtggtg acgcgggtct 152580
gaggtcatag agctttgctt gtaaccgcta agcgccatat attctttttt atccgttggg 152640
tactgttcaa tgtcaaggtg ggaaaaatgt gttttaacgg caagattaaa ggcggcatgc 152700
tttcgtccta tgcccttttt aatatagata tcctctataa tcaacgattt tccgggttgt 152760
aggaagccaa tctcaaaggt aggattaaaa atcgggtatt taagcttagg gcctgccacc 152820
tggatgagat cgcggctata gatggtttta acctcacagc tattgtttaa actccgcaga 152880
gcaaatacca gtgtctcgtt tttcgcataa atcggaatga aattaatgcg gtttctaata 152940
aattgttccg tcataaacag gtccgtggaa tcctcgatct tatacccacc gggcttaata 153000
tctagcatat aattgggaat ttcatcttgc aagacccgcg acaggccgtg gaccgcggct 153060
ctgctaatgc ccttaaagtc cataacaaca ttgaccggga cgaggggcaa ctgctcctcg 153120
agctgaaata gttttttggc cgcattttta ataaagaggt tggaaaagtc tatcaaaaac 153180
ggtttgattt ccacgttttg gaaaattttt tccatttgta ttataaatat atctatatat 153240
attcaaatta tggtagttta tgacttgctc gtttctttaa gtaaggaatc catagatgtg 153300
ctacggtttg tagaggcaaa ccttgcggcg tttaaccagc agtatatttt tttcaatatc 153360
caaagaaaaa actcgatcac gacacccctt ctcattacgc cgcagcagga aaaaatttcg 153420
caaattgttg agtttttaat ggatgaatat aataagaaca atagaaggcc ctccgggccg 153480
ccgcgtgagc agcccatgca cccattattg ccgtatcaac aatcctcgga cgaacagccc 153540
atgatgccgt atcaacagcc cccggggaat gatgatcagc catatgagca aatataccat 153600
aaaaaacacg cgtcgcagca agtaaatact gaactgaacg attattatca acatattctt 153660
gcattaggcg atgaagacaa aggtatggac agcatgttaa aacttccaga aaaggcaaaa 153720
agggatagcg atgatgagga cgacatgttt tctataaaaa actaacgacg taacaattaa 153780
acaaaaaata aaaatcatta taaaatgaat cttgaatacg tccaagttgt tcaaaaattt 153840
aatcaagtac tcctagaact taccaaaaaa gtatgtaccg ttgtgggcgg gagcaaaccc 153900
acctattggt atcaccacat tagaagggtt tgctcagaat gtccatccat gccgatgagt 153960
atgataggtc cgtatctgaa tgtctataaa gcccaaattc taacaaggga caagaatttt 154020
tttatgaatt tcgatcccgc gcataatgag tacaccttta tcattcaaaa actaaaagaa 154080
gcagcccgaa atatgccgga agacgaatta gaacagtact gggtaaaact tttattttta 154140
cttaaaagct acataaaatg taagcccttt attaattaaa gaattgatgc ataactaata 154200
aatggccggt cgtgttaaaa taaaacagaa agagctcata gactctactg taaaaaacaa 154260
aaatgtgatg aatctgttcc atgaaattat aggctcaaaa ggcaatatta attttagcgt 154320
tgtctggccc aagtttaaaa aaatcaaaca gagcgtttat gactacattt ccactctttc 154380
tgtgctggaa aaagcaaacg ttatgcaaaa ctttgaagct gataagaaac tgttggaact 154440
ttttgtacaa aagctgtggg ctgcctatga aggctatttc aaatatcccg agattgaaaa 154500
atatgaggtg gaaggccagg taaatttcaa tctcgtacct cagtgcgtcc tcgaaaagtt 154560
tagccagttg tataggataa gaatcaattc agagcttgtc acactcatcc taaacagctg 154620
tgcctttatg agtaaatata acgattatat tctcaaaaaa gatccctaca tactaaccat 154680
aacccccggc ctatgctttt cccccattcc caacttcgag gacctaaatt ttaaacatct 154740
ttacaacagt gataaaaatt ctcagcatga caaagagttt atcatgttta tattatataa 154800
gctttatacg gctgccctag gagtgtacaa tgccatctcg attccagaca tcgacgtaga 154860
agaccttgaa aatatcatcc tatcctcggt gagccagatt aaaaaacaaa ttccgcgctg 154920
caaagacgcc ttcaacaaaa ttgaatcttc ggtacacctg ttgcgcaaaa attttaacac 154980
atattacagt gactatgtgg gctcaggcta caacccaacc atcattatgg aacagtacat 155040
taaagacata tcacaggatt ccaagaacat atcaccacgc atttcctacc agtttagaac 155100
catcatcaag tattaccgcg acatgattgc caccaggcat caaacgatgg acccccaggt 155160
attaaacctc gtaaagcacg tcgaaaagaa attagatatg cttgatagag aaaaaaatta 155220
gtatatatag ttatggtgaa tctttttcct gtttttacct taattgtgat tattacaatt 155280
ttaattacga ctcgagaact atccaccacg atgcttattg tttctcttgt aacagattat 155340
attattatta atacacagta tacggaacag cagcatgaaa acaatacatt tttcatgccg 155400
caaaaaaatt cttttaacga atcttataat aaagacaaaa aatctaatat acatattccc 155460
taccagtggc tggcgcctga actgaaggaa gctgagagca agtactggtg gggcaattat 155520
gatcctcata gcgagcccgt tctcgctggc gcatcttgaa tatcttcata cgtggcacgt 155580
caccatcaaa aacattgccc aacagcacgg gcttgatata aaggtggcca ttgtggtctc 155640
aacatcgcat ttaaataatt ttttgccaat ttccggggcg cttaacatcg aatgtataac 155700
cttccccagt tgcggcatca aggagataga cctcctatgg gcgcgcatta aactatttca 155760
acattactgc gccatcggtg cccgtctttt atggctggta agtgctgaca tcaggccccc 155820
tgtttcagcg tggccagcca tcgccgacag tctaaaaaag ggagcagatg cggtcgttat 155880
tccctacccc tcccgatgga acaatcttat acctaccgtc atcaaagaaa tagttgtcca 155940
ccaaaaaaaa tgccttgtgg cggtggatgc acgccacctt gatacagata cccagattgt 156000
aggggccggg atgggctgca tcgtcctaac cctaaaggcc cttatggtgc gcctaagtat 156060
tggcaaacag cccgttaaga tactgtggcc cgaccttcac ggcactgccg agggcattcc 156120
tctggagggg gtggaggttg gctggttttt aaacgcttat gcgcataaat taaatatacg 156180
ctgcctaggg gctgatcata ttgcgcagca cttaacttaa ttctttattt aaaaagtcca 156240
cgcatccagt ggcggcctac attaagggcc tacgcacata aatatacact ggctagaagt 156300
acgccttcat ttaaaccatt gaattattta tataatggct gcaaacatta ttgcaacaag 156360
agccgtgcca aagatggcca gcaaaaaaga gcatcaatac tgtctgctag actcccagga 156420
aaagcgtcat gggcattatc ccttttcatt tgaattaaag ccttatgggc aaacaggcgc 156480
aaatatcata ggagtacagg gctcacttac ccatgttatc aaaatgacag tatttccatt 156540
tatgattcct tttcctttac aaaaaactca tatagatgat tttattggtg gacgcattta 156600
tttatttttt aaggaactgg acatgcaagc agtttctgat gtaaatggaa tgcaatacca 156660
cttcgagttc aaggttgttc ctgtaagccc caaccaagta gagcttcttc ctgtgaataa 156720
taaatataaa tttacatatg ctataccggt agtgcaatac cttaccccaa tcttttatga 156780
tctttcggga ccgctagatt tcccattaga tactctttcg gtccatgtgg atatcctctc 156840
caatcatata cagcttccta tccaaaacca taacctaaca acgggtgatc gtgtttttat 156900
ttctggatat aaacacctgc aaacgattga attatgtaaa aataacaaga tttttatcaa 156960
aaatataccg ccgctttcat ccgaaaaaat aaaactatat atactaaaaa atcgaatcag 157020
aattccgcta tactttaaat ctttaaaaac gtctaagtaa taacattttt atagtctact 157080
cctagttccg aaataggctg aatttctttt ttaagtcctt taaaccaagg atgtgataca 157140
agactcttaa aggaaagccg cttattttca ttaattgtta aacattccgt gataaactgt 157200
tttcccgtct ctgaaatgtt ctcgggaata taattttccc gtttcaggat atcatttaaa 157260
taaaaatttt ctgcacgaaa tctaaaaaga ttaaccgcga ccatacctat cgtccacacg 157320
gttaaaggaa gctggtagta ataaccataa taataaaatt ctggacacac gtattcccat 157380
gttccaaaca tattatattg gggacgggtt tcgtctaatc taacagcgct tccaaagtca 157440
atgaccttaa tgatcttttg atttatgtct ataataaggt tctcatcctt aatatcccca 157500
tggataaagc ccttctcata aatgttttgt ataataagaa taagctggaa tattattttt 157560
ttggcttcgg tttcctcaag ttttttaaag taatgataat gaagtagatc aacactattt 157620
ggaatatatt ctatgattag tatatgatac atagcatttt cggtatattc gataagctta 157680
ataacaccgg gagtatcttg cagggctttc aacacgatga cttcatttcc tggaatttct 157740
tttttagaaa cgtacttaaa tataatgggt tgccctactt gatgacccaa aaagacgtta 157800
tttctgccac cctcaaacat gggtctcgtc gcaatgaaat acatgtgctg cgttgtggag 157860
atcctttcca cctttgctgt aggataaaac gcatattgtg cctggggatt ttttaacatt 157920
tttttaagct gttgttccgg cctggacatg ttttattagc tttatatata aagggttaga 157980
aggtttaatt tcaatatatg ccttaatgat gggattatat tcgtaaaagg tatagcctaa 158040
tcctacgtct ttgttttttt ggtaaaaaaa ctgtttgccc tcgtaggata tgctataggc 158100
ttttacttcg gcttttacaa gcggttggca gggattgggc aaacgtaaat cgcgttcaaa 158160
gttttcatga aaaagcaaag catttgtggg ctgacacatc agacagccgc tttcgccatt 158220
gaaggcacat tcaatggccg cccttttttag taaatcgcgg aaagcagaat taagatggct 158280
cttttcaagc cccctttcgt gaaaacgctc atcaatcgtt ttttgttcct gactgccttc 158340
gggaatacta taaaacattt tttgattagc caccgcgatg tacaaaaaag gctgtacggt 158400
tttctcctcg ggcggtagcg catcgtggct accaatgcgt ataatgcgcg ccttcacttg 158460
atcctctcgg gccttatccc agtacggctc taggatatga acctgccgcc cgtatttgag 158520
atccaatccc tcagctcctg ttttagagac gagtaaaatt ttaataacct ctccgtgtat 158580
attcagcggc gaattccaaa gctgctggat catgtcgcgc tctttagata aaattttccc 158640
tgtaataagc gtaaatcgtg ttattttgga ggacaggact aacgtatggg tcggcccatc 158700
ttccgcaaag tttttcacca taagatcttt cccatcctta tgaaggagga tggtgttgtg 158760
cccttcttcc aatactttta ggggctgaag gcactggtag ccctctattt ctaaaaagcg 158820
ggccacgacg tgaaggccca attccacaaa ctgtgagtaa atgagcacag ggcccggaga 158880
cgttttaata ttttttagca tgcgtactat tttgggacta gaattttctg tgaaggcctc 158940
tttgggcagc tgctgaacag cctctgataa tttttcatcc tcctttactg ttagcatttc 159000
ggacgcgaag atgctgatca tacgggaacg cacatagtag gaggagcctg actcttgctc 159060
cgatcctggc aggcagaggg cggcggcatt tattttttca tacattcctg agctggcgtg 159120
cttttccgcg ttttcaacgt ctcgggccag cagatattgc ctatactgct cgggtgacat 159180
ttcaaccttt tctataataa gaggaagctc tgtggggaat agcttgttga gctcattctg 159240
gtttccagcg tagcttatca tacccactag gcggtttagt agtttgtccg cgtttaaagg 159300
gctattcgtt gttttattga cataagcggt gtagaatctt tcatagtgaa gaggtaataa 159360

-continued gattcgcccg cttagcatat taaaacaggg caccatttca aaggggtcct tcgaacacgg 159420
ggtgcctgtt aaaaacagaa tacgaatatt tttagcttgc ataatattat tgtacagctg 159480
gcgggcattt gttttatcat tggcgctatt gataattcct ctaaagaggt tgtgtgcctc 159540
gtcaacgatg agcaggcatc catttaggga ccctcccgcc tttatgatct gctgccccat 159600
gttgtaagcg tctagggaca caaacctgaa gcgccgcgag attttttgta gctctttgga 159660
gtgatccgtc gtttccggat ataaaagttt aataagcttt aacaaagact gttggaagtt 159720
tgagtgcaac gacttgggtg cgatcagaat cgggttgtaa atatgtgaaa gtgagatggc 159780
aagcgacagg ctcaaaatgg ttttccccat gcccatctgg tgatagatga ggaggccccg 159840
tgtgttttcc ccctggccta tcccaaattt aggatccgaa aaggcggtgt aaattaaaaa 159900
ctggtagtat ttcagggctc gtgcaaagcg ggcagtgagt gaggtgtctt tgctttcctg 159960
aagctcttta tatttttcat atacctcttt taggtatgct tctatttgga cggggaagga 160020
ggtgttgttg tgcacgcaag acatgactcg ttataaggat cccatattaa aacttcatta 160080
gaagaatagg gctgctgata gctagcgctg cacttaaaaa tggggtagcc ctttttcttg 160140
taaatccggt gcctgtcgta gacctggcta gaaagcgggc ttagtgtatc tttaatgtcc 160200
acaacgatgc gtaccttttt ttcatccgat ccctgccggg taatacgtcc caagatttgc 160260
tccatgttgt ttctgcgggg cgttgccatg atgatcgatg tcatatgctt gaaggaaatg 160320
cctctacgcc cgtagccata ggtcagcaag ataatggaag cgctgtgtgc ctgagaaaga 160380
gcggtatttg aaaccccgcc gcataggagc gccacctccg gaacgataat ttgaacatct 160440
ttgaattctt tggaaagcgc ctgataaaaa atttctaaaa gtttgcgaaa ttccacgaaa 160500
atgatgatgc catacggctc atcggtcccc catttgtgag gctcagcggt atgcagggag 160560
taaagccgct ttgcctcatt tacgacaagt tgtatacgcg aaggatcttg aagtagttta 160620
tcaatggtgg caatggccga taccttttca ttaatataca cagggctaac gaagtcagga 160680
tgtccctgat attcgatttc cctcacgtac ccggaaaagg ttgtggtggg acttacagtc 160740
ctctggggct gtcctagatg gtgaataata atcttgtcca taccatcggg ccggtccagg 160800
ggtgtagcgg acagtcctaa tatccgacta agttgtattt tccaaaaaat tttgtaattc 160860
tccggcgagt gtaattcatg tgcctcatct aacacgacta gaccaaaggg ctcaaagaac 160920
tgctcaggct tcttgcgcag ggtattaatg attcccacga tgacgtcgta ctctttgctc 160980
gtcatgtcct ttttcttgca cgctgcatta ttgtaagcag ctacacgtag gtggggcagg 161040
agcaatgtta gctcgtcgat ccactgtatt tgaatcgcct tggtgggcac gatgaccagg 161100
gtagggtaca aaagtttttg aataatgctg atcgcaatac gcgttttccc caaaccggta 161160
tttagatgta ggtaaaagcg cccatagggg gacaggagct ttttatgaat cttatcgacc 161220
atttcttgct ggtagttaaa tagtggaaat tctgtttcaa cgcatgggag ggcccgcagc 161280
gacacggggc gcgtcgtgta aaccatgtta aacatttcaa actgcttttg cagcaatatg 161340
ggaaaataaa tgtattcccc ctgcagcgtg aaggcagttt cctgtcttat ggctatgtgc 161400
tttggctgcc cgggtaatgc ccgcgccgta acggtgagcg ccttaagaac gcgcccgaaa 161460
tcatgttgta atttactttg tagcttctta taatttattc ctattccagc aaaggatata 161520
atggcctcca ttctcacgct ggacgggtta tatgcagagg ttccaaaatt cttaccagag 161580
gcgttacgag agggctgtgc tggcaagaat cctctaagct tttatattca acaaatttta 161640
aatttaatgg gatgtgacgg taacgagtac catgttcttt ttaccagcag ctccgaggaa 161700
gcaaatactc atatgatcat ggccgccgtg cgtcgccatt tgctgcggac gcagcaaagg 161760
cctcatgtca ttatcggagc agccgagccc cctagcgtca ccgaatgtgt gaaggcattg 161820
gcgcaggaaa aacgctgcgt atacaccatc atccccctaa aaaattttga aatagatcct 161880
gttgcggtat acgatgccat acaaagcaat acctgcttag cgtgcatttc aggcactaat 161940
gctgttgtca aaacgttcaa caaactccag gacatcagca acgtgttaaa aggtattccc 162000
ctgcactcag aagtgagtga tcttgtttat caaggatgta ttcaacaaaa tccgcccgct 162060
gatagttttt caataaatag tctctacggc ttcctgggag tcggtgtttt gggaatgaag 162120
aaaaaggtca tgcaaggatt ggggccgctc atttttggag gagggctgag aggcggaagc 162180
cctaatatac ccggaattca tgccatgtat aaaacgctaa cccagcaaag gccttctatg 162240
aaaaaaataa atacaataca tacgctgttc atgaaaactt taaaaaaaca tcagcatgta 162300
tatctaccca tagggggcgt gtctgcagag gacacgtctg cagaaaacat atctacaaaa 162360
gacatgcctg ttgaaggccc gaagggactc ccgggctata ttttatttag cgttggccgt 162420
cgcgccgagg agctacaaaa aaaaattttc actaaattta atataaaggt tggccgtgtt 162480
gttgacttac aagagatact gtttcgtatc aaaataccac aaaaatactg ggagacatta 162540
ttgttcatcc aattaagaga taatttgacc aaagaggaca taaaaagagt tatggttgtt 162600
ttgatgcatt tagataccat cactcctcgt ggctctcttc ctcctccgag ccactcttct 162660
tctttttctt aatcgttttt gtttgttcta taataaggga aaagaactcc gtgggatctt 162720
gttccccgta caggttatct gcgaccataa ggatgcttag aatggtaaac aggtgagaat 162780
acataagggt ttgcgtttta agaaaaccct gacgttgaat cataattgaa aacaccttgc 162840
aaagccgact catcagttgt tctgtaatgg cgttaagcat tttctggaat ttttcttggt 162900
tttcgggtgt gattttatat tcatgtagaa agtgtttcac acctgaggag aagaatcttt 162960
cctccttcga gagcccatct ttgatgatgg gaagttcctt gatcagggca aaccattcct 163020
cctcttgggc ttgcggattc tgaagatact gatggcagat atggtttaga atggtgcaca 163080
cgtagctaat aagctctgag ctgattcttt ggttggtttt caaatgttgg cgaaagtagt 163140
ttttcaccga agtgcatgta ataaacgtct tcattttctt ataatataca acagtatgtt 163200
gagtctttaa tttaaaatta caaggagttt tctaggtctt tatgcgtata ggtgtttctt 163260
tgtcgtaaat tttcaatagc cgacattgtt tgtgaagcag tgttctgagt agtgactgtc 163320
gtgtaaggct cagccggatg agcaggagca ctcgcggccg caggtgcggc cgccggcccg 163380
ccagttgcca tgactagtct gtccgtaact gggttgtccg taactggttt gtttgttgct 163440
ggtctgtttg ttgccggtct gcccgtgact ggcttgccta cacttgctgt agtcgctcca 163500
gctggtttag aggtacctgg ttgtggagtg acttctaccc actgctgatc ttgataagga 163560
tttataaact gtatatcttc ctcctcaata gcagcagctt ttttctttct tgaagagaat 163620
agatagatta gaacgatgat aatgatgact aagaccacga tagcaatgag aatagtatac 163680
atatgtgtgg agaagaagct tggtgtagtg actggtgaca aacactcacc ataatgccgc 163740
ggataaaccg gttgaaaaaa ttcagaatcc atttaagata ctattataaa taatatataa 163800
aaatgttgtg gcgcaatgaa attacagaat ttatggacca actttccaag tattctcaag 163860
aaatcttaaa aacgtttaag caattgcgtc ctagtgaata taaacaatac aatgaatttt 163920
taacacaagt tacaccgttg ctgcaaaaaa cccctgaaaa aattccagag ttggttgacc 163980
atatattcaa ttacctagac aacgttgaaa aaatttgtga gctcctcgtg aatgctagct 164040
caattattat tagttcaaaa atacgagaac aagtaaaaca cggaatgagc ttcagctata 164100
aagccgacct cgactccttg gcggacattc tctctcaaaa acagtacgtg cttatgcatc 164160
tttcaaaaaa tattgcggcc gagtatttta atacgtgttt aaaccaaggg aaatccaagt 164220
tagatctcaa agctgcctct gtattttata gtagtcgttc ccgaacggca agctcagcag 164280
aactctatag aaaaatgcta tacgcctatg gttcaccgca ggaaattaat tattatactg 164340
aaaaagcccg aaataagacg ttggatgtgg aggagagcga cagcatggcc atcatcgaac 164400
gaacggcccg acacaacctt tcccttatgc acccgctaga agccatgggg cttacctttg 164460
gggcaaccaa cacggacgcc gacccggagg atctgaagga caaaacggtg ataaatttaa 164520
cgctcccgca ggcaacagaa agcatcacct accatcttaa atccctaatg cagctaaaaa 164580
aagtaagtac ggcttcagga ctaaatacaa acattttgaa agcatttgat aatattattt 164640
ccacccctgt gaaaaaaaat aaaatggcct ccaagttggc gcccgggatg gatgtcgtgt 164700
tcactagcga taacggaaaa acatttttta ctaaaaacat tttaagcaaa aacatgctag 164760
cggggcccaa agagcgggtg tttgcatata ataatctcat tagtaattta aataactcct 164820
gtttcataca aaatcacaac gatttttaa gacagcagga ctcttggccc ttctatgacg 164880
cgcacaattt taccaacaag tttttaatgc agcctatttt ttcggggcag acccgtcctc 164940
ggcttcaggg agccatggag gcggcgcatg tggaaacgca tctcacggca tttttacaaa 165000
gtattcagcc ctctaggcca caagatccct ctgttttggc ttcccccaag ttatctgctc 165060
taatcttgaa ctaaaaacag cctttcttgg acttaaatga tggtctacca gtttttgaaa 165120
taacttagag aactatgaag attttcatga aatttaaatt agagatttgc aaaggttact 165180
tgcggtcatt ttctgttgaa ttaaataatt attcgaatag tataatgtct gaagatattc 165240
gtcgtggtcc tggcagaccg ccaaagaaaa gggttgttcc caactttgag cgcaagggca 165300
ttctggaaaa accagttcgg ccacaaagcc gtctcgagtt ttcctatgat aacccgctga 165360
tatttaaaaa tctttttatt tactttaaaa accttaaaag taaaaaatatt ttggtgcgat 165420
gtacccccac cgagattacc tttttttcac gtgaccagtc gcaggcaagc tttgttattg 165480
ccaccatcga cggaaaaaac gtgaaccatt attacgccag tgatgtcttt tggctaggca 165540
tcaacagaga gctcgttgaa aaaatgttta acagcattga tcgctctttt ttaaaaatta 165600
ccatcgttca ccgctatgac aagcctgaaa ccctgttttt tatctttacg gattttgaca 165660
ttgacaagga gtgcacgtat cagattacgg tctcggagcc cgagctcgat atggacctta 165720
tcgaaatgga aaaaagcatc agtgaagaaa gactcaagaa ctatcctctg cgctgggagt 165780
ttacctccaa gcagctcaag aaaacattta gcgacttatc aaactacacc gagctcgtga 165840
ccattgaaaa actcggcggc gatacgccgc tgcacctgta tttccaaaag tttaactcca 165900
tctcatacca cgagatgtat aaatcttcca acaagatcaa cctgacctcg accattccta 165960
agtcgcaggt gttccagata aatgttaaaa ttgctcacat caagtcgctg gcctcggcta 166020
tggtcaccga caagatccgc attctgtgcg aagaaaatgg gaacctaatc tttcaatcgg 166080
aaatggatgc ccttatgtta aatacgatta ccttgaacac cacgatatag ttcggtaaca 166140
ttagatgttc taatatttag catctaaata atacgctgta gtccggtcag ggttgcgtca 166200
cagttttccc attttttgc ctcgtcggcg gtggccaccg ttgccctatc atttacgccc 166260
ggtaagacaa agctaaaggc gttcagcggg gcttggcaat gcccgcccag cgtgaaggag 166320
ctcggaggat tttgcgcatc ccgaaatccc ttagccatgt tgtttaacac ttcggttacg 166380
tcaatcgagt gaagggatcc cttgggatcc gtgaatgtaa agacgcagtt tctaaagcgc 166440
atgtatgcga tggacgattc atcgggggtt ttgaaggtaa cagtgttccc cttgctgtac 166500
ttaaaggggg accatccggt aaaattatac caaatgaaag caataataat taaaataacc 166560
aacacaatag ttatagacaa cacaaagtct gtagtgccgc ccattattaa ataaaaatat 166620
tttagaccgc cggcttaaaa tttacttatt gctcatagct taagtctatt ttattcatag 166680
cttaagttta ttgctcatgg cttaagtcta ttgcttatag cttaagtcta ttttattcat 166740
agcttaagtc tattgttcat ggcttaagtt tgttgctcat agcttaactc cattactgat 166800
agcttactga tcatgactta aataaaaata ttttgcccgc ttaaaaattg tttaggtttg 166860
aaaaaataag agatggaggg ggcaacttat cgtcattgtg tttacccccca ctggaagaca 166920 tcaaacggta aataattata agaatcaaaa tgattaatat aagggttaaa aaaggatgat 166980
tcatcacatt aattaaaaac gtatttataa cgctgttgca gttgaaattt tggtataggt 167040
cggaaatatt gcccgagcct ccgtattctg caatgttctg acatatggtg agtccggagg 167100
ggcactgctt gttggtcaaa atatttcttt gctccgttgt tttataggca tttttatttc 167160
cattacacgg agcaaacgca cattcagccc atagggtgcc ggagttcaca caggcacaat 167220
actggctata cgcatactca tcctttgagc acaatccctg tttatcgcat atgctcccaa 167280
taatattgtc atcctccgcc gtttgttgat ttgtatgcga gcgtaaaata gcggcccagg 167340
ccttgggctc cttttttttgc agctcggaaa tcgaagggcc tgtacagcta aagtcgaccc 167400
aaatatcatt gcatttcgtg gaaactggca tgcaagacat aattgaaata attaataagt 167460
atatatcatg gcaacaaatt tttttattca acctatcacc gaagaagctg aagcatacta 167520
cccaccttcc gtgataacga ataaacggaa ggacctgggg gtagacgtat actgttgctc 167580
cgacctagtg cttcaacctg gactaaatat tgttcgcctg catattaaag tagcatgcga 167640
acacatgggc aaaaaatgcg gttttaaaat catggcgaga agcagtatgt gcacccatga 167700
acggctgctc atccttgcaa acggaattgg tttaatagac ccgggttatg tgggcgagct 167760
catgctcaag atcattaatc ttggcgacac cccggtccaa atatgggcca aagaatgttt 167820
ggtgcagttg gtggcccaag gtgaccatgt gcctgaccat atcaacatcc taaaaagaaa 167880
ccaaatattt ccgctgtttg cgcctacccc aagaggcgag ggtagatttg ggagcacggg 167940
cgaggccggg attatgagaa cttaatttta tttttttttct taacataatg ggaggctcta 168000
caagcaaaaa ttcctttaaa aatacgacca acattatcag caattccatt ttcaatcaga 168060
tgcaaagttg tatttccatg ttggatggca aaaattacat aggcgtattc ggtgatggaa 168120
atattttaaa ccacgttttc caggatttaa acttatcatt aaacacaagt tgcgtgcaaa 168180
agcacgtaaa cgaggaaaat ttcattacaa atctttcgaa ccaaattact caaaatttaa 168240
aagaccaaga agttgcgtta acccaatgga tggacgcagg aactcacgat cagaaaacgg 168300
atatagaaga aaatataaag gtaaacttaa caaccacact tattcaaaac tgcgtttcat 168360
ccctgtcggg tatgaacgtg ctggtggtga aggggaatgg caacattgtt gaaaacgcaa 168420
ctcagaagca gtcgcagcaa atcatctcta actgcttgca ggggagcaag caggccatag 168480
acaccacaac cggcatcact aacacggtaa atcagtactc acactacacc tcaaaaaact 168540
tttttgactt cattgcagac gcaatttcgg ctgtttttaa aaacatcatg gtcgcggctg 168600
tagttatcgt tctaatcatc gtagggttta tagccgtctt ttactttttg cattcacggc 168660
accgccatga ggaggaagaa gaagctgaac cactcataag caacaaggta ttaaaaaatg 168720
ctgccgtttc gtaataattt aattaaaagt aaaaaaaaaa ggtattgtta tagtgatggc 168780
agattttaat tctccaatcc agtatttgaa agaagattcg agggaccgga cctctatagg 168840
ttctctagaa tacgatgaaa atgccgacac gatgataccg agcttcgcag caggcttgga 168900
agagtttgaa cccattcccg actatgaccc taccacatca acttccctgt attcacaatt 168960
gacccacaac atggaaaaaa tcgcagagga agaggatagt aattttctac acgatactag 169020
ggagtttact tcactggtcc ccgatgaggc agacaataaa ccggaagatg acgaagaaag 169080
cggtgcaaaa cctaaaaaga aaaaacattt gtttccaaaa ttaagctcgc ataaatcgaa 169140
gtaaaaattg aagcgaaaaa aagtagaaaa aaaatgtttg gagcttttgt aagccaccgt 169200
ttgtggtcag atagtggttg tacgaccacc tgcatcacaa acagcattgc taattatgta 169260
gccttcggcg aacaaattgg atttcccttt aaatcagctc aggtatttat tgccggccct 169320
agaaaggctg tgataaatat tcaggaagat gataaagttg agcttttaaa gatgattgtt 169380
aagcacaatc tttgggttgt tgctcatgga acctacttag atgtgccctg gtcccgtaag 169440
agtgcgtttg ttacacattt tatacaacaa gaactactta tatgcaagga agtcggtatt 169500
aaagggttag ttttacacct aggcgctgtg gagcctgaac ttattatgga aggactaaaa 169560
aaaattaagc cggttgaggg ggttgtcatt tacctggaaa ccccgcataa caaacatcat 169620
acatataaat acagtacaat tgagcagatc aaagaattgt ttttacggat acgaaatacc 169680
aggttgaaac agattggttt atgcattgat acggctcaca tctggtcttc cggtgtcaac 169740
atctccagct ataatgacgc ggggcaatgg ctgcgctcgc tggaaaacat tcattccgtg 169800
atcccaccaa gccacattat gttccaccta aatgatgccg ccacagaatg cggaagcggt 169860
atagaccgac atgcaagtct ttttgaagga atgatttgga aatcatatag ccataaaata 169920
aagcaaagcg gtttatattg ttttgttgaa tacgttacgc gacaccagtg tccggctata 169980
ttggagagaa acctcgggtc ttccatgcaa ttacaaaccg ctttaaccgc agaatttact 170040
acattaaaat cgttattaaa ataaggatga gttttagcga atgtccctta gttattagtg 170100
catgcaaaaa atttctacaa aagcgtatta caatagagaa tgaagcactt ataaatgcct 170160
taataaccgc tttagcgcag accagcacgt tgaatgatct ttgtttatta cctattcaaa 170220
cctatttgct tagttataaa aatgcttttg agtggataca cttcgtatgt attgcaatca 170280
ccactatttt ggataataag tataactgga aggactgtac ggtagatatt aattatattt 170340
ttctccatgt aacctatatt tacaatatta aaaccaagga atacctagac tactgttctt 170400
aaactttatt ttttctatat ttacgccaaa gagaatattt aaagtttttt ttgaaaaaaa 170460
ataatatatg tagataaaat tcagttacat gatatatgtg taaacatgtg tggtaaacaa 170520
catatggtta tgctttataa gataaatgcg cataatatat gtaaacaaaa tatggttatg 170580
tgttaaatgc atataaatgt attttaacgt atatcttgtg ataatggata tatgcattta 170640
ttaaaagagg ctgtatttat tataaatctt gctaaggatg ccattgtcaa catatatccc 170700
atgttggaca aattgcgttg cgatccagtt cttttttttt tgattttgtt taatgctatc 170760
ctttttgaag ggatggttgt ccaccatatt tattcgatgt tcaatgaata ggtctgcttt 170820
ttcgtaaggc agtgaaggtc gttccaagac tccttgaacg atggacgtgt tttcttggat 170880
ccacttaaaa agcacgtggc attcaaaaac aggacagtga ttggatcctt ggatatgctt 170940
tggacagcca atgcttgaag agatgtagtc ccttttcttt aggacaagct tctccacgct 171000
ggggcaacag agatcgttca agttctggac ggtcgcattt ggaatgttga aacttcgtat 171060
ccattcaccc tcgggtcctc ccttatgaag aaggagtatt tgctcatggt ccttagtaat 171120
cttaaccaaa tgttggaaga tcattttttt acctgcttta aaggcctgaa gggtgtcagt 171180
tggcaaagct attgaattcg ggagtgggct ttcatcaagc gtgaaatggt gaatgtgacg 171240
cgactggaaa gaaaacgacc gttgatttat tttttcaaag attgggtcga ttccgccatg 171300
aaagaacagc tgcaagattt tagaaggcgt attttttttcc caataaaaaa tgaccacttc 171360
tcgtgggatt aaaatcgtct gtgtcccatt ttcattatat aattggccca taaagccatc 171420
aacgtcaatc aacaccaaaa gcatggtata gagagctttt agaaccggag ttcgttaaaa 171480
aaatacaaag ttcgtttaaa acgtgtaatg ttactaaaaa aatgtaatgt ttaaatgata 171540
atgataccac atgcattaat gaaaaaaact tttaaatttt tgttttaata tttgcatgaa 171600
aatggaaaca tttttagtct gtttatttca caatgcagat ggtttacatc aacagattca 171660
ggaaattttg tatttattgc ggatgcatat ttacgaaaca aatctttact taaagcagga 171720
actatcacgg cttatatatc caaataggca actttctttt gtgttactta tgcccctttc 171780
ccttctaaga aactgggatg acattgaata tttaacggac gttgtagatg ataagcagac 171840
tctacattac gcggcaaatt tgctgacaaa ctacgttcta catctatcca tgtttcaaaa 171900
gctgacaaaa ccatacttcc ttttagcggt caagcgggtc agcgaaaaac tcaacaaaaa 171960
gcagcgacat tcattttacg aggtattggt aacctccgaa accttgaata attatgaaaa 172020
cctatctaaa aacattttaa atacgttgat gtttgccgtg cgctacgtat ttaaacctac 172080
gccgaactat tcagaaattc tcgcagagtt ggaaaaaaaa aataaaattc accatattat 172140
ttttaatatg gtaattacgg attttgcgca aatccgtgaa caacaaatgg ataaacatct 172200
gtgtgaaaca aataatgagc ttcgtcagga atgtaaagaa actatttttg atttaaaggt 172260
ggtaggaaat gtttagccaa taaactcatg cccgcatttt ttacaggtac aaaatatcgt 172320
ggatggctca tcgagggcgc gtgtttgtac ttctctgtag gtacacatac gctgcttgca 172380
gttgggacac ttataaagtt gtgacgtctt ttcggcgacc ttttgctgcg aacgtagagt 172440
aatttctgtc ttctccttta aggcggcaga ggggcaaagc tcggcgaacg tcatgctacc 172500
aattgcctcc ggttttagct cgccagaaat tagcttatta agggcatcgt tatcctgttg 172560
ttggtgactt ttttttcgc agttaataat atgattgatc gtcccacaac gggttgaata 172620
ttcttctaaa aaggtttttt cttgttgctg gtacgtataa tgataacacg aggcctcgat 172680
tttttgcgcg tattcggtgc ataaatcagt atgttcctta aaaaacatat gtttttgaag 172740
cgttctaaaa aacatcattt ggatgatatc acgcatttcc aaaataatat agggttctag 172800
tcttttggaa tctttcataa ctagatcggt ggtaatattc ttagtcatac aatttattaa 172860
aaatggttta atatattgta aatatttttt aggcgtgtca gcctgtaaaa aacattcttg 172920
ttcaatctta tttgtaagga tagtattttg caaatactta tttagcaaaa atacgataga 172980
atcgcgggct atatgcattt tcatataatt tttttttaa aatttaatac aaaaaaaaga 173040
agtatagact cttcttctag tccggttagt tcgttggttg cctcaacatg gagactcaga 173100
agttgatttc catggttaag gaagccttag aaaaatatca ataccctctt actgctaaaa 173160
atattaaagt agtgatacaa aaagagcaca atgtcgtctt acctacagga tctataaata 173220
gcatactgta cagtaactca gaactttttg agaagattga taagacaaat accatttatc 173280
ccccgctttg gatacggaaa aactaattgt aaccagtagt acatttaagg atagtttaag 173340
cagtaaatgt agaataacac agttaagcaa taaataacaa gtatatagga atatatagga 173400
atatatagaa atatatagaa atagctaagc ttaatactaa ttcagctttt tttttaacta 173460
aaacctgaat agatgcgaag tagcggacat atacatacta aaataagcca tacatttact 173520
ttcttcttga acatgaaacc tttttttctt ctgttgttgg tatataaaca ataggactgt 173580
ttgctgaggt tgtatgatct tctacaactg ctgtctcagg atgacgatgt tttttaaac 173640 taaaagtgta ggatggaatg agtggaatat agttatggct cgacttatcc tgtttcgtac 173700
aggaatattt tttacaaata gaacgcaaca agcatatgaa taaaaacaga aatgatatac 173760
aggagcataa aatagatatg aacactaagg ggtagcagct tttataacgt tccgtatttt 173820
tcttagctat caattgattt accgtaatat ttatctcggg aaactttgtt ctacaatatt 173880
ttgtttggta ttccagaaac tcatgtcctg gcttattccc gcagcttaaa aaatgataca 173940
aaaatgtgtt attgttacta aaattaattc ttcttaagaa aaactgcgga agacgcttta 174000
ggtacgtctg ttcctgtttt agtaggaagt agtataaggg acaatttctt tttccacaca 174060
ttagattatt gtaatatagg taggttgggg tgttggagcg aataagtttt ctgagtatgt 174120
tataatctat gacttgtaaa tcgttatacc ttaggtccaa aaacttgagt tctttaccaa 174180
agccacctgc aatttcagaa atatttttca tcccgcagcg gataatacgg atgtcctgaa 174240
acgtctttaa aatacttgta ttgtagtgaa tacttatgtt atttttttgt aaataatcta 174300
tgtcatgaca agtgcatgaa atgccagcag cattgcttgg tatagtatta tatgcaggaa 174360
gaactatact actattgaga atagtcacat tgtacttata ccatgtatta ttttctgata 174420
taaagtattt gcaggtgacc tgtggtttaa tcctacctgt taagccactt cctaaaaaaa 174480
caaaaaatat gaaaaccctt agcatcctgt atatactatt aaaaatttat aaaattttct 174540
gtttaaattt catttagaca aaaaaaataa tatatataca tcagcaagaa attatataca 174600
gattatataa ttttctgatt tttttttgcc acaataagca tcattatatg cattaaaatc 174660
tcaatactaa acactaaaat ctaaattcta agcattaaat tctaagcatt aaattctatg 174720
cactaaactg taagcactaa aatctaagta actaaaatca acactaaatg tatgcaacct 174780
aaaatgtaaa gcattactca tcatcctcct cttcttcatc ctcatcatca taggttaaga 174840
tatatgtgtc atcctccatt tcttcacatt catcttcata agcatcactg ggtattggtg 174900
gaacattgga tgcagcattt ttaaaatatt ctatgtcttc tggtgaacac tcatctaatg 174960
attttttgac agtcctttta acttccatgg gatatgattc caaatcctct ttatataaga 175020
gtttacggta gcttttagct gcatccacat ttgctggaga atctggattt ggctcattga 175080
gcagtgaaat tacactaaga agaatggtat caatcttttg agccggagac caagtcattc 175140
cctgttcttc agcattgtct ccgtgtaaga tagagataca tagttttcca tcagagtaaa 175200
tattaggatg ccacatttca gaggtgaatg ttaatctggg tggtgcatat gggtattctg 175260
gaggaaaggc gatttttgcc ttgaataagc ctccctcata aaaagtgtca ggtgggcccc 175320
ttaagatcac atcccattca gtcatatcct tctcattcac cgaaattttg aaattctcag 175380
agggattctc tatcaggtgt ctgtactctg ctattaaaaa cctggaaacc atggttattt 175440
aatattaatt aaattccctg gtttattcct ccttaaaagt agatgaacct cttttgtttt 175500
ttattgggtt catttttact aaatttatga actggaaaaa actttaacgg cataattatc 175560
aaatgcgaag ggggatccgt ataaaatcct agcttgccgg taatggctat taagttaaat 175620
ttggtaccag taacactaat atttaaaaag ccctgatcat taactttcca cattaaaaga 175680
ttattatatt cgaatgtttg tccaatatgg acaactttgt caccagatgt tacatttgat 175740
ttggttgtta gtggctgaag cttggcacaa tcaaaaataa gcccattaac actaagatat 175800
agaggagtgg gttgatctat tttctcatag tttaatattc catctttcca cgtaatagct 175860
tgataattat ccgcagcaat gagttgaaat tttataaata gtacaggggt tttagttgtc 175920
gttatacatt taaagggtgt tttataaaaa taaaaaataa taattgttaa aagtatgata 175980

```
ataatcgcca aaataatttc atacattttt tataagaatt atacatagta tggtatttaa 176040
aatattagct aaatttaaaa aaacttcatg atttttaaaa cagggaaaaa ggggattagg 176100
ttgaataaaa aaggtaagca cttgtctata tatttttttt acaatgttgc cttgagtcgc 176160
atttttaact ggctggggag tatcagagtg gaatatcact gtagtaggtc tataaggtct 176220
tgttaaaata tgatcggtca ttgttttcgt actagtgtca tttagggtcg acctgatagc 176280
tcgatataaa gttatagggg ataacctatc aaatacagtc ttatctgtgc tgaaatgtat 176340
atcgtcttct ttatcactaa taatattagg aatggctgtc attaaataat tactacttgt 176400
tgttgtgggt gaaatagttg tactggtatt attggaaatg gctgtcatta aataattact 176460
acttgttgtt gtgggtgaaa tagttgtact agtattatta gaaatggctg tcgttaaata 176520
attactacct attacaagta aactaatgct aactacattt ttaacctcaa taaacctaaa 176580
aagccatact aaatacctaa acaacatcct gttataatat gagcagaaaa aaaaaataag 176640
tataattagg gaattattct tattcgctta ctattaagaa taattcagaa tcttatttag 176700
ttagaaacta tcataaagtg aataggactc atcgtcggat gaagattccg tttcagagat 176760
agtttctttt tcttcctcag aataatctgt tcctacaata gaatcggtgt catcctcaga 176820
aagagaagta tttaaatatg gactatctat agcaatatcc tcttctatct cgcaatcctc 176880
ctcctccatt tccatagtgt gtaggagaat atttttatca tcatgctcac ttcttttttt 176940
gttgaaagat gaaccgtcct caatacggtt catgttaagt tccttcatct tatgtataat 177000
ttccgtaatc cgtgatgttt ttgacatgta agatggtttt aaggttatat ccacaataac 177060
aggagaatct ctatcatttt catttgataa actttgatct ttgatttctt cgtctaaaat 177120
tcttgtcttt ttttgggtac tagatgaaat agaggaattc atattctgaa acgatatatc 177180
aaggggagct ggacgctttt ttccaattaa accgtttttc gagatactat gattagatga 177240
atgatcttta gccaagctgt ccttggatat actatagtta gatattttac ctttaaataa 177300
tattcttcta tacaagttat tcttaggtaa agaattagta tggattccta tatttttatc 177360
tgaaggagtg tccatatcgg agaacgtcct cttacgaata ttttgaccac gagccatttc 177420
atccactata ggcagtattt tggctggcta tggttctttg ttgtgacaat tctatgagat 177480
ttgattgcaa atcaattttt agttttaaat atattggtac ctaggacaaa gaaagtatat 177540
atagccaata attattccac taaattgatt tccagactga tgggtatgga gccatgttgt 177600
ctctgcagac gatcgcaaaa atggccgtag caacaaacac ctactccaag tatcactatc 177660
caatactgaa ggtctttggg ctgtggtgga aaaacaatac gctaaatggc cctattaaaa 177720
tatgtaacca ttgcaacaac ataatggtag gagaatatcc tatgtgttac aatcatggaa 177780
tgagtctgga tatagctttg attcgggcag taaaggagcg taatatatcc ttagtccagc 177840
ttttcaccga atgggggggga aatattgact atggggcact ttgtgctaac actccatcta 177900
tgcaaagatt atgtaaaagt ttgggagcca aaccaccaaa gggccgaatg tatatggatg 177960
ctcttataca tctttcagat accttgaatg ataatgatct gattaggggg tatgagattt 178020
ttgatgataa tagcgtgttg gattgtgtca atctcatacg actcaaaata atgcttacct 178080
tgaaggcccg tatacctctc atggaacaac tagaccaaat tgccttaaaa caacttctgc 178140
agcgatactg gtatgccatg gctgtacaac acaacttaac aatcgctatc cactattttg 178200
ataatcatat tcctaatata aagccattta gtctgcgctg tgctttgtat tttaatgatc 178260
cctttaaaat ccatgatgct tgcagaactg taaatatgga tcctaatgag atgatgaaca 178320
```

ttgcttgtca acaggattta aactttcaaa gcatttacta ttgttatctt ttaggggctg 178380
atattaatca ggctatgcta atgtctttaa agtatggtca tctttctaat atgtggtttt 178440
gcatagattt gggggcggat gcctttaaag aggcaggggc gcttgctgag aaaaaaaata 178500
aaagagtgtt acaacacata ttaggtctta atatctttaa gcgagagttg attccccccct 178560 gtaaagatcc tgatccttat caaatccaaa ttctgttaaa aaactacatt ctaaaaaatg 178620
tctcaactgt ttttacatat tattgccagt agccattgtt tatatcagaa aataacccat 178680
ttgtttatct ttttttgtgg ggcaaccatt aagacccgac gcaaaaaaag attaatcttt 178740
tatcagatac ctaaaacgtt ctataaggga gtctatgaga tggatcatat tttgatggtc 178800
atagtaagaa gcaagctttt tggcgaaaac aacggagtta aagaatttaa cccgctcatg 178860
tttggatagg acttttaaca gcgagccaaa acagtattta aaaatttggc aatagttttt 178920
ttgggatgca ataaacaaac acttgatcag tgcccgcttc actttctgat cagacatgtt 178980
tgccgcataa caggcctttt taaacttagt aatataatta tgttccgcaa gcaccattaa 179040
caagggaacg atgggaagct gcttttcttg gtgaaattta cgtaaatatt cgatggccac 179100
cgcttggacg actgtgtaat ttactaagtt agaaatgata gctttcatgg ttgtaaaaat 179160
atacatagga ttttcttttt ctgtatacag tttgaaaagc ttatgattac gtgaaatgat 179220
ggccattttt aatacaagat ggtatagtgt atctttaggt aaaaatgcct tgcaagccgc 179280
gatgatgtcg atgttgtctc catgaacagc gatagaaact aatgtttcca atctaaatgt 179340
ttttatctgc attaatagaa gaatgcagtc aatgttatta tacttaataa tactgtaata 179400
caccgaatca atgaccgtca tctgagaatc aagctgactt attagtaaat ttaacgtttt 179460
tttggaggca tgacctttga tcgcggcact aagtgcacac agtatagcaa aattgttaaa 179520
tacattttga tttaggagaa ggagtaatat tttccttcgg ttatagtacg cagcatctgt 179580
gatgattatt ggccgataaa tgttaaaatg tgttaacagc tttttaaaaa aacggaagta 179640
attttttggg atcgctgttt gcatcatcga aataatgaga taatcagggt atataatggg 179700
taggtcacat gctacctcta acaaagaata gtcgcccaat ctaaaggctg tgttgaaaag 179760
cgtactatca tcatacgtat cgagtacccc tgctgttaca aaccaagcga taagatgaat 179820
gtgccgttcc ttgcaagcta tcgcaaatag ggagtttcct atggaatgtc gaataatgta 179880
ctccctattt ttttccaaaa tgtttggaaa attgtatagc gttgcggcat acagtagaca 179940
ctccattctg gcgttataat ttttactttt acatatgaat aggtggaaga actcgaataa 180000
ttcttgagaa cttgttaaat gcataaatatg gtgatatttt ggtgtcgtta aatggtatga 180060
gaaaatgcat tctaatacat cttttcggtt atgctttagc gcctgagcta aggcatattc 180120
aggctcgacc cataggacta gtgtttctat aattgagata ttcgcctgct ttgccagggc 180180
atactttaag acgctccggt tagaaaaaat gttgttatga agatggataa ccgtatccat 180240
ttttacgatg ggaccattcc agtatagtcc taaatgctgt agcagatctt ttgttagttg 180300
tgaagcgttc tcgggtgtca tataaatatg ttgcagggct tttttctgta aggagaacat 180360
ttcgtcgtaa tcgtacaaaa aaaaattaaa atttgggcat ggatgattca aacataacaa 180420
aatcaagatt ttataacagt ttgcattaac ctatacatat atgcaagtaa atgagatatt 180480
atctatcata acgaatcaag ggatatttgt atatatcagg agtttctgaa ataaagatat 180540
gaagattatc atagtagtat ccatcaatca caatgcaact tcctttaagg cataatttag 180600
taaactcagc actcccatct tctggatgct ttacaactaa cattaaaaac tcctcagtca 180660
tattatctgt aataaaataa gatcctcctg gagccatttg tagcatgtct cttattccta 180720
caaaatcttt tttgggatgg taaaaactca gcagtttcaa actctttttt agtttttttt 180780
cctggtattt aagccatttg ttataaaaca gttttcttat gaaaatgcat ttgaaaatat 180840
tgggaatgtt taaccatgct tcttccgagc acatctccag atacttactt tctttgtttc 180900
ccatgtctaa tttattgctc actaagttag taatgaatct attttaataa tctactttac 180960
taatctatct taataaccta tcttataatc tatcttaata acctaattat aacctattta 181020
taattggcta atgctgccgg catttcatgc ctatctaaac aactcctact aagcaatcta 181080
ctattacata tatagattca ctttttatat ttgtaaatca tgagaattat aaaatcatta 181140
ctcattttta ttgtaaatta gtgggtattt gtaaaaatct tcaaacgttt taagatagtt 181200
ttctagagag aagtaatctt tgccatcaat atataatgct tttcctttaa actccagttt 181260
tgctatgttt agtgagccgt ttctagatct ttttgggcaa taaatagatt ttcattggtt 181320
gcatcgtccg taagcagaaa ggtaccacta ggcacgttaa aaaacatacg ttctatttca 181380
tggtcggatt tttgagaata gaaaaaatct aattttttaa tccgcgttaa ctctttttta 181440
tcaatctttc cagactgttt tatatatact ttattgcaaa tcttacaatc ctctatggct 181500
tcattatact tattttgctt atcctctatt gacatgtccg tatttgatag gtaacttccg 181560
ttaaggcggt tccccatggt tttagataga tttttaattc agttgtatac ttttattatg 181620
aggctaaaat atagaagttt gatcctaaaa aaataaaaag attttgtaca tttatttatg 181680
gtttatagcg gtatagaggc cgataaaagg tatccgggta gtctcctatg atatcgtcaa 181740
ttttggtata ataacagttg ttatggtagt attgtccaaa ccgagtatgt atgcgccggt 181800
gaagcgtccg cccgctaatg gtacagttcc aggttaagac aatcatatca cacccaaaaa 181860
gagaggaaac agcataggtg cccaaaggtt cattatataa catacgccgc atatatttta 181920
gttttttttc tccatggtaa taatcacagg ttttcatgtc ctgcttaata ggatgattcc 181980
ccatgtatga taatatataa taaatttagt ttttagcttt ttcaaaaaat tgggcgctcg 182040
aaactaaatt ttccttatca cagcgtttgg agaaagcgta tttaaagata tatcttcttc 182100
taacaagact gcaaaaaaaa tcttacccct tatttttata atgttcatca tagcgtttga 182160
agatatcaga aggtgccagg ttttataaaa atatccttta ggatttataa cgatacaagg 182220
gtctataaaa tatatgcggg tataatctta taaaatcatc gattttttca taatattctc 182280
cgtttataca ataaagatca taacagatat tgatgcgtag atgcattatt cgcgtgttcg 182340
ttgggcagct aaaggatatc acaacgtagt ttttttttaag aaaagacgaa actacataag 182400
tccctaaggg ttcattgaat agtaaacgcc atatttgttt taaattttgt tgttcaccat 182460
agtagtattc gcactttttc aagtcttttt taataagcct attccccatg tatgcttata 182520
aataaaaatt tagaaatgtg ctatattatt tgttgatgaa tcatgaacac gtcttatatg 182580
ttgatatgtt actttaaaaa catttgtatt ttcaacagac gcgttctatt cttattaaga 182640
atgatgccgt ctttatttta aaccttggtt taaaatttaa agaagtattt ataaactata 182700
atcatgggaa ctttttcagt aactgcctct gcaaaaagtg acgatgctgt ttgtaagtat 182760
ttagaagaac caatagatga aaattacaga aacatattaa gaaatgagca tgttaaaaaa 182820
aatttaaatg aggctctgaa tcgacatatt actacctata atccagtagt tgattggtgt 182880
aataactatt caacattttc atctcaggat ttcgatgaat ataaaattta tatacatagc 182940
gatcttatgg atggacgacc tcgtccaaaa aaaacatggt gtgtcatcat gtaatgtttg 183000
ttagttttat ataaacgcaa aaatattctt ctaggagatg ttgatatact acctattgaa 183060

-continued ttcaatatat taaagtacat ttctggctat tcccattacg gtattattat tactattttt 183120
aagagctaga tgtggattta agtaataata acattctccc gttcctccta gagacacctc 183180
atcaaattcc catcctatgc aacctttatg ttgtaaacat aatgattgac agcattcatc 183240
ttcttttgac caagtcgtcc aaatcctacc aagatctata cgtgtttttc caaatggaga 183300
ttgaagatca gcagtagtgg cattaaacct ataaaaacca ggtgcataat cacatgaacg 183360
gatcgtagga tctaatttaa tatcttttat atcttgtttt actgcttcta gacaactttt 183420
atcagtacat gttccacgta cacagtggtg tcctttatcc ttacaatccg tatctgtctt 183480
acattttttt ttcggcggtt tatgtttcag atggtaaaaa cccagtatta aaataatcac 183540
aagaataatt cctataagta cttgaacaac aggataaaac attttaatat taaatatatt 183600
ttttaattaa atgaatagat ttaatccaag tagtattaaa attttttaga aatagtgttc 183660
tacaaataat gaaatgaatg gtccaaaaaa aataaggtgt acaataatgt aatatattgt 183720
taggctaagt aaatttaata ttttaaagta tttggaaaaa tattttttaa catatgatgt 183780
ctaggaatat tttttagaca tttaaaacca tatagttact ttatttatta cactgaactt 183840
gaaaagactt attacctaaa atattaatag atgaagtaat attgtgtaat tgagtccata 183900
acatgggtgg gaaacaaaaa tctcgtaata tgaaaaataa acatcctaaa aagagtgcaa 183960
ttgttataag tttatgtaac tttattttaa agtaagaata taaaaatatg agtacaagag 184020 gaatagggg cattactaac attggctcca acatcctgtt gtctacaaaa aaaaatattt 184080
tttttagcaa aaaaaaatcc atggaaggat attaatacac ataattattt gacatcacat 184140
tagtgtactt accaaatagt aatatacaac catcctaata ttcaccttta tgaaatgatc 184200
ccaacctata cggtaaaata gtataggttt taataaagaa aaaagatatt ctgtggtttt 184260
tatttttgta tagtgtgtga atacaaaata aaatcccaaa ttttaacctt ttcttttttt 184320
ttctatacag gatgttagaa atagtattgg caacgctgct aggcgacctg cagcggctcc 184380
gggttcttac ccctcagcag cgggcagttg ccttctttcg agccaatact aaggagctag 184440
aggacttctt atgctcagat gggcagtctg aggaggtact gtctggcccc cttcttaacc 184500
gtctactaga accctcaggc cctcttgata ttttaaccgg atatcaccta tttcgtcaga 184560
atcccaaggc aggtcagttg cgcggccttg aggtcaagat gcttgaacgg ttatacgatg 184620
ctaatattta caatatactg tctcggctgc ggcctgaaaa agttcgcaac aaggctattg 184680
agctatactg ggttttccga gctatccata tttgtcatgc tcctttagtt ttagatattg 184740
tacgatatga ggaaccggac tttgctgaac tggcctttat ttgtgctgct tactttggtg 184800
aacctcaggt aatgtatttg ctctacaaat atatgcctct gacccgcgca gttcttacgg 184860
atgccatccg gataagtctt gagagcaaca accaggtagg gatttgctat gcttacttga 184920
tgggaggcag cctcaaggga ctagtctccg ccccactgcg taaacgtctg cgcgccaaac 184980
tacgctcgca gcgcaaaaag aaggacgttc tttcacccca cgacttctta ctgctgctcc 185040
agtagctttt tttgccgcag gagcaccgcg gataggagct cctccacgct cgcgatccgg 185100
cgctggaagc ggaaccgatc gaccgccacc tgctcccagg gacccttgcg ctcgatgtcg 185160
tcggcttccc acacctcgac ggctgtggca aaatggacat gcttcgcgtc gttcgtccgt 185220
tttttgcgcc gcctccccat tattcttcct gtaagattag tgtttaatac ctataataac 185280
ataattttaa gatttaatat accaaaactt aaactatttt tgtatagtaa ctattagcat 185340
gtctacacat gattgttctc taaaagagaa accggttgat atgaacgata tatctgagaa 185400
atcagttgtc gtggataatg cacccgagaa accagctgga gcgaatcata tacctgagaa 185460
gtcggcccgc gaaatgacat catcagaatg gattgctgaa tattggaaag gtataaaacg 185520
tggaaatgac gtgccatgtt gttgtccaag aaaaatgacc agtgcagaca aaaagttttc 185580
agtatttggt aagggatccc taatgcgctc catccagaag aataattaaa aaaaatattt 185640
tttttagcaa gtttttaaac tatttaaata aatgtggtaa aaaaattcac ataataatta 185700
aagtgaacgt gttagaatta atattttttt ataatcggat ataatatcca ttaaatcaat 185760
aaatgatagt gttgctacca cactaaacaa taacaaacag aaacgcacga tacctttcct 185820
catgatttat aatagcgtgt tatctaaaga ttttttgaa aaaaatatta aattttagtt 185880
gattattttt ttcagttaca acattgcttt agaaaaaata cctaattact acatagcaaa 185940
taaagcgagc gcattgttac aaacaacatt tttttgcgcc tggatactcc tatatatgag 186000
aactataata cggtatatta atcctattac caacattgtc aataatagta tgtaggcaat 186060
gacatacttt aaataccaaa tatccatggt tatttctaaa aatcttgaaa aaacgttaaa 186120
ttttagatcg gtcacctacg acagtaatac taattttaat aattgatgac tgaaatcata 186180
atataatgcc gtgcgaaaaa taattatttt tcggttaaag ataccattac ataaaaaata 186240
tgccatctac tctacaagtg cttgctaaaa aggtattggc cttaggggag cataaagaaa 186300
atgaacatat atctagagaa tattattatc atatattaaa gtgttgcggt ttatggtggc 186360
atgaagctcc gattatactt tgttatgatg ggagtgagca aatgatgata aagactccaa 186420
tctttgaaga aggcatatta cttaatactg cattaatgaa agctgtacag gagaataatt 186480
atgaattaat aaagttgttt actgaatggg gagcaaacat caattatgga ttaatttcca 186540
ttaataccga gcatgcccgg gatctatgtc gaaaattagg agctaaagaa atgcttgaag 186600
gaaatgaatt tatacaaatt atattcaaaa cattagatga taccaccagt agtaatataa 186660
ttttatgtca tgaattattc accaacaatc ctcttttaga gaatgtaaat atgggggaaa 186720
tgaggatgat aatttattgg aggatgaaaa atttaacgaa cctattatta aataatgact 186780
ctattagtga aatattaact aaattctggt atggtatagc agtaaaatat aatcttaagg 186840
atgcgatcca atatttttac cagagattca tggacttcaa cgagtggcga gtaacatgtg 186900
ctctttcttt taataatgtg aatgatcttc ataagatgta tataacagag aaggttcata 186960
tgaataatga cgaaatgatg aatctagcct gcagcattca agacagaaat ttatcaacca 187020
tttactattg ttttctattg gggggctaac atcaatcaag caatgttaac ctcagtatta 187080
aattataata tttttaactt attcttttgt atagacttag gggctgatgc ctttgaagag 187140
ggtaagaccc tggcgaaaca aaaggggtat aatgaaatag tggaaatctt atcattagat 187200
atcatttata gtccaaatac tgacttctca tcaaaaatag aacctgaaca tattagttct 187260
ttgttaaaaa acttttatcc aaaaaatctg ttcgcttttg atcgttgcaa ccccggttta 187320
tattattctt agaggaccgc tacaaaaatt attttttttt cttgatcaaa gctccaaaat 187380
aattattaga ttaaagtcgc ctatagcagc agcccactcc aaaaaaagta ttttatagta 187440
caaaaaacac gaaaaatagt ttgcggccgg cggcaaacta tttgttgttg tctaaaactt 187500
aatgtttttt taatattttt aaatgcaacc atggattgtt ggactatcag ggagaagaac 187560
tatagctaca tcatattgtc aatactggta atactattaa tatggtatct tatacttaac 187620
tattgtcgat cgaaaaaaaa tgcagttaca aacaacatgc cgccaccata cacggtgtca 187680
agtagctgtt ctcaataata gggttgattg acgctcttcg taataatatg ttgattgacg 187740
catcataaaa tgctgtggtt gattaatatg ttgattgtcg cctactttat tatataagta 187800
atgatttttg tataaaatac gggtttgtga gggctttatt ttttcttatt agaacaaagc 187860
atgcaattta aggcctacag caagagtaat ttaacaccta caacagtaat tttaaggtca 187920
gtaataatgt ttaattaagg cctgaccact aaaacttaaa cgattttgta aaaaaaaatg 187980
tctactccac tttctctaca gactcttgtt aaaaaagtgc tggccacaca gcacatatct 188040
aaagaacact actttatttt gaaatattgt ggtttatggt ggcatgaagc gccgattacg 188100
atttgcattg atgaggatag ccaaatattg ataaaatcgg caagcttcaa agaaggctta 188160
tctttagata tcgcattaat gaaagtcgtg caagaaaata accatgattt aatagagttg 188220
tttaccaagt ggggtgcaga tatcaactct agcttagtta ctgttaatac ggagtatacc 188280
cggaaccttt gtcagaaatt aggcgcaaag gaagctttga atgaaaggga tattttacaa 188340
atattttata aaacacgtca tcttaaaact agcagtaata ttattttata taatgaattg 188400
ttttctaata atctcctttt ccaaaatata gagagattga gtttaatagt ttataggggc 188460
ttgaaaaact tatcaatcaa ctttatattg gatgatattt catttagcga aatgttaact 188520
agatactggt atagtatggc gatattatat aaccttactg aagccatcca atatttttat 188580
caacgatata ggcattttaa agattggcgg cttatatgtg ggctttcttt taacaatttg 188640
tctgaccttc atgaagtata taacttagag aagacggata tagacattga tgaaatgatg 188700
aagttgacct gtagtacgta tgatggtaat tattcgacta tttattattg ttttatgttg 188760
ggggctgaca tcaatcgggc aatgttaacc tcggtaataa actttcatat tggtaacttg 188820
ttcctttgta tagatttagg agctgatgct ttcgaagaca gcatggaact agcaaaacaa 188880
aagaataata atatattagt agaaatatta tcatttaaaa attattatag ttcaaatacc 188940
tctcttttat caataaaaac gacagatccg gaaaaaatta atgccttatt agatgaagaa 189000
aagtatgagt caaaaaatat gttaatgtat gaagaattat ctcattgata caaaattatt 189060
ttttataaca gaactctctg atggtgacaa atctccgata ggaatatatg acgtaacata 189120
attatttttt tcgcccagaa aaaaattata aatgttatta ttgccagcac ttttatcaac 189180
tatacgtaca aaaaggtgtt gaccaaaaaa ataatttttt ttcttgatca aagtatgtaa 189240
acgcccgctt acagcaagga tcttaagtga gagccattaa attttattga tagctgcttg 189300
ccaccagtag aatacggcca aaccacctaa caggaaatac aaggcggccc ttcggccaat 189360
aaggtggata aaaatcacgc ataagacggt tgtaacatag cactttagtg cgaatatcag 189420
gaatgccaat agcatgtaga taaggcacca aacatcgcag ctatacatgg ctaaagatca 189480
accagaaaag gtttaaattt taacgccggc ccaaaactta aacttttttt gatattttta 189540
agtgcagcca tggattggtc cggccatagg atgacctatg cctacgtggc attctcattg 189600
atggcaatag caataatatg gtatattcta cttatctatt gccgatcgaa aaaaaatgtt 189660
gttacaagcg gtaatacgct cgctttagcg ccaatatcgc atatgtgaaa aatgttcgcc 189720
gaaaaaaaca ttaaaattta gaaccgccgc ggcatctcag gggcggcaac attttttttt 189780
atatggatat tgtcacacac cacctcatct atgacgcaat atattactgc taatatcagg 189840
ttccccaata gtatgtagag aaaccacaca agatagatat tcatggcgat ttttgacgaa 189900
aaaacattaa gttttagctt ctttgacgcc tgtgtactaa taatgtttaa cgcctgtagt 189960
ataataattg atacctacag cagtaattga tacctacggc gataatgtct ctctggccgc 190020
cccaaaaaaa agtatttacg gtagggttta ttaccggcgg cgtaacacca gttatggtca 190080
attttgtctg gcccgccgcc cagccgcaaa aaaaaatcaa ttacaaccgc aaaaaaaaat 190140
atttccggcc gcggcgtttc aaaaaataat ctttgcgaaa taattccgca tcttgtgaaa 190200
tgaacgccta cagtaataat tttaatcttt gacacctaca gcagtagtaa taattttaat 190260
ctttaacgcc tgcagcagta ctaatatttt taatctttaa cgcctacagc agtagtaata 190320
attttaatgt ttaacgccta cagcagtagt aataatttta atctttgacg cctacagcag 190380
tagtaataat tttaatgttt aacgcctaca gcagtacaat aattttaatg tttaacgcct 190440
gcagcagtac taatattttt aatctttaac gcctgcagca gtactaatat ttttaatctt 190500
taacgcctac agcagtagta ataattttaa tgtttaacgc ctacagcagt agtaataatt 190560
ttaatctttg acgcctacag cagt 190584

<210> SEQ ID NO 4
<211> LENGTH: 476
<212> TYPE: PRT
<213> ORGANISM: Artificial Sequence
<220> FEATURE:
<223> OTHER INFORMATION: Chemically Synthesized

<400> SEQUENCE: 4

Met Leu Pro Ser Leu Gln Ser Leu Thr Lys Lys Val Leu Ala Gly Gln
1 5 10 15

Cys Ile Pro Val Asp Gln Tyr His Val Leu Lys Cys Cys Gly Leu Trp
20 25 30

Trp His Asn Gly Pro Ile Met Leu His Ile Arg Arg Asn Lys Leu Phe
35 40 45

Ile Arg Ser Thr Cys Phe Ser Gln Gly Ile Glu Leu Asn Ile Gly Leu
50 55 60

Met Lys Ala Val Lys Glu Asn Asn His Asp Leu Ile Lys Leu Phe Thr
65 70 75 80

Glu Trp Gly Ala Asp Ile Asn Tyr Gly Met Ile Cys Ala Leu Thr Glu
85 90 95

Asn Thr Arg Asp Leu Cys Lys Glu Leu Gly Ala Lys Glu Tyr Leu Glu
100 105 110

Arg Glu Tyr Ile Leu Lys Ile Phe Phe Asp Thr Thr Arg Asp Lys Thr
115 120 125

Ser Ser Asn Ile Ile Phe Cys His Glu Val Phe Ser Asn Asn Pro Asn
130 135 140

Leu Arg Ile Ile Asp Asn Leu Asp Leu Arg Gly Glu Ile Met Trp Glu
145 150 155 160

Leu Arg Gly Leu Met Glu Ile Thr Phe Met Leu Asp His Asp Asp Ser
165 170 175

Phe Ser Thr Val Leu Thr Lys Tyr Trp Tyr Ala Ile Ala Val Asp Tyr
180 185 190

Asp Leu Lys Asp Ala Ile Arg Tyr Phe Tyr Gln Lys Tyr Pro Arg Leu
195 200 205

His Arg Trp Arg Leu Met Cys Ala Leu Phe Tyr Asn Asn Val Phe Asp
210 215 220

Leu His Glu Leu Tyr Glu Ile Glu Arg Val Arg Met Asp Ile Asp Glu
225 230 235 240

Met Met His Ile Ala Cys Ile Gln Asp Tyr Ser Tyr Ser Ala Ile Tyr
245 250 255

Tyr Cys Phe Ile Met Gly Ala Asn Ile Asn Gln Ala Met Leu Val Ser
260 265 270

Ile Gln Asn Tyr Asn Leu Gly Ile Ala Ile Asp Phe Asn Leu Thr Lys
275 280 285

-continued

```
Pro Ile His Tyr Leu Ser Lys Lys Phe Pro His Leu Asp Leu Trp Arg
    290                 295                 300

Leu Gln Thr Ala Ile Tyr Leu Gly Asn Ile Asp Glu Val His His Ala
305                 310                 315                 320

Tyr Phe Gln Glu Asn Ile Arg Leu Gly Leu Asn Val Met Met Phe Leu
                325                 330                 335

Ala Cys Ala Arg Pro Gly Asn Lys Leu Gly Ile Tyr Tyr Cys Phe Ala
            340                 345                 350

Leu Gly Ala Asp Leu Asp Arg Ala Leu Glu Arg Leu Ile Ser Phe Asn
        355                 360                 365

Ser Ile Asn Arg Glu Ile Asn Arg Lys Ile Arg Gly Glu Lys Arg Leu
    370                 375                 380

Cys Ile Glu Gly Ser Tyr Leu Ser Asn Val Tyr Phe Cys Ile Gly Leu
385                 390                 395                 400

Gly Ala Asn Pro Tyr Thr Lys Lys Ile Gln Glu Ile Ile Lys Gln Lys
                405                 410                 415

His Ser Asn Ile Met Ile Leu Leu Phe Ser Lys Lys Lys Ile Leu Ser
            420                 425                 430

Pro His Ser Val Leu Gln Asn Lys Ile Leu Asp Pro Ser Asp Val His
        435                 440                 445

Lys Met Ile Ser Thr Tyr Lys Asn Thr Glu Ser Phe Tyr Pro Phe Ser
    450                 455                 460

Ser Leu Ala Val Lys Leu Ile Gln Gln Ala Asn Ile
465                 470                 475
```

GENOMIC DELETION IN AFRICAN SWINE FEVER VACCINE ALLOWING EFFICIENT GROWTH IN STABLE CELL LINES

BACKGROUND OF THE INVENTION

Field of Invention

The present disclosure provides details on the construction of a recombinant African Swine Fever Virus (ASFV) live attenuated vaccine for prevention of ASF caused by various strains of ASFV, such as the highly virulent Georgia 2007 isolate ("ASFV-G"). An exemplary vaccine comprises a deletion resulting in efficient growth in a stable cell line, allowing for industrial-level production of ASFV vaccines.

Background

African swine fever virus (ASFV) strain Georgia (ASFV-G), the only member of the virus family Asfarviridae, is the causative agent of a pandemic disease currently affecting a large contiguous geographical area extended from central Europe to China and South Asia (Costard et al, Philos. Trans. R. Soc. London B Biol. Sci., (2009) 364:2683-96; O'Donnell et al, J. Virol., (2015a) 89:6048-56). This pandemic is causing important economic losses devastating swine industry and provoking worldwide protein availability shortages (O'Donnell et al, (2015a) supra). ASFV is a very large with a complex structure, and a 180-190 kilobases double-stranded DNA genome which encodes for over 150 open reading frames (ORFs).

There is no commercial vaccine available therefore the disease control is exclusively based in managing geographical movements of susceptible animals and culling infected animals (Costard et al, supra). Effective experimental vaccines have been obtained based on the development of attenuated virus strains via genetic manipulation of parental virulent virus deleting specific virus genes associated with virus virulence (O'Donnell et al, (2015a) supra; O'Donnell et al, J. Virol., (2015b) 89:8556-66; O'Donnell et al, J. Virol., (2017) 91:e01760-16; Borca et al, J. Virol., (2020) 94:e02017-19). Understanding the function of viral genes in the process of virus virulence in the natural host is a critical step in the rational development of experimental vaccine using genetic manipulation. These experimental live attenuated vaccines constitute by far the more advanced approach towards the development of an effective countermeasure to control ASF.

A main technical problem in developing commercially viable ASF vaccines is that these virus strains only efficiently replicate in primary cultures of swine macrophage hampering large-scale production at industrial level. To address this problem, we herein disclose a mutation that allows for growth of ASFV vaccines in a stable cell line, while maintaining the ability to replicate in swine macrophages, and a complete attenuation when inoculated in domestic swine.

SUMMARY OF THE INVENTION

The present disclosure provides, in one embodiment, a genetically modified virus, in which the virus genome has a viral genome at least 95% identical to SEQ ID NO: 1. In a particular embodiment, the viral genome is identical to SEQ ID NO:1.

Further provided herein is a vaccine composition against African Swine Fever Virus (ASFV), comprising a genetically modified virus with a viral genome at least 95% identical to SEQ ID NO: 1. In particular embodiments, the ASFV is an ASFV-Georgia 2007 isolate (ASFV-G).

The present disclosure further provides, in an additional embodiment, a method for the protection of swine against ASFV, comprising administering to a swine a live attenuated vaccine comprising a genetically modified virus with a viral genome at least 95% identical to SEQ ID NO: 1 in an amount effective to protect said swine from clinical ASFV disease. In particular embodiments, the ASFV is ASFV-G. In a specific embodiment, the amount effective to protect a vaccinated swine from clinical ASFV disease is a vaccine comprising $10^2$-$10^6$ $HAD_{50}$ of a genetically modified virus with a viral genome at least 95% identical to SEQ ID NO: 1.

An additional embodiment provided by the present disclosure is a recombinant ASFV mutant virus having a deletion, or partial deletion of each of ORFs MGF360-4L, MGF360-6L, X69R, MGF300-1L, MGF300-2R, MGF300-4L, MGF3608L, MGF360-9L, MGF360-10L, MGF360-11L. In a particular embodiment, the virus comprises a deletion of a genomic fragment at least 95% identical to SEQ ID NO:2. In some embodiments, the mutant ASFV is an ASFV-Georgia isolate. In some embodiments, the mutant ASFV has a genome at least 99% identical to SEQ ID NO: 1. Such viruses can also be part of a vaccine composition against ASFV-G.

An additional embodiment provided by this disclosure is a method for the protection of swine against ASFV, comprising administering to a swine a live attenuated vaccine comprising the recombinant having a deletion, or partial deletion of each of ORFs MGF360-4L, MGF360-6L, X69R, MGF300-1L, MGF300-2R, MGF300-4L, MGF3608L, MGF360-9L, MGF360-10L, MGF360-11L in an amount effective to protect said swine from clinical ASFV disease. In a particular embodiment, the ASFV is ASFV-G. In some embodiments, the amount effective to protect inoculated swine from clinical ASFV disease is a vaccine comprising $10^2$-$10^6$ $HAD_{50}$ of the genetically modified virus.

Further provided herein is an embodiment for a method of producing ASFV at titers of $10^4$-$10^7$ $HAD_{50}$/mL in a cultured stable cell line, comprising inoculating a genetically modified virus, in which the virus genome has a viral genome at least 95% identical to SEQ ID NO: 1 into the cultured stable cell line; incubating the inoculated cell line under conditions allowing for viral replication, and; growing said viruses to a titer of $10^4$-$10^7$ $HAD_{50}$/mL. In some embodiments, the stable cell line is a porcine fetal kidney cell line engineered to express bovine $\alpha_v\beta_6$ integrin. In a particular embodiment, the ASFV virus genome comprises a viral genome at least 99% identical to SEQ ID NO: 1.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

DETAILED DESCRIPTION OF THE INVENTION

Figure 1:
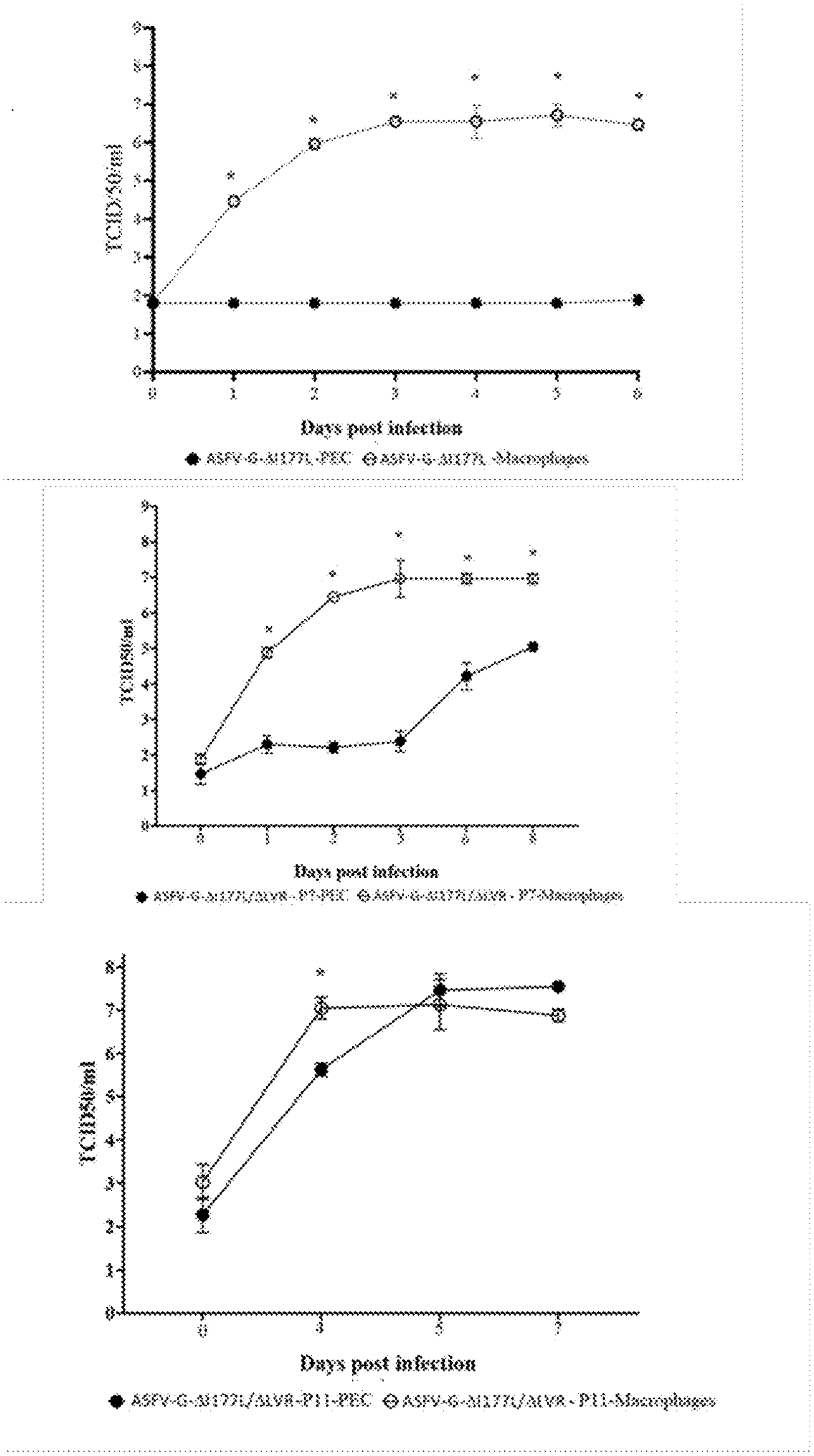
FIG. 1 provides graphically represented data showing in vitro growth characteristics of ASFV-G-ΔI177L/ΔLVR (top), ASFV-G-ΔI177L/ΔLVR p7 (middle) and ASFV-G-ΔI177L/ΔLVR p11 (bottom) in a stable porcine cell line and primary swine macrophage cultures. Cell cultures were infected (MOI=0.01) with each of the viruses and the virus yield titrated at the indicated times postinfection. Data represent the means of the results from three independent experiments. The sensitivity of virus detection is ≥1.8 $\log_{10}$ $HAD_{50}$/ml. Significant differences (*) in viral yields between the two viruses at specific times points were determined using the Holm-Sidak method (α=0.05), without assuming a consistent standard deviation. All calculations were conducted on the software GraphPad Prism version 8. $TCID_{50}$, 50% tissue culture infective dose.

Highly virulent African swine fever virus (ASFV) strain Georgia (ASFV-G) is the causative agent of the current pandemic covering a contiguous geographical area from central Europe to Asia and South Asia causing enormous economic losses. There is no commercial vaccine available and live attenuated strains, developed from virulent parental virus by genetic manipulation, are the most advanced experimental vaccines. Recently we developed a vaccine candidate by deleting the I177L gene from the genome of ASFV-G (see, U.S. patent application Ser. No. 16/580,058). This mutant strain was shown to be very safe and highly efficacious in inducing protection against challenge with ASFV-G. An important technical limitation of transferring this mutant (and other recombinant ASFV vaccines) to industrial production is that replicates exclusively in primary cultures of swine macrophages. Here we present the development of a derivative strain (ASFV-G-ΔI177LΔLVR) that contains a deletion of 10.8 kb in the Left variable region (LVR) which allows for efficient grows in a stable porcine cell line (see, U.S. Pat. No. 9,121,010). The deletion in the LVR affects 10 viral genes in the left end of the genome. This deletion remained stable after more than 30 additional passages in a continuous stable porcine cell line. Importantly, ASFV-G-ΔI177LΔLVR maintained the same level of attenuation, immunogenic characteristics and protective efficacy against challenge with virulent ASFV-G as the parental vaccine. This is the first time a rationally designed highly efficacious ASF vaccine candidate has been shown to grow in a stable cell line, while maintaining genomic stability, allowing for ASFV vaccine production at industrial levels.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for producing genetically altered strains of ASFV.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

The term "adjuvant" means a substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules.

The term "administer"/"administration" means any method of providing a subject with a substance, such as a therapeutic agent by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

The terms "coding sequence" and "coding region" as used herein refer to nucleotide sequences and nucleic acid sequences, including both RNA and DNA, that encode genetic information for the synthesis of an RNA, a protein, or any portion of an RNA or protein.

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

The terms "I177L", "ASFV I177L", and "genomic I177L" are synonyms and refer to the ASFV-G open reading frame I177L that encodes a 177 amino acid protein and is positioned on the reverse strand between nucleotide positions 175473 and 176006 of SEQ ID NO:3.

Figure 2:
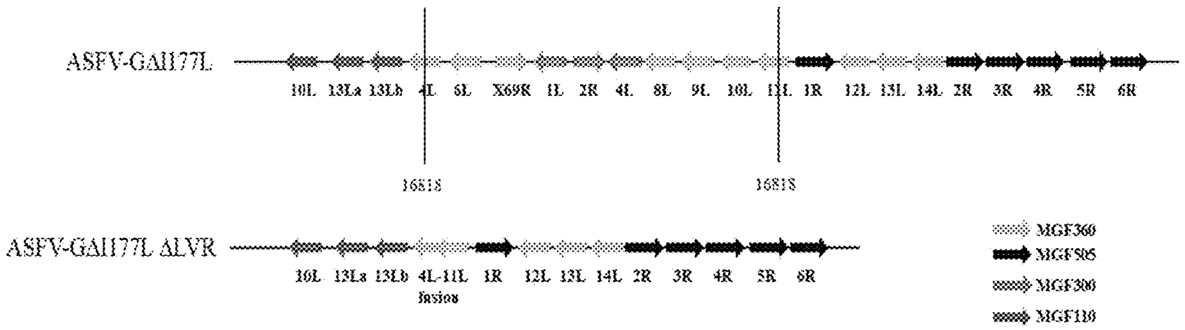
FIG. 2 provides a graphically represented comparison of the genomes of two viruses—ASFV-G-ΔI177LΔLVR and parental ASFV-G-ΔI177L.

In the context of the present invention, the term "cell line adaptation mutation" refers to a modification of the ASFV genome resulting in the full or partial deletion of ORFs MGF360-4L, MGF360-6L, X69R, MGF300-1L, MGF300-2R, MGF300-4L, MGF3608L, MGF360-9L, MGF360-10L, MGF360-11L (FIG. 2). In a specific embodiment, this term refers to deletion of the ASFV-G genomic sequence disclosed as SEQ ID NO:2.

In the context of the present invention, the term "non-functional genomic" MGF360-4L, MGF360-6L, X69R, MGF300-1L, MGF300-2R, MGF300-4L, MGF3608L, MGF360-9L, MGF360-10L, or MGF360-11L refers to a modified gene or ORF, located in the genome of an ASFV, wherein such modification of the ASFV gene results in no gene product at all or a biologically non-functional gene product as compared to an unmodified functional ASFV gene. Such modifications can include, but are not limited to, full or partial deletion of the coding sequence, disruption of the open reading frame (e.g., by insertion of a shift mutation or insertion of a nonsense codon), modification of upstream or downstream regulatory elements, and/or any other currently known or conceivable method of inactivating or knocking-out functional expression of such ASFV gene(s).

The term "ASFV-G-ΔI177LΔLVR" is used to describe a specific embodiment of the present disclosure, namely the vaccine/virus having the genomic sequence of SEQ ID NO: 1. The term "ASFV-G ΔI177L" is used to refer to the parental strain of "ASFV-G-ΔI177LΔLVR", but which lacks the "cell line adaptation mutation".

The term "immunize" means to render a subject protected from an infectious disease, such as by vaccination.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

The phrase "high percent identical" or "high percent identity", and grammatical variations thereof in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In one exemplary embodiment, the sequences are high percent identical over the entire length of the polynucleotide or polypeptide sequences.

The term "swine" can generally refer to any member of the Suidae family and includes domesticated and wild pigs, hogs and boars.

A "vaccine" is herein defined as a biological agent capable of providing a protective response in an animal to which it has been delivered but not capable of causing a serious disease. Administration of the vaccine results in immunity from the disease. Thus, the vaccine stimulates antibody production or cellular immunity against the disease-causing pathogen (e.g., ASFV). Immunity is herein defined as the induction of significantly higher levels of protection against lethality and clinical symptoms following vaccination in a swine population, as compared to the non-vaccinated group. In particular, the vaccine according to the invention protects most of the vaccinated animals against the development of clinical symptoms and lethality of the disease. The vaccine of the present disclosure is typically a genetically engineered (recombinant) mutant virus vaccine.

In the context of the present disclosure, the term "non-deficient in its replication" refers to a non-naturally occurring recombinant ASFV which is able to replicate in vitro and/or in vivo and/or is capable of producing viral progeny although such replication and/or viral progeny production may also occur at reduced levels compared to the unmodified parent strain. Therefore, it can be the case that such ASFV is non deficient in its replication in vitro, e.g. in a cell culture, although in vivo in a mammal such ASFV is at least partially impaired in its replication, e.g. resulting in a replication and/or viral progeny production below detection limits.

As used herein, the term "minimal dose" or "minimal effective dose" refers to a dose that demonstrates the absence of, or minimal presence of, toxicity to the recipient, but still results in producing a desired result (e.g., protective immunity).

Viruses/Vaccines

Provided herein is a novel mutant ASFV-G virus (SEQ ID NO: 1), resulting from the recombinant deletion of a portion of the I177L gene of the parental ASFV-G genome (described in U.S. patent application Ser. No. 16/580,058) and deletion of an approximately 9 kb genomic region. The genomic nucleotide sequence of a specific recombinant mutant ASFV-G ΔI177L (SEQ ID NO: 1) is described herein and differs from the genomic nucleotide sequence encoding the parental ASFV-G.

The exemplary mutant strain of ASFV-G (SEQ ID NO: 1) is representative of the genus of recombinant vaccines in which the cell line adaptation mutation is present, which includes, without limitation, deletion mutants, nonsense mutants, insertional mutants, frameshift mutants and other mutants resulting in deletion, non-functionality, and non-expression of the various ORFs within the mutation (SEQ ID NO: 2). An exemplary virus disclosed herein also has a non-functional I177L ORF, but other recombinant viruses envisioned include mutants in other ORFs, including regulatory elements for those ORFs resulting in non-expression or non-translation of their respective proteins. Such variants can be in the ASFV-G wild type genomic background (SEQ ID NO: 3).

Modifications intended to preclude functional expression of a target protein or reduced expression or reduced activity of a target protein can involve mutations of the DNA or gene encoding the target protein, including deletion of all or a portion of a target gene, including but not limited to the open reading frame of a target locus, transcriptional regulators such as promoters of a target locus, and any other regulatory nucleic acid sequences positioned 5' or 3' from the open reading frame, insertion of premature stop codons in the open reading frame, and insertions or deletions that shift the reading frame leading to premature termination of translation. Such deletional mutations can be achieved using any technique known to those of skill in the art. Reduced levels of the target protein or reduced activity of the target protein may also be achieved with point mutations or insertions in the DNA or gene encoding the target protein. Mutational, insertional, and deletional variants of the disclosed nucleotide sequences and genes can be readily prepared by methods which are well known to those skilled in the art. Techniques used to achieve reduced levels and/or reduced activity of the target protein may include CRISPR/Cas, TALEN, and Zn-finger nuclease. It is well within the skill of a person trained in this art to make mutational, insertional, and deletional mutations which are equivalent in function to the specific ones disclosed herein.

The approaches described herein that were used to create a deletion mutant in ASFV-G can be used in different isolates of ASFV (such as isolates circulating in Asia, Europe or Africa), including naturally occurring and recombinant strains. Such approaches can be varied by methodologies known in the art, such as using different selection markers that can select recombinant virus by purification such as, but not limited to, fluorescent proteins, enzymes such as beta-glucuronidase or beta-galactosidase that can be used with chromogenic substrates, and drug selection makers. Such approaches can also be used to create any mutation to any of the individual ORFs within the larger mutation described herein. For example, any single ORF selected from MGF360-4L, MGF360-6L, X69R, MGF300-1L, MGF300-2R, MGF300-4L, MGF3608L, MGF360-9L, MGF360-10L, or MGF360-11L, as well as to regulatory elements controlling the expression and translation of these ORFs that results in a non-functional protein produced by that ORF. For all usages herein, the nomenclature utilized for these ORFs will be recognized by the skilled artisan as utilizing the standard names for these ASFV ORFs.

Mutants in other ASFV strains and genotypes is also encompassed by the present disclosure. ASFV strains comprising synthetic mutations in nucleic acid sequences that exhibit at least 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 2 are encompassed in the instant invention. ASFV strains comprising entire genomes with 95%, 96%, 97%, 98%, 99% or higher identity to SEQ ID NO: 1 are also encompassed in the instant invention.

The present disclosure further contemplates the combination of a cell-line adaptation mutation with other recombinant mutations. As such, it is not only wild-type viruses that can be modified as disclosed herein, but also strains containing non-naturally occurring mutations in other genes or genomic regions (see, e.g., U.S. Pat. No. 9,814,771).

The present disclosure provides that such rationally-designed, live, attenuated ASFV-G mutants can be incorporated into immunogenic compositions to produce a vaccine effective to protect an animal, such as a pig, from clinical ASF disease when challenged with ASFV-G. Thus, one object of the invention is to provide a method for protecting an animal against ASFV-G by administering an effective amount of rationally designed live attenuated vaccine. In another embodiment, the present disclosure provides a method for eliciting a protective immune response in an animal, preferably of the family Suidae (e.g., domestic pigs (*Sus scrofa domesticus*), wild pigs (*Sus scrofa scrofa*), warthogs (*Potamochoerus porcus*), bushpigs (*Potamochoerus larvatus*), giant forest hogs (*Hylochoerus meinertzhageni*) as well as feral pigs), Such methods will typically comprise administering to such animal the one or more ASFV immunogenic compositions and vaccines described herein.

The immunogenically effective amounts of immunogenic compositions disclosed herein can vary based upon multiple parameters. In general, however, effective amounts per dosage unit for intramuscular application can be about $10^2$ 50% hemadsorption dose ("$HAD_{50}$") to $10^6$ $HAD_{50}$. One, two, or more dosage units can be utilized in practicing the methodologies of the present invention. A dosage unit can readily be modified to fit a desired volume or mass by one of skill in the art. Regardless of the dosage unit parameters, immunogenic compositions disclosed herein can be administered in an amount effective to produce an immune response.

Dosage levels of active ingredients in vaccines disclosed herein, can be varied by one of skill in the art to achieve a desired result in a subject or per application. As such, a selected dosage level can depend upon a variety of factors including, but not limited to, formulation, combination with other treatments, severity of a pre-existing condition, and the presence or absence of adjuvants. In preferred embodiments, a minimal dose of an immunogenic composition is administered. Determination of a minimal dose is well within the capabilities of one skilled in the art.

Vaccines of the present invention can be prepared by conventional methods used for commercially available live attenuated ASFV vaccines. In a specific embodiment, a susceptible substrate is inoculated with an ASFV mutant disclosed herein and propagated until the virus has replicated to a desired titer after which ASFV-containing material is harvested. Following this, the harvested material can be formulated into a vaccine preparation with immunogenic properties. Every substrate which is able to support the replication of the recombinant viruses provided herein can be used in the present invention, including primary cultures of swine peripheral blood macrophages or blood from infected swine.

Virus Replication and Production in Stable Cell Lines

The vaccines provided herein containing a cell line adaptation mutation of the present disclosure replicate and grow at increased rates in stable cell lines compared to viruses lacking the mutation. ASFV-G-I177L can grow increasing titer 4-5 logs in swine macrophages (over 3-5 days), however was unable to grow in stable cell lines tested. When the adaptation mutation was added to the vaccine, the vaccine could grow to comparable rates to the parental vaccine in macrophages increasing the titer of the vaccine 4-5 logs (over 3-6 days).

Formulations and Administration

A vaccine provided herein comprises one of the recombinant viruses as defined above in a live form, and a pharmaceutically acceptable carrier or diluent customarily used for such compositions. Carriers include stabilizers, preservatives and buffers. Suitable stabilizers include, for example, SPGA (sucrose, phosphate, glutamate and albumin), carbohydrates (sorbitol, mannitol, starch, sucrose, dextran, glutamate, and glucose), proteins (dried milk, serum, albumin, casein), or degradation products thereof. Suitable buffers include, for example alkali metal phosphates. Preservatives that can be utilized, include, but are not limited to, thimerosal, merthiolate and gentamicin. Diluents include water, aqueous buffers (e.g., buffered saline), alcohols and polyols (e.g., glycerol).

In some instances, vaccines of the present invention also contain or comprise one or more adjuvants, which includes any material included in the immunogenic composition formulation that enhances an immune response in the recipient that is induced by the immunogenic composition. In some instances, such adjuvants can include proteins other components included with the recombinant virus. Other adjuvants can be included as an extra component of the immunogenic compositions, and include such categories as aluminum salts (alum), oil emulsions, saponins, immune-stimulating complexes (ISCOMs), liposomes, microparticles, nonionic block copolymers, derivatized polysaccharides, cytokines, and a wide variety of bacterial derivatives. Any relevant adjuvant known in the art can be utilized in practicing the inventions disclosed herein. Factors influencing the selection of an adjuvant include animal species, specific pathogen, antigen, route of immunization, and type of immunity needed and can be readily determined by one of skill in the art.

Immunogenic compositions of the present disclosure can also comprise carriers in addition to the recombinant virus. Carriers utilized in practicing the immunogenic compositions provided herein can be any known in the art and can be liquid, solid, semi-solid, or gel. The type of formulation can be modified depending on the route of administration of the antigen. Preferably, carriers are non-toxic to the recipient. One of skill in the art is readily able to choose such carriers for application to recipient animals such as poultry.

Vaccines provided herein may be administered by intramuscular, subcutaneous, intranasal or injection in an amount which is effective to protect the animal against challenge by a virulent strain of ASFV. The vaccine may be administered orally, through direct oral inoculation, dosed in drinking water, or though bait delivery systems. The effective amount of recombinant virus may vary according to parameters considered by those skilled in the art. Effective amounts can be experimentally determined as necessary by those of skill in the art by following any known method or the guidance provided in the Examples herein.

Having generally described this invention, the same will be better understood by reference to certain specific examples, which are included herein to further illustrate the invention and are not intended to limit the scope of the invention as defined by the claims.

EXAMPLES

Example 1

Cell Culture and Viruses.

Primary cultures of swine macrophage were prepared from swine blood, following procedures previously described (O'Donnell et al, (2015b), supra) Preparation of macrophage cultures in 96-well plates for virus titration also was performed as previously described (O'Donnell et al, (2015b), supra).

Porcine Epithelial Cells (PEC) are a cell subclone derived after over 60 passages from the parental LFPK$\alpha_V\beta_6$ cell line, a porcine fetal kidney cell line engineered to express bovine $\alpha_V\beta_6$ integrin (U.S. Pat. No. 9,121,010). Cell cultures were passaged in culture using DMEM medium (Life Technologies, Grand Island, N.Y.) with 10% heat-inactivated fetal bovine serum (HI-FBS; Thermo Fisher Scientific, Waltham, Mass.) and 1% antibiotic-antimycotic (Thermo Fisher Scientific) at 37° C. under 5% $CO_2$.

ASFV-G-ΔI177LΔLVR (SEQ ID NO: 1) was generated after sequential passages of the live attenuated vaccine candidate strain ASFV-G-ΔI177L (U.S. patent application Ser. No. 16/580,058) as described below.

Comparative growth curves between ASFV-G-ΔI177L (parental strain) and ASFV-G-ΔI177LΔLVR (SEQ ID NO: 1) were performed in primary swine macrophage and stable porcine cell cultures. Preformed monolayers were prepared in 24-well plates and infected at an MOI of 0.01 (based on the $HAD_{50}$ previously determined in primary swine macrophage cell cultures). After 1 h of adsorption at 37° C. under 5% $CO_2$, the inoculum was removed, and the cells were rinsed two times with PBS. The monolayers were then rinsed with macrophage medium and incubated for 2, 24, 48, 72, and 96 h at 37° C. under 5% $CO_2$. At appropriate times postinfection, the cells were frozen at <−70° C., and the thawed lysates were used to determine titers by $HAD_{50}$/ml in primary swine macrophage cell cultures. All samples were run simultaneously to avoid intraassay variability.

Virus titration was performed on primary swine macrophage cell cultures in 96-well plates. Virus dilutions and cultures were performed using macrophage medium. The presence of virus was assessed by hemadsorption (HA), and virus titers were calculated by the Reed and Muench method (Reed & Muench, Am. J. Hygiene, (1938), 27:493-497). ASFV Georgia (ASFV-G) used in the animal challenge experiments is a field isolate kindly provided by Nino Vepkhvadze from the Laboratory of the Ministry of Agriculture (LMA) in Tbilisi, Republic of Georgia. ASFV DNA was extracted from infected cells and quantified as described earlier. The full-length sequence of the virus genome was determined as described previously (Borca et al, Sci. Rep., (2018), 8:3154) using an Illumina NextSeq 500 sequencer.

Example 2

Cell Line Mutation and Adaptation.

ASFV-G ΔI177L did not significantly replicate in more than 30 cell lines tested in our laboratory, including commercially available cell lines of swine origin. In most of the cases only the initial replication steps, evidenced by presence of intracellular expression of fluorescence due to the expression of the recombinant RFP present in the ASFV-G ΔI177L genome, were perceived with minor or no virus yield detected (data not shown).

ASFV-G ΔI177L after 6 successive passages in stable porcine cell line cells showed a clear cytopathic effect occurring. The first passage of ASFV-G-ΔI177L was performed using a MOI of 10. By passage six, ASFV-G-ΔI177L yield reached a titer of approximately $10^5$ $HAD_{50}$/ml. Further successive passages reached virus yields of approximately $10^7$ $HAD_{50}$/ml (FIG. 1).

Assessment of genomic changes accompanying the passage of ASFV-G-ΔI177L (ASFV-G-ΔI177LΔLVR) was performed in virus obtained after the sixth passage by next-generation sequencing (NGS). Compared to parental virus, a deletion occurred between positions 16818 and 27660 of the viral genome, resulting in a deletion of 10842 bp. This genomic modification fully deletes the following genes: MGF360-6L, X69R, MGF300-1L, MGF300-1L, MGF300-2R, MGF300-4L, MGF360-8L, MGF360-9L, and MGF360-10L. In addition, the genomic modification also causes the deletion of the N-terminal portion of MGF 360-4L gene, and the C-terminus of MGF360-11L gene (FIG. 2). This deletion results in the creation of a novel hybrid protein, MGF360-4l/11L. This resulting ORF, which resides on the reverse coding strand, has 839nt of MGF-360-11L combined with 592nt MGF-360-4L. The resulting ORF is composed by 1432nt that encodes a novel 476 amino acid protein (SEQ ID NO: 4).

The genomic stability of ASFV-G-ΔI177LΔLVR was further assessed in the population of virus obtained after passage twenty and passage thirty. Surprisingly, NGS analysis demonstrated no major additional genomic changes when compared with the genome of the virus obtained after the sixth passage. This result indicates that the viral genome of ASFV-G-ΔI177LΔLVR remains stable with continuous passage in the stable porcine cell line cells.

Replication of ASFV-G-Δ1177LΔLVR in Primary Swine Macrophages.

The goal of developing aptASFV-G-ΔI177L is to use it as vaccine strain. Therefore, it is important to assess its ability to replicate in swine macrophages, the primary cell targeted by ASFV during infection in swine. Then, the in vitro growth characteristics of ASFV-G-ΔI177LΔLVR were evaluated in primary swine macrophage cell cultures in a multistep growth curve. Two different passages of ASFV-G-ΔI177LΔLVR in PEC, the sixth and twelfth passages, were tested. Cell cultures were infected at a multiplicity of infection (MOI) of 0.01, and samples were collected at 2 h, and every 24 hours for the next 6-8 days after infection. The results demonstrated that both strains of ASFV-G-ΔI177LΔLVR displayed a similar growth kinetic compared to that of parental ASFV-G-ΔI177L (FIG. 1). Therefore, the ability of ASFV-G-ΔI177LΔLVR to grow in stable porcine cell line cells does not affect the ability of ASFV-G-ΔI177ΔLVR to replicate in vitro in primary swine macrophage cell cultures.

Example 3

Animal Experiments

Animal experiments were performed under biosafety level 3-Agriculture (3-AG) conditions in the animal facilities at Plum Island Animal Disease Center (PIADC) following a protocol approved by the PIADC Institutional Animal Care and Use Committee of the U.S. Department of Agriculture and U.S. Department of Homeland Security (protocol number 225.04-16-R, 09-07-16).

To evaluate if changes in the genome of ASFV-G-ΔI177LΔLVR produced any alteration in the attenuated phenotype of the parental virus, ASFV-G-ΔI177L, a group of 80- to 90-pound pigs were inoculated via intramuscularly (IM) with a high dose, $10^6$ hemadsorbing doses ($HAD_{50}$), and the clinical evolution of the animals were observed for a 28 day period. The five animals inoculated did not present with any ASF-related signs, remaining clinically normal during the entire observation period indicating that ASFV-G-ΔI177LΔLVR remains completely attenuated (Table 1). Therefore, ASFV-G-ΔI177LΔLVR maintains the complete attenuation phenotype of the parental virus.

TABLE 1

Swine survival and fever response following infection with different doses of ASFV-G-ΔI177LΔLVR.

| | | | Fever | | |
|---|---|---|---|---|---|
| Virus and dose ($HAD_{50}$) [(1)] | No. of survivors/ total | Mean time to death (days ± SD) | No. of days to onset (days ± SD | Duration No. of days (days ± SD) | Maximum daily temp (° F. ± SD) |
| ASFV-G-ΔI177LΔLVR $10^6$ | 5/5 | — | — | — | 103 (0.64) |
| ASFV-G-ΔI177LΔLVR $10^2$ | 5/5 | — | — | — | 103.8 (1.04) |
| ASFV-G-ΔI177LΔLVR $10^4$ | 5/5 | — | — | — | 103.2 (1.68) |
| ASFV-G-ΔI177LΔLVR $10^6$ | 5/5 | — | — | — | 102.9 (0.46) |

Protective Efficacy of ASFV-G-Δ1177L Against Challenge with Parental ASFV-G

To assess the ability of ASFV-G-ΔI177LΔLVR infection to induce protection against challenge with highly virulent parental virus ASFV-G, all animals infected with ASFV-G-ΔI177LΔLVR were challenged 28 days later with $10^2$ $HAD_{50}$ of ASFV-G by the IM route. An additional group of five naive animals were challenged as a mock-inoculated control group. All mock animals started showing disease-related signs by 3 to 4 days post challenge (dpc), with rapidly increasing disease severity in the following hours; they were euthanized around 5 dpc (Table 2). On the other hand, the group of animals infected with ASFV-G-ΔI177LΔLVR remained clinically healthy, not showing any significant signs of disease during the 21-day observational period. Therefore, ASFV-G-ΔI177LΔLVR-treated animals are protected against clinical disease when challenged with the highly virulent parental virus.

In order to quantify the effectivity of ASFV-G-ΔI177LΔLVR in protecting swine against the challenge with the parental virulent ASFV-G, three groups of pigs were IM inoculated with either $10^2$, $10^4$ or $10^6$ $HAD_{50}$ of ASFV-G-ΔI177LΔLVR, respectively. All animals remained clinical normal during the 28-day period before they were challenge IM with $10^2$ $HAD_{50}$ of parental virulent ASFV-G. Animals were observed for 21 days. All animals remained clinically normal after the challenge without showing any ASF clinical related sign (Table 2). Therefore, ASFV-G-ΔI177LΔLVR efficacy is comparable to that reported for ASFV-G-ΔI177L (U.S. patent application Ser. No. 16/580,058).

TABLE 2

Swine survival and fever response in ASFV-G-ΔI177LΔLVR-infected animals challenged with parental ASFV-G virus.

| | | | Fever | | |
|---|---|---|---|---|---|
| Virus and dose ($HAD_{50}$) | No. of survivors/total | Mean time to death (days ± SD) | No. of days to onset (days ± SD | Duration No. of days (days ± SD) | Maximum daily temp (° F. ± SD) |
| ASFV-G-ΔI177LΔLVR $10^6$ | 5/5 | — | — | — | 103 (0.59) |
| ASFV-G-ΔI177LΔLVR $10^2$ | 5/5 | — | — | — | 103 (0.29) |
| ASFV-G-ΔI177LΔLVR $10^4$ | 5/5 | — | — | — | 103 (0.28) |
| ASFV-G-ΔI177LΔLVR $10^6$ | 5/5 | — | — | — | |
| AI177L ($10^2$) | 5/5 | — | — | — | 102.7 (0.44) |
| Mock | 10/10 | — | — | — | 102.8 (0.52) |

Example 4

Recombinant Virus Construction

Figure 3:
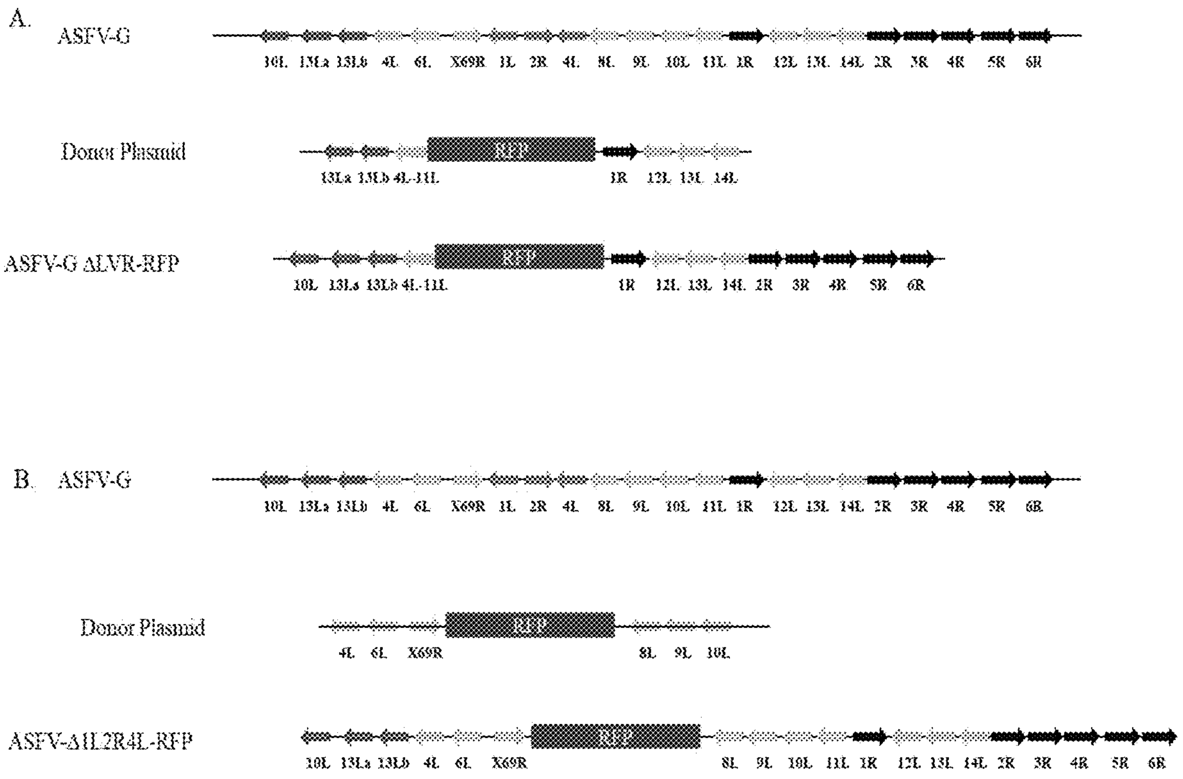
FIG. 3 provides a schematic of gene deletion approaches to construct cell line adaptation mutants of ASFV. ΔLVR or a partial deletion in ΔLVR deleting just MGF300 1L, 2R, 4L. The indicated donor plasmid serves as a template for homologous recombination, a standard method for producing recombinant viruses.

Recombinant ASFV lacking one or more genes have been produced by us and other laboratories. A donor plasmid is made containing flanking arms of identical DNA (typically 1000 bp) of both sides of the area that is targeted for deletion, between these two arms is a reporter cassette (i.e. GFP, RFP) that allows for selection of the recombinant ASFV. Introduction of this plasmid into virally infected cells allows for exchange of the donor plasmid for ASFV DNA. This occurs specifically in the homologous DNA arms. Examples of this deleting individual genes I177L, 9GL, UK (O'Donnell et al, (2015b), supra; O'Donnell et al, (2017), supra; Borca et al; (2020), supra) or deleting multiple MGF genes (O'Donnell et al, (2015a), supra). FIG. 3 shows a schematic of how this could be done, making the exact deletion of the ΔLVR in the ASFV-G genome in 4A and a partial deletion in the ΔLVR region deleting only 3 genes MGF3001L, 2R, 4. The same methodology can be applied to delete any gene or any group of genes in the cell line adaptation mutation region (SEQ ID NO: 2) or other parts of the genome. Selection and screening of recombinant viruses can be performed as described herein, or by any means known in the art.

While the invention has been described with reference to details of the illustrated embodiments, these details are not intended to limit the scope of the invention as defined in the appended claims. The embodiments of the disclosure in which exclusive property or privilege is claimed is defined as follows:

What is claimed is:

1. A genetically modified virus, wherein the virus genome comprises a viral genome at least 95% identical to SEQ ID NO: 1.

2. The virus of claim 1, wherein the viral genome comprises SEQ ID NO:1.

3. A vaccine composition against African Swine Fever Virus (ASFV), comprising the genetically modified virus of claim 1.

4. The vaccine composition of claim 3, wherein the ASFV is ASFV-Georgia 2007 isolate (ASFV-G).

5. A method for the protection of swine against ASFV, comprising administering to a swine a live attenuated vaccine comprising the genetically modified virus of claim 1 in an amount effective to protect said swine from clinical ASFV disease, wherein the ASFV is ASFV-G.

6. The method of claim 5, wherein the amount effective to protect said swine from clinical ASFV disease is a vaccine comprising $10^2$-$10^6$ $HAD_{50}$ of the genetically modified virus of claim 1.

7. A recombinant ASFV mutant virus, comprising a genome with a deletion, or partial deletion of each of ORFs MGF360-4L, MGF360-6L, X69R, MGF300-1L, MGF300-2R, MGF300-4L, MGF3608L, MGF360-9L, MGF360-10L, and MGF360-11L.

8. The recombinant virus of claim 7, wherein the virus comprises a deletion of a genomic fragment at least 95% identical to SEQ ID NO:2.

9. The recombinant virus of claim 7, wherein the mutant ASFV is an ASFV-Georgia isolate.

10. The recombinant virus of claim 7, wherein the mutant ASFV comprises a genome at least 99% identical to SEQ ID NO: 1.

11. A vaccine composition against ASFV-G, comprising the recombinant virus of claim 7.

12. A method for the protection of swine against ASFV, comprising administering to a swine a live attenuated vaccine comprising the recombinant virus of claim 7 in an amount effective to protect said swine from clinical ASFV disease, wherein the ASFV is ASFV-G.

13. The method of claim 12, wherein the amount effective to protect said swine from clinical ASFV disease is a vaccine comprising $10^2$-$10^6$ $HAD_{50}$ of the genetically modified virus of claim 7.

14. A method of producing ASFV at titers of $10^4$-$10^7$ $HAD_{50}$/mL in a cultured stable cell line, comprising inoculating the virus of claim 1 into said cultured stable cell line; incubating the inoculated cell line under conditions allowing for viral replication; and, growing said viruses to a titer of $10^4$-$10^7$ $HAD_{50}$/mL.

15. The method of claim 14, wherein the stable cell line is a porcine fetal kidney cell line engineered to express bovine $\alpha_V\beta_6$ integrin.

16. The method of claim 14, wherein the ASFV comprises a viral genome at least 99% identical to SEQ ID NO: 1.

* * * * *